(12) United States Patent
Chan et al.

(10) Patent No.: US 7,084,139 B2
(45) Date of Patent: Aug. 1, 2006

(54) PYRROLIDIN-2-ONE DERIVATIVES AS INHIBITORS OF FACTOR XA

(75) Inventors: Chuen Chan, Stevenage (GB); Julie Nicole Hamblin, Stevenage (GB); Henry Anderson Kelly, Stevenage (GB); Nigel Paul King, Harlow (GB); Andrew McMurtrie Mason, Stevenage (GB); Vipulkumar Kantibhai Patel, Stevenage (GB); Stefan Senger, Stevenage (GB); Gita Punjabhai Shah, Stevenage (GB); Nigel Stephen Watson, Stevenage (GB); Helen Elisabeth Weston, Stevenage (GB); Caroline Whitworth, Stevenage (GB); Robert John Young, Stevenage (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 33 days.

(21) Appl. No.: 10/479,534

(22) PCT Filed: Jun. 6, 2002

(86) PCT No.: PCT/GB02/02586

§ 371 (c)(1),
(2), (4) Date: Dec. 3, 2003

(87) PCT Pub. No.: WO02/100886

PCT Pub. Date: Dec. 19, 2002

(65) Prior Publication Data

US 2004/0152697 A1    Aug. 5, 2004

(30) Foreign Application Priority Data

Jun. 8, 2001    (GB) .................................. 0114004.5

(51) Int. Cl.
| | | |
|---|---|---|
| *A61K 51/5377* | (2006.01) | |
| *A61K 31/4015* | (2006.01) | |
| *C07D 413/414* | (2006.01) | |
| *C07D 207/12* | (2006.01) | |

(52) U.S. Cl. .............................. 514/235.5; 514/236.2; 514/424; 544/141; 544/124; 544/134; 548/538

(58) Field of Classification Search ................. 544/141
See application file for complete search history.

(56) References Cited

U.S. PATENT DOCUMENTS 5,489,583 A * 2/1996 Mack et al. ................. 514/183

| 6,034,215 | A  | 3/2000 | Semple et al. |
| 6,187,797 | B1 | 2/2001 | Pruitt et al. |
| 6,281,227 | B1 | 8/2001 | Choi-Sledeski et al. |

FOREIGN PATENT DOCUMENTS

| DE | 41 21 947 | 1/1993 |
| EP | 365992 | 5/1990 |
| EP | 0 483 667 | 5/1992 |
| EP | 1 031 563 | 8/2000 |
| WO | 93/01208 | 1/1993 |
| WO | 98/16523 | 4/1998 |
| WO | 98/25611 | 6/1998 |
| WO | 98/47876 | 10/1998 |
| WO | 99/37304 | 7/1999 |
| WO | 99/62904 | 12/1999 |
| WO | 00/40578 | 7/2000 |
| WO | 00/47563 | 8/2000 |
| WO | 00/55188 | 9/2000 |
| WO | 00/69465 | 11/2000 |
| WO | 01/07436 | 2/2001 |
| WO | 01/39759 | 6/2001 |
| WO | 02/060894 | 8/2002 |

OTHER PUBLICATIONS

J. Enzyme Inhibition, 1995, 9(1), pp. 73-86.

* cited by examiner

*Primary Examiner*—Golam M. M. Shameem
*Assistant Examiner*—Andrew B. Freistein
(74) *Attorney, Agent, or Firm*—Amy H. Fix

(57) ABSTRACT

The invention relates to compounds of formula (Ic)

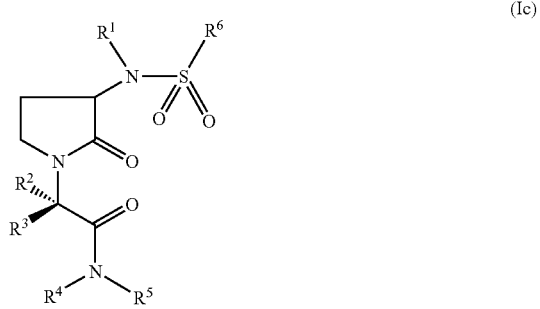

processes for their preparation, pharmaceutical compositions containing them and to their use in medicine, particularly use in the amelioration of a clinical condition for which a Factor Xa inhibitor is indicated.

11 Claims, No Drawings

PYRROLIDIN-2-ONE DERIVATIVES AS INHIBITORS OF FACTOR XA

This This application is filed pursuant to 35 U.S.C. § 371 as a United States National Phase Application of International Application No. PCT/GB02/02586 filed Jun. 6, 2002, which claims priority from GB 0114004.5 filed Jun. 8, 2001.

FIELD OF THE INVENTION

The present invention relates to a novel class of chemical compounds, to processes for their preparation, to pharmaceutical compositions containing them and to their use in medicine, particularly use in the amelioration of a clinical condition for which a Factor Xa inhibitor is indicated.

BACKGROUND OF THE INVENTION

Factor Xa is a member of the trypsin-like serine protease class of enzymes. It is a key enzyme in the coagulation cascade. A one-to-one binding of Factors Xa and Va with calcium ions and phospholipid converts prothrombin into thrombin. Thrombin plays a central role in the mechanism of blood coagulation by converting the soluble plasma protein, fibrinogen, into insoluble fibrin. The insoluble fibrin matrix is required for the stabilisation of the primary hemostatic plug. Many significant disease states are related to abnormal hemostasis. With respect to the coronary arterial vasculature, abnormal thrombus formation due to the rupture of an established atherosclerotic plaque is the major cause of acute myocardial infarction and unstable angina. Both treatment of an occlusive coronary thrombus by thrombolytic therapy and percutaneous transluminal coronary angioplasty (PTCA) are often accompanied by an acute thrombotic reclosure of the affected vessel which requires immediate resolution. With respect to the venous vasculature, a high percentage of patients undergoing major surgery in the lower extremities or the abdominal area suffer from thrombus formation in the venous vasculature which can result in reduced blood flow to the affected extremity and a predisposition to pulmonary embolism. Disseminated intravascular coagulopathy commonly occurs within both vascular systems during septic shock, certain viral infections and cancer and is characterised by the rapid consumption of coagulation factors and systemic coagulation which results in the formation of life-threatening thrombi occurring throughout the vasculature leading to widespread organ failure.

Beyond its direct role in the formation of fibrin rich blood clots, thrombin has been reported to have profound bioregulatory effects on a number of cellular components within the vasculature and blood, (Shuman, M. A., Ann. NY Acad. Sci., 405: 349 (1986)).

A Factor Xa inhibitor may be useful in the treatment of acute vascular diseases such as coronary thrombosis (for example myocardial infarction and unstable angina), thromboembolism, acute vessel closure associated with thrombolytic therapy and percutaneous transluminal coronary angioplasty, transient ischemic attacks, pulmonary embolism, deep vein thrombosis, peripheral arterial occlusion, prevention of vessel luminal narrowing (restenosis), and the prevention of thromboembolic events associated with atrial fibrillation, e.g. stroke. They may also have utility as anticoagulant agents both in-vivo and ex-vivo, and in oedema and inflammation. Thrombin has been reported to contribute to lung fibroblast proliferation, thus, Factor Xa inhibitors could be useful for the treatment of some pulmonary fibrotic diseases. Factor Xa inhibitors could also be useful in the treatment of tumour metastasis, preventing the fibrin deposition and metastasis caused by the inappropriate activation of Factor Xa by cysteine proteinases produced by certain tumour cells. Thrombin can induce neurite retraction and thus Factor Xa inhibitors may have potential in neurogenerative diseases such as Parkinson's and Alzheimer's disease. They have also been reported for use in conjunction with thrombolytic agents, thus permitting the use of a lower dose of thrombolytic agent.

The present invention provides novel Factor Xa inhibitors. Compounds of the present invention have oral bioavailability and PK profiles suitable for acute and chronic therapies.

SUMMARY OF THE INVENTION

The present invention provides compounds of formula (Ic):

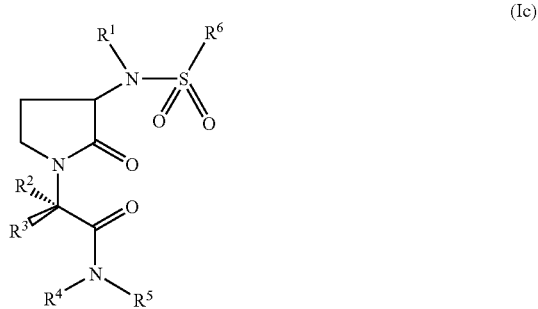

wherein:
$R^1$ represents hydrogen, —$C_{1-6}$alkyl, —$C_{3-6}$alkenyl, —$C_{3-6}$alkynyl, —$C_{2-3}$alkylOH, —$C_{2-3}$alkylNR$^b$R$^a$, —$C_{2-3}$alkylNHCOR$^a$, —$C_{2-3}$alkylNHCO$_2$R$^b$, —$C_{2-3}$alkylNHSO$_2$R$^b$, —$C_{2-3}$alkylNHCONR$^b$R$^c$, —$C_{2-3}$alkylOCONR$^b$R$^c$, —$C_{2-3}$alkylOC$_{1-6}$alkyl, —$C_{2-3}$alkylOCH$_2$phenyl, phenyl or 5- or 6-membered aromatic heterocyclic group containing at least one heteroatom selected from O, N or S, the phenyl or aromatic heterocyclic group being optionally substituted by one or more substitutents selected from: —$C_{1-3}$alkyl, —$C_{1-3}$alkoxy, —$C_{1-3}$alkylOH, halogen, —CN, —$CF_3$, —$NH_2$, —$CO_2H$ and —OH, or $R^1$ represents a group X—W;
X represents —$C_{1-3}$alkylene-, propenylene, propynylene;
W represents —CN, —$CO_2H$, —CONR$^b$R$^c$, —COC$_{1-6}$alkyl, —$CO_2C_{1-6}$alkyl, —$CO_2C_{3-6}$alkenyl, phenyl or 5- or 6-membered aromatic or non-aromatic heterocyclic group containing at least one heteroatom selected from O, N or S, the phenyl or aromatic or non-aromatic heterocyclic group being optionally substituted by one or more substitutents selected from: —$C_{1-3}$alkyl, —$C_{1-3}$alkoxy, —$C_{1-3}$alkylOH, halogen, —CN, —$CF_3$, —$NH_2$, —$CO_2H$ and —OH;
$R^a$ represents hydrogen, —$C_{1-3}$alkyl, phenyl or a 5- or 6-membered heterocyclic group containing at least one heteroatom selected from O, N or S, the phenyl or heterocyclic group being optionally substituted by one or more substituents selected from: —$C_{1-3}$alkyl, —$C_{1-3}$alkoxy, —$C_{1-3}$alkylOH, halogen, —CN, —$CF_3$, —$NH_2$, —$CO_2H$ and —OH;
$R^b$ and $R^c$ independently represent hydrogen or —$C_{1-4}$alkyl;

$R^2$ and $R^3$ independently represent hydrogen, —$C_{1-3}$alkyl or —$CF_3$, with the proviso that one of $R^2$ and $R^3$ is —$C_{1-3}$alkyl or —$CF_3$ and the other is hydrogen;

$R^4$ and $R^5$, together with the N atom to which they are bonded, form a 4-, 5-, 6-, 7- or 8-membered non-aromatic heterocyclic ring, bridged or unbridged, optionally containing an additional heteroatom selected from O, N or S, and optionally substituted by:

(i) one or more substitutents selected from: —$NH_2$, —$CF_3$, F, —OH, =O, —$CO_2H$, —$C_{1-6}$alkyl, —$C_{1-6}$alkoxy, —$C_{1-6}$alkylOH, —($C_{1-3}$alkyl)$NR^bR^c$, —($C_{0-3}$alkyl)$CONR^bR^c$, —$NHSO_2CF_3$, —$NHSO_2(C_{0-3}$alkyl)$R^a$, —$NHCH_2COCH_2O(C_{1-3}$alkyl), —($C_{0-3}$alkyl)$CO_2C_{1-4}$alkyl, —$CONHC_{2-3}$alkylOH, —$CH_2NHC_{2-3}$alkylOH, —$CH_2OC_{1-3}$alkyl, —$COCH_2NR^bR^c$, —$COCH_2N^+(CH_3)_3$ and —$CH_2SO_2C_{1-3}$alkyl;

(ii) a group —$NHCOR^d$ or —$NR^bR^d$, $R^d$ represents —$C_{1-6}$alkyl, —$C_{2-6}$alkynyl, —$C_{1-6}$alkoxy, —$C_{1-6}$alkylOH, —$C_{1-3}$alkylCO_2H$, —$C_{1-3}$alkyl$NR^bR^c$, —$C_{1-3}$alkylCO$_2C_{1-3}$alkyl, —$C_{1-3}$alkyl$CONR^bR^c$ and —$C_{1-3}$alkylOC$_{1-3}$alkyl;

(iii) a group —Y—$R^e$,

Y represents —$C_{1-3}$alkylene-, —NHCO—, —$NHCO_2C_{1-3}$alkylene-, —NHC$_{1-3}$alkylene-, —CO—, —$C_{1-3}$alkylNH—, —$C_{1-3}$alkylNHCO—, —$C_{1-3}$alkylNHSO$_2$—, —$CH_2NHSO_2CH_2$— or a direct link, $R^e$ represents phenyl, a 5- or 6-membered heterocycle containing at least one heteroatom selected from O, N or S, or a 5- or 6-membered cycloalkyl, each of which is optionally substituted by one or more substituents selected from: —$C_{1-3}$alkyl, —$C_{1-3}$alkoxy, —$C_{1-3}$alkylOH, halogen, —CN, —$CF_3$, —$NH_2$, —$CO_2H$ and —OH; or (iv) a second ring $R^f$ which is fused to the non-aromatic heterocyclic ring formed by $R^4$ and $R^5$, wherein $R^f$ represents phenyl, a 5- or 6-membered cycloalkyl group or a 5- or 6-membered aromatic heterocyclic group containing at least one heteroatom selected from O, N or S, and the fused bicyclic group is optionally substituted by one or more substituents selected from: —$C_{1-3}$alkyl, —$C_{1-3}$alkoxy, —$C_{1-3}$alkylOH, halogen, —CN, —$CF_3$, —$NH_2$, —$CO_2H$ and —OH; with the proviso that where the substituent on the non-aromatic ring formed by $R^4$ and $R^5$ is —$NH_2$, —OH, —$C_{1-6}$alkoxy, —$NHSO_2CF_3$, —$NHSO_2(C_{0-3}$alkyl)$R^a$, —$NHCOR^d$, —$NR^bR^d$, —$NHCOR^e$, —$NHCO_2C_{1-3}$alkylene$R^e$ or —$NHC_{1-3}$alkylene$R^e$, —$NHCH_2COCH_2O(C_{1-3}$alkyl), the substituent is not attached to a ring carbon atom adjacent to a heteroatom;

$R^6$ represents:

(i) a fused bicyclic group —$R^gR^h$;

(ii) a group —$R^g$—$R^h$;

(iii) a group -Z-$R^h$ wherein Z represents —$C_{1-3}$alkylene-, —$C_{2-3}$alkenylene- or a direct link;

wherein $R^g$ and $R^h$ independently represent phenyl or a 5- or 6-membered aromatic heterocyclic group containing at least one heteroatom selected from O, N or S, the phenyl or aromatic heterocyclic group being optionally substituted by one or more substituents selected from: —$C_{1-3}$alkyl, —$C_{1-3}$alkoxy, halogen, —CN, —$CF_3$, —$NH_2$, —$CO_2H$ and —OH;

and pharmaceutically acceptable derivatives thereof.

Further aspects of the invention are:

A pharmaceutical composition comprising a compound of the invention together with a pharmaceutical carrier and/or excipient.

A compound of the invention for use in therapy.

Use of a compound of the invention for the manufacture of a medicament for the treatment of a patient suffering from a condition susceptible to amelioration by a Factor Xa inhibitor.

A method of treating a patient suffering from a condition susceptible to amelioration by a Factor Xa inhibitor comprising administering a therapeutically effective amount of a compound of the invention.

DETAILED DESCRIPTION OF THE INVENTION

The present invention provides compounds of formula (I):

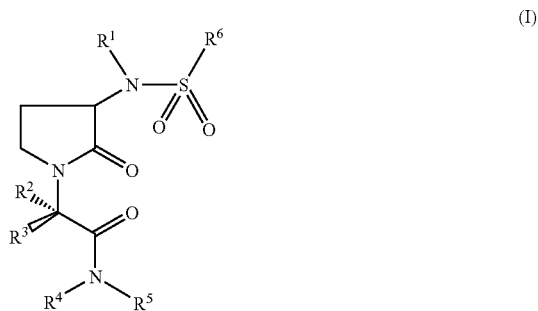

wherein:

$R^1$ represents hydrogen, —$C_{1-6}$alkyl, —$C_{2-6}$alkenyl, —$C_{2-6}$alkynyl, —$C_{2-3}$alkylOH, —$C_{2-3}$alkyl$NR^bR^a$, —$C_{2-3}$alkylNHCOR$^a$, —$C_{2-3}$alkylNHCO$_2R^b$, —$C_{2-3}$alkylNHSO$_2R^b$, —$C_{2-3}$alkylNHCONR$^bR^c$, or a group X—W;

X represents —$C_{1-3}$alkylene-, propenylene, propynylene;

W represents —CN, —$CO_2H$, —$CONR^bR^c$, —$COC_{1-6}$alkyl, —$CO_2C_{1-6}$alkyl, —$CO_2C_{2-6}$alkenyl, —$OCONR^bR^c$, —$OC_{1-6}$alkyl, —$OCH_2$phenyl, phenyl or 5- or 6-membered aromatic heterocyclic group containing at least one heteroatom selected from O, N or S, the phenyl or aromatic heterocyclic group being optionally substituted by one or more substitutents selected from: —$C_{1-3}$alkyl, —$C_{1-3}$alkoxy, —$C_{1-3}$alkylOH, halogen, —CN, —$CF_3$, —$NH_2$, —$CO_2H$ and —OH;

$R^a$ represents hydrogen, —$C_{1-3}$alkyl, phenyl or a 5- or 6-membered heterocyclic group containing at least one heteroatom selected from O, N or S, the phenyl or heterocyclic group being optionally substituted by one or more substituents selected from: —$C_{1-3}$alkyl, —$C_{1-3}$alkoxy, —$C_{1-3}$alkylOH, halogen, —CN, —$CF_3$, —$NH_2$, —$CO_2H$ and —OH;

$R^b$ and $R^c$ independently represent hydrogen or —$C_{1-3}$alkyl;

$R^2$ and $R^3$ independently represent hydrogen, —$C_{1-3}$alkyl or —$CF_3$, with the proviso that when one of $R^2$ and $R^3$ is —$C_{1-3}$alkyl or —$CF_3$, the other is hydrogen;

$R^4$ and $R^5$, together with the N atom to which they are bonded, form a 5-, 6- or 7-membered non-aromatic heterocyclic ring, bridged or unbridged, optionally containing an additional heteroatom selected from O, N or S, and optionally substituted by: (i) one or more substituents selected from: —$NH_2$, —$CF_3$, F, —OH, =O, —$CO_2H$, —$C_{1-6}$alkyl, —$C_{1-6}$alkoxy, —$C_{1-6}$alkylOH, —($C_{1-3}$alkyl)$NR^bR^c$, —($C_{0-3}$alkyl)$CONR^bR^c$, —$NHSO_2CF_3$, —$NHSO^2(C_{0-3}$alkyl)$R^a$ and —($CO_{0-3}$alkyl)$CO_2C_{1-3}$alkyl;

(ii) a group —$NHCOR^d$ or —$NR^bR^d$, $R^d$ represents —$C_{1-6}$alkyl, —$C_{2-6}$alkynyl, —$C_{1-6}$alkoxy, —$C_{1-6}$alkylOH, —$C_{1-3}$alkylCO$_2$H, —$C_{1-3}$alkylNR$^b$R$^c$, —$C_{1-3}$alkylCO$_2$C$_{1-3}$alkyl or —$C_{1-3}$alkylCONR$^b$R$^c$;

(iii) a group —Y—$R^e$,
Y represents —$C_{1-3}$alkylene-, —NHCO—, —NHCO$_2$C$_{1-3}$alkylene-, —NHC$_{1-3}$alkylene-, —CO—, —$C_{1-3}$alkylNH—, —$C_{1-3}$alkylNHCO—, —$C_{1-3}$alkylNHSO$_2$—, —CH$_2$NHSO$_2$CH$_2$— or a direct link, $R^e$ represents phenyl, a 5- or 6-membered cycloalkyl or a 5- or 6-membered heterocycle containing at least one heteroatom selected from O, N or S, each of which is optionally substituted by one or more substituents selected from: —$C_{1-3}$alkyl, —$C_{1-3}$alkoxy, —$C_{1-3}$alkylOH, halogen, —CN, —CF$_3$, —NH$_2$, —CO$_2$H and —OH; or (iv) a second ring $R^f$ which is fused to the non-aromatic heterocyclic ring formed by $R^4$ and $R^5$, wherein $R^f$ represents phenyl, a 5- or 6-membered cycloalkyl group or a 5- or 6-membered aromatic heterocyclic group containing at least one heteroatom selected from O, N or S, and the fused bicyclic group is optionally substituted by one or more substituents selected from: —$C_{1-3}$alkyl, —$C_{1-3}$alkoxy, —$C_{1-3}$alkylOH, halogen, —CN, —CF$_3$, —NH$_2$, —CO$_2$H and —OH;

with the proviso that where the substituent on the non-aromatic ring formed by $R^4$ and $R^5$ is —NH$_2$, —OH, —$C_{1-6}$alkoxy, —NHSO$_2$CF$_3$, —NHSO$_2$(C$_{0-3}$alkyl)R$^a$, —NHCOR$^d$, —NR$^b$R$^d$, —NHCOR$^e$, —NHCO$_2$C$_{1-3}$alkyleneR$^e$ or —NHC$_{1-3}$alkyleneR$^e$, the substituent is not attached to a ring carbon atom adjacent to a heteroatom;

$R^6$ represents:
(i) a fused bicyclic group —$R^g R^h$;
(ii) a group —$R^g$—$R^h$;
(iii) a group -Z-$R^h$ wherein Z represents —$C_{1-3}$alkylene-, —$C_{2-3}$alkenylene- or a direct link;
wherein $R^g$ and $R^h$ independently represent phenyl or a 5- or 6-membered aromatic heterocyclic group containing at least one heteroatom selected from O, N or S, each of which is optionally substituted by one or more substituents selected from: —$C_{1-3}$alkyl, —$C_{1-3}$alkoxy, halogen, —CN, —CF$_3$, —NH$_2$, —CO$_2$H and —OH;

and pharmaceutically acceptable salts or solvates thereof.

When $R^1$ represents a group X—W:
Preferably, X represents —$C_{1-3}$alkylene-, more preferably-methylene-.
Preferably, W represents —CN, —CO$_2$H, —CONR$^b$R$^c$, —COC$_{1-6}$alkyl, —CO$_2$C$_{1-6}$alkyl or a 5- or 6-membered aromatic heterocyclic group containing at least one heteroatom selected from O, N or S.
Preferably, $R^1$ represents hydrogen, —$C_{1-6}$alkyl, —$C_{2-6}$alkenyl or a group X—W wherein X represents —$C_{1-3}$alkylene- and W represents —CN, —CO$_2$H, —CONR$^b$R$^c$, —COC$_{1-6}$alkyl, —CO$_2$C$_{1-6}$alkyl or a 5- or 6-membered aromatic heterocyclic group containing at least one heteroatom selected from O, N or S. More preferably, $R^1$ represents a group selected from hydrogen, —CH$_2$CN, —CH$_2$CONH$_2$, —CH$_2$COC$_{1-6}$alkyl and —CH$_2$CO$_2$C$_{1-6}$alkyl.

In another preferred aspect, $R^1$ represents hydrogen, —$C_{1-6}$alkyl, —$C_{3-6}$alkenyl, —$C_{2-3}$alkylNR$^b$R$^a$, —$C_{2-3}$alkylNHCOR$^a$, phenyl or a 5- or 6-membered aromatic heterocycle, or $R^1$ represents a group X—W wherein X represents —$C_{1-3}$alkylene- and W represents —CN, —CO$_2$H, —CONR$^b$R$^c$, —COC$_{1-6}$alkyl, —CO$_2$C$_{1-6}$alkyl or a 5- or 6-membered aromatic or non-aromatic heterocyclic group containing at least one heteroatom selected from O, N or S. More preferably, $R^1$ represents hydrogen, —$C_{1-6}$alkyl, —$C_{3-6}$alkenyl, —$C_{2-3}$alkylNR$^b$R$^a$, —$C_{2-3}$alkylNHCOR$^a$, or $R^1$ represents a group X—W wherein X represents —$C_{1-3}$alkylene- and W represents —CN, —CO$_2$H, —CONR$^b$R$^c$, —COC$_{1-6}$alkyl, —CO$_2$C$_{1-6}$alkyl or a 5- or 6-membered aromatic or non-aromatic heterocyclic group containing at least one heteroatom selected from O, N or S. Even more preferably, $R^1$ represents a group selected from: hydrogen, —$C_{1-6}$alkyl, —CH$_2$CH=CH$_2$, —CH$_2$CH$_2$N(CH$_3$)$_2$, —CH$_2$CH$_2$NHCOCH$_3$, —CH$_2$CN, —CH$_2$CO$_2$H, —CH$_2$CO$_2$CH$_3$, —CH$_2$CO$_2$t-Butyl, —CH$_2$CONH$_2$, —CH$_2$COCH$_2$CH$_3$, —CH$_2$COt-Butyl, —CH$_2$CO$_2$CH$_2$CH$_3$,

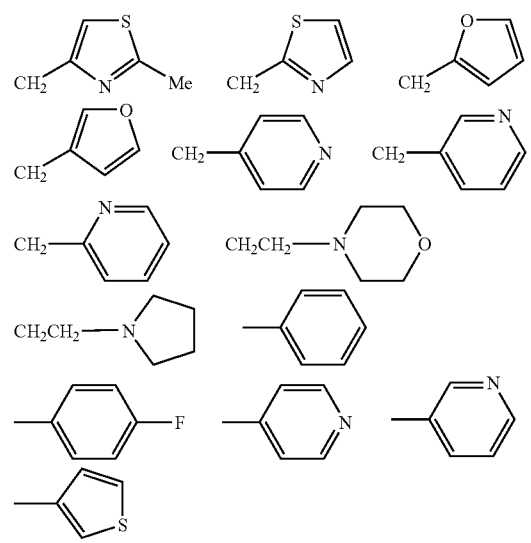

Most preferably, $R^1$ represents a group selected from: hydrogen, —$C_{1-6}$alkyl, —CH$_2$CH=CH$_2$, —CH$_2$CH$_2$N(CH$_3$)$_2$, —CH$_2$CH$_2$NHCOCH$_3$, —CH$_2$CN, —CH$_2$CO$_2$H, —CH$_2$CO$_2$CH$_3$, —CH$_2$CO$_2$t-Butyl, —CH$_2$CONH$_2$, —CH$_2$COCH$_2$CH$_3$, —CH$_2$COt-Butyl,

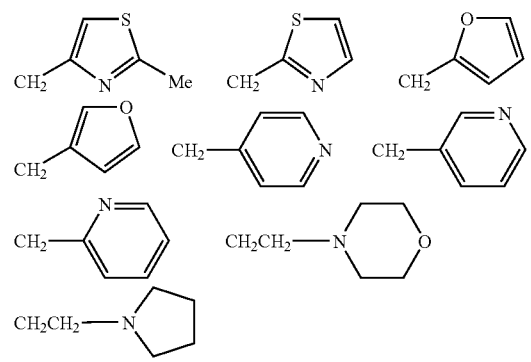

In another preferred aspect, $R^1$ represents a group selected from hydrogen, —CH$_2$CN, —CH$_2$CONH$_2$, —CH$_2$COC$_{1-6}$alkyl and —CH$_2$CO$_2$C$_{1-6}$alkyl.

Preferably, $R^2$ represents —$C_{1-3}$alkyl or hydrogen, more preferably methyl or hydrogen.

Preferably, $R^3$ represents —$C_{1-3}$alkyl or hydrogen, more preferably methyl or hydrogen.

When the 5-, 6- or 7-membered non-aromatic heterocyclic ring formed by $R^4$ and $R^5$, optionally containing an additional heteroatom, is substituted by one or more substituents selected from group (i):

preferably, the substituents in group (i) are —$NH_2$, —$CF_3$, —OH, —$CO_2H$, —$C_{1-6}$alkyl, —$C_{1-6}$alkoxy, —$C_{1-6}$alkylOH, —($C_{1-3}$alkyl)$NR^bR^c$, —($C_{0-3}$alkyl)$CONR^bR^c$ and —$NHSO_2CF_3$, more preferably —$NH_2$, —$C_{1-6}$alkyl, —$C_{1-6}$alkylOH and —($C_{1-3}$alkyl)$NR^bR^c$.

When, the 5-, 6- or 7-membered non-aromatic heterocyclic ring formed by $R^4$ and $R^5$, optionally containing an additional heteroatom, is substituted —$NHCOR^d$:

preferably, $R^d$ represents —$C_{1-6}$alkyl, —$C_{2-6}$alkynyl, —$C_{1-3}$alkyl$CO_2H$, —$C_{1-3}$alkyl$NR^bR^c$, —$C_{1-3}$alkyl$CO_2C_{1-3}$alkyl, or —$C_{1-3}$alkyl$CONR^bR^c$, more preferably —$C_{1-3}$alkyl$CO_2H$, —$C_{1-3}$alkyl$NR^bR^c$ or —$C_{1-3}$alkyl$CO_2C_{1-3}$alkyl.

When, the 5-, 6- or 7-membered non-aromatic heterocyclic ring formed by $R^4$ and $R^5$, optionally containing an additional heteroatom, is substituted by —$NR^bR^d$:

preferably, $R^b$ represents hydrogen;
preferably, $R^d$ represents —$C_{1-6}$alkyl or —$C_{1-4}$alkylOH.

When the 5-, 6- or 7-membered non-aromatic heterocyclic ring formed by $R^4$ and $R^5$, optionally containing an additional heteroatom, is substituted by Y—$R^e$:

preferably, Y represents —$C_{1-3}$alkylene-, —NHCO—, —$NHCO_2C_{1-3}$alkylene-, —$NHC_{1-3}$alkylene- or —$C_{1-3}$alkyl$NHSO_2$—, more preferably —$C_{1-3}$alkylene-, —NHCO— or —$NHC_{1-3}$alkylene-, most preferably —$C_{1-3}$alkylene-;

preferably, $R^e$ represents imidazole, pyrrole, pyrazole, pyridine, pyrimidine, furan, oxazole, 1,2,4-triazole, phenyl or pyrrolidine, more preferably pyrrole, pyrazole, pyridine, pyrimidine, 1,2,4-triazole or pyrrolidine, most preferably pyrrolidine; preferably, $R^e$ is unsubstituted or substituted by —$C_{1-3}$alkyl, —$NH_2$ or —$C_{1-3}$alkylOH. A preferred Y—$R^e$ is —$C_{1-3}$alkylene-pyrrolidine.

When the 5-, 6- or 7-membered non-aromatic heterocyclic ring formed by $R^4$ and $R^5$, optionally containing an additional heteroatom, is substituted by a group (iv):

preferably, $R^f$ represents cyclohexyl. Preferably, $R^f$ is unsubstituted.

Preferably, $R^4$ and $R^5$, together with the N atom to which they are bonded, form a 5- or 6-membered non-aromatic heterocyclic ring, optionally containing an additional heteroatom selected from O, N or S, and optionally substituted by:

(i) one or more substituents selected from: —$NH_2$, —$CF_3$, —OH, —$CO_2H$, —$C_{1-6}$alkyl, —$C_{1-6}$alkoxy, —$C_{1-6}$alkylOH, —($C_{1-3}$alkyl)$NR^bR^c$, —($C_{0-3}$alkyl)$CONR^bR^c$ and —$NHSO_2CF_3$;

(ii) a group —$NHCOR^d$ wherein $R^d$ represents —$C_{1-6}$alkyl, —$C_{2-6}$alkynyl, —$C_{1-3}$alkyl$CO_2H$, —$C_{1-3}$alkyl$NR^bR^c$, —$C_{1-3}$alkyl$CO_2C_{1-3}$alkyl or —$C_{1-3}$alkyl$CONR^bR^c$ or a group —$NHR^d$ wherein $R^d$ represents —$C_{1-6}$alkyl or —$C_{1-6}$alkylOH;

(iii) a group —Y—$R^e$, Y represents —$C_{1-3}$alkylene-, —NHCO—, —$NHCO_2C_{1-3}$alkylene-, —$NHC_{1-3}$alkylene- or —$C_{1-3}$alkyl$NHSO_2$, $R^e$ represents imidazole, pyrrole, pyrazole, pyridine, pyrimidine, furan, oxazole, 1,2,4-triazole, phenyl or pyrrolidine optionally substituted by —$C_{1-3}$alkyl, —$NH_2$ or —$C_{1-3}$alkylOH;

(iv) a second ring $R^f$ which is fused to the non-aromatic heterocyclic ring formed by $R^4$ and $R^5$, wherein $R^f$ represents cyclohexyl;

with the proviso that where the substituent on the non-aromatic ring formed by $R^4$ and $R^5$ is —$NH_2$, —OH, —$C_{1-6}$alkoxy, —$NHSO_2CF_3$, —$NHCOR^d$, —$NR^bR^d$, —$NHCOR^e$, —$NHCO_2C_{1-3}$alkylene$R^e$ or —$NHC_{1-3}$alkylene$R^e$, the substituent is not attached to a ring carbon atom adjacent to a heteroatom. More preferably, $R^4$ and $R^5$, together with the N atom to which they are bonded, represent piperidine, 2-(pyrrolidin-1-ylmethyl) pyrrolidine or morpholine.

In another preferred aspect, $R^4$ and $R^5$, together with the N atom to which they are bonded, form a 4-, 5-, 6-, 7- or 8-membered non-aromatic heterocyclic ring, selected from: piperidine; pyrrolidine; hexamethyleneimine (homopiperidine); morpholine; thiomorpholine; diazepine; tetrahydro-1,6-naphthyridine; 2-azabicyclo[2.2.1]heptane; 2-oxa-5-azabicyclo[2.2.1]heptane; 3,7-diazabicyclo[3.3.1]nonane; 9-oxa-3,7-diazabicyclo[3.3.1]nonane; 2-azabicyclo[2.2.2]octane; 4,6,7,8-tetrahydro-5H-thieno[3,2-c]azepine; 1,2,5,6-tetrahydropyridine; azetidine; 2,5dihydro-1H-pyrrole; piperazine; hexahydropyrimidine; tetrahydroquinoline; decahydroquinoline; tetrahydroquinoxaline; dihydroisoindole; tetrahydroisoquinoline; tetrahydro-5H-imidazo[4,5-c]pyridine; 1,3,4,5-tetrahydro-2H-2-benzazepine; 2,5-diazabicyclo[2.2.1]heptane; optionally substituted by:

(i) one or more substitutents selected from: —$NH_2$, —$CF_3$, F, —OH, =O, —$C_{1-6}$alkyl, —$C_{1-6}$alkoxy, —$C_{1-6}$alkylOH, —($C_{1-3}$alkyl)$NR^bR^c$, —($C_{0-3}$alkyl)$CONR^bR^c$, —$NHSO_2CF_3$, —$NHCH_2COCH_2O(C_{1-3}$alkyl), —($C_{0-3}$alkyl)$CO_2C_{1-4}$alkyl, —$CONHC_{2-3}$alkylOH, —$COCH_2NR^bR^c$, —$COCH_2N^+(CH_3)_3$, —$CH_2OC_{1-3}$alkyl and —$CH_2SO_2C_{1-3}$alkyl;

(ii) a group —$NHCOR^d$ or —$NR^bR^d$,
$R^d$ represents —$C_{1-6}$alkyl, —$C_{2-6}$alkynyl, —$C_{1-6}$alkylOH, —$C_{1-3}$alkyl$CO_2H$, —$C_{1-3}$alkyl$NR^bR^c$, —$C_{1-3}$alkyl$CO_2C_{1-3}$alkyl, —$C_{1-3}$alkyl$OC_{1-3}$alkyl and —$C_{1-3}$alkyl$CONR^bR_c$;

(iii) a group —Y—$R^e$,
Y represents —$C_{1-3}$alkylene-, —NHCO—, —$NHC_{1-3}$alkylene-, —$NHCO_2C_{1-3}$alkylene-, —$C_{1-3}$alkylNHCO—, —$C_{1-3}$alkyl$NHSO_2$—, —CO— or a direct link, $R^e$ represents phenyl, pyridine, pyrrole, isoxazole, pyrazole, pyrrolidine, cyclopentyl, triazole, pyrazine, furan, thiazole, imidazole, morpholine, piperazine, pyrimidine, piperidine, each of which is optionally substituted by one or more substituents selected from: —$C_{1-3}$alkyl, halogen, —$NH_2$;

with the proviso that where the substituent on the non-aromatic ring formed by $R^4$ and $R^5$ is —$NH_2$, —OH, —$C_{1-6}$alkoxy, —$NHSO_2CF_3$, —$NHCOR^d$, —$NR^bR^d$, —$NHCOR^e$, or —$NHC_{1-3}$alkylene$R^e$, —$NHCO_2C_{1-3}$alkylene$R^e$, —$NHCH_2COCH_2O(C_{1-3}$alkyl), the substituent is not attached to a ring carbon atom adjacent to a heteroatom.

More preferably $R^4$ and $R^5$, together with the N atom to which they are bonded, form a 5-, 6-, 7- or 8-membered non-aromatic heterocyclic ring, selected from: piperidine; pyrrolidine; hexamethyleneimine (homopiperidine); morpholine; thiomorpholine; diazepine; tetrahydro-1,6-naphthyridine; 2-azabicyclo[2.2.1]heptane; 2-oxa-5-azabicyclo[2.2.1]heptane; 3,7-diazabicyclo[3.3.1]nonane; 9-oxa-3,7-diazabicyclo[3.3.1]nonane; 2-azabicyclo[2.2.2]octane; 4,6,7,8-tetrahydro-5H-thieno[3,2-c]azepine; 1,2,5,6-tetrahydropyridine; and optionally substituted by:

(i) one or more substitutents selected from: —$NH_2$, —$CF_3$, F, —OH, =O, —$C_{1-6}$alkyl, —$C_{1-6}$alkoxy, —$C_{1-6}$alkylOH, —($C_{1-3}$alkyl)$NR^bR^c$, —($C_{0-3}$alkyl)$CO_2C_{1-4}$alkyl, —$COCH_2NR^bR^c$ and —$COCH_2N^+(CH_3)_3$;

(ii) a group —$NHCOR^d$ or —$NR^bR^d$, $R^d$ represents —$C_{1-6}$alkyl, —$C_{2-6}$alkynyl, —$C_{1-6}$alkylOH, —$C_{1-3}$alkylCO$_2$H, —$C_{1-3}$alkylNR$^b$R$^c$, —$C_{1-3}$alkylCO$_2$C$_{1-3}$alkyl, —$C_{1-3}$alkylOC$_{1-3}$alkyl and —$C_{1-3}$alkylCONR$^b$R$^c$;

(iii) a group —Y—R$^e$,

Y represents —$C_{1-3}$alkylene-, —NHCO—, —NHC$_{1-3}$alkylene-, —NHCO$_2$C$_{1-3}$alkylene-, —C$_{1-3}$alkylNHSO$_2$— or a direct link, R$^e$ represents phenyl, pyridine, pyrrole, isoxazole, pyrazole, pyrrolidine, cyclopentyl, triazole, pyrazine, furan, thiazole, imidazole, morpholine, piperazine, pyrimidine, each of which is optionally substituted by one or more substituents selected from: —$C_{1-3}$alkyl, halogen, —NH$_2$;

with the proviso that where the substituent on the non-aromatic ring formed by R$^4$ and R$^5$ is —NH$_2$, —OH, —$C_{1-6}$alkoxy, —NHCOR$^d$, —NR$^b$R$^d$, —NHCOR$^e$, or —NHC$_{1-3}$alkyleneR$^e$, —NHCO$_2$C$_{1-3}$alkyleneR$^e$, the substituent is not attached to a ring carbon atom adjacent to a heteroatom;

Even more preferably R$^4$ and R$^5$, together with the N atom to which they are bonded, form a 5-, 6-, 7-, 8-membered non-aromatic heterocyclic ring, selected from: piperidine; pyrrolidine; hexamethyleneimine (homopiperidine); morpholine; thiomorpholine; diazepine; tetrahydro-1,6-naphthyridine; 2-azabicyclo[2.2.1]heptane; 2-oxa-5-azabicyclo[2.2.1]heptane; 3,7-diazabicyclo[3.3.1]nonane; 9-oxa-3,7-diazabicyclo[3.3.1]nonane; 2-azabicyclo[2.2.2]octane; optionally substituted by a subsituent selected from: —CH$_3$, =O, —NH$_2$, F, —CH$_2$OH, —CH$_2$CH$_2$NHCH$_3$, —NH-COC$_{1-3}$alkyl, —NHCOC≡CH, —NHCOCH$_2$CH$_2$CO$_2$H; —NHCOCH$_2$N(CH$_3$)$_2$, —NHCOC$_{1-3}$alkylCO$_2$CH$_3$,

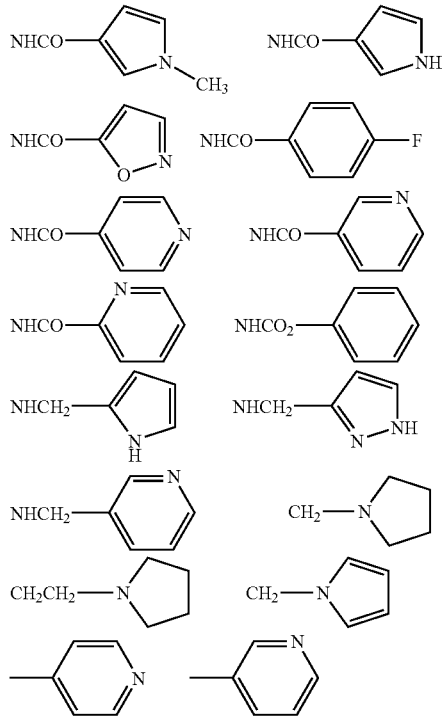

with the proviso that where the substituent on the non-aromatic ring formed by R$^4$ and R$^5$ is —NH$_2$, NHCO$_2$C$_{1-3}$alkyleneR$^e$, —NHCO— or —NHCH$_2$— the substituent is not attached to a ring carbon atom adjacent to a heteroatom.

When R$^6$ represents a fused bicyclic group —R$^g$R$^h$:

Preferably, R$^g$ represents phenyl or thiophene, more preferably phenyl. Preferably, R$^g$ is unsubstituted. When R$^g$ is thiophene, preferably it is attached to the sulphonyl group at the 2-position.

Preferably, R$^h$ represents phenyl. Preferably, R$^h$ is substituted by halogen, more preferably Cl. Preferably, R$^h$ is monosubstituted.

When R$^6$ represents a group —R$^g$—R$^h$:

Preferably, R$^g$ represents thiophene or phenyl, more preferably thiophene. Preferably, R$^g$ is unsubstituted. When R$^g$ is thiophene, preferably it is attached to the sulphonyl group at the 2-position.

Preferably, R$^h$ represents thiophene or phenyl, more preferably thiophene. Preferably, R$^h$ is substituted by halogen, more preferably Cl. Preferably, R$^h$ is monosubstituted.

When R$^6$ represents a group -Z-R$^h$:

Preferably, Z represents —$C_{2-3}$alkenyl-, more preferably —CH=CH—.

Preferably, R$^h$ represents phenyl. Preferably, R$^h$ is substituted by halogen, more preferably Cl. Preferably, R$^h$ is monosubstituted.

(iii) In another preferred aspect, R$^6$ represents:

(i) a fused bicyclic group —R$^g$R$^h$ wherein R$^g$ represents phenyl, thiophene, imidazole, thiazole, pyrrole or furan optionally substituted by one or more substituents selected from: —$C_{1-3}$alkyl and R$^h$ represents phenyl or pyridine optionally substituted by one or more substituents selected from: halogen and —OH;

(ii) a group —R$^g$—R$^h$ wherein R$^g$ represents thiophene or phenyl and R$^h$ represents phenyl, pyridine, thiophene, thiadiazole, tetrazole, isoxazole or furan optionally substituted by one or more substituents selected from: —$C_{1-3}$alkyl, halogen, —NH$_2$, —OC$_{1-3}$alkyl and —OH;

(iii) a group -Z-R$^h$ wherein Z represents —$C_{2-3}$alkenylene- or a direct link wherein R$^h$ represents phenyl or thiophene optionally substituted by one or more substituents selected from: halogen, OH and —CN;

Preferably, R$^6$ represents a substituent selected from:

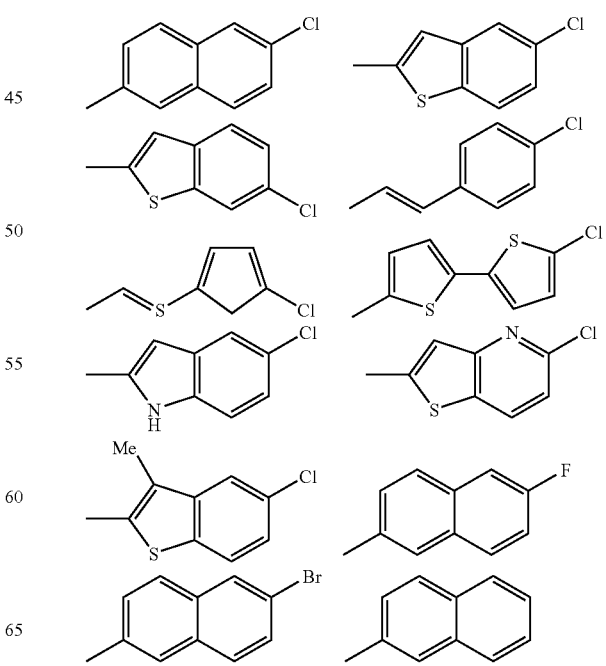

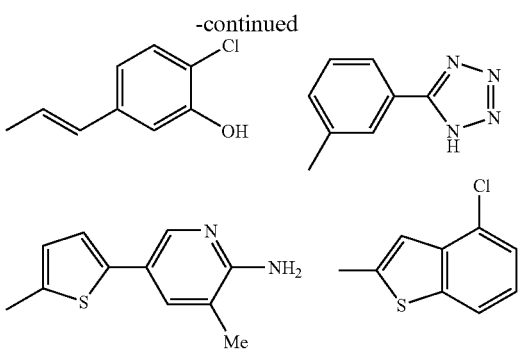

More preferably, $R^6$ represents a substituent selected from:

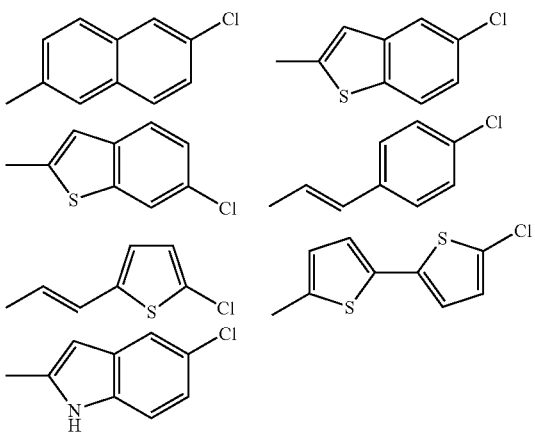

Even more preferably, $R^6$ represent a substituent selected from:

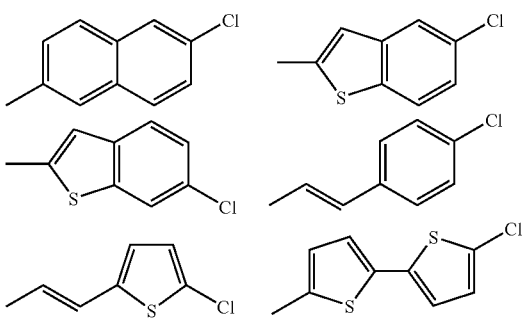

Most preferably, $R^6$ represents (chlorothienyl)ethene.

In another preferred aspect of the invention, $R^6$ represents chloronaphthylene, chlorobenzothiophene, chlorobithiophene or chlorophenylethene. More preferably, A represents a group selected from: 6-chloronaphthyl, 5'-chloro-2,2'-biothiophene, (4-chlorophenyl)ethene, 6-chloro-1-benzothiophene.

It is to be understood that the present invention covers all combinations of suitable, convenient and preferred groups described hereinabove.

Hence, in a preferred aspect the invention provides compounds of formula (I) wherein:

$R^1$ represents hydrogen, —$C_{1-6}$alkyl, —$C_{3-6}$alkenyl, —$C_{2-3}$alkylNR$^b$R$^a$, —$C_{2-3}$alkylNHCOR$^a$, phenyl or a 5- or 6-membered aromatic heterocycle, or $R^1$ represents a group X—W wherein X represents —$C_{1-3}$alkylene- and W represents —CN, —$CO_2$H, —CONR$^b$R$^c$, —COC$_{1-6}$alkyl, —$CO_2C_{1-6}$alkyl or a 5- or 6-membered aromatic or non-aromatic heterocyclic group containing at least one heteroatom selected from O, N or S.

$R^2$ and $R^3$ independently represent hydrogen, or —$C_{1-3}$alkyl, with the proviso that one of $R^2$ and $R^3$ is —$C_{1-3}$alkyl and the other is hydrogen;

$R^4$ and $R^5$, together with the N atom to which they are bonded, form a 4-, 5-, 6-, 7- or 8-membered non-aromatic heterocyclic ring, selected from: piperidine; pyrrolidine; hexamethyleneimine (homopiperidine); morpholine; thiomorpholine; diazepine; tetrahydro-1,6-naphthyridine; 2-azabicyclo[2.2.1]heptane; 2-oxa-5-azabicyclo[2.2.1]heptane; 3,7-diazabicyclo[3.3.1]nonane; 9-oxa-3,7-diazabicyclo[3.3.1]nonane; 2-azabicyclo[2.2.2]octane; 4,6,7,8-tetrahydro-5H-thieno[3,2-c]azepine; 1,2,5,6-tetrahydropyridine; azetidine; 2,5-dihydro-1H-pyrrole; piperazine; hexahydropyrimidine; tetrahydroquinoline; decahydroquinoline; tetrahydroquinoxaline; dihydroisoindole; tetrahydroisoquinoline; tetrahydro-5H-imidazo[4,5c]pyridine; 1,3,4,5-tetrahydro-2H-2-benzazepine; 2,5-diazabicyclo[2.2.1]heptane; 3,5,6,7,-tetrahydro-4H-[1,2,3]triazolo[4,5-b]pyridine; 2,3-dihydro-1H-indole; optionally substituted by:

(i) one or more substitutents selected from: —$NH_2$, —$CF_3$, F, —OH, =O, —$C_{1-6}$alkyl, —$C_{1-6}$alkoxy, —$C_{1-6}$alkylOH, —$(C_{1-3}$alkyl)NR$^b$R$^c$, —$(C_{0-3}$alkyl)CONR$^b$R$^c$, —$NHSO_2CF_3$, —$NHCH_2COCH_2O(C_{1-3}$alkyl), —$(C_{0-3}$alkyl)$CO_2C_{1-4}$alkyl, —CONHC$_{2-3}$alkylOH, —COCH$_2$NR$^b$R$^c$, —COCH$_2$N$^+$(CH$_3$)$_3$, —$CH_2OC_{1-3}$alkyl and —$CH_2SO_2C_{1-3}$alkyl;

(ii) a group —NHCOR$^d$ or —NR$^b$R$^d$, $R^d$ represents —$C_{1-6}$alkyl, —$C_{2-6}$alkynyl, —$C_{1-6}$alkylOH, —$C_{1-3}$alkylCO$_2$H, —$C_{1-3}$alkylNR$^b$R$^c$, —$C_{1-3}$alkylCO$_2C_{1-3}$alkyl, —$C_{1-3}$alkylOC$_{1-3}$alkyl and —$C_{1-3}$alkylCONR$^b$R$^c$;

(iii) a group —Y—R$^e$,

Y represents —$C_{1-3}$alkylene-, —NHCO—, —NHC$_{1-3}$alkylene-, —NHCO$_2C_{1-3}$alkylene-, —$C_{1-3}$alkylNHCO—, —$C_{1-3}$alkylNHSO$_2$—, —$CH_2$NHSO$_2$CH$_2$—, —CO— or a direct link, R$^e$ represents phenyl, pyridine, pyrrole, isoxazole, pyrazole, pyrrolidine, cyclopentyl, triazole, pyrazine, furan, thiazole, imidazole, morpholine, piperazine, pyrimidine, piperidine, each of which is optionally substituted by one or more substituents selected from: —$C_{1-3}$alkyl, halogen, —$NH_2$;

with the proviso that where the substituent on the non-aromatic ring formed by $R^4$ and $R^5$ is —$NH_2$, —OH, —$C_{1-6}$alkoxy, —$NHSO_2CF_3$, —NHCOR$_d$, —NR$^b$R$^d$, —NHCOR$^e$, or —NHC$_{1-3}$alkyleneR$^e$, —NHCO$_2C_{1-3}$alkyleneR$^e$, —NHCH$_2$COCH$_2$O(C$_{1-3}$alkyl), the substituent is not attached to a ring carbon atom adjacent to a heteroatom;

$R^a$ represents hydrogen, —$C_{1-3}$alkyl, phenyl or a 5- or 6-membered heterocyclic group containing at least one heteroatom selected from O, N or S, the phenyl or heterocyclic group being optionally substituted by one or more substituents selected from: —$C_{1-3}$alkyl, —$C_{1-3}$alkoxy, —$C_{1-3}$alkylOH, halogen, —CN, —$CF_3$, —$NH_2$, —$CO_2$H and —OH;

$R^b$ and $R^c$ independently represent hydrogen or —$C_{1-3}$alkyl;

R⁶ represents:
(i) a fused bicyclic group —RᵍRʰ wherein Rᵍ represents phenyl, thiophene, imidazole, thiazole, pyrrole or furan optionally substituted by one or more substituents selected from: —C₁₋₃alkyl and Rʰ represents phenyl or pyridine optionally substituted by one or more substituents selected from: halogen and —OH;
(ii) a group —Rᵍ—Rʰ wherein Rᵍ represents thiophene or phenyl and Rʰ represents phenyl, pyridine, thiophene, thiadiazole, tetrazole, isoxazole or furan optionally substituted by one or more substituents selected from: —C₁₋₃ alkyl, halogen, —NH₂, —OC₁₋₃alkyl and —OH;
(iii) a group -Z-Rʰ wherein Z represents —C₂₋₃alkenylene- or a direct link wherein Rʰ represents phenyl or thiophene optionally substituted by one or more substituents selected from: halogen, OH and —CN;

and pharmaceutically acceptable salts or solvates thereof.

In a more preferred aspect the invention provides compounds of formula (I) wherein:
R¹ represents hydrogen, —C₁₋₆alkyl, —C₃₋₆alkenyl, —C₂₋₃alkylNRᵇRᵃ, —C₂₋₃alkylNHCORᵃ, phenyl or a 5- or 6-membered aromatic heterocycle, or R¹ represents a group X—W wherein X represents —C₁₋₃alkylene- and W represents —CN, —CO₂H, —CONRᵇRᶜ, —COC₁₋₆ alkyl, —CO₂C₁₋₆alkyl or a 5- or 6-membered aromatic or non-aromatic heterocyclic group containing at least one heteroatom selected from O, N or S.
R² and R³ independently represent hydrogen, or —C₁₋₃alkyl, with the proviso that one of R² and R³ is —C₁₋₃alkyl and the other is hydrogen;
R⁴ and R⁵, together with the N atom to which they are bonded, form a 4-, 5-, 6-, 7- or 8-membered non-aromatic heterocyclic ring, selected from: piperidine; pyrrolidine; hexamethyleneimine (homopiperidine); morpholine; thiomorpholine; diazepine; tetrahydro-1,6-naphthyridine; 2-azabicyclo[2.2.1]heptane; 2-oxa-5-azabicyclo[2.2.1]heptane; 3,7-diazabicyclo[3.3.1]nonane; 9-oxa-3,7-diazabicyclo[3.3.1]nonane; 2-azabicyclo[2.2.2]octane; 4,6,7,8-tetrahydro-5h-thieno[3,2-c]azepine; 1,2,5,6-tetrahydropyridine; azetidine; 2,5-dihydro-1h-pyrrole; piperazine; hexahydropyrimidine; tetrahydroquinoline; decahydroquinoline; tetrahydroquinoxaline; dihydroisoindole; tetrahydroisoquinoline; tetrahydro-5h-imidazo[4,5-c]pyridine; 1,3,4,5-tetrahydro-2h-2-benzazepine; 2,5-diazabicyclo[2.2.1]heptane; optionally substituted by:
(i) one or more substitutents selected from: —NH₂, —CF₃, F, —OH, =O, —C₁₋₆alkyl, —C₁₋₃alkoxy, —C₁₋₆alkylOH, —(C₁₋₃alkyl)NRᵇRᶜ, —(C₀₋₃alkyl)CONRᵇRᶜ, —NHSO₂CF₃, —NHCH₂COCH₂O(C₁₋₃alkyl), —(C₀₋₃alkyl)CO₂C₁₋₄alkyl, —CONHC₂₋₃alkylOH, —COCH₂NRᵇRᶜ, —COCH₂N⁺(CH₃)₃, —CH₂OC₁₋₃alkyl and —CH₂SO₂C₁₋₃alkyl;
(ii) a group —NHCORᵈ or —NRᵇRᵈ,
Rᵈ represents —C₁₋₆alkyl, —C₂₋₆alkynyl, —C₁₋₆alkylOH, —C₁₋₃alkylCO₂H, —C₁₋₃alkylNRᵇRᶜ, —C₁₋₃alkylCO₂C₁₋₃alkyl, —C₁₋₃alkylOC₁₋₃alkyl and —C₁₋₃alkylCONRᵇRᶜ;
(iii) a group —Y—Rᵉ,
Y represents —C₁₋₃alkylene-, —NHCO—, —NHC₁₋₃alkylene-, —NHCO₂C₁₋₃alkylene-, —C₁₋₃alkylNHCO—, —C₁₋₃alkylNHSO₂,—CO— or a direct link,
Rᵉ represents phenyl, pyridine, pyrrole, isoxazole, pyrazole, pyrrolidine, cyclopentyl, triazole, pyrazine, furan, thiazole, imidazole, morpholine, piperazine, pyrimidine, piperidine, each of which is optionally substituted by one or more substituents selected from: —C₁₋₃alkyl, halogen, —NH₂;

with the proviso that where the substituent on the non-aromatic ring formed by R⁴ and R⁵ is —NH₂, —OH, —C₁₋₆alkoxy, —NHSO₂CF₃, —NHCORᵈ, —NRᵇRᵈ, —NHCORᵉ, or —NHC₁₋₃alkyleneRᵉ, —NHCO₂C₁₋₃alkyleneRᵉ, —NHCH₂COCH₂O(C₁₋₃alkyl), the substituent is not attached to a ring carbon atom adjacent to a heteroatom;
Rᵃ represents hydrogen, —C₁₋₃alkyl, phenyl or a 5- or 6-membered heterocyclic group containing at least one heteroatom selected from O, N or S, the phenyl or heterocyclic group being optionally substituted by one or more substituents selected from: —C₁₋₃alkyl, —C₁₋₃alkoxy, —C₁₋₃alkylOH, halogen, —CN, —CF₃, —NH₂, —CO₂H and —OH;
Rᵇ and Rᶜ independently represent hydrogen or —C₁₋₃alkyl;
R⁶ represents a substituent selected from:

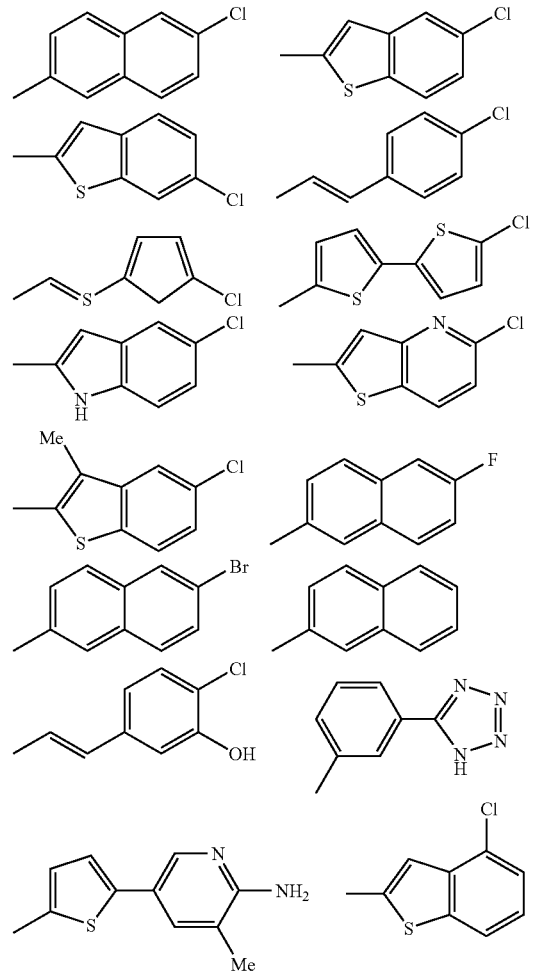

and pharmaceutically acceptable salts or solvates thereof.

In an even more preferred aspect the invention provides compounds of formula (I) wherein:
R¹ represents a group selected from: hydrogen, —C₁₋₆alkyl, —CH₂CH=CH₂, —CH₂CH₂N(CH₃)₂, —CH₂CH₂NHCOCH₃, —CH₂CN, —CH₂CO₂H, —CH₂CO₂CH₃, —CH₂CO₂t-Butyl, —CH₂CONH₂, —CH₂COCH₂CH₃, —CH₂COt-Butyl,

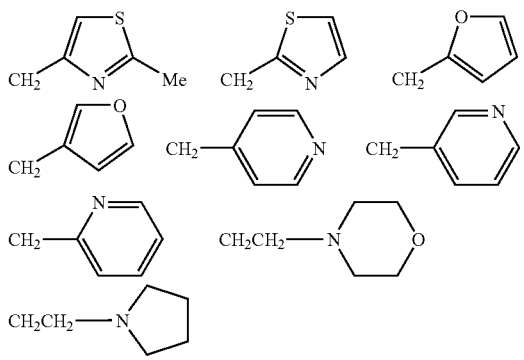

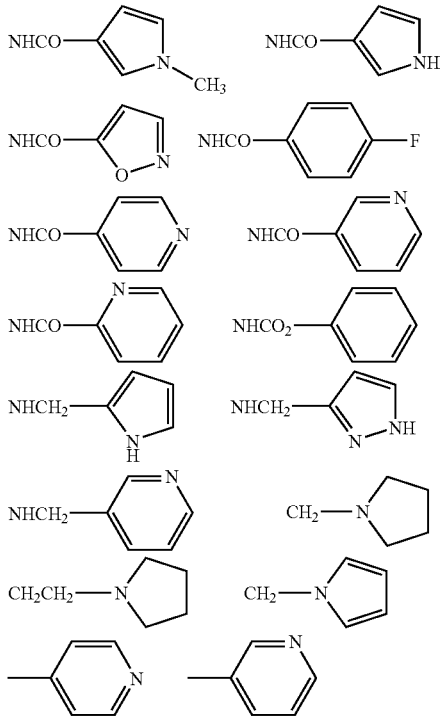

with the proviso that where the substituent on the non-aromatic ring formed by $R^4$ and $R^5$ is —$NH_2$, $NHCO_2C_{1-3}$ alkyleneR$^e$, —NHCO— or —NHCH$_2$— the substituent is not attached to a ring carbon atom adjacent to a heteroatom;

$R^a$ represents hydrogen, —$C_{1-3}$alkyl, phenyl or a 5- or 6-membered heterocyclic group containing at least one heteroatom selected from O, N or S, the phenyl or heterocyclic group being optionally substituted by one or more substituents selected from: —$C_{1-3}$alkyl, —$C_{1-3}$alkoxy, —$C_{1-3}$alkylOH, halogen, —CN, —$CF_3$, —$NH_2$, —$CO_2H$ and —OH;

$R^b$ and $R^c$ independently represent hydrogen or —$C_{1-3}$alkyl;

$R^6$ represent a substituent selected from:

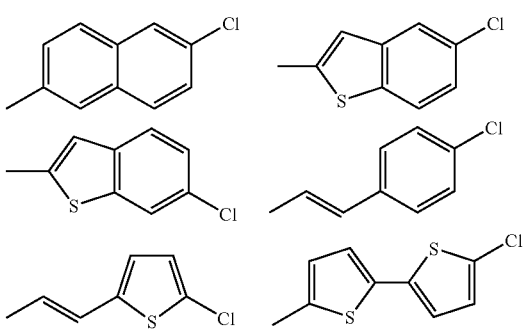

and pharmaceutically acceptable salts or solvates thereof.

The present invention also provides compounds of formula (Ia):

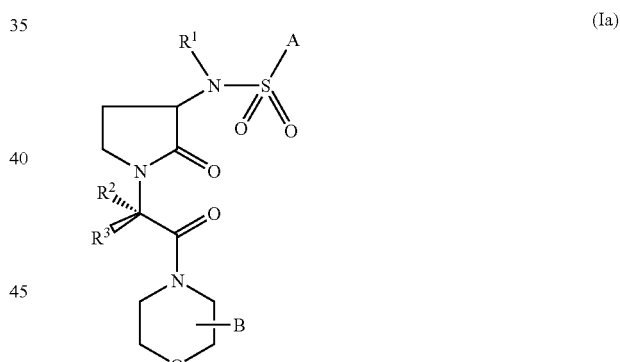

(Ia)

wherein:

$R^1$ represents hydrogen, —$C_{1-6}$alkyl, —$C_{2-6}$alkenyl or a group X—W, wherein X represents —$C_{1-3}$alkylene- and W represents —CN, —$CO_2H$, —$CONR^bR^c$, —$COC_{1-6}$alkyl, —$CO_2C_{1-6}$alkyl, phenyl or 5- or 6-membered aromatic heterocyclic group containing at least one heteroatom selected from O, N or S, the phenyl or aromatic heterocyclic group being optionally substituted by one or more substitutents selected from: —$C_{1-3}$alkyl, —$C_{1-3}$alkoxy, —$C_{1-3}$alkylOH, halogen, —CN, —$CF_3$, —$NH_2$, —$CO_2H$ and —OH;

$R^2$ and $R^3$ independently represent hydrogen, —$C_{1-3}$alkyl or $CF_3$ with the proviso that when one of $R^2$ and $R^3$ is —$C_{1-3}$alkyl or $CF_3$, the other is hydrogen;

$R^b$ and $R^c$ independently represent hydrogen or —$C_{1-3}$alkyl;

A represents a group selected from:

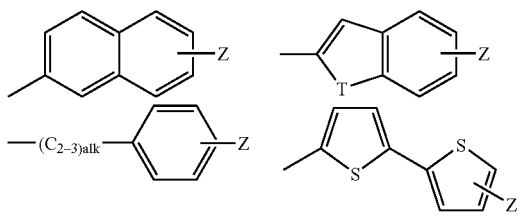

Z represents an optional substituent halogen,
alk represents alkylene or alkenylene,
T represents a heteroatom selected from S or N;
B represents one or more optional substituents on ring carbon atoms selected from: (i) one or more substituents selected from —$CF_3$, —F, =O, —$CO_2H$, —$C_{1-6}$alkyl, —$C_{1-6}$alkylOH, —($C_{1-3}$alkyl)$NR^bR^c$, —($C^{0-3}$alkyl)$CONR^bR^c$ and —($C_{0-3}$alkyl)$CO_2C_{1-3}$alkyl;
(ii) a group —Y—$R^e$,
Y represents —$C_{1-3}$alkylene-, —CO—, —$C_{1-3}$alkylNH—, —$C_{1-3}$alkylNHCO—, —$C_{1-3}$alkylNHSO_2—, —$CH_2NHSO_2CH_2$— or a direct link,
$R^e$ represents phenyl, a 5- or 6-membered cycloalkyl or a 5- or 6-membered heterocycle containing at least one heteroatom selected from O, N or S, each of which is optionally substituted by one or more substituents selected from: —$C_{1-3}$alkyl, —$C_{1-3}$alkoxy, —$C_{1-3}$alkylOH, halogen, —CN, —$CF_3$, —$NH_2$, —$CO_2H$ and —OH; or
(iii) a second ring $R^f$ which is fused to the heterocyclic ring, wherein $R^f$ represents phenyl, a 5- or 6-membered cycloalkyl group or a 5- or 6-membered aromatic heterocyclic group containing at least one heteroatom selected from O, N or S, and the fused bicyclic group is optionally substituted by one or more substituents selected from: —$C_{1-3}$alkyl, —$C_{1-3}$alkoxy, —$C_{1-3}$alkylOH, halogen, —CN, —$CF_3$, —$NH_2$, —$CO_2H$ and —OH;
and pharmaceutically acceptable salts and solvates thereof.

The present invention also provides compounds of formula (Ib):

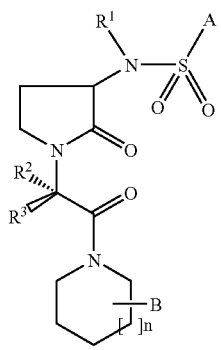

(Ib)

wherein:
$R^1$ represents hydrogen, —$C_{1-6}$alkyl, —$C_{2-6}$alkenyl or a group X—W, wherein X represents —$C_{1-3}$alkylene- and W represents —CN, —$CO_2H$, —$CONR^bR^c$, —$COC_{1-6}$alkyl, —$CO_2C_{1-6}$alkyl, phenyl or 5- or 6-membered aromatic heterocyclic group containing at least one heteroatom selected from O, N or S, the phenyl or aromatic heterocyclic group being optionally substituted by one or more substitutents selected from: —$C^{1-3}$alkyl, —$C_{1-3}$alkoxy, —$C_{1-3}$alkylOH, halogen, —CN, —$CF_3$, —$NH_2$, —$CO_2H$ and —OH;
$R^2$ and $R^3$ independently represent hydrogen, —$C_{1-3}$alkyl or $CF_3$ with the proviso that when one of $R^2$ and $R^3$ is —$C_{1-3}$alkyl or $CF_3$, the other is hydrogen;
$R^b$ and $R^c$ independently represent hydrogen or —$C_{1-3}$alkyl;

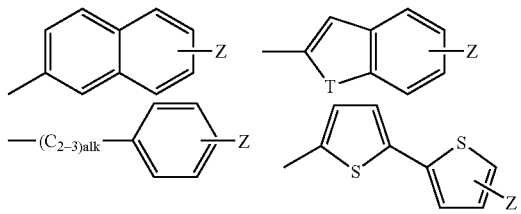

A represents a group selected from:
Z represents an optional substituent halogen,
alk represents alkylene or alkenylene,
T represents a heteroatom selected from S or N;
n represents 0 or 1;
B represents one or more optional substituents on ring carbon atoms selected from:
(i) one or more substitutents selected from: —$NH_2$, —$CF_3$, F, —OH, =O, —$CO_2H$, —$C_{1-6}$alkyl, —$C_{1-6}$alkoxy, —$C_{1-6}$alkylOH, —($C_{1-3}$alkyl)$N^bR^c$, —($C_{0-3}$alkyl)$CONR^bR^c$, —$NHSO_2CF_3$, —$NHSO_2(C_{0-3}$alkyl)$R^a$ and —($CO_3$alkyl)$CO_2C_{1-3}$alkyl;
$R^a$ represents hydrogen, —$C_{1-3}$alkyl, phenyl or a 5- or 6-membered heterocyclic group containing at least one heteroatom selected from O, N or S, the phenyl or heterocyclic group being optionally substituted by one or more substituents selected from: —$C_{1-3}$alkyl, —$C_{1-3}$alkoxy, —$C_{1-3}$alkylOH, halogen, —CN, —$CF_3$, —$NH_2$, —$CO_2H$ and —OH;
(ii) a group —$NHCOR^d$ or —$NR^bR^d$,
$R^d$ represents —$C_{1-6}$alkyl, —$C_{2-6}$alkynyl, —$C_{1-6}$alkoxy, —$C_{1-6}$alkylOH, —$C_{1-3}$alkylCO_2H, —$C_{1-3}$alkylNR^bR^c$, —$C_{1-3}$alkylCO_2C_{1-3}$alkyl or —$C_{1-3}$alkylCONR^bR^c$;
(iii) a group —Y—$R^e$,
Y represents —$C_{1-3}$alkylene-, —NHCO—, —$NHCO_2C_{1-3}$alkylene-, —$NHC_{1-3}$alkylene-, —CO—, —$C_{1-3}$alkylNH—, —$C_{1-3}$alkylNHCO—, —$C_{1-3}$alkylNHSO_2—, —$CH_2NHSO_2CH_2$— or a direct link,
$R^e$ represents phenyl, a 5- or 6-membered cycloalkyl or a 5- or 6-membered heterocycle containing at least one heteroatom selected from O, N or S, each of which is optionally substituted by one or more substituents selected from: —$C_{1-3}$alkyl, —$C_{1-3}$alkoxy, —$C_{1-3}$alkylOH, halogen, —CN, —$CF_3$, —$NH_2$, —$CO_2H$ and —OH; or
(iv) a second ring $R^f$ which is fused to the heterocyclic ring, wherein $R^f$ represents phenyl, a 5- or 6-membered cycloalkyl group or a 5- or 6-membered aromatic heterocyclic group containing at least one heteroatom selected from O, N or S, and the fused bicyclic group is optionally substituted by one or more substituents selected from: —$C_{1-3}$alkyl, —$C_{1-3}$alkoxy, —$C_{1-3}$alkylOH, halogen, —CN, —$CF_3$, —$NH_2$, —$CO_2H$ and —OH;
with the proviso that where B is —$NH_2$, —OH, —$C_{1-6}$alkoxy, —$NHSO_2CF_3$, —$NHSO_2(C_{0-3}$alkyl)$R^a$, —$NHCOR^d$, —$NR^bR^d$, —$NHCOR^e$, —$NHCO_2C_{1-3}$alkyleneR^e$ or —NHC$_{1-3}$alkyleneR$^e$, it is not attached to a ring carbon atom adjacent to a heteroatom;

and pharmaceutically acceptable derivatives thereof.

The present invention also provides compounds of formula (I) wherein:

R$^1$ represents hydrogen, —C$_{1-6}$alkyl, —C$_{2-6}$alkenyl, —C$_{2-6}$alkynyl, —C$_{2-3}$alkylOH, —C$_{2-3}$alkylNR$^b$R$^a$, —C$_{2-3}$alkylNHCOR$^a$, —C$_{2-3}$alkylNHCO$_2$R$^b$, —C$_{2-3}$alkylNHSO$_2$R$^b$, —C$_{2-3}$alkylNHCONR$^b$R$^c$ or a group X—W;

X represents —C$_{1-3}$alkylene-, propenylene, propynylene;

W represents —CN, —CO$_2$H, —CONR$^b$R$^c$, —COC$_{1-6}$alkyl, —CO$_2$C$_{1-6}$alkyl, —CO$_2$C$_{2-6}$alkenyl, —OCONR$^b$R$^c$, —OC$_{1-6}$alkyl, —OCH$_2$phenyl, phenyl or 5- or 6-membered aromatic heterocyclic group containing at least one heteroatom selected from O, N or S, the phenyl or aromatic heterocyclic group being optionally substituted by one or more substitutents selected from: —C$_{1-3}$alkyl, —C$_{1-3}$alkoxy, —C$_{1-3}$alkylOH, halogen, —CN, —CF$_3$, —NH$_2$, —CO$_2$H and —OH;

R$^2$ and R$^3$ independently represent hydrogen or —C$_{1-3}$alkyl, with the proviso that when one of R$^2$ and R$^3$ is —C$_{1-3}$alkyl, the other is hydrogen;

R$^4$ and R$^5$, together with the N atom to which they are bonded, form a 5- or 6-membered non-aromatic heterocyclic ring, optionally containing an additional heteroatom, and optionally substituted by:

(i) one or more substituents selected from —NH$_2$, —CF$_3$, —OH, —CO$_2$H, —C$_{1-6}$alkyl, —C$_{1-6}$alkoxy, —C$_{1-6}$alkylOH, —(C$_{1-3}$alkyl)NR$^b$R$^c$, —(C$_{0-3}$alkyl)CONR$^b$R$^c$ and NHSO$_2$CF$_3$;

(ii) a group —NHCOR$^d$ or —NR$^b$R$^d$,

R$^d$ represents —C$_{1-6}$alkyl, —C$_{2-6}$alkynyl, —C$_{1-6}$alkylOH, —C$_{1-3}$alkylCO$_2$H, —C$_{1-3}$alkylNR$^b$R$^c$, —C$_{1-3}$alkylCO$_2$CH$_3$ or —C$_{1-3}$alkylCONR$^b$R$^c$;

(iii) a group —Y—R$^e$,

Y represents —C$_{1-3}$alkylene-, —NHCO—, —NHCO$_2$C$_{1-3}$alkylene-, —NHC$_{1-3}$alkylene- or —C$_{1-3}$alkylNHSO$_2$—, R$^e$ represents imidazole, pyrrole, pyrazole, pyridine, pyrimidine, furan, oxazole, 1,2,4-triazole, phenyl or pyrrolidine optionally substituted by —C$_{1-3}$alkyl, NH$_2$ or —C$_{1-3}$alkylOH;

with the proviso that where the substituent on the non-aromatic ring formed by R$^4$ and R$^5$ is —NH$_2$, —OH, —C$_{1-6}$alkoxy, —NHSO$_2$CF$_3$, —NHCOR$^d$, —NR$^b$R$^d$, —NHCOR$^e$, —NHCO$_2$C$_{1-3}$alkyleneR$^e$ or —NHC$_{1-3}$alkyleneR$^e$, the substituent is not attached to a ring carbon atom adjacent to a heteroatom;

R$^b$ and R$^c$ independently represent hydrogen or —C$_{1-3}$alkyl;

R$^6$ represents a group selected from:

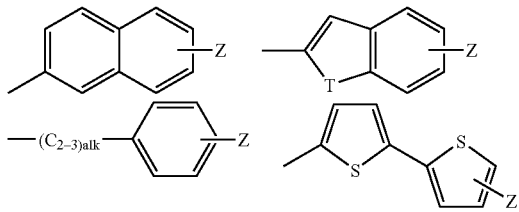

Z represents an optional substituent halogen, alk represents alkylene or alkenylene, T represents a heteroatom selected from S or N;

The present invention also provides compounds of formula (I) wherein:

R$^1$ represents hydrogen, —C$_{1-6}$alkyl, —C$_{2-6}$alkenyl or a group X—W wherein X represents —C$_{1-3}$alkylene- and W represents —CN, —CO$_2$H, —CONR$^b$R$^c$, —COC$_{1-6}$alkyl, —CO$_2$C$_{1-6}$alkyl or a 5- or 6-membered aromatic heterocyclic group containing at least one heteroatom selected from O, N or S;

R$^2$ and R$^3$ independently represent hydrogen or —C$_{1-3}$alkyl, with the proviso that when one of R$^2$ and R$^3$ is —C$_{1-3}$alkyl, the other is hydrogen;

R$^4$ and R$^5$, together with the N atom to which they are bonded, form a 5- or 6-membered non-aromatic heterocyclic ring, optionally containing an additional heteroatom, and optionally substituted by:

(i) one or more substituents selected from —NH$_2$, —CF$_3$, —OH, —CO$_2$H, —C$_{1-6}$alkyl, —C$_{1-6}$alkoxy, —C$_{1-6}$alkylOH, —(C$_{1-3}$alkyl)NR$^b$R$^c$, —(C$_{0-3}$alkyl)CONR$^b$R$^c$ and —NHSO$_2$CF$_3$;

(ii) a group —NHCOR$^d$ or —NR$^b$R$^d$,

R$^d$ represents —C$_{1-6}$alkyl, —C$_{2-6}$alkynyl, —C$_{1-6}$alkylOH, —C$_{1-6}$alkylCO$_2$H, —C$_{1-3}$alkylNR$^b$R$^c$, —C$_{1-3}$alkylCO$_2$CH$_3$ or —C$_{1-3}$alkylCONR$^b$R$^c$, (iii) a group —Y—R$^e$, Y represents —C$_{1-3}$alkylene-, —NHCO—, —NHCO$_2$C$_{1-3}$alkylene- or —NHC$_{1-3}$alkylene-, —C$_{1-3}$alkylNHSO$_2$—, R$^e$ represents imidazole, pyrrole, pyrazole, pyridine, pyrimidine, furan, oxazole, 1,2,4-triazole, phenyl or pyrrolidine optionally substituted by —C$_{1-3}$alkyl, NH$_2$ or —C$_{1-3}$alkylOH;

with the proviso that where the substituent on the non-aromatic ring formed by R$^4$ and R$^5$ is —NH$_2$, —OH, —C$_{1-6}$alkoxy, —NHSO$_2$CF$_3$, —NHCOR$^d$, —NR$^b$R$^d$, —NHCOR$^e$, —NHCO$_2$C$_{1-3}$alkyleneR$^e$ or —NHC$_{1-3}$alkyleneR$^e$, the substituent is not attached to a ring carbon atom adjacent to a heteroatom;

R$^b$ and R$^c$ independently represent hydrogen or —C$_{1-3}$alkyl;

R$^6$ represents a group selected from:

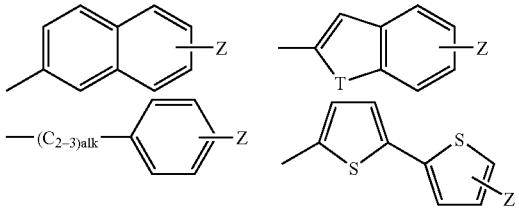

Z represents an optional substituent halogen, alk represents alkylene or alkenylene, T represents a heteroatom selected from S or N;

The present invention also provides compounds of formula (I) wherein:

R$^1$ represents hydrogen, —C$_{1-6}$alkyl, —C$_{2-6}$alkenyl, —C$_{2-6}$alkynyl, —C$_{2-3}$alkylOH, —C$_{2-3}$alkyNR$^b$R$^a$, —C$_{2-3}$alkylNHCOR$^a$, —C$_{2-3}$alkylNHCO$_2$R$^b$, —C$_{2-3}$alkylNHSO$_2$R$^b$, —C$_{2-3}$alkylNHCONR$^b$R$^c$ or a group X—W;

X represents —C$_{1-3}$alkylene-, propenylene, propynylene;

W represents —CN, —CO$_2$H, —CONR$^b$R$^c$, —COC$_{1-6}$alkyl, —CO$_2$C$_{1-6}$alkyl, —CO$_2$C$_{2-6}$alkenyl, —OCONR$^b$R$^c$, —OC$_{1-6}$alkyl, —OCH$_2$phenyl, phenyl or 5- or 6-membered aromatic heterocyclic group containing at least one heteroatom selected from O, N or S, the phenyl or aromatic heterocyclic group being optionally substituted by one or more substitutents selected from: —C$_{1-3}$ alkyl, —C$_{1-3}$alkoxy, —C$_{1-3}$alkylOH, halogen, —CN, —CF$_3$, —NH$_2$, —CO$_2$H and —OH;

R$^2$ and R$^3$ independently represent hydrogen or —C$_{1-3}$alkyl, with the proviso that when one of R$^2$ and R$^3$ is —C$_{1-3}$ alkyl, the other is hydrogen;

R$^4$ and R$^5$, together with the N atom to which they are bonded, represent piperidine, 2-(pyrrolidin-1-ylmethyl) pyrrolidine or morpholine;

R$^b$ and R$^c$ independently represent hydrogen or —C$_{1-3}$alkyl;

R$^6$ represents a group selected from:

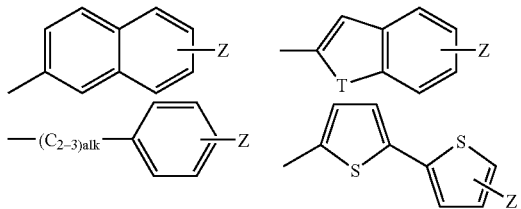

Z represents an optional substituent halogen,
alk represents alkylene or alkenylene,
T represents a heteroatom selected from S or N;

The present invention also provides compounds of formula (I) wherein:

R$^1$ represents hydrogen, —C$_{1-6}$alkyl, —C$_{2-6}$alkenyl, —C$_{2-6}$ alkynyl, —C$_{2-3}$alkylOH, —C$_{2-3}$alkylNR$^b$R$^a$, —C$_{2-3}$ alkylNHCOR$^a$, —C$_{2-3}$alkylNHCO$_2$R$^b$, —C$_{2-3}$ alkylNHSO$_2$R$^b$, —C$_{2-3}$alkylNHCONR$^b$R$^c$ or a group X—W;

X represents —C$_{1-3}$alkylene-, propenylene, propynylene;

W represents —CN, —CO$_2$H, —CONR$^b$R$^c$, —COC$_{1-6}$ alkyl, —CO$_2$C$_{1-6}$alkyl, —CO$_2$C$_{2-6}$alkenyl, —OCONR$^b$R$^c$, —OC$_{1-6}$alkyl, —OCH$_2$phenyl, phenyl or 5- or 6-membered aromatic heterocyclic group containing at least one heteroatom selected from O, N or S, the phenyl or aromatic heterocyclic group being optionally substituted by one or more substitutents selected from: —C$_{1-3}$ alkyl, —C$_{1-3}$alkoxy, —C$_{1-3}$alkylOH, halogen, —CN, —CF$_3$, —NH$_2$, —CO$_2$H and —OH;

R$^2$ and R$^3$ independently represent hydrogen or —C$_{1-3}$alkyl, with the proviso that when one of R$^2$ and R$^3$ is —C$_{1-3}$ alkyl, the other is hydrogen;

R$^4$ and R$^5$, together with the N atom to which they are bonded, form a 5- or 6-membered non-aromatic heterocyclic ring, optionally containing an additional heteroatom, and optionally substituted by:

(i) one or more substituents selected from —NH$_2$, —CF$_3$, —OH, —CO$_2$H, —C$_{1-6}$alkyl, —C$_{1-6}$alkoxy, —C$_{1-6}$alkylOH, —(C$_{1-3}$alkyl)NR$^b$R$^c$, —(C$_{0-3}$alkyl)CONR$^b$R$^c$ or —NHSO$_2$CF$_3$;

(ii) a group —NHCOR$^d$ or —NR$^b$R$^d$,

R$^d$ represents —C$_{1-6}$alkyl, —C$_{2-6}$alkynyl, —C$_{1-6}$alkylOH, —C$_{1-6}$alkylCO$_2$H, —C$_{1-3}$alkylNR$^b$R$^c$, —C$_{1-3}$ alkylCO$_2$CH$_3$ or —C$_{1-3}$alkylCONR$^b$R$^c$, (iii) a group —Y—R$^e$, Y represents —C$_{1-3}$alkylene-, —NHCO—, —NHCO$_2$C$_{1-3}$ alkylene-, —NHC$_{1-3}$alkylene- or —C$_{1-3}$alkylNHSO$_2$—, R$^e$ represents imidazole, pyrrole, pyrazole, pyridine, pyrimidine, furan, oxazole, 1,2,4-triazole, phenyl or pyrrolidine optionally substituted by —C$_{1-3}$alkyl, NH$_2$ or —C$_{1-3}$ alkylOH;

with the proviso that where the substituent on the non-aromatic ring formed by R$^4$ and R$^5$ is —NH$_2$, —OH, —C$_{1-6}$alkoxy, —NHSO$_2$CF$_3$, —NHCOR$^d$, —NR$^b$R$^d$, —NHCOR$^e$, —NHCO$_2$C$_{1-3}$alkyleneR$^e$ or —NHC$_{1-3}$ alkyleneR$^e$, the substituent is not attached to a ring carbon atom adjacent to a heteroatom;

R$^b$ and R$^c$ independently represent hydrogen or —C$_{1-3}$alkyl;

R$^6$ represents 6-chloronaphthyl, 5'-chloro-2,2'-bithiophene, (4-chlorophenyl)ethene or 6-chloro-1-benzothiophene.

The present invention also provides compounds of formula (I) wherein:

R$^1$ represents hydrogen, —C$_{1-6}$alkyl, —C$_{2-6}$alkenyl or a group X—W wherein X represents —C$_{1-3}$alkylene- and W represents —CN, —CO$_2$H, —CONR$^b$R$^c$, —COC$_{1-6}$ alkyl, —CO$_2$C$_{1-6}$alkyl or a 5- or 6-membered aromatic heterocyclic group containing at least one heteroatom selected from O, N or S;

R$^2$ and R$^3$ independently represent hydrogen or —C$_{1-3}$alkyl, with the proviso that when one of R$^2$ and R$^3$ is —C$_{1-3}$ alkyl, the other is hydrogen;

R$^4$ and R$^5$, together with the N atom to which they are bonded, represent piperidine, 2-(pyrrolidin-1-ylmethyl) pyrrolidine or morpholine, R$^b$ and R$^c$ independently represent hydrogen or —C$_{1-3}$alkyl, R$^6$ represents a group selected from:

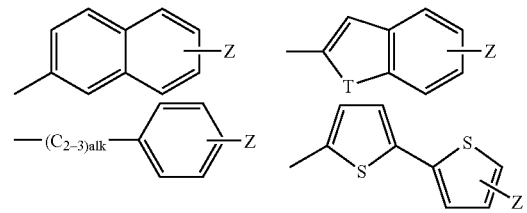

Z represents an optional substituent halogen,
alk represents alkylene or alkenylene,
T represents a heteroatom selected from S or N;

The present invention also provides compounds of formula (I) wherein:

R$^1$ represents hydrogen, —C$_{1-6}$alkyl, —C$_{2-6}$alkenyl or a group X—W wherein X represents —C$_{1-3}$alkylene- and W represents —CN, —CO$_2$H, —CONR$^b$R$^c$, —COC$_{1-6}$ alkyl, —CO$_2$C$_{1-6}$alkyl or a 5- or 6-membered aromatic heterocyclic group containing at least one heteroatom selected from O, N or S;

R$^2$ and R$^3$ independently represent hydrogen or —C$_{1-3}$alkyl, with the proviso that when one of R$^2$ and R$^3$ is —C$_{1-3}$ alkyl, the other is hydrogen;

R$^4$ and R$^5$, together with the N atom to which they are bonded, form a 5- or 6-membered non-aromatic heterocyclic ring, optionally containing an additional heteroatom, and optionally substituted by:

(i) one or more substituents selected from —NH$_2$, —CF$_3$, —OH, —CO$_2$H, —C$_{1-6}$alkyl, —C$_{1-6}$alkoxy, —C$_{1-6}$alkylOH, —(C$_{1-3}$alkyl)NR$^b$R$^c$, —(C$_{0-3}$alkyl)CONR$^b$R$^c$ and —NHSO$_2$CF$_3$;

(ii) a group —NHCOR$^d$ or —NR$^b$R$^d$,

R$^d$ represents —C$_{1-6}$alkyl, —C$_{2-6}$alkynyl, —C$_{1-6}$alkylOH, —C$_{1-6}$alkylCO$_2$H, —C$_{1-3}$alkylNR$^b$R$^c$, —C$_{1-3}$ alkylCO$_2$CH$_3$ or —C$_{1-3}$alkylCONR$^b$R$^c$, (iii) a group —Y—R$^e$, Y represents —C$_{1-3}$alkylene-, —NHCO—, —NHCO$_2$C$_{1-3}$ alkylene-, —NHC$_{1-3}$alkylene- or —C$_{1-3}$alkylNHSO$_2$—, R$^e$ represents imidazole, pyrrole, pyrazole, pyridine, pyrimidine, furan, oxazole, 1,2,4-triazole, phenyl or pyrrolidine optionally substituted by —C$_{1-3}$alkyl, NH$_2$ or —C$_{1-3}$ alkylOH;

with the proviso that where the substituent on the non-aromatic ring formed by $R^4$ and $R^5$ is —$NH_2$, —OH, —$C_{1-6}$alkoxy, —$NHSO_2CF_3$, —$NHCOR^d$, —$NR^bR^d$, —$NHCOR^e$, —$NHCO_2C_{1-3}$alkyleneR$^e$ or —$NHC_{1-3}$alkyleneR$^e$, the substituent is not attached to a ring carbon atom adjacent to a heteroatom;

$R^b$ and $R^c$ independently represent hydrogen or —$C_{1-3}$alkyl;

$R^6$ represents 6-chloronaphthyl, 5'-chloro-2,2'-bithiophene, (4-chlorophenyl)ethene or 6-chloro-1-benzothiophene.

The present invention also provides compounds of formula (I) wherein:

$R^1$ represents hydrogen, —$C_{1-6}$alkyl, —$C_{2-6}$alkenyl, —$C_{2-6}$ alkynyl, —$C_{2-3}$alkylOH, —$C_{2-3}$alkylNR$^bR^a$, —$C_{2-3}$ alkylNHCOR$^a$, —$C_{2-3}$alkylNHCO$_2R^b$, —$C_{2-3}$ alkylNHSO$_2R^b$, —$C_{2-3}$alkylNHCONR$^bR^c$ or a group X—W;

X represents —$C_{1-3}$alkylene-, propenylene, propynylene;

W represents —CN, —$CO_2H$, —CONR$^bR^c$, —$COC_{1-6}$ alkyl, —$CO_2C_{1-6}$alkyl, —$CO_2C_{2-6}$alkenyl, —OCONR$^b$ $R^c$, —$OC_{1-6}$alkyl, —OCH$_2$phenyl, phenyl or 5- or 6-membered aromatic heterocyclic group containing at least one heteroatom selected from O, N or S, the phenyl or aromatic heterocyclic group being optionally substituted by one or more substitutents selected from: —$C_{1-3}$ alkyl, —$C_{1-3}$alkoxy, —$C_{1-3}$alkylOH, halogen, —CN, —$CF_3$, —$NH_2$, —$CO_2H$ and —OH;

$R^2$ and $R^3$ independently represent hydrogen or —$C_{1-3}$alkyl, with the proviso that when one of $R^2$ and $R^3$ is —$C_{1-3}$ alkyl, the other is hydrogen;

$R^4$ and $R^5$, together with the N atom to which they are bonded, represent piperidine, 2-(pyrrolidin-1-ylmethyl) pyrrolidine or morpholine;

$R^b$ and $R^c$ independently represent hydrogen or —$C_{1-3}$alkyl, $R^6$ represents 6-chloronaphthyl, 5'-chloro-2,2'-bithiophene, (4-chlorophenyl)ethene or 6-chloro-1-benzothiophene.

The present invention also provides compounds of formula (I) wherein:

$R^1$ represents hydrogen, —$C_{1-6}$alkyl, —$C_{2-6}$alkenyl or a group X—W wherein X represents —$C_{1-3}$alkylene- and W represents —CN, —$CO_2H$, —CONR$^bR^c$, —$COC_{1-6}$ alkyl, —$CO_2C_{1-6}$alkyl or a 5- or 6-membered aromatic heterocyclic group containing at least one heteroatom selected from O, N or S;

$R^2$ and $R^3$ independently represent hydrogen or —$C_{1-3}$alkyl, with the proviso that when one of $R^2$ and $R^3$ is —$C_{1-3}$ alkyl, the other is hydrogen;

$R^4$ and $R^5$, together with the N atom to which they are bonded, represent piperidine, 2-(pyrrolidin-1-ylmethyl) pyrrolidine or morpholine, $R^b$ and $R^c$ independently represent hydrogen or —$C_{1-3}$alkyl, $R^6$ represents 6-chloronaphthyl, 5'-chloro-2,2'-bithiophene, (4-chlorophenyl)ethene or 6-chloro-1-benzothiophene.

The compounds of formula (I), (Ia), (Ib), (Ic) contain chiral (asymmetric) centres. The individual stereoisomers (enantiomers and diastereoisomers) and mixtures of these are within the scope of the present invention.

As used herein, the terms "alkyl" and "alkoxy" mean both straight and branched chain saturated hydrocarbon groups. Examples of alkyl groups include methyl (—$CH_3$), ethyl (—$C_2H_5$), propyl (—$C_3H_7$) and butyl (—$C_4H_9$). Examples of alkoxy groups include methoxy (—$OCH_3$) and ethoxy (—$OC_2H_5$).

As used herein, the term "alkylene" means both straight and branched chain saturated hydrocarbon linker groups. Examples of alkylene groups include methylene (—$CH_2$—) and ethylene (—$CH_2CH_2$—).

As used herein, the term "alkenyl" means both straight and branched chain unsaturated hydrocarbon groups, wherein the unsaturation is present only as double bonds. Examples of alkenyl groups include ethenyl (—CH=$CH_2$) and propenyl (—CH=CHCH$_3$ or —$CH_2$CH=$CH_2$).

As used herein, the term "alkenylene" means both straight and branched chain unsaturated hydrocarbon linker groups, wherein the unsaturation is present only as double bonds. Examples of alkenylene groups includes ethenylene (—CH=CH—) and propenylene (—$CH_2$—CH=CH— or —CH=CH—$CH_2$—).

As used herein, the term "alkynyl" means both straight and branched chain unsaturated hydrocarbon groups, wherein the unsaturation is present only as triple bonds. Examples of alkynyl groups include propynyl (e.g. —$CH_2$—C≡CH, —C≡C—$CH_3$).

As used herein, the term "propynylene" means a straight chain unsaturated hydrocarbon linker group, wherein the unsaturation is present as a triple bond (—$CH_2$—C≡C—).

As used herein, the term "halogen" means fluorine, chlorine, bromine and iodine.

As used herein, the term "cycloalkyl group" means an aliphatic ring (a saturated carbocyclic group). Examples of cycloalkyl groups include cyclopentyl and cyclohexyl.

As used herein, the term "heterocyclic group" means rings containing one or more heteroatoms selected from: N, S and O. The heterocycle may be aromatic or non-aromatic, i.e., may be saturated, partially or fully unsaturated. Examples of 5-membered groups include thienyl, pyrrolyl, pyrrolidinyl, pyrazolyl, imidazolyl, triazolyl, tetrazolyl, thiazolyl, thiadiazolyl, oxazolyl, oxadiazolyl, isoxazolyl and furanyl, 6-membered groups include pyridyl, pyrazyl and pyrimidyl, morpholinyl, thiomorpholinyl, 7-membered groups include azepinyl.

As used herein, the term "pharmaceutically acceptable" means a compound which is suitable for pharmaceutical use.

As used herein, the term "pharmaceutically acceptable derivative", means any pharmaceutically acceptable salt, solvate, or prodrug e.g. ester or carbamate, or salt or solvate of such a prodrug, of a compound of formula (I), (Ia), (Ib), or (Ic), which upon administration to the recipient is capable of providing (directly or indirectly) a compound of formula (I), (Ia), (Ib), or (Ic), or an active metabolite or residue thereof. Preferred pharmaceutically acceptable derivatives are salts and solvates.

Suitable salts according to the invention include those formed with both organic and inorganic acids and bases. Pharmaceutically acceptable acid addition salts include those formed from mineral acids such as: hydrochloric, hydrobromic, sulphuric, phosphoric, acid; and organic acids such as: citric, tartaric, lactic, pyruvic, acetic, trifluoroacetic, succinic, oxalic, formic, fumaric, maleic, oxaloacetic, methanesulphonic, ethanesulphonic, p-toluenesulphonic, benzenesulphonic and isethionic acids. Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine. Particularly preferred pharmaceutically acceptable salts include those formed from hydrochloric, trifluoroacetic and formic acids.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of formula (I), (Ia), (Ib), or (Ic) are within the scope of the invention.

Salts and solvates of compounds of formula (I), (Ia), (Ib), or (Ic) which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of formula (I), (Ia), (Ib), or (Ic) and their pharmaceutically acceptable salts and solvates.

As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference. Esters may be active in their own right and/or be hydrolysable under in vivo conditions in the human body. Suitable pharmaceutically acceptable in vivo hydrolysable ester groups include those which break down readily in the human body to leave the parent acid or its salt.

Preferred compounds of the invention include:

6-Chloro-N{(3S)-1-[(1S)-1-methyl-2-oxo-2-(5-oxo-1,4-diazepan-1-yl)ethyl]-2-oxopyrrolidin-3-yl}naphthalene-2-sulfonamide;

6-Chloro-N{(3S)-1-[(1S)-1-methyl-2-(4-methyl-5-oxo-1,4-diazepan-1-yl)-2-oxoethyl]-2-oxopyrrolidin-3-yl}naphthalene-2-sulfonamide;

6-Chloro-N-[(3S)-1-((1S)-1-methyl-2-{2-[(4-methylpiperazin-1-yl)methyl]pyrrolidin-1-yl}-2-oxoethyl)-2-oxopyrrolidin-3-yl]naphthalene-2-sulfonamide formate;

6-Chloro-N-((3S)-1-{(1S)-1-methyl-2-[2-(morpholin-4-ylmethyl)pyrrolidin-1-yl]-2-oxoethyl}-2-oxopyrrolidin-3-yl)naphthalene-2-sulfonamide formate;

6-Chloro-N-{(3S)-1-[(1S)-1-methyl-2-oxo-2-pyrrolidin-1-ylethyl]-2-oxopyrrolidin-3-yl}naphthalene-2-sulfonamide;

6-Chloro-N-{(3S)-1-[(1S)-2-(2,6-dimethylmorpholin-4-yl)-1-methyl-2-oxoethyl]-2-oxopyrrolidin-3-yl}naphthalene-2-sulfonamide;

6-Chloro-N-{(3S)-1-[(1S)-1-methyl-2-(3-methylmorpholin-4-yl)-2-oxoethyl]-2-oxopyrrolidin-3-yl}naphthalene-2-sulfonamide;

6-Chloro-N-((3S)-1-{(1S)-1-methyl-2-oxo-2-[2-(2-pyrrolidin-1-ylethyl)piperidin-1-yl]ethyl}-2-oxopyrrolidin-3-yl)naphthalene-2-sulfonamide;

6-Chloro-N-((3S)-1-{(1S)-1-methyl-2-oxo-2-[2-(2-pyrrolidin-1-ylethyl)piperidin-1-yl]ethyl}-2-oxopyrrolidin-3-yl)naphthalene-2-sulfonamide;

6-Chloro-N-[(3S)-1-((1S)-1-methyl-2-{2-[(methylsulfonyl)methyl]morpholin-4-yl}-2-oxoethyl)-2-oxopyrrolidin-3-yl]naphthalene-2-sulfonamide;

6-Chloro-N-((3S)-{(1S)-2-[2-(methoxymethyl)morpholin-4-yl]-1-methyl-2-oxoethyl}-2-oxopyrrolidin-3-yl)naphthalene-2-sulfonamide;

4-[(2S)-2-((3S)-3-{[(6-Chloro-2-naphthyl)sulfonyl]amino}-2-oxopyrrolidin-1-yl)propanoyl]-N-methylmorpholine-2-carboxamide;

4-[(2S)-2-((3S)-3-{[(6-Chloro-2-naphthyl)sulfonyl]amino}-2-oxopyrrolidin-1-yl)propanoyl]-N-(2-hydroxypropyl) morpholine-2-carboxamide;

6-Chloro-N-((3S)-1-{(1S)-1-methyl-2-oxo-2-[2-(pyrrolidin-1-ylmethyl)morpholin-4-yl]ethyl}-2-oxopyrrolidin-3-yl)naphthalene-2-sulfonamide formate;

6-Chloro-N-{(3S)-1-[(1S)-2-(2-{[(2-hydroxypropyl)amino]methyl}morpholin-4yl)-1-methyl-2-oxoethyl]-2-oxopyrrolidin-3-yl}naphthalene-2-sulfonamide formate;

6-Chloro-N-[(3S)-1-((1S)-2-{2-[(dimethylamino)methyl]morpholin-4-yl}-1-methyl-2-oxoethyl)-2-oxopyrrolidin-3-yl]naphthalene-2-sulfonamide formate;

6-Chloro-N-((3S)-1-{(1S)-1-methyl-2-oxo-2-[2-(piperidin-1-ylmethyl)morpholin-4-yl]ethyl}-2-oxopyrrolidin-3-yl)naphthalene-2-sulfonamide formate;

6-Chloro-N-{(3S)-1-[(1S)-1-methyl-2-oxo-2-(2-pyridin-3-ylpyrrolidin-1-yl)ethyl]-2-oxopyrrolidin-3-yl}naphthalene-2-sulfonamide;

6-Chloro-N-{(3S)-1-[(1S)-2-(3,3-difluoropiperidin-1-yl)-1-methyl-2-oxoethyl]-2-oxopyrrolidin-3-yl}naphthalene-2-sulfonamide;

6-Chloro-N-{(3S)-1-[(1S)-2-(4,4-difluoropiperidin-1-yl)-1-methyl-2-oxoethyl]-2-oxopyrrolidin-3-yl}naphthalene-2-sulfonamide;

N-{(3S)-1-[(1S)-2-Azetidin-1-yl-1-methyl-2-oxoethyl]-2-oxopyrrolidin-3-yl}-6-chloronaphthalene-2-sulfonamide;

6-Chloro-N-{(3S)-1-[(1S)-2-(3,4-dihydro-1,6-naphthyridin-1-(2H)-yl)-1-methyl-2-oxoethyl]-2-oxopyrrolidin-3-yl}naphthalene-2-sulfonamide;

6-Chloro-N-((3S)-1-{(1S)-1-methyl-2-[(1S,4S)-2-oxa-5-azabicyclo[2.2.1]hept-5-yl]-2-oxoethyl}-2-oxopyrrolidin-3-yl)naphthalene-2-sulfonamide;

N-((3S)-1-{(1S)-2-[(1R,4S)-2-Azabicyclo[2.2.1]hept-2-yl]-1-methyl-2-oxoethyl}-2-oxopyrrolidin-3-yl)-6-chloronaphthalene-2-sulfonamide;

6-Chloro-N-{(3S)-1-[(1S)-1-methyl-2-oxo-2-(2-pyridin-4-ylpyrrolidin-1-yl)ethyl]-2-oxopyrrolidin-3-yl}naphthalene-2-sulfonamide formate;

6-Chloro-N-{(3S)-1-[(1S)-1-methyl-2-oxo-2-(2-pyridin-4-ylpyrrolidin-1-yl)ethyl]-2-oxopyrrolidin-3-yl}naphthalene-2-sulfonamide formate;

N-{1-[(1S)-2-Azepan-1-yl-1-methyl-2-oxoethyl]-2-oxopyrrolidin-3-yl}-6-chloronaphthalene-2-sulfonamide;

N-{(3S)-1-[(1S)-2-(2-Azabicyclo[2.2.2]oct-2-yl)-1-methyl-2-oxoethyl]-2-oxopyrrolidin-3-yl}-6-chloronaphthalene-2-sulfonamide;

6-Chloro-N-{(3R)-1-[(1S)-1-methyl-2-oxo-2-piperidin-1-ylethyl]-2-oxopyrrolidin-3-yl}naphthalene-2-sulfonamide;

6-Chloro-N-{(3R)-1-[(1S)-1-methyl-2-morpholin-4-yl-2-oxoethyl]-2-oxopyrrolidin-3-yl}naphthalene-2-sulfonamide;

6-Chloro-N-{(3R)-1-[(1S)-1-methyl-2-oxo-2-pyrrolidin-1-ylethyl]-2-oxopyrrolidin-3-yl}naphthalene-2-sulfonamide;

6-Chloro-N-((3R)-1-{(1S)-1-methyl-2-[(2R)-2-methylpiperidin-1-yl]-2-oxoethyl}-2-oxopyrrolidin-3-yl)naphthalene-2-sulfonamide;

6-Chloro-N-[(3R)-1-((1S)-2-{2-[(diethylamino)methyl]piperidin-1-yl}-1-methyl-2-oxoethyl)-2-oxopyrrolidin-3-yl]naphthalene-2-sulfonamide;

5'-Chloro-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)-N-(2-oxobutyl)-2,2'-bithiophene-5-sulfonamide;

(E)-2-(4-Chlorophenyl)-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)-N-(2-oxobutyl)ethenesulfonamide formate;

6-Chloro-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)-N-(2-oxobutyl)-1-benzothiophene-2-sulfonamide;

5-Chloro-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)-N-(2-oxobutyl)-1-benzothiophene-2-sulfonamide;

N2-{[(E)-2-(4-Chlorophenyl)ethenyl]sulfonyl}-N2-{(3S)-1-[(1S)-1-methyl-2-morpholin-4-yl-2-oxoethyl]-2-oxopyrrolidin-3-yl}glycinamide;

N2-[(5'-Chloro-2,2'-bithien-5-yl)sulfonyl]-N2-{(3S)-1-[(1S)-1-methyl-2-morpholin-4-yl-2-oxoethyl]-2-oxopyrrolidin-3-yl}glycinamide;

N-[(5'-Chloro-2,2'-bithien-5-yl)sulfonyl]-N-{(3S)-1-[(1S)-1-methyl-2-morpholin-4-yl-2-oxoethyl]-2-oxopyrrolidin-3-yl}glycine;

(E)-2-(4-Chlorophenyl)-N-(cyanomethyl)-N-{(3S)-1-[(1S)-1-methyl-2-morpholin-4-yl-2-oxoethyl]-2-oxopyrrolidin-3-yl}ethenesulfonamide;

(E)-2-(4-Chlorophenyl)-N-{(3S)-1-[(1S)-1-methyl-2-morpholin-4-yl-2-oxoethyl]-2-oxopyrrolidin-3-yl}-N-(2-oxobutyl)ethenesulfonamide;

Methyl N-{[(E)-2-(4-chlorophenyl)ethenyl]sulfonyl}-N-{(3S)-1-[(1S)-1-methyl-2-morpholin-4-yl-2-oxoethyl]-2-oxopyrrolidin-3-yl}glycinate;

N-{[(E)-2-(4-Chlorophenyl)ethenyl]sulfonyl}-N-{(3S)-1-[(1S)-1-methyl-2-morpholin-4-yl-2-oxoethyl]-2-oxopyrrolidin-3-yl}glycine;

N-{[(E)-2-(4-Chlorophenyl)ethenyl]sulfonyl}-N-{(3S)-1-[(1S)-1-methyl-2-oxo-2-piperidin-1-ylethyl]-2-oxopyrrolidin-3-yl}glycine;

N-{(3S)-1-[(1S)-2-(3-Aminopiperidin-1-yl)-1-methyl-2-oxoethyl]-2-oxopyrrolidin-3-yl}-6-chloronaphthalene-2-sulfonamide;

6-Chloro-N-((3S)-1-{(1S)-2-[2-(hydroxymethyl)piperidin-1-yl]-1-methyl-2-oxoethyl}-2-oxopyrrolidin-3-yl)naphthalene-2-sulfonamide;

6-Chloro-N-{(3S)-1-[(1S)-1-methyl-2-oxo-2-(3-phenylpiperidin-1-yl)ethyl]-2-oxopyrrolidin-3-yl}naphthalene-2-sulfonamide;

6-Chloro-N-((3S)-1-{(1S)-1-methyl-2-oxo-2-[2-(pyrrolidin-1-ylcarbonyl)piperidin-1-yl]ethyl}-2-oxopyrrolidin-3-yl)naphthalene-2-sulfonamide;

1-[(2S)-2-((3S)-3-{[(6-Chloro-2-naphthyl)sulfonyl]amino}-2-oxopyrrolidin-1-yl)propanoyl]-N,N-dimethylprolinamide;

Methyl 1-[(2S)-2-((3S)-3-{[(6-chloro-2-naphthyl)sulfonyl]amino}-2-oxopyrrolidin-1-yl)propanoyl]-L-prolinate;

6-Chloro-N-((3S)-1-{(1S)-2-[4-(hydroxymethyl)piperidin-1-yl]-1-methyl-2-oxoethyl}-2-oxopyrrolidin-3-yl)naphthalene-2-sulfonamide;

Methyl 1-[(2S)-2-((3S)-3-{[(6-chloro-2-naphthyl)sulfonyl]amino}-2-oxopyrrolidin-1-yl)propanoyl]piperidine-3-carboxylate;

N-{(3S)-1-[(1S)-2-(4-Acetylpiperidin-1-yl)-1-methyl-2-oxoethyl]-2-oxopyrrolidin-3-yl}-6-chloronaphthalene-2-sulfonamide;

6-Chloro-N-((3S)-1-{(1S)-2-[(2R)-2-(methoxymethyl)pyrrolidin-1-yl]-1-methyl-2-oxoethyl}-2-oxopyrrolidin-3-yl)naphthalene-2-sulfonamide;

6-Chloro-N-{(3S)-1-[(1S)-1-methyl-2-(2-methylpyrrolidin-1-yl)-2-oxoethyl]-2-oxopyrrolidin-3-yl}naphthalene-2-sulfonamide;

1-[(2S)-2-((3S)-3-{[(6-Chloro-2-naphthyl)sulfonyl]amino}-2-oxopyrrolidin-1-yl)propanoyl]prolinamide;

6-Chloro-N-{(3S)-1-[(1S)-2-(3-isopropyltetrahydropyrimidin-1(2H)-yl)-1-methyl-2-oxoethyl]-2-oxopyrrolidin-3-yl}naphthalene-2-sulfonamide;

6-Chloro-N-((3S)-1-{(1S)-1-methyl-2-[(2S)-2-(morpholin-4-ylmethyl)pyrrolidin-1-yl]-2-oxoethyl}-2-oxopyrrolidin-3-yl)naphthalene-2-sulfonamide;

6-Chloro-N-{(3S)-1-[(1S)-1-methyl-2-oxo-2-(4,6,7,8-tetrahydro-5H-thieno[3,2-c]azepin-5-yl)ethyl]-2-oxopyrrolidin-3-yl}naphthalene-2-sulfonamide;

6-Chloro-N-{(3S)-1-[(1S)-1-methyl-2-oxo-2-(3,4,6,7-tetrahydro-5H-imidazo[4,5-c]pyridin-5-yl)ethyl]-2-oxopyrrolidin-3-yl}naphthalene-2-sulfonamide;

6-Chloro-N-{(3S)-1-[(1S)-2-(3,4-dihydroquinolin-1(2H)-yl)-1-methyl-2-oxoethyl]-2-oxopyrrolidin-3-yl}naphthalene-2-sulfonamide;

6-Chloro-N-{(3S)-1-[(1S)-2-(3,4-dihydroisoquinolin-2(1H)-yl)-1-methyl-2-oxoethyl]-2-oxopyrrolidin-3-yl}naphthalene-2-sulfonamide;

6-Chloro-N-{(3S)-1-[(1S)-2-(1,3-dihydro-2H-isoindol-2-yl)-1-methyl-2-oxoethyl]-2-oxopyrrolidin-3-yl}naphthalene-2-sulfonamide;

6-Chloro-N-{(3S)-1-[(1S)-1-methyl-2-oxo-2-(1,3,4,5-tetrahydro-2H-2-benzazepin-2-yl)ethyl]-2-oxopyrrolidin-3-yl}naphthalene-2-sulfonamide 6-Chloro-N-{(3S)-1-[(1S)-1-methyl-2-(4-methyl-5-oxo-1,4-diazepan-1-yl)-2-oxoethyl]-2-oxopyrrolidin-3-yl}naphthalene-2-sulfonamide;

6-Chloro-N-{(3S)-1-[(1S)-1-methyl-2-oxo-2-(5-oxo-1,4-diazepan-1-yl)ethyl]-2-oxopyrrolidin-3-yl}naphthalene-2-sulfonamide;

6-Chloro-N-{(3S)-1-[(1S)-1-methyl-2-oxo-2-thiomorpholin-4-ylethyl]-2-oxopyrrolidin-3-yl}naphthalene-2-sulfonamide;

6-Chloro-N-{(3S)-1-[(1S)-2-(2,5-dihydro-1H-pyrrol-1-yl)-1-methyl-2-oxoethyl]-2-oxopyrrolidin-3-yl}naphthalene-2-sulfonamide;

6-Chloro-N-{(3S)-1-[(1S)-1-methyl-2-(2-methylmorpholin-4-yl)-2-oxoethyl]-2-oxopyrrolidin-3-yl}naphthalene-2-sulfonamide;

6-Chloro-N-{(3S)-1-[(1S)-1-methyl-2-(4methyl-1,4-diazepan-1-yl)-2-oxoethyl]-2-oxopyrrolidin-3-yl}naphthalene-2-sulfonamide;

6-Chloro-N-{(3S)-1-[(1S)-2-(3,6-dihydropyridin-1(2H)-yl)-1-methyl-2-oxoethyl]-2-oxopyrrolidin-3-yl}naphthalene-2-sulfonamide;

6-Chloro-N-{(3S)-1-[(1S)-2-(3-hydroxyquinoxalin-1(2H)-yl)-1-methyl-2-oxoethyl]-2-oxopyrrolidin-3-yl}naphthalene-2-sulfonamide;

N-{1-[(2S)-2-((3S)-3-{[(6-Chloro-2-naphthyl)sulfonyl]amino}-2-oxopyrrolidin-1-yl)propanoyl]piperidin-3-yl}prop-2-ynamide;

N-{1-[(2S)-2-((3S)-3-{[(6-Chloro-2-naphthyl)sulfonyl]amino}-2-oxopyrrolidin-1-yl)propanoyl]piperidin-3-yl}-1H-pyrrole-2-carboxamide;

N-{1-[(2S)-2-((3S)-3-{[(6-Chloro-2-naphthyl)sulfonyl]amino}-2-oxopyrrolidin-1-yl)propanoyl]piperidin-3-yl}-1-methyl-1H-1,2,3-triazole-4-carboxamide;

N-{1-[(2S)-2-((3S)-3-{[(6-Chloro-2-naphthyl)sulfonyl]amino}-2-oxopyrrolidin-1-yl)propanoyl]piperidin-3-yl}-1,3-thiazole-2-carboxamide;

N1-{1-[(2S)-2-((3S)-3-{[(6-Chloro-2-naphthyl)sulfonyl]amino}-2-oxopyrrolidin-1-yl)propanoyl]piperidin-3-yl}-N2,N2-dimethylglycinamide;

Methyl 3-({1-[(2S)-2-((3S)-3-{[(6-chloro-2-naphthyl)sulfonyl]amino}-2-oxopyrrolidin-1-yl)propanoyl]piperidin-3-yl}amino)-3-oxopropanoate;

N-{1-[(2S)-2-((3S)-3-{[(6-Chloro-2-naphthyl)sulfonyl]amino}-2-oxopyrrolidin-1-yl)propanoyl]piperidin-3-yl}nicotinamide;
N-{1-[(2S)-2-((3S)-3-{[(6-Chloro-2-naphthyl)sulfonyl]amino}-2-oxopyrrolidin-1-yl)propanoyl]piperidin-3-yl}pyridine-2-carboxamide;
N-{1-[(2S)-2-((3S)-3-{[(6-Chloro-2-naphthyl)sulfonyl]amino}-2-oxopyrrolidin-1-yl)propanoyl]piperidin-3-yl}-4H-1,2,4-triazole-3-carboxamide;
N-{1-[(2S)-2-((3S)-3-{[(6-Chloro-2-naphthyl)sulfonyl]amino}-2-oxopyrrolidin-1-yl)propanoyl]piperidin-3-yl}-2-ethylbutanamide;
N-{1-[(2S)-2-((3S)-3-{[(6-Chloro-2-naphthyl)sulfonyl]amino{-2-oxopyrrolidin-1-yl)propanoyl]piperidin-3-yl}prop-2-ynamide;
6-Chloro-N-{(3S)-1-[(1R)-1-methyl-2-oxo-2-piperidin-1-ylethyl-2-oxopyrrolidin-3-yl}-1-benzothiophene-2-sulfonamide compound with 4-chloro-N-{(3S)-1-[(1R)-1-methyl-2-oxo-2-piperidin-1-ylethyl]-2-oxopyrrolidin-3-yl}-1-benzothiophene-2-sulphonamide;
5'-Chloro-N-{(3S)-1-[(1R)-1-methyl-2-oxo-2-piperidin-1-ylethyl]-2-oxopyrrolidin-3-yl}-2,2'-bithiophene-5-sulfonamide;
(E)-2-(4-Chlorophenyl)-N-{(3S)-1-[(1R)-1-methyl-2-oxo-2-piperidin-1-ylethyl]-2-oxopyrrolidin-3-yl}ethenesulfonamide;
5-Chloro-N-{(3S)-1-[(1R)-1-methyl-2-oxo-2-piperidin-1-ylethyl]-2-oxopyrrolidin-3-yl}-1-benzothiophene-2-sulfonamide;
N-{(3S)-1-[(1S)-1-Methyl-2-oxo-2-piperidin-1-ylethyl]-2-oxopyrrolidin-3-yl}-3-(1H-tetraazol-5-yl)benzenesulfonamide;
4-Chloro-N-{(3S)-1-[(1S)-1-methyl-2-oxo-2-piperidin-1-ylethyl]-2-oxopyrrolidin-3-yl}-1-benzothiophene-2-sulfonamide;
(E)-2-(4-Chlorophenyl)-N-{(3R)-1-[(1R)-1-methyl-2-oxo-2-piperidin-1-ylethyl]-2-oxopyrrolidin-3-yl}ethenesulfonamide;
5'-Chloro-N-{(3R)-1-[(1R)-1-methyl-2-oxo-2-piperidin-1-ylethyl]-2-oxopyrrolidin-3-yl}-2,2'-bithiophene-5-sulfonamide;
5-Chloro-N-{(3S)-1-[(1S)-1-methyl-2-oxo-2-piperidin-1-ylethyl]-2-oxopyrrolidin-3-yl}-1-benzothiophene-2-sulfonamide;
5-Chloro-N-{(3R)-1-[(1S)-1-methyl-2-oxo-2-piperidin-1-ylethyl]-2-oxopyrrolidin-3-yl}-1-benzothiophene-2-sulfonamide;
6-Fluoro-N-{(3S)-1-[(1S)-1-methyl-2-oxo-2-piperidin-1-ylethyl]-2-oxopyrrolidin-3-yl}naphthalene-2-sulfonamide;
5-Chloro-3-methyl-N-{(3S)-1-[(1S)-1-methyl-2-oxo-2-piperidin-1-ylethyl]-2-oxopyrrolidin-3-yl}-1-benzothiophene-2-sulfonamide;
6-Chloro-N-ethyl-N-{(3S)-1-[(1S)-1-methyl-2-morpholin-4-yl-2-oxoethyl]-2-oxopyrrolidin-3-yl}naphthalene-2-sulfonamide;
N2-[(6-Chloro-2-naphthyl)sulfonyl]-N2-{(3S)-1-[(1S)-1-methyl-2-oxo-2-(5-oxo-1,4-diazepan-1-yl)ethyl]-2-oxopyrrolidin-1-yl}glycinamide;
N2-[(6-Chloro-2-naphthyl)sulfonyl]-N2-{(3S)-1-[(1S)-1-methyl-2-(4-methyl-5-oxo-1,4-diazepan-1-yl)-2-oxoethyl]-2-oxopyrrolidin-3-yl}glycinamide;
N2-[(6-Chloro-2-naphthyl)sulfonyl]-N2-{(3S)-1-[(1S)-1-methyl-2-oxo-2-(2-pyridin-3-ylpyrrolidin-1-yl)ethyl]-2-oxopyrrolidin-3-yl}glycinamide;
N2-[(6-Chloro-2-naphthyl)sulfonyl]-N2-}(3S)-1-[(1S)-1-methyl-2-oxo-2-(2-pyridin-3-ylpiperidin-1-yl)ethyl]-2-oxopyrrolidin-3-yl}glycinamide;
N2-[(6-Chloro-2-naphthyl)sulfonyl]-N2-}(3S)-1-[(1S)-1-methyl-2-oxo-2-(2-pyridin-4-ylpyrrolidin-1-yl)ethyl]-2-oxopyrrolidin-3-yl}glycinamide;
N2-[(6-Chloro-2-naphthyl)sulfonyl]-N2-((3S)-1-{(1S)-2-[(1S,4S)-2,5-diazabicyclo[2.2.1]hept-2-yl]-1-methyl-2-oxoethyl}-2-oxopyrrolidin-3-yl)glycinamide;
N2-[(6-Chloro-2-naphthyl)sulfonyl]-N2-((3S)-1-{(1S)-1-methyl-2-[(1S,4S)-5-methyl-2,5-diazabicyclo[2.2.1]hept-2-yl]-2-oxoethyl}-2-oxopyrrolidin-3-yl)glycinamide hydrobromide;
N2-[(6-Chloro-2-naphthyl)sulfonyl]-N2-{(3S)-1-[(1S)-1-methyl-2-(4-methyl-1,4-diazepan-1-yl)-2-oxoethyl]-2-oxopyrrolidin-3-yl}glycinamide;
N2-[(6-Chloro-2-naphthyl)sulfonyl]-N2-{(3S)-1-[(1S)-2-(1,4-diazepan-1-yl)-1-methyl-2-oxoethyl]-2-oxopyrrolidin-3-yl}glycinamide;
N2-[(6-Chloro-2-naphthyl)sulfonyl]-N2-((3S)-1-{(1S)-2-[(2R,6S)-2,6-dimethylmorpholin-4-yl]-1-methyl-2-oxoethyl}-2-oxopyrrolidin-3-yl)glycinamide;
N2-[(6-Chloro-2-naphthyl)sulfonyl]-N2-((3S)-1-{(1S)-1-methyl-2-[(1S,4S)-2-oxa-5-azabicyclo[2.2.1]hept-5-yl]-2-oxoethyl}-2-oxopyrrolidin-3-yl)glycinamide;
6-Chloro-N-{(3S)-1-[(1S)-1-methyl-2-morpholin-4-yl-2-oxoethyl]-2-oxopyrrolidin-3-yl}-N-[(2-methyl-1,3-thiazol-4-yl)methyl]naphthalene-2-sulfonamide;
6-Chloro-N-{(3S)-1-[(1S)-1-methyl-2-morpholin-4-yl-2-oxoethyl]-2-oxopyrrolidin-3-yl}-N-(pyridin-2-ylmethyl)naphthalene-2-sulfonamide formate;
6-Chloro-N-{(3S)-1-[(1S)-1-methyl-2-morpholin-4-yl-2-oxoethyl]-2-oxopyrrolidin-3-yl}-N-(pyridin-4-ylmethyl)naphthalene-2-sulfonamide formate;
6-Chloro-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)-N-[(2-methyl-1,3-thiazol4-yl)methyl]naphthalene-2-sulfonamide formate;
6-Chloro-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)-N-(pyridin-4-ylmethyl)naphthalene-2-sulfonamide formate;
N-[(5'-Chloro-2,2'-bithien-5-yl)sulfonyl]-N-{(3S)-1-[(1S)-1-methyl-2-oxo-2-piperidin-1-ylethyl]-2-oxopyrrolidin-3-yl}glycine;
6-Chloro-N-((3S)-1-{(1R)-1-methyl-2-[(2R)-2-methylpiperidin-1-yl]-2-oxoethyl}-2-oxopyrrolidin-3-yl)naphthalene-2-sulfonamide;
6-Chloro-N-((3S)-1-{(1R)-1-methyl-2-[(2S)-2-methylpiperidin-1-yl]-2-oxoethyl}-2-oxopyrrolidin-3-yl)naphthalene-2-sulfonamide;
6-Chloro-N-[(3S)-1-((1R)-2-{2-[(diethylamino)methyl]piperidin-1-yl}-1-methyl-2-oxoethyl)-2-oxopyrrolidin-3-yl]naphthalene-2-sulfonamide;
6-Chloro-N-{(3S)-1-[(1R)-1-methyl-2-oxo-2-pyrrolidin-1-ylethyl]-2-oxopyrrolidin-3-yl}naphthalene-2-sulfonamide;
6-Chloro-N-{(3S)-1-[(1R)-1-methyl-2-morpholin-4-yl-2-oxoethyl]-2-oxopyrrolidin-3-yl}naphthalene-2-sulfonamide;
6-Chloro-N-((3S)-1-{(1R)-2-[3-(hydroxymethyl)piperidin-1-yl]-1-methyl-2-oxoethyl}-2-oxopyrrolidin-3-yl)naphthalene-2-sulfonamide;
6-Chloro-N-methyl-N-{(3S)-1-[(1R)-1-methyl-2-oxo-2-piperidin-1-ylethyl]-2-oxopyrrolidin-3-yl}naphthalene-2-sulfonamide;
N-[1-((2R)-2-{(3S)-3-[[(6-Chloro-2-naphthyl)sulfonyl](methyl)amino]-2-oxopyrrolidin-1-yl}propanoyl)piperidin-3-yl]benzamide;

6-Chloro-N-[(3S)-1-((1R)-2-{2-[(diethylamino)methyl]piperidin-1-yl}-1-methyl-2-oxoethyl)-2-oxopyrrolidin-3-yl]-N-methylnaphthalene-2-sulfonamide;
6-Chloro-N-methyl-N-{(3S)-1-[(1R)-1-methyl-2-oxo-2-pyrrolidin-1-ylethyl]-2-oxopyrrolidin-3-yl}naphthalene-2-sulfonamide;
6-Chloro-N-methyl-N-((3S)-1-{(1R)-1-methyl-2-[(2S)-2-methylpiperidin-1-yl]-2-oxoethyl}-2-oxopyrrolidin-3-yl)naphthalene-2-sulfonamide;
N-{(3S)-1-[(1R)-2-Azepan-1-yl-1-methyl-2-oxoethyl]-2-oxopyrrolidin-3-yl}-6-chloro-N-methylnaphthalene-2-sulfonamide;
6-Chloro-N-methyl-N-((3S)-1-{(1R)-1-methyl-2-oxo-2-[2-(pyrrolidin-1-ylmethyl)piperidin-1-yl]ethyl}-2-oxopyrrolidin-3-yl)naphthalene-2-sulfonamide;
6-Chloro-N-methyl-N-{(3S)-1-[(1R)-1-methyl-2-(4-methylpiperidin-1-yl)-2-oxoethyl]-2-oxopyrrolidin-3-yl}naphthalene-2-sulfonamide;
N-{[1-((2R)-2-{(3S)-3-[[(6-Chloro-2-naphthyl)sulfonyl](methyl)amino]-2-oxopyrrolidin-1-yl}propanoyl)piperidin-2-yl]methyl}benzamide;
6-Chloro-N-{(3S)-1-[(1R)-2-(3-methoxypiperidin-1-yl)-1-methyl-2-oxoethyl]-2-oxopyrrolidin-3-yl}-N-methylnaphthalene-2-sulfonamide;
6-Chloro-N-methyl-N-{(3S)-1-[(1R)-1-methyl-2-morpholin-4-yl-2-oxoethyl]-2-oxopyrrolidin-3-yl}naphthalene-2-sulfonamide;
6-Chloro-N-methyl-N-{(3R)-1-[(1S)-1-methyl-2-oxo-2-pyrrolidin-1-ylethyl]-2-oxopyrrolidin-3-yl}naphthalene-2-sulfonamide;
6-Chloro-N-methyl-N-((3R)-1-{(1S)-1-methyl-2-[(2R)-2-methylpiperidin-1-yl]-2-oxoethyl}-2-oxopyrrolidin-3-yl)naphthalene-2-sulfonamide;
6-Chloro-N-[(3R)-1-((1S)-2-{2-[(diethylamino)methyl]piperidin-1-yl}-1-methyl-2-oxoethyl-2-oxopyrrolidin-3-yl]-N-methylnaphthalene-2-sulfonamide;
6-Chloro-N-(3,3-dimethyl-2-oxobutyl)-N-{(3S)-1-[(1S)-1-methyl-2-morpholin-4-yl-2-oxoethyl]-2-oxopyrrolidin-3-yl}naphthalene-2-sulfonamide;
Ethyl N-[(6-chloro-2-naphthyl)sulfonyl]-N-{(3S)-1-[(1S)-1-methyl-2-morpholin-4-yl-2-oxoethyl]-2-oxopyrrolidin-3-yl}glycinate;
tert-Butyl N-[(6-chloro-2-naphthyl)sulfonyl]-N-{(3S)-1-[(1S)-1-methyl-2-morpholin-4-yl-2-oxoethyl]-2-oxopyrrolidin-3-yl}glycinate;
N-[1((2R)-2-{(3R)-3-[[(6-Chloro-2-naphthyl)sulfonyl](methyl)amino]-2-oxopyrrolidin-1-yl}propanoyl)piperidin-3-yl]benzamide;
N-{(3R)-1-[(1R)-2-Azepan-1-yl-1-methyl-2-oxoethyl]-2-oxopyrrolidin-3-yl}-6-chloro-N-methylnaphthalene-2-sulfonamide;
6-Chloro-N-methyl-N-{(3S)-1-[(1S)-1-methyl-2-oxo-2-pyrrolidin-1-ylethyl]-2-oxopyrrolidin-3-yl}naphthalene-2-sulfonamide;
N-Allyl-6-Chloro-N-{1-[(1S)-1-methyl-2-oxo-2-piperidin-1-ylethyl]-2-oxopyrrolidin-3-yl}naphthalene-2-sulfonamide;
Methyl N-[(6-chloro-2-naphthyl)sulfonyl]-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)glycinate formate;
N-[(6-Chloro-2-naphthyl)sulfonyl]-N-(1-{1-methyl-2-oxo-2-[2-(pyrrolidin-1-ylmethyl)pyrrolidin-1-yl]ethyl}-2-oxopyrrolidin-3-yl)glycine formate;
N-[(6-Chloro-2-naphthyl)sulfonyl]-N-((3S)-1-{(1S)-1-methyl-2-oxo-2-((2S)-2-(pyrrolidin-1-ylmethyl)pyrrolidin-1-yl]ethyl}-2-oxopyrrolidin-3-yl)glycine;
6-Chloro-N-{(3R)-1-[(1R)-1-methyl-2-oxo-2-piperidin-1-ylethyl]-2-oxopyrrolidin-3-yl}naphthalene-2-sulfonamide;
N-{1-[(2R)-2-((3R)-3-{[(6-Chloro-2-naphthyl)sulfonyl]amino}-2-oxopyrrolidin-1-yl)propanoyl]piperidin-3-yl}benzamide;
N-{(3R)-1-[(1R)-2-Azepan-1-yl-1-methyl-2-oxoethyl]-2-oxopyrrolidin-3-yl}-6-chloronaphthalene-2-sulfonamide;
6-Chloro-N-{(3R)-1-[(1R)-1-methyl-2-morpholin-4-yl-2-oxoethyl]-2-oxopyrrolidin-3-yl}naphthalene-2-sulfonamide;
6-Chloro-N-{(3R)-1-[(1R)-1-methyl-2-oxo-2-pyrrolidin-1-ylethyl]-2-oxopyrrolidin-3-yl}naphthalene-2-sulfonamide;
6-Chloro-N-((3R)-1-{(1R)-1-methyl-2-[(2R)-2-methylpiperidin-1-yl]-2-oxoethyl}-2-oxopyrrolidin-3-yl)naphthalene-2-sulfonamide;
6-Chloro-N-[(3R)-1-((1R)-2-{2-[(diethylamino)methyl]piperidin-1-yl}-1-methyl-2-oxoethyl)-2-oxopyrrolidin-3-yl]naphthalene-2-sulfonamide;
N-((3R)-1-{(1R)-2-[(1R,4S)-2-Azabicyclo[2.2.1]hept-2-yl]-1-methyl-2-oxoethyl}-2-oxopyrrolidin-3-yl)-6-chloronaphthalene-2-sulfonamide;
6-Bromo-N{1-[(1R)-1-methyl-2-oxo-2-piperidin-1-ylethyl]-2-oxopyrrolidin-3-yl}naphthalene-2-sulfonamide;
6-Chloro-N-methyl-N-{(3R)-1-[(1R)-1-methyl-2-oxo-2-pyrrolidin-1-ylethyl]-2-oxopyrrolidin-3-yl}naphthalene-2-sulfonamide;
6-Chloro-N-[(3R)-1-((1R)-2-{2-[(diethylamino)methyl]piperidin-1-yl}-1-methyl-2-oxoethyl)-2-oxopyrrolidin-3-yl]-N-methylnaphthalene-2-sulfonamide;
N-((3R)-1-(1R)-2-[(1R,4S)-2-Azabicyclo[2.2.1]hept-2-yl]-1-methyl-2-oxoethyl}-2-oxopyrrolidin-3-yl)-6-chloro-N-methylnaphthalene-2-sulfonamide;
6-Chloro-N-methyl-N-((3R)-1-{(1R)-1-methyl-2-[(2R)-2-methylpiperidin-1-yl]-2-oxoethyl}-2-oxopyrrolidin-3-yl)naphthalene-2-sulfonamide;
6-Chloro-N-[(3S)-1-((1S)-2-{3-[(3-ethoxy-2-oxopropyl)amino]piperidin-1-yl}-1-methyl-2-oxoethyl)-2-oxopyrrolidin-3-yl]naphthalene-2-sulfonamide;
6-Chloro-N-[(3S)-1-((1S)-2-{3-[(3-methoxypropyl)amino]piperidin-1-yl}-1-methyl-2-oxoethyl)-2-oxopyrrolidin-3-yl]naphthalene-2-sulfonamide;
4[({1-[(2S)-2-((3S)-3-{[(6-Chloro-2-naphthyl)sulfonyl]amino}-2-oxopyrrolidin-1-yl)propanoyl]piperidin-3-yl}amino)methyl]-1-methylpyridinium iodide;
5-(6-Amino-5-methylpyridin-3-yl)-N-{(3S)-1-[(1S)-1-methyl-2-oxo-2-piperidin-1-ylethyl]-2-oxopyrrolidin-3-yl}thiophene-2-sulfonamide;
N-[(6-Chloro-2-naphthyl)sulfonyl]-N-(1-{1-methyl-2-oxo-2-[2-(pyrrolidin-1-ylmethyl)pyrrolidin-1-yl]ethyl}-2-oxopyrrolidin-3-yl)glycine formate;
(E)-2-(5-Chlorothien-2-yl)-N-{(3S)-1-[(1S)-1-methyl-2-morpholin-4-yl-2-oxoethyl]-2-oxopyrrolidin-3-yl}ethenesulfonamide;
5-Chloro-N-{(3S)-1-[(1S)-1-methyl-2-morpholin-4-yl-2-oxoethyl]-2-oxopyrrolidin-3-yl}-1-benzothiophene-2-sulfonamide;
6-Chloro-N-{(3S)-1-[(1S)-1-methyl-2-morpholin-4-yl-2-oxoethyl]-2-oxopyrrolidin-3-yl}-1-benzothiophene-2-sulfonamide;
5-Chloro-3-methyl-N-{(3S)-1-[(1S)-1-methyl-2-morpholin-4-yl-2-oxoethyl]-2-oxopyrrolidin-3-yl}-1-benzothiophene-2-sulfonamide;
6-Chloro-N-{(3S)-1-[(1S)-1-methyl-2-morpholin-4-yl-2-oxoethyl]-2-oxopyrrolidin-3-yl}-N-(2-oxobutyl)-1-benzothiophene-2-sulfonamide;

N2-[(6-Chloro-1-benzothien-2-yl)sulfonyl]-N2-{(3S)-1-[(1S)-1-methyl-2-morpholin-4-yl-2-oxoethyl]-2-oxopyrrolidin-3-yl}glycinamide;

5-Chloro-N-{(3S)-1-[(1S)-1-methyl-2-morpholin-4-yl-2-oxoethyl]-2-oxopyrrolidin-3-yl}-N-(2-oxobutyl)-1-benzothiophene-2-sulfonamide;

N2-[(5-Chloro-1-benzothien-2-yl)sulfonyl]-N2-{(3S)-1-[(1S)-1-methyl-2-morpholin-4-yl-2-oxoethyl]-2-oxopyrrolidin-3-yl}glycinamide;

6-Chloro-N-{(3S)-1-[(1S)-1-methyl-2-morpholin-4-yl-2-oxoethyl]-2-oxopyrrolidin-3-yl}-N-phenylnaphthalene-2-sulfonamide;

6-Chloro-N-(4-fluorophenyl)-N-{(3S)-1-[(1S)-1-methyl-2-morpholin-4-yl-2-oxoethyl]-2-oxopyrrolidin-3-yl}naphthalene-2-sulfonamide;

6-Chloro-N-{(3S)-1-[(1S)-1-methyl-2-morpholin-4-yl-2-oxoethyl]-2-oxopyrrolidin-3-yl}-N-pyridin-4-ylnaphthalene-2-sulfonamide;

6-Chloro-N-{(3S)-1-[(1S)-1-methyl-2-morpholin-4-yl-2-oxoethyl]-2-oxopyrrolidin-3-yl}-N-pyridin-3-ylnaphthalene-2-sulfonamide;

6-Chloro-N-{(3S)-1-[(1S)-1-methyl-2-morpholin-4-yl-2-oxoethyl]-2-oxopyrrolidin-3-yl}-N-thien-3-ylnaphthalene-2-sulfonamide;

N-((3S)-1-{(1S)-2-[(3S)-3-Aminopiperidin-1-yl]-1-methyl-2-oxoethyl}-2-oxopyrrolidin-3-yl)naphthalene-2-sulfonamide formate;

Benzyl (3S)-1-((2S)-2-{(3S)-3-[(2-naphthylsulfonyl)amino]-2-oxopyrrolidin-1-yl}propanoyl)piperidin-3-yl-carbamate;

tert-Butyl (1R,5S)-7-[(2S)-2-((3S)-3-{[(6-chloro-2-naphthyl)sulfonyl]amino}-2-oxopyrrolidin-1-yl)propanoyl]-3,7-diazabicyclo[3.3.1]nonane-3-carboxylate;

6-Chloro-N-((3S)-1-{(1S)-2-[(1R,5S)-3,7-diazabicyclo[3.3.1]non-3-yl]-1-methyl-2-oxoethyl}-2-oxopyrrolidin-3-yl)naphthalene-2-sulfonamide;

N1-[(1R,5S)-7-[(2S)-2-((3S)-3-{[(6-Chloro-2-naphthyl)sulfonyl]amino}-2-oxopyrrolidin-1-yl)propanoyl]-3-(N,N-dimethylglycyl)-3,7-diazabicyclo[3.3.1]non-2-yl]-N1-[(1S,5R)-7-[(2S)-2-((3S)-3-{[(6-chloro-2-naphthyl)sulfonamide;

2-{(1R,5S)-7-[(2S)-2-((3S)-3-{[(6-Chloro-2-naphthyl)sulfonyl]amino}-2-oxopyrrolidin-1-yl)propanoyl]-3,7-diazabicyclo[3.3.1]non-3-yl}-N,N,N-trimethyl-2-oxoethanaminium chloride;

6-Chloro-N-((3S)-1-{(1S)-2-[(1R,5S)-3-(N-methylglycyl)-7-diazabicyclo[3.3.1]non-3-yl]-1-methyl-2-oxoethyl}-2-oxopyrrolidin-3-yl)naphthalene-2-sulfonamide;

N2-[(6-Chloro-2-naphthyl)sulfonyl]-N2-((3S)-1-{(1S)-2-[(1R,5S)-3,7-diazabicyclo[3.3.1]non-3-yl]-1-methyl-2-oxoethyl}-2-oxopyrrolidin-3-yl)glycinamide formate;

6-Chloro-N-[(3S)-1-((1S)-1-methyl-2-{(1R,5S)-7-[2-(methylamino)ethyl]-3,7-diazabicyclo[3.3.1]non-3-yl}-2-oxoethyl)-2-oxopyrrolidin-3-yl]naphthalene-2-sulfonamide;

6-Chloro-N-[2-(dimethylamino)ethyl]-N-[(3S)-1-((1S)-2-{(1R,5S)-7-[2-(dimethylamino)ethyl]-3,7-diazabicyclo[3.3.1]non-3-yl}-1-methyl-2-oxoethyl)-2-oxopyrrolidin-3-yl]naphthalene-2-sulfonamide;

6-Chloro-N-((3S)-1-{(1S)-1-methyl-2-[(1R,5S)-9-oxa-3,7-diazabicyclo[3.3.1]non-3-yl]-2-oxoethyl}-2-oxopyrrolidin-3-yl)naphthalene-2-sulfonamide trifluoroacetate;

N2-[(6-Chloro-2-naphthyl)sulfonyl]-N2-{(3S)-1-[(1S)-1-methyl-2-oxo-2-piperazin-1-ylethyl]-2-oxopyrrolidin-3-yl}glycinamide trifluoroacetate;

N2-[(6-Chloro-2-naphthyl)sulfonyl]-N2-{(3S)-1-[(1S)-1-methyl-2-(4-methyl-1,4-diazepan-1-yl)-2-oxoethyl]-2-oxopyrrolidin-3-yl}glycinamide formate;

N2-[(6-Chloro-2-naphthyl)sulfonyl]-N2-((3S)-1-{(1S)-2-[(2R,6S)-2,6-dimethylmorpholin-4-yl]-1-methyl-2-oxoethyl}-2-oxopyrrolidin-3-yl)glycinamide;

N2-[(6-Chloro-2-naphthyl)sulfonyl]-N2-((3S)-1-{(1S)-1-methyl-2-[(1S,4S)-2-oxa-5-azabicyclo[2.2.1]hept-5-yl]-2-oxoethyl}-2-oxopyrrolidin-3-yl)glycinamide;

N2-[(6-Chloro-2-naphthyl)sulfonyl]-N2-{(3S)-1-[(1S)-1-methyl-2-oxo-2-(2-pyridin-4-ylpyrrolidin-1-yl)ethyl]-2-oxopyrrolidin-3-yl}glycinamide;

N2-[(6-Chloro-2-naphthyl)sulfonyl]-N2-{(3S)-1-[(1S)-1-methyl-2-(4-methyl-5oxo-1,4-diazepan-1-yl)-2-oxoethyl]-2-oxopyrrolidin-3-yl}glycinamide;

N2-[(6-Chloro-2-naphthyl)sulfonyl]-N2-{(3S)-1-[(1S)-1-methyl-2-oxo-2-(2-pyridin-3-ylpyrrolidin-1-yl)ethyl]-2-oxopyrrolidin-3-yl}glycinamide;

N2-[(6-Chloro-2-naphthyl)sulfonyl]-N2-((3S)-1-{(1S)-1-methyl-2-[2-(4-methylpyridin-2-yl)pyrrolidin-1-yl]-2-oxoethyl)-2-oxopyrrolidin-3-yl)glycinamide;

(E)-2-(4-Chloro-3-hydroxyphenyl)-N-{(3S)-1-[(1S)-1-methyl-2-morpholin-4-yl-2-oxoethyl]-2-oxopyrrolidin-3-yl}ethenesulfonamide;

6-Chloro-N-{(3S)-1-[(1S)-1-methyl-2-morpholin-4-yl-2-oxoethyl]-2-oxopyrrolidin-3-yl}-N-(2-morpholin-4-ylethyl)naphthalene-2-sulfonamide formate;

6-Chloro-N-{(3S)-1-[(1S)-1-methyl-2-morpholin-4-yl-2-oxoethyl]-2-oxopyrrolidin-3-yl}-N-(2-pyrrolidin-1-ylethyl)naphthalene-2-sulfonamide formate;

6-Chloro-N-[2-(dimethylamino)ethyl]-N-{(3S)-1-[(1S)-1-methyl-2-morpholin-4-yl-2-oxoethyl]-2-oxopyrrolidin-3-yl}naphthalene-2-sulfonamide formate;

N-[2-([(6-Chloro-2-naphthyl)sulfonyl]{(3S)-1-[(1S)-1-methyl-2-morpholinyl-2-oxoethyl]-2-oxopyrrolidin-3-yl}amino)ethyl]acetamide;

6-Chloro-N-{2-oxo-1-[1-(pyrrolidin-1-ylcarbonyl)propyl]pyrrolidin-3-yl}naphthalene-2-sulfonamide;

6-Chloro-N-((3R)-1-{(1S)-1-methyl-2-oxo-2-[(2S)-2-(pyrrolidin-1-ylmethyl)pyrrolidin-1-yl]ethyl}-2-oxopyrrolidin-3-yl)naphthalene-2-sulfonamide formate;

5-Chloro-N-{(3S)-1-[(1S)-1-methyl-2-morpholin-4-yl-2-oxoethyl]-2-oxopyrrolidin-3-yl}-1H-indole-2-sulfonamide;

6-Chloro-N-{(3S)-1-[(1S)-1-methyl-2-morpholin-4-yl-2-oxoethyl]-2-oxopyrrolidin-3-yl}naphthalene-2-sulfonamide;

6-Chloro-N-{(3S)-1-[(1S)-1-methyl-2-oxo-2-piperidin-1-ylethyl]-2-oxopyrrolidin-3-yl}naphthalene-2-sulfonamide;

6-Chloro-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)naphthalene-2-sulfonamide formate;

6-Chloro-N-((3S)-1-{(1S)-1-methyl-2-[(2R)-2-methylpiperidin-1-yl]-2-oxoethyl}-2-oxopyrrolidin-3-yl)naphthalene-2-sulfonamide;

6-Chloro-N-[(3S)-1-((1S)-2-{2-[(diethylamino)methyl]piperidin-1-yl}-1-methyl-2-oxoethyl)-2-oxopyrrolidin-3-yl]naphthalene-2-sulfonamide;

6-Chloro-N-((3S)-1-{(1S)-1-methyl-2-oxo-2-[2-(pyrrolidin-1-ylmethyl)piperidin-1-yl]ethyl}-2-oxopyrrolidin-3-yl)naphthalene-2-sulfonamide formate;

1-[(2S)-2-((3S)-3-{[(6-Chloro-2-naphthyl)sulfonyl]amino}-2-oxopyrrolidin-1-yl)propanoyl]piperidine-3-carboxamide;

6-Chloro-N-{(3S)-1-[(1S)-1-methyl-2-oxo-2-(3-{[(trifluoromethyl)sulfonyl]amino}piperidin-1-yl)ethyl]-2-oxopyrrolidin-3-yl}naphthalene-2-sulfonamide;

1-[(2S)-2-((3S)-3-{[(6-Chloro-2-naphthyl)sulfonyl]amino}-2-oxopyrrolidin-1-yl)propanoyl]piperidine-2-carboxamide;

1-[(2S)-2-((3S)-3-{[(6-Chloro-2-naphthyl)sulfonyl]amino}-2-oxopyrrolidin-1-yl)propanoyl]piperidine-4-carboxamide;

5'-Chloro-N-{(3S)-1-[(1S)-1-methyl-2-morpholin-4-yl-2-oxoethyl]-2-oxopyrrolidin-3-yl}-2,2'-bithiophene-5-sulfonamide;

5'-Chloro-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)-2,2'-bithiophene-5-sulfonamide;

(E)-2-(4-Chlorophenyl)-N-{(3S)-1-[(1S)-1-methyl-2-morpholinyl-4-yl-2-oxoethyl]-2-oxopyrrolidin-3-yl}ethenesulfonamide;

(E)-2-(4-Chlorophenyl)-N-((3S)-1-{(1S)-1-methyl-2-oxo-2-[(2S)-2-(pyrrolidin-1-ylmethyl)pyrrolidin-1-yl]ethyl)}-2-oxopyrrolidin-3-yl)ethenesulfonamide;

5'-Chloro-N-(cyanomethyl)-N-{(3S)-1-[(1S)-1-methyl-2-morpholinyl-2-oxoethyl]-2-oxopyrrolidin-3-yl}-2,2'-bithiophene-5-sulfonamide;

Methyl N-[(5'-chloro-2,2'-bithien-5-yl)sulfonyl]-N-{(3S)-1-[(1S)-1-methyl-2-morpholin-4-yl-2-oxoethyl]-2-oxopyrrolidin-3-yl}glycinate;

5'-Chloro-N-{(3S)-1-[(1S)-1-methyl-2-morpholin-4-yl-2-oxoethyl]-2-oxopyrrolidin-3-yl}-N-(2-oxobutyl)-2,2'-bithiophene-5-sulfonamide;

N-{(3S)-1-[(1S)-2-(3-Aminopiperidin-1-yl)-1-methyl-2-oxoethyl]-2-oxopyrrolidin-3-yl}-6-chloronaphthalene-2-sulfonamide;

(E)-2-(4-Chlorophenyl)-N-{(3S)-1-[(1S)-1-methyl-2-oxo-2-piperidin-1-ylethyl]-2-oxopyrrolidin-3-yl}ethenesulfonamide;

Methyl N{[(E)-2-(4-chlorophenyl)ethenyl]sulfonyl}-N-{(3S)-1-[(1S)-1-methyl-2-oxo-2-piperidin-1-ylethyl]-2-oxopyrrolidin-3-yl}glycinate;

(E)-2-(4-Chlorophenyl)-N-(cyanomethyl)-N-{(3S)-1-[(1S)-1-methyl-2-oxo-2-piperidin-1-ylethyl]-2-oxopyrrolidin-3-yl}ethenesulfonamide;

6-Chloro-N-{(3S)-1-[(1S)-1-methyl-2-(3-methylpiperidin-1-yl)-2-oxoethyl]-2-oxopyrrolidin-3-yl}naphthalene-2-sulfonamide;

6-Chloro-N-((3S)-1-{(1S)-2-(3-(hydroxymethyl)piperidin-1-yl]-1-methyl-2-oxoethyl}-2-oxopyrrolidin-3-yl)naphthalene-2-sulfonamide;

N-{1-[(2S)-2-((3S)-3-{[(6-Chloro-2-naphthyl)sulfonyl]amino}-2-oxopyrrolidin-1-yl)propanoyl]piperidin-3-yl}acetamide;

6-Chloro-N-((3S)-1-{(1S)-1-methyl-2-oxo-2-[3-(1H-pyrrol-1-ylmethyl)piperidin-1-yl]ethyl}-2-oxopyrrolidin-3-yl)naphthalene-2-sulfonamide;

6-Chloro-N-{(3S)-1-[(1S)-2-(3,3-dimethylpiperidin-1-yl)-1-methyl-2-oxoethyl]-2-oxopyrrolidin-3-yl}naphthalene-2-sulfonamide;

6-Chloro-N-{(3S)-1-[(1S)-1-methyl-2-(2-methylpiperidin-1-yl)-2-oxoethyl]-2-oxopyrrolidin-3-yl}naphthalene-2-sulfonamide;

6-Chloro-N-((3S)-1-{(1S)-1-methyl-2-oxo-2-[3-(trifluoromethyl)piperidin-1-yl]ethyl}-2-oxopyrrolidin-3-yl)naphthalene-2-sulfonamide;

6-Chloro-N-((3S)-1-(1S)-1-methyl-2-oxo-2-[2-(2-pyrrolidin-1-ylethyl)piperidin-1-yl]ethyl}-2-oxopyrrolidin-3-yl)naphthalene-2-sulfonamide formate;

6-Chloro-N-{(3S)-1-[(1S)-2-(3-methoxypiperidin-1-yl)-1-methyl-2-oxoethyl]-2-oxopyrrolidin-3-yl}naphthalene-2-sulfonamide;

6-Chloro-N-{(3S)-1-[(1S)-1-methyl-2-(4methylpiperidin-1-yl)-2-oxoethyl]-2-oxopyrrolidin-3-yl}naphthalene-2-sulfonamide;

6-Chloro-N-{(3S)-1-[(1S)-2-(3-hydroxypiperidin-1-yl)-1-methyl-2-oxoethyl]-2-oxopyrrolidin-3-yl}naphthalene-2-sulfonamide;

6-Chloro-N-{(3S)-1-[(1S)-1-methyl-2-octahydroquinolin-1(2H)-yl-2-oxoethyl]-2-oxopyrrolidin-3-yl}naphthalene-2-sulfonamide;

6-Chloro-N-{(3S)-1-[(1S)-2-(4-hydroxypiperidin-1-yl)-1-methyl-2-oxoethyl]-2-oxopyrrolidin-3-yl}naphthalene-2-sulfonamide;

5'-Chloro-N{(3R)-1-[(1S)-1-methyl-2-oxo-2-piperidin-1-ylethyl]-2-oxopyrrolidin-3-yl)-2,2'-bithiophene-5-sulfonamide;

(E)-2-(4-Chlorophenyl)-N-{(3R)-1-[(1S)-1-methyl-2-oxo-2-piperidin-1-ylethyl]-2-oxopyrrolidin-3-yl}ethenesulfonamide;

N-{1-[(2S)-2-((3S)-3-{[(6-Chloro-2-naphthyl)sulfonyl]amino}-2-oxopyrrolidin-1-yl)propanoyl]piperidin-3-yl}prop-2-ynamide;

N-{1-[(2S)-2-((3S)-3-{[(6-Chloro-2-naphthyl)sulfonyl]amino}-2-oxopyrrolidin-1-yl)propanoyl]piperidin-3-yl}-1-methyl-1H-pyrrole-3-carboxamide;

Methyl 4-({1-[(2S)-2-((3S)-3-{[(6-chloro-2-naphthyl)sulfonyl]amino}-2-oxopyrrolidin-1-yl)propanoyl]piperidin-3-yl}amino)-4-oxobutanoate;

4-({1-[(2S)-2-((3S)-3-{[(6-Chloro-2-naphthyl)sulfonyl]amino}-2-oxopyrrolidin-1-yl)propanoyl]piperidin-3-yl}amino)-4-oxobutanoic acid;

N-{1-[(2S)-2-((3S)-3-{[(6-Chloro-2-naphthyl)sulfonyl]amino}-2-oxopyrrolidin-1-yl)propanoyl]piperidin-3-yl}-1H-1,2,4-triazole-3-carboxamide;

N-{1-[(2S)-2-((3S)-3-{[(6-Chloro-2-naphthyl)sulfonyl]amino}-2-oxopyrrolidin-1-yl)propanoyl]piperidin-3-yl}-1-methyl-1H-pyrrole-2-carboxamide;

N-{1-[(2S)-2-((3S)-3-{[(6-Chloro-2-naphthyl)sulfonyl]amino}-2-oxopyrrolidin-1-yl)propanoyl]piperidin-3-yl}propanamide;

N-{1-[(2S)-2-((3S)-3-{[(6-Chloro-2-naphthyl)sulfonyl]amino}-2-oxopyrrolidin-1-yl)propanoyl]piperidin-3-yl}-1H-pyrazole-3-carboxamide;

N-{1-[(2S)-2-((3S)-3-{[(6-Chloro-2-naphthyl)sulfonyl]amino}-2-oxopyrrolidin-1-yl)propanoyl]piperidin-3-yl}-2-ethylbutanamide;

N-{1-[(2S)-2-((3S)-3-{[(6-Chloro-2-naphthyl)sulfonyl]amino}-2-oxopyrrolidin-1-yl)propanoyl]piperidin-3-yl}cyclopentanecarboxamide;

N-{1-[(2S)-2-((3S)-3-{[(6-Chloro-2-naphthyl)sulfonyl]amino}-2-oxopyrrolidin-1-yl)propanoyl]piperidin-3-yl}pentanediamide;

N-{1-[(2S)-2-((3S)-3-{[(6-Chloro-2-naphthyl)sulfonyl]amino}-2-oxopyrrolidin-1-yl)propanoyl]piperidin-3-yl}pyrazine-2-carboxamide;

N-{1-[(2S)-2-((3S)-3-{[(6-Chloro-2-naphthyl)sulfonyl]amino}-2-oxopyrrolidin-1-yl)propanoyl]piperidin-3-yl}-1H-pyrazole-4-carboxamide;

N-{1-[(2S)-2-((3S)-3-{[(6-chloro-2-naphthyl)sulfonyl]amino}-2-oxopyrrolidin-1-yl)propanoyl]piperidin-3-yl}malonamide;

N-{1-[(2S)-2-((3S)-3-{[(6-Chloro-2-naphthyl)sulfonyl]amino}-2-oxopyrrolidin-1-yl)propanoyl]piperidin-3-yl}-2-methylpropanamide;

N-1-{1-[(2S)-2-((3S)-3-{[(6-Chloro-2-naphthyl)sulfonyl]amino}-2-oxopyrrolidin-1-yl)propanoyl]piperidin-3-yl}-N-3-,N-3-dimethyl-beta-alaninamide;
N-}1-[(2S)-2-((3S)-3-{[(6-Chloro-2-naphthyl)sulfonyl]amino}-2-oxopyrrolidin-1-yl)propanoyl]piperidin-3-yl}succinamide;
N-{(3S)-1-[(2S)-2-((3S)-3-{[(6-Chloro-2-naphthyl)sulfonyl]amino}-2-oxopyrrolidin-1-yl)propanoyl]piperidin-3-yl}nicotinamide;
N-{(3S)-1-[(2S)-2-((3S)-3-{[(6-Chloro-2-naphthyl)sulfonyl]amino}-2-oxopyrrolidin-1-yl)propanoyl]piperidin-3-yl}pyridine-2-carboxamide;
N-{(3S)-1-[(2S)-2-((3S)-3-{[(6-Chloro-2-naphthyl)sulfonyl]amino}-2-oxopyrrolidin-1-yl)propanoyl]piperidin-3-yl}isonicotinamide;
Methyl 3-({(3S)-1-[(2S)-2-((3S)-3-{[(6-chloro-2-naphthyl)sulfonyl]amino2-oxopyrrolidin-1-yl)propanoyl]piperidin-3-yl}amino)-3-oxopropanoate;
N-1-{(3S)-1-[(2S)-2-((3S)-3-{[(6-Chloro-2-naphthyl)sulfonyl]amino}-2-oxopyrrolidin-1-yl)propanoyl]piperidin-3-yl}-N-2-,N-2-dimethylglycinamide;
Benzyl (3R)-1-[(2S)-2-((3S)-3-{[(6-chloro-2-naphthyl)sulfonyl]amino}-2-oxopyrrolidin-1-yl)propanoyl]piperidin-3-ylcarbamate;
N-{(3R)-1-[(2S)-2-((3S)-3-{[(6-Chloro-2-naphthyl)sulfonyl]amino}-2-oxopyrrolidin-1-yl)propanoyl]piperidin-3-yl}nicotinamide;
N-{(3R)-1-[(2S)-2-((3S)-3-{[(6-Chloro-2-naphthyl)sulfonyl]amino}-2-oxopyrrolidin-1-yl)propanoyl]piperidin-3-yl}pyridine-2-carboxamide;
N-{(3R)-1-[(2S)-2-((3S)-3-{[(6-Chloro-2-naphthyl)sulfonyl]amino}-2-oxopyrrolidin-1-yl)propanoyl]piperidin-3-yl}isonicotinamide;
Methyl 3-({(3R)-1-[(2S)-2-((3S)-3-{[(6-chloro-2-naphthyl)sulfonyl]amino}-2-oxopyrrolidin-1-yl)propanoyl]piperidin-3-yl}amino)-3-oxopropanoate;
N-1-{(3R)-1-[(2S)-2-((3S)-3-{[(6-Chloro-2-naphthyl)sulfonyl]amino}-2-oxopyrrolidin-1-yl)propanoyl]piperidin-3-yl}-N-2-N-2-dimethylglycinamide;
5'-Chloro-N-{(3S)-1-[(1S)-1-methyl-2-oxo-2-piperidin-1-ylethyl]-2-oxopyrrolidin-3-yl}-2,2'-bithiophene-5-sulfonamide;
6-Chloro-N-{(3S)-1-[(1S)-1-methyl-2-oxo-2-piperidin-1-ylethyl]-2-oxopyrrolidin-3-yl}-1-benzothiophene-2-sulfonamide;
(E)-2-(4-Chlorophenyl)-N-{(3S)-1-[(1S)-1-methyl-2-oxo-2-piperidin-1-ylethyl]-2-oxopyrrolidin-3-yl}ethenesulfonamide;
6-Chloro-N-{(3S)-1-[(1S)-1-methyl-2-oxo-2-piperidin-1-ylethyl]-2-oxopyrrolidin-3-yl}-1-benzothiophene-2-sulfonamide compound with 4-chloro-N-{(3S)-1-[(1S)-1-methyl-2-oxo-2-piperidin-1-ylethyl]-2-oxopyrrolidin-3-yl}-1-benzothiophene-2-sulfonamide (1:1);
6-Fluoro-N-{(3S)-1-[(1S)-1-methyl-2-oxo-2-piperidin-1-ylethyl]-2-oxopyrrolidin-3-yl}naphthalene-2-sulfonamide;
6-Chloro-N-(3-furylmethyl)-N-{(3S)-1-[(1S)-1-methyl-2-morpholin-4-yl-2-oxoethyl]-2-oxopyrrolidin-3-yl}naphthalene-2-sulfonamide;
6-Chloro-N-{(3S)-1-[(1S)-1-methyl-2-morpholin-4-yl-2-oxoethyl]-2-oxopyrrolidin-3-yl}-N-(pyridin-3-ylmethyl)naphthalene-2-sulfonamide formate;
N-{1-[(2R)-2-((3S)-3-{[(6-Chloro-2-naphthyl)sulfonyl]amino}-2-oxopyrrolidin-1-yl)propanoyl]piperidin-3-yl}benzamide;
6-Chloro-N-{(3S)-1-[(1S)-1-methyl-2-morpholin-4-yl-2-oxoethyl]-2-oxopyrrolidin-3-yl}-N-(2-oxobutyl)naphthalene-2-sulfonamide;
N-2-[(6-Chloro-2-naphthyl)sulfonyl]-N-2-{(3S)-1-[(1S)-1-methyl-2-morpholin-4-yl-2-oxoethyl]-2-oxopyrrolidin-3-yl}glycinamide;
6-Chloro-N-(2-furylmethyl)-N-{(3S)-1-[(1S)-1-methyl-2-morpholin-4-yl-2-oxoethyl]-2-oxopyrrolidin-3-yl}naphthalene-2-sulfonamide;
6-Chloro-N-{(3S)-1-[(1S)-1-methyl-2-morpholin-4-yl-2-oxoethyl]-2-oxopyrrolidin-3-yl}-N-(1,3-thiazol-2-ylmethyl)naphthalene-2-sulfonamide;
Methyl N-[(5'-chloro-2,2'-bithien-5-yl)sulfonyl]-N-{(3S)-1-[(1S)-1-methyl-2-oxo-2-piperidin-1-ylethyl]-2-oxopyrrolidin-3-yl}glycinate;
5'-Chloro-N-(cyanomethyl)-N-{(3S)-1-[(1S)-1-methyl-2-oxo-2-piperidin-1-ylethyl]-2-oxopyrrolidin-3-yl}-2,2'-bithiophene-5-sulfonamide;
6-Chloro-N-{(3S)-1-[(1R)-1-methyl-2-(3-methylpiperidin-1-yl)-2-oxoethyl]-2-oxoethyl]-2-oxopyrrolidin-3-yl}naphthalene-2-sulfonamide;
N-{1-[(2R)-2-((3S)-3-{[(6-Chloro-2-naphthyl)sulfonyl]amino}-2-oxopyrrolidin-1-yl)propanoyl]piperidin-3-yl}acetamide;
6-Chloro-N-methyl-N-{(3R)-1-[(1S)-1-methyl-2-oxo-2-piperidin-1-ylethyl]-2-oxopyrrolidin-3-yl}naphthalene-2-sulfonamide;
6-Chloro-N-methyl-N-{(3S)-1-[(1R)-1-methyl-2-(3-methylpiperidin-1-yl)-2-oxoethyl]-2-oxopyrrolidin-3-yl}naphthalene-2-sulfonamide;
N-[1-((2R)-2-{(3S)-3-[[(6-chloro-2-naphthyl)sulfonyl](methyl)amino]-2-oxopyrrolidin-1-yl}propanoyl)piperidin-3-yl]acetamide;
6-Chloro-N-methyl-N-{(3S)-1-[(1R)-1-methyl-2-oxo-2-(3-{[(phenylsulfonyl)amino]methyl}piperidin-1-yl)ethyl]-2-oxopyrrolidin-3-yl}naphthalene-2-sulfonamide;
6-Chloro-N-((3S)-1-{(1R)-2-[3-(hydroxymethyl)piperidin-1-yl]-1-methyl-2-oxoethyl}-2-oxopyrrolidin-3-yl)-N-methylnaphthalene-2-sulfonamide;
6-Chloro-N-((3S)-1-{(1R)-2-[2-(hydroxymethyl)piperidin-1-yl]-1-methyl-2-oxoethyl}-2-oxopyrrolidin-3-yl)-N-methylnaphthalene-2-sulfonamide;
6-Chloro-N-(cyanomethyl)-N-{(3S)-1-[(1S)-1-methyl-2-morpholin-4-yl-2-oxoethyl]-2-oxopyrrolidin-3-yl}naphthalene-2-sulfonamide;
6-Chloro-N-methyl-N-{(3S)-1-[(1S)-1-methyl-2-morpholin-4-yl-2-oxoethyl]-2-oxopyrrolidin-3-yl}naphthalene-2-sulfonamide;
N-Allyl-6-chloro-N-{(3S)-1-[(1S)-1-methyl-2-morpholin-4-yl-2-oxoethyl]-2-oxopyrrolidin-3-yl}naphthalene-2-sulfonamide;
Methyl N-[(6-chloro-2-naphthyl)sulfonyl]-N(3S)-1-[(1S)-1-methyl-2-morpholin-4-yl-2-oxoethyl]-2-oxopyrrolidin-3-yl}glycinate;
N-[(6-Chloro-2-naphthyl)sulfonyl]-N-{(3S)-1-[(1S)-1-methyl-2-morpholin-4-yl-2-oxoethyl]-2-oxopyrrolidin-3-yl}glycine;
6-Chloro-N-{(3)-1-[(1R)-1-methyl-2-oxo-2-piperidin-1-ylethyl]-2-oxopyrrolidin-3-yl}naphthalene-2-sulfonamide;
6-Chloro-N-methyl-N-{(3S)-1-[(1S)-1-methyl-2-oxo-2-piperidin-1-ylethyl]-2-oxopyrrolidin-3-yl}naphthalene-2-sulfonamide;
6-Chloro-N-methyl-N-((3S)-1-{(1S)-1-methyl-2-[(2R)-2-methylpiperidin-1-yl]-2-oxoethyl}-2-oxopyrrolidin-3-yl)naphthalene-2-sulfonamide;
6-Chloro-N-[(3S)-1-((1S)-2-{2-[(diethylamino)methyl]piperidin-1-yl}-1-methyl-2-oxoethyl)-2-oxopyrrolidin-3-yl]-N-methylnaphthalene-2-sulfonamide;

Methyl N-[(6-chloro-2-naphthyl)sulfonyl]-N-{(3S)-1-[(1S)-1-methyl-2-oxo-2-piperidin-1-ylethyl]-2-oxopyrrolidin-3-yl}glycinate;

N-[(6-Chloro-2-naphthyl)sulfonyl]-N-{(3S)-1-[(1S)-1-methyl-2-oxo-2-piperidin-1-ylethyl]-2-oxopyrrolidin-3-yl}glycine;

N-2-[(6-Chloro-2-naphthyl)sulfonyl]-N-2-{(3S)-1-[(1S)-1-methyl-2-oxo-2-piperidin-1ylethyl]-2-oxopyrrolidin-3-yl}glycinamide;

6-Chloro-N-{(3S)-1-[(1S)-1-methyl-2-oxo-2-piperidin-1-ylethyl]-2-oxopyrrolidin-3-yl}-N-(2-oxobutyl)naphthalene-2-sulfonamide;

N-2-[(6-Chloro-2-naphthyl)sulfonyl]-N-2-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)glycinamide;

Methyl N-[(6-chloro-2-naphthyl)sulfonyl]-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)glycinate formate;

6-Chloro-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)-N-(2-oxobutyl)naphthalene-2-sulfonamide;

N-[1-((2R)-2-{(3S)-3-[[(6-Chloro-2-naphthyl)sulfonyl](methyl)amino]-2-oxopyrrolidin-1-yl}propanoyl)piperidin-3-yl]benzamide;

6-Chloro-N-methyl-N-{(3R)-[(1R)-1-methyl-2-oxo-2-piperidin-1-ylethyl]-2-oxopyrrolidin-3-yl}naphthalene-2-sulfonamide;

6-Chloro-N-methyl-N-((3S)-{(1R)-1-methyl-2-[(2R)-2-methylpiperidin-1-yl]-2-oxoethyl}-2-oxopyrrolidin-3-yl)naphthalene-2-sulfonamide;

N-((3S)-1-{(1R)-2-[(1R,4S)-2-Azabicyclo[2.2.1]hept-2-yl]-1-methyl-2-oxoethyl}-2-oxopyrrolidin-3-yl)-6-chloro-N-methylnaphthalene-2-sulfonamide;

6-Chloro-N-((3S)-1-{(1S)-2-[3-(ethylamino)piperidin-1-yl]-1-methyl-2-oxoethyl}-2-oxopyrrolidin-3-yl)naphthalene-2-sulfonamide;

6-Chloro-N-[(3S)-1-((1S)-1-methyl-2-oxo-2-{3-[(1H-pyrrol-2-ylmethyl)amino]piperidin-1-yl}ethyl)-2-oxopyrrolidin-3-yl]naphthalene-2-sulfonamide;

6-Chloro-N-[(3S)-1-((1S)-1-methyl-2-oxo-2-{3-[(pyridin-3-ylmethyl)amino]piperidin-1-yl}ethyl)-2-oxopyrrolidin-3-yl]naphthalene-2-sulfonamide;

6-Chloro-N-[(3S)-1-((1S)-2-{3-[(3-hydroxybutyl)amino]piperidin-1-yl}-1-methyl-2-oxoethyl)-2-oxopyrrolidin-3-yl]naphthalene-2-sulfonamide;

6-Chloro-N-[(3S)-1-((1S)-1-methyl-2-oxo-2-{3-[(pyridin4-ylmethyl)amino]piperidin-1-yl}ethyl)-2-oxopyrrolidin-3-yl]naphthalene-2-sulfonamide;

N-{(3S)-1-[(1S)-2-(3-{[(2-Aminopyrimidin-5-yl)methyl]amino}piperidin-1-yl)-1-methyl-2-oxoethyl]-2-oxopyrrolidin-3-yl}-6-chloronaphthalene-2-sulfonamide;

6-Chloro-N-[(3S)-1-((1S)-1-methyl-2-oxo-2-{3-[(pyridin-2-ylmethyl)amino]piperidin-1-yl}ethyl)-2-oxopyrrolidin-3-yl]naphthalene-2-sulfonamide;

6-Chloro-N-[(3S)-1-((1S)-1-methyl-2-oxo-2-{3-[(1H-pyrazol-3-ylmethyl)amino]piperidin-1-yl}ethyl)-2-oxopyrrolidin-3-yl]naphthalene-2-sulfonamide;

6-Chloro-N-[(3S)-1-((1S)-1-methyl-2-oxo-2-{3-[(pyridin-4-ylmethyl)amino]piperidin-1-yl}ethyl)-2-oxopyrrolidin-3-yl]naphthalene-2-sulfonamide;

6-Chloro-N-((3S)-1-{(1S)-2-[3-({[5-(hydroxymethyl)-2-furyl]methyl}amino)piperidin-1-yl]-1-methyl-2-oxoethyl}-2-oxopyrrolidin-3-yl)naphthalene-2-sulfonamide;

6-Chloro-N-[(3S)-1-((1S)-1-methyl-2-oxo-2-{3-[(1,3-thiazol-2-ylmethyl)amino]piperidin-1-yl}ethyl)-2-oxopyrrolidin-3-yl]naphthalene-2-sulfonamide;

6-Chloro-N-{(3S)-1-[(1S)-1-methyl-2-(3-{[(1-methyl-1H-imidazol-2-yl)methyl]amino}piperidin-1-yl)-2-oxoethyl]-2-oxopyrrolidin-3-yl}naphthalene-2-sulfonamide;

6-Chloro-N-[(3S)-1-((1S)-2-{3-[(3-hydroxy-2,2-dimethylpropyl)amino]piperidin-1-yl}-1-methyl-2-oxoethyl)-2-oxopyrrolidin-3-yl]naphthalene-2-sulfonamide;

6-Chloro-N-[(3S)-1-((1S)-2-{3-[(1H-imidazol-4-ylmethyl)amino]piperidin-1-yl}-1-methyl-2-oxoethyl)-2-oxopyrrolidin-3-yl]naphthalene-2-sulfonamide;

Benzyl (3S)-1-[(2S)-2-((3S)-3-{[(6-chloro-2-naphthyl)sulfonyl]amino}-2-oxopyrrolidin-1-yl)propanoyl]piperidin-3-ylcarbamate;

N-((3S)-1-{(1S)-2-[(3S)-3-Aminopiperidin-1-yl]-1-methyl-2-oxoethyl}-2-oxopyrrolidin-3-yl)-6-chloronaphthalene-2-sulfonamide;

N-((3S)-1-{(1S)-2-[(3R)-3-Aminopiperidin-1-yl]-1-methyl-2-oxoethyl}-2-oxopyrrolidin-3-yl)-6-chloronaphthalene-2-sulfonamide;

(E)-2-(5-Chlorothien-2-yl)-N-methyl-N-{(3S)-1-[(1S)-1-methyl-2-morpholin-4-yl-2-oxoethyl]-2-oxopyrrolidin-3-yl}ethenesulfonamide;

5-Chloro-N-{(3S)-1-[(1S)-1-methyl-2-morpholin-4-yl-2-oxoethyl]-2-oxopyrrolidin-3-yl}thieno[3,2-b]pyridine-2-sulfonamide;

More preferred compounds of the invention include:

6-Chloro-N-{(3S)-1-[(1S)-1-methyl-2-(4-methyl-5-oxo-1,4-diazepan-1-yl)-2-oxoethyl]-2-oxopyrrolidin-3-yl}naphthalene-2-sulfonamide;

6-Chloro-N-((3S)-1-{(1S)-1-methyl-2-oxo-2-[2-(2-pyrrolidin-1-ylethyl)piperidin-1-yl]ethyl}-2-oxopyrrolidin-3-yl)naphthalene-2-sulfonamide;

6-Chloro-N-((3S)-1-{(1S)-1-methyl-2-oxo-2-[2-(2-pyrrolidin-1-ylethyl)piperidin-1-yl]ethyl}-2-oxopyrrolidin-3-yl)naphthalene-2-sulfonamide;

6-Chloro-N-{(3S)-1-[(1S)-1-methyl-2-oxo-2-(2-pyridin-3-ylpyrrolidin-1-yl)ethyl]-2-oxopyrrolidin-3-ylnaphthalene-2-sulfonamide;

6-Chloro-N-{(3S)-1-[(1S)-2-(3,3-difluoropiperidin-1-yl)-1-methyl-2-oxoethyl]-2-oxopyrrolidin-3-yl}naphthalene-2-sulfonamide;

6-Chloro-N-{(3S)-1-[(1S)-2-(4,4-difluoropiperidin-1-yl)-1-methyl-2-oxoethyl]-2-oxopyrrolidin-3-yl}naphthalene-2-sulfonamide;

6-Chloro-N-{(3S)-1-[(1S)-2-(3,4-dihydro-1,6-naphthyridin-1(2H)-yl)-1-methyl-2-oxoethyl]-2-oxopyrrolidin-3-yl}naphthalene-2-sulfonamide;

N-((3S)-1-{(1S)-2-[(1R,4S)-2-Azabicyclo[2.2.1]hept-2-yl]-1-methyl-2-oxoethyl}-2-oxopyrrolidin-3-yl)6-chloronaphthalene-2-sulfonamide;

6-Chloro-N-{(3S)-1-[(1S)-1-methyl-2-oxo-2-(2-pyridin-4-ylpyrrolidin-1-yl)ethyl]-2-oxopyrrolidin-3-yl}naphthalene-2-sulfonamide formate;

N-{1-[(1S)-2-Azepan-1-yl-1-methyl-2-oxoethyl]-2-oxopyrrolidin-3-yl}-6-chloronaphthalene-2-sulfonamide;

N-{(3S)-1-[(1S)-2-(2-Azabicyclo[2.2.2]oct-2-yl)-1-methyl-2-oxoethyl]-2-oxopyrrolidin-2-oxopyrrolidin-3-yl}-6-chloronaphthalene-2-sulfonamide;

5'-Chloro-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)-N-(2-oxobutyl)-2,2'-bithiophene-5-sulfonamide;

(E)-2-(4-Chlorophenyl)-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)-N-(2-oxobutyl)ethenesulfonamide formate;

6-Chloro-N-((3S)-1-{(1S)-1-methyl-2-oxo-2-[(2S)-2-(pyr-rolidin-1-ylmethyl)pyrrolidin-1-yl]ethyl}-2-oxopyrroli-din-3-yl)-N-(2-oxobutyl)-1-benzothiophene-2-sulfona-mide;

5-Chloro-N-((3S)-1-{(1S)-1-methyl-2-oxo-2-[(2S)-2-(pyr-rolidin-1-ylmethyl)pyrrolidin-1-yl]ethyl}-2-oxopyrroli-din-3-yl)-N-(2-oxobutyl)-1-benzothiophene-2-sulfona-mide;

N2-{[(E)-2-(4-Chlorophenyl)ethenyl]sulfonyl}-N2-{(3S)-1-[(1S)-1-methyl-2-morpholin-4-yl-2-oxoethyl]-2-ox-opyrrolidin-3-yl}glycinamide;

N2-[(5'-Chloro-2,2'-bithien-5-yl)sulfonyl]-N2-{(3S)-1-[(1S)-1-methyl-2-morpholin-4-yl-2-oxoethyl]-2-oxopyr-rolidin-3-yl}glycinamide;

N-[(5'-Chloro-2,2'-bithien-5-yl)sulfonyl]-N-{(3S)-1-[(1S)-1-methyl-2-morpholin-4-yl-2-oxoethyl]-2-oxopyrrolidin-3-yl}glycine;

(E)-2-(4-Chlorophenyl)-N-(cyanomethyl)-N-{(3S)-1-[(1S)-1-methyl-2-morpholin-4-yl-2-oxoethyl]-2-oxopyrrolidin-3-yl}ethenesulfonamide;

(E)-2-(4-Chlorophenyl)-N-{(3S)-1-[(1S)-1-methyl-2-mor-pholin-4-yl-2-oxoethyl]-2-oxopyrrolidin-3-yl}-N-(2-ox-obutyl)ethenesulfonamide;

Methyl N-{[(E)-2-(4-chlorophenyl)ethenyl]sulfonyl}-N-{(3S)-1-[(1S)-1-methyl-2-morpholin-4-yl-2-oxoethyl]-2-oxopyrrolidin-3-yl}glycinate;

N-{[(E)-2-(4-Chlorophenyl)ethenyl]sulfonyl}-N-{(3S)-1-[(1S)-1-methyl-2-oxo-2-piperidin-1-ylethyl]-2-oxopyrro-lidin-3-yl}glycine;

N-{(3S)-1-[(1S)-2-(3-Aminopiperidin-1-yl)-1-methyl-2-oxoethyl]-2-oxopyrrolidin-3-yl}-6-chloronaphthalene-2-sulfonamide;

6-Chloro-N-{(3S)-1-[(1S)-1-methyl-2-oxo-2-thiomorpho-lin-4-ylethyl]-2-oxopyrrolidin-3-yl}naphthalene-2-sul-fonamide;

N-{1-[(2S)-2-((3S)-3-{[(6-Chloro-2-naphthyl)sulfonyl]amino}-2-oxopyrrolidin-1-yl)propanoyl]piperidin-3-yl}prop-2-ynamide;

N1-{1-[(2S)-2-((3S)-3-{[(6-Chloro-2-naphthyl)sulfonyl]amino}-2-oxopyrrolidin-1-yl)propanoyl]piperidin-3-yl}-N2,N2-dimethylglycinamide;

Methyl 3-({1-[(2S)-2-((3S)-3-{[(6-chloro-2-naphthyl)sulfo-nyl]amino}-2-oxopyrrolidin-1-yl)propanoyl]piperidin-3-yl}amino)-3-oxopropanoate;

N-{1-[(2S)-2-((3S)-3-{[(6-Chloro-2-naphthyl)sulfonyl]amino}-2-oxopyrrolidin-1-yl)propanoyl]piperidin-3-yl}nicotinamide;

N-{1-[(2S)-2-((3S)-3-{[(6-Chloro-2-naphthyl)sulfonyl]amino}-2-oxopyrrolidin-1-yl)propanoyl]piperidin-3-yl}pyridine-2-carboxamide;

6-Chloro-N-ethyl-N-{(3S)-1-[(1S)-1-methyl-2-morpholin-4-yl-2-oxoethyl]-2-oxopyrrolidin-3-yl}naphthalene-2-sulfonamide;

N2-[(6-Chloro-2-naphthyl)sulfonyl]-N2-{(3S)-1-[(1S)-1-methyl-2-oxo-2-(5-oxo-1,4-diazepan-1-yl)ethyl]-2-ox-opyrrolidin-3-yl}glycinamide;

N2-[(6-Chloro-2-naphthyl)sulfonyl]-N2-{(3S)-1-[(1S)-1-methyl-2-(4-methyl-5-oxo-1,4-diazepan-1-yl)-2-oxoet-hyl]-2-oxopyrrolidin-3-yl}glycinamide;

N2-[(6-Chloro-2-naphthyl)sulfonyl]-N2-{(3S)-1-[(1S)-1-methyl-2-oxo-2-(2-pyridin-3-ylpyrrolidin-1-yl)ethyl]-2-oxopyrrolidin-3-yl}glycinamide;

N2-[(6-Chloro-2-naphthyl)sulfonyl]-N2-{(3S)-1-[(1S)-1-methyl-2-oxo-2-(2-pyridin-4-ylpyrrolidin-1-yl)ethyl]-2-oxopyrrolidin-3-yl}glycinamide;

N2-[(6-Chloro-2-naphthyl)sulfonyl]-N2-((3S)-1-{(1S)-2-[(2R,6S)-2,6-dimethylmorpholin-4-yl]-1-methyl-2-oxo-ethyl}-2-oxopyrrolidin-3-yl)glycinamide;

6-Chloro-N-{(3S)-1-[(1S)-1-methyl-2-morpholin-4-yl-2-oxoethyl]-2-oxopyrrolidin-3-yl}-N-[(2-methyl-1,3-thia-zol-4-yl)methyl]naphthalene-2-sulfonamide;

6-Chloro-N-{(3S)-1-[(1S)-1-methyl-2-morpholin-4-yl-2-oxoethyl]-2-oxopyrrolidin-3-yl}-N-(pyridin-2-ylmethyl)naphthalene-2-sulfonamide formate;

6-Chloro-N-{(3S)-1-[(1S)-1-methyl-2-morpholin-4-yl-2-oxoethyl]-2-oxopyrrolidin-3-yl}-N-(pyridin-4-ylmethyl)naphthalene-2-sulfonamide formate;

6-Chloro-N-((3S)-1-((1S)-1-methyl-2-oxo-2-[(2S)-2-(pyr-rolidin-1-ylmethyl)pyrrolidin-1-yl]ethyl}-2-oxopyrroli-din-3-yl)-N-[(2-methyl-1,3-thiazol-4-yl)methyl]naphtha-lene-2-sulfonamide formate;

6-Chloro-N-((3S)-1-{(1S)-1-methyl-2-oxo-2-[(2S)-2-(pyr-rolidin-1-ylmethyl)pyrrolidin-1-yl]ethyl)-2-oxopyrroli-din-3-yl)-N-(pyridin-4-ylmethyl)naphthalene-2-sulfona-mide formate;

N-[(5'-Chloro-2,2'-bithien-5-yl)sulfonyl]-N-{(3S)-1-[(1S)-1-methyl-2-oxo-2-piperidin-1-ylethyl]-2-oxopyrrolidin-3-yl}glycine;

N-[1-((2R)-2-{(3S)-3-[[(6-Chloro-2-naphthyl)sulfonyl](methyl)amino]-2-oxopyrrolidin-1-yl}propanoyl)piperi-din-3-yl]benzamide;

6-Chloro-N-(3,3-dimethyl-2-oxobutyl)-N-{(3S)-1-[(1S)-1-methyl-2-morpholin-4-yl-2-oxoethyl]-2-oxopyrrolidin-3-yl}naphthalene-2-sulfonamide;

tert-Butyl N-[(6-chloro-2-naphthyl)sulfonyl]-N-{(3S)-1-[(1S)-1-methyl-2-morpholinyl-4-yl-2-oxoethyl]-2-ox-opyrrolidin-3-yl}glycinate;

N-Allyl-6-chloro-N{1-[(1S)-1-methyl-2-oxo-2-piperidin-1-ylethyl]-2-oxopyrrolidin-3-yl}naphthalene-2-sulfona-mide;

N-[(6-Chloro-2-naphthyl)sulfonyl]-N-(1-{1-methyl-2-oxo-2-[2-(pyrrolidin-1-ylmethyl)pyrrolidin-1-yl]ethyl}-2-ox-opyrrolidin-3-yl)glycine formate;

N-[(6-Chloro-2-naphthyl)sulfonyl]-N-((3S)-1-(1S)-1-me-thyl-2-oxo-2-[(2S)-2-(pyrrolidin-1-ylmethyl)pyrrolidin-1-yl]ethyl}-2-oxopyrrolidin-3-yl)glycine;

6-Chloro-N-methyl-N-{(3R)-1-[(1R)-1-methyl-2-oxo-2-pi-peridin-1-ylethyl]-2-oxopyrrolidin-3-yl}naphthalene-2-sulfonamide;

N-[(6-Chloro-2-naphthyl)sulfonyl]-N-(1-{1-methyl-2-oxo-2-[2-(pyrrolidin-1-ylmethyl)pyrrolidin-1-yl]ethyl}-2-ox-opyrrolidin-3-yl)glycine formate;

(E)-2-(5-Chlorothien-2-yl)-N-{(3S)-1-[(1S)-1-methyl-2-morpholin-4-yl-2-oxoethyl]-2-oxopyrrolidin-3-yl}ethenesulfonamide;

6-Chloro-N-{(3S)-1-[(1S)-1-methyl-2-morpholin-4-yl-2-oxoethyl]-2-oxopyrrolidin-3-yl}-N-(2-oxobutyl)-1-ben-zothiophene-2-sulfonamide;

N2-[(6-Chloro-1-benzothien-2-yl)sulfonyl]-N2-{(3S)-1-[(1S)-1-methyl-2-morpholin-4-yl-2-oxoethyl]-2-oxopyr-rolidin-3-yl}glycinamide;

6-Chloro-N-((3S)-1-{(1S)-2-[(1R,5S)-3,7-diazabicyclo[3.3.1]non-3-yl]-1-methyl-2-oxoethyl}-2-oxopyrrolidin-3-yl)naphthalene-2-sulfonamide;

6-Chloro-N-[(3S)-1-((1S)-1-methyl-2-{(1R,5S)-7-[2-(me-thylamino)ethyl]-3,7-diazabicyclo[3.3.1]non-3-yl}-2-oxoethyl)-2-oxopyrrolidin-3-yl]naphthalene-2-sulfona-mide;

6-Chloro-N-((3S)-1-{(1S)-1-methyl-2-[(1R,5S)-9-oxa-3,7-diazabicyclo[3.3.1]non-3-yl]-2-oxoethyl}-2-oxopyrroli-din-3-yl)naphthalene-2-sulfonamide trifluoroacetate;

N2-[(6-Chloro-2-naphthyl)sulfonyl]-N2-{(3S)-[(1S)-1-methyl-2-(4-methyl-1,4-diazepan-1-yl)-2-oxoethyl]-2-oxopyrrolidin-3-yl}glycinamide formate;
N2-[(6-Chloro-2-naphthyl)sulfonyl]-N2-((3S)-1-{(1S)-2-[(2R,6S)-2,6-dimethylmorpholin-4-yl]-1-methyl-2-oxoethyl}-2-oxopyrrolidin-3-yl)glycinamide;
N2-[(6-Chloro-2-naphthyl)sulfonyl]-N2-((3S)-1-{(1S)-1-methyl-2-[(1S,4S)-2-oxa-5-azabicyclo[2.2.1]hept-5-yl]-2-oxoethyl}-2-oxopyrrolidin-3-yl)glycinamide;
N2-[(6-Chloro-2-naphthyl)sulfonyl]-N2-{(3S)-1-[(1S)-1-methyl-2-oxo-2-(2-pyridin-4-ylpyrrolidin-1-yl)ethyl]-2-oxopyrrolidin-3-yl}glycinamide;
N2-[(6-Chloro-2-naphthyl)sulfonyl]-N2-{(3S)-1-[(1S)-1-methyl-2-(4-methyl-5-oxo-1,4-diazepan-1-yl)-2-oxoethyl]-2-oxopyrrolidin-3-yl}glycinamide;
N2-[(6-Chloro-2-naphthyl)sulfonyl]-N2-{(3S)-1-[(1S)-1-methyl-2-oxo-2-(2-pyridin-3-ylpyrrolidin-1-yl)ethyl]-2-oxopyrrolidin-3-yl}glycinamide;
6-Chloro-N-{(3S)-1-[(1S)-1-methyl-2-morpholin-4-yl-2-oxoethyl]-2-oxopyrrolidin-3-yl}-N-(2-morpholin-4-ylethyl)naphthalene-2-sulfonamide formate;
6-Chloro-N-{(3S)-1-[(1S)-1-methyl-2-morpholin-4-yl-2-oxoethyl]-2-oxopyrrolidin-3-yl}-N-(2-pyrrolidin-1-ylethyl)naphthalene-2-sulfonamide formate;
6-Chloro-N-[2-(dimethylamino)ethyl]-N-{(3S)-1-[(1S)-1-methyl-2-morpholin-4-yl-2-oxoethyl]-2-oxopyrrolidin-3-yl}naphthalene-2-sulfonamide formate;
N-[2-([(6-Chloro-2-naphthyl)sulfonyl]{(3S)-1-[(1S)-1-methyl-2-morpholinyl-2-oxoethyl]-2-oxopyrrolidin-3-yl}amino)ethyl]acetamide;
6-Chloro-N-{(3S)-1-[(1S)-1-methyl-2-morpholin-4-yl-2-oxoethyl]-2-oxopyrrolidin-3-yl}naphthalene-2-sulfonamide;
6-Chloro-N-{(3S)-1-[(1S)-1-methyl-2-oxo-2-piperidin-1-ylethyl]-2-oxopyrrolidin-3-yl}naphthalene-2-sulfonamide;
6-Chloro-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)naphthalene-2-sulfonamide formate;
6-Chloro-N-((3S)-1-{(1S)-1-methyl-2-[(2R)-2-methylpiperidin-1-yl]-2-oxoethyl}-2-oxopyrrolidin-3-yl)naphthalene-2-sulfonamide;
5'-Chloro-N-{(3S)-1-[(1S)-1-methyl-2-morpholin-4-yl-2-oxoethyl]-2-oxopyrrolidin-3-yl}-2,2'-bithiophene-5-sulfonamide;
5'-Chloro-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)-2,2'-bithiophene-5-sulfonamide;
(E)-2-(4-Chlorophenyl)-N-{(3S)-1-[(1S)-1-methyl-2-morpholin-4-yl-2-oxoethyl]-2-oxopyrrolidin-3-yl}ethenesulfonamide;
5'-Chloro-N-(cyanomethyl)-N-{(3S)-1-[(1S)-1-methyl-2-morpholin-4-yl-2-oxoethyl]-2-oxopyrrolidin-3-yl}-2,2'-bithiophene-5-sulfonamide;
Methyl N-[(5'-chloro-2,2'-bithien-5-yl)sulfonyl]-N-{(3S)-1-[(1S)-1-methyl-2-morpholin-4-yl-2-oxoethyl]-2-oxopyrrolidin-3-yl}glycinate;
5'-Chloro-N-{(3S)-1-[(1S)-1-methyl-2-morpholin-4-yl-2-oxoethyl]-2-oxopyrrolidin-3-yl}-N-(2-oxobutyl)-2,2'-bithiophene-5-sulfonamide;
N-{(3S)-1-[(1S)-2-(3-Aminopiperidin-1-yl)-1-methyl-2-oxoethyl]-2-oxopyrrolidin-3-yl}-6-chloronaphthalene-2-sulfonamide;
(E)-2-(4-Chlorophenyl)-N-{(3S)-1-[(1S)-1-methyl-2-oxo-2-piperidin-1-ylethyl]-2-oxopyrrolidin-3-yl}ethenesulfonamide;
Methyl N-{[(E)-2-(4-chlorophenyl)ethenyl]sulfonyl}-N-{(3S)-[(1S)-1-methyl-2-oxo-2-piperidin-1-ylethyl]-2-oxopyrrolidin-3-yl}glycinate;
(E)-2-(4-Chlorophenyl)-N-(cyanomethyl)-N-{(3S)-1-[(1S)-1-methyl-2-oxo-2-piperidin-1-ylethyl]-2-oxopyrrolidin-3-yl}ethenesulfonamide;
6-Chloro-N-{(3S)-1-[(1S)-1-methyl-2-(3-methylpiperidin-1-yl)-2-oxoethyl]-2-oxopyrrolidin-3-yl}naphthalene-2-sulfonamide;
6-Chloro-N-((3S)-1-{(1S)-2-[3-(hydroxymethyl)piperidin-1-yl]-1-methyl-2-oxoethyl}-2-oxopyrrolidin-3-yl)naphthalene-2-sulfonamide;
N-{1-[(2S)-2-((3S)-3-{[(6-Chloro-2-naphthyl)sulfonyl]amino}-2-oxopyrrolidin-1-yl)propanoyl]piperidin-3-yl}acetamide;
6-Chloro-N-((3S)-1-{(1S)-1-methyl-2-oxo-2-[3-(1H-pyrrol-1-ylmethyl)piperidin-1-yl]ethyl}-2-oxopyrrolidin-3-yl)naphthalene-2-sulfonamide;
6-Chloro-N-{(3S)-1-[(1S)-2-(3,3-dimethylpiperidin-1-yl)-1-methyl-2-oxoethyl]-2-oxopyrrolidin-3-yl}naphthalene-2-sulfonamide;
N-{1-[(2S)-2-((3S)-3-{[(6-Chloro-2-naphthyl)sulfonyl]amino}-2-oxopyrrolidin-1-yl)propanoyl]piperidin-3-yl}prop-2-ynamide;
N-{1-[(2S)-2-((3S)-3-{[(6-Chloro-2-naphthyl)sulfonyl]amino}-2-oxopyrrolidin-1-yl)propanoyl]piperidin-3-yl}-1-methyl-1H-pyrrole-3carboxamide;
Methyl 4-({1-[(2S)-2-((3S)-3-{[(6-chloro2-naphthyl)sulfonyl]amino}-2-oxopyrrolidin-1-yl)propanoyl]piperidin-3-yl}amino)4-oxobutanoate;
4-({1-[(2S)-2-((3S)-3-{[(6-Chloro-2-naphthyl)sulfonyl]amino}-2-oxopyrrolidin-1-yl)propanoyl]piperidin-3-yl}amino)4-oxobutanoic acid;
N-{(3S)-1-[(2S)-2-((3S)-3-{[(6-Chloro-2-naphthyl)sulfonyl]amino}-2-oxopyrrolidin-1-yl)propanoyl]piperidin-3-yl}nicotinamide;
N-{(3S)-1-[(2S)-2-((3S)-3-{[(6-Chloro-2-naphthyl)sulfonyl]amino}-2-oxopyrrolidin-1-yl)propanoyl]piperidin-3-yl}pyridine-2-carboxamide;
N-{(3S)-1-[(2S)-2-((3S)-3-{[(6-Chloro-2-naphthyl)sulfonyl]amino}-2-oxopyrrolidin-1-yl)propanoyl]piperidin-3-yl}isonicotinamide;
Methyl 3-({(3S)-1-[(2S)-2-((3S)-3-{[(6-chloro-2-naphthyl)sulfonyl]amino}-2-oxopyrrolidin-1-yl)propanoyl]piperidin-3-yl}amino)-3-oxopropanoate;
N-1{(3S)-1-[(2S)-2-((3S)-3-{[(6-Chloro-2-naphthyl)sulfonyl]amino}-2-oxopyrrolidin-1-yl)propanoyl]piperidin-3-yl}-N-2-,N-2-dimethylglycinamide;
Benzyl (3R)-1-[(2S)-2-((3S)-3-{[(6-chloro-2-naphthyl)sulfonyl]amino}-2-oxopyrrolidin-1-yl)propanoyl]piperidin-3-ylcarbamate;
N-{(3R)-1-[(2S)-2-((3S)-3-{[(6-Chloro-2-naphthyl)sulfonyl]amino}-2-oxopyrrolidin-1-yl)propanoyl]piperidin-3-yl}nicotinamide;
N-{(3R)-1-[(2S)-2-((3S)-3-{[(6-Chloro-2-naphthyl)sulfonyl]amino}-2-oxopyrrolidin-1-yl)propanoyl]piperidin-3-yl}isonicotinamide;
5'-Chloro-N-{(3S)-1-[(1S)-1-methyl-2-oxo-2-piperidin-1-ylethyl]-2-oxopyrrolidin-3-yl}-2,2'-bithiophene-5-sulfonamide;
6-Chloro-N-{(3S)-1-[(1S)-1-methyl-2-oxo-2-piperidin-1-ylethyl]-2-oxopyrrolidin-3-yl}-1-benzothiophene-2-sulfonamide;
(E)-2-(4-Chlorophenyl)-N-{(3S)-1-[(1S)-1-methyl-2-oxo-2-piperidin-1-ylethyl]-2-oxopyrrolidin-3-yl}ethenesulfonamide;

6-Chloro-N-{(3S)-1-[(1S)-1-methyl-2oxo-2-piperidin-1-yl-ethyl]-2-oxopyrrolidin-3-yl}-1-benzothiophene-2-sulfonamide compound with 4-chloro-N-{(3S)-1-[(1S)-1-methyl-2-oxo-2-piperidin-1-ylethyl]-2-oxopyrrolidin-3-yl}-1-benzothiophene-2-sulfonamide (1:1);

6-Chloro-N-(3-furylmethyl)-N-{(3S)-1-[(1S)-1-methyl-2-morpholin-4-yl-2-oxoethyl]-2-oxopyrrolidin-3-yl}naphthalene-2-sulfonamide;

6-Chloro-N-{(3S)-1-[(1S)-1-methyl-2-morpholin-4-yl-2-oxoethyl]-2-oxopyrrolidin-3-yl}-N-(pyridin-3-ylmethyl)naphthalene-2-sulfonamide formate;

6-Chloro-N-{(3S)-1-[(1S)-1-methyl-2-morpholin-4-yl-2-oxoethyl]-2-oxopyrrolidin-3-yl}-N-(2-oxobutyl)naphthalene-2-sulfonamide;

N-2-[(6-Chloro-2-naphthyl)sulfonyl]-N-2-{(3S)-1-[(1S)-1-methyl-2-morpholin-4-yl-2-oxoethyl]-2-oxopyrrolidin-3-yl}glycinamide;

6-Chloro-N-(2-furylmethyl)-N-{(3S)-1-[(1S)-1-methyl-2-morpholin-4-yl-2-oxoethyl]-2-oxopyrrolidin-3-yl}naphthalene-2-sulfonamide;

6-Chloro-N-{(3S)-1-[(1S)-1-methyl-2-morpholin-4-yl-2-oxoethyl]-2-oxopyrrolidin-3-yl}-N-(1,3-thiazol-2-ylmethyl)naphthalene-2-sulfonamide;

Methyl N-[(5'-chloro-2,2'-bithien-5-yl)sulfonyl]-N-{(3S)-1-[(1S)-1-methyl-2-oxo-2-piperidin-1-ylethyl]-2-oxopyrrolidin-3-yl}glycinate;

5'-Chloro-N-(cyanomethyl)-N-{(3S)-1-[(1S)-1-methyl-2-oxo-2-piperidin-1-ylethyl]-2-oxopyrrolidin-3-yl}-2,2'-bithiophene-5-sulfonamide;

6-Chloro-N-{(3S)-1-[(1R)-1-methyl-2-(3-methylpiperidin-1-yl)-2-oxoethyl]-2-oxopyrrolidin-3-yl}naphthalene-2-sulfonamide;

6-Chloro-N-methyl-N-{(3R)-1-[(1S)-1-methyl-2-oxo-2-piperidin-1-ylethyl]-2-oxopyrrolidin-3-yl}naphthalene-2-sulfonamide;

6-Chloro-N-methyl-N-{(3S)-1-[(1R)-1-methyl-2-(3-methylpiperidin-1-yl)-2-oxoethyl]-2-oxopyrrolidin-3-yl}naphthalene-2-sulfonamide;

N-[1-((2R)-2-{(3S)-3-[[(6-chloro-2-naphthyl)sulfonyl](methyl)amino]-2-oxopyrrolidin-1-yl}propanoyl)piperidin-3-yl]acetamide;

6-Chloro-N-(cyanomethyl)-N-{(3S)-1-[(1S)-1-methyl-2-morpholin-4-yl-2-oxoethyl]-2-oxopyrrolidin-3-yl}naphthalene-2-sulfonamide;

6-Chloro-N-methyl-N-{(3S)-1-[(1S)-1-methyl-2-morpholin-4-yl-2-oxoethyl]-2-oxopyrrolidin-3-yl}naphthalene-2-sulfonamide;

N-Allyl-6-chloro-N-{(3S)-1-[(1S)-1-methyl-2-morpholin-4-yl-2-oxoethyl]-2-oxopyrrolidin-3-yl}naphthalene-2-sulfonamide;

Methyl N-[(6-chloro-2-naphthyl)sulfonyl]-N-{(3S)-1-[(1S)-1-methyl-2-morpholin-4-yl-2-oxoethyl]-2-oxopyrrolidin-3-yl}glycinate;

N-[(6-Chloro-2-naphthyl)sulfonyl]-N-{(3S)-1-[(1S)-1-methyl-2-morpholin-4-yl-2-oxoethyl]-2-oxopyrrolidin-3-yl}glycine;

6-Chloro-N-methyl-N-{(3S)-1-[(1S)-1-methyl-2-oxo-2-piperidin-1-ylethyl]-2-oxopyrrolidin-3-yl}naphthalene-2-sulfonamide;

6-Chloro-N-methyl-N-((3S)-1-{(1S)-1-methyl-2-[(2R)-2-methylpiperidin-1-yl]-2-oxoethyl}-2-oxopyrrolidin-3-yl)naphthalene-2-sulfonamide;

Methyl N-[(6-chloro-2-naphthyl)sulfonyl]-N-{(3S)-1-[(1S)-1-methyl-2-oxo-2-piperidin-1-ylethyl]-2-oxopyrrolidin-3-yl}glycinate;

N-[(6-Chloro-2-naphthyl)sulfonyl]-N-{(3S)-1-[(1S)-1-methyl-2-oxo-2-piperidin-1-ylethyl]-2-oxopyrrolidin-3-yl}glycine;

N-2-[(6-Chloro-2-naphthyl)sulfonyl]-N-2-{(3S)-1-[(1S)-1-methyl-2-oxo-2-piperidin-1-ylethyl]-2-oxopyrrolidin-3-yl}glycinamide;

6-Chloro-N-{(3S)-1-[(1S)-1-methyl-2-oxo-2-piperidin-1-ylethyl]-2-oxopyrrolidin-3-yl}-N-(2-oxobutyl)naphthalene-2-sulfonamide;

N-2-[(6-Chloro-2-naphthyl)sulfonyl]-N-2-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)glycinamide;

Methyl N-[(6-chloro-2-naphthyl)sulfonyl]-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)glycinate formate;

6-Chloro-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)-N-(2-oxobutyl)naphthalene-2-sulfonamide;

N-[1-((2R)-2-{(3S)-3-[[(6-Chloro-2-naphthyl)sulfonyl](methyl)amino]-2-oxopyrrolidin-1-yl}propanoyl)piperidin-3-yl]benzamide;

6-Chloro-N-[(3S)-1-((1S)-1-methyl-2-oxo-2-{3-[(1H-pyrrol-2-ylmethyl)amino]piperidin-1-yl}ethyl)-2-oxopyrrolidin-3-yl]naphthalene-2-sulfonamide;

6-Chloro-N-[(3S)-1-((1S)-1-methyl-2-oxo-2-{3-[(pyridin-3-ylmethyl)amino]piperidin-1-yl}ethyl)-2-oxopyrrolidin-3-yl]naphthalene-2-sulfonamide;

6-Chloro-N-[(3S)-1-((1S)-1-methyl-2-oxo-2-{3-[(1H-pyrazol-3-ylmethyl)amino]piperidin-1-yl}ethyl)-2-oxopyrrolidin-3-yl]naphthalene-2-sulfonamide;

Benzyl (3S)-1-[(2S)-2-((3S)-3-{[(6-chloro-2-naphthyl)sulfonyl]amino}-2-oxopyrrolidin-1-yl)propanoyl]piperidin-3-ylcarbamate;

N-((3S)-1-{(1S)-2-[(3S)-3-Aminopiperidin-1-yl]-1-methyl-2-oxoethyl}-2-oxopyrrolidin-3-yl)-6-chloronaphthalene-2-sulfonamide; and N-((3S)-1-{(1S)-2-[(3R)-3-Aminopiperidin-1-yl]-1-methyl-2-oxoethyl}-2-oxopyrrolidin-3-yl)-6-chloronaphthalene-2-sulfonamide.

Preferred compounds of the invention also include:

6-Chloro-N-{(3S)-1-[(1S)-1-methyl-2-morpholin-4-yl-2-oxoethyl]-2-oxopyrrolidin-3-yl}naphthalene-2-sulfonamide;

6-Chloro-N-{(3S)-1-[(1S)-1-methyl-2-oxo-2-piperidin-1-ylethyl]-2-oxopyrrolidin-3-yl}naphthalene-2-sulfonamide;

6-Chloro-N-{(3S)-1-{(1S)-1-methyl-2-oxo-2-[(2S)-2-(pyrrolidin-1-ylmethyl)pyrrolidin-1-yl]ethyl}-2-oxopyrrolidin-3-yl)naphthalene-2-sulfonamide formate;

6-Chloro-N-((3S)-1-{(1S)-1-methyl-2-[(2R)-2-methylpiperidin-1-yl]-2-oxoethyl}-2-oxopyrrolidin-3-yl)naphthalene-2-sulfonamide;

6-Chloro-N-[(3S)-1-((1S)-2-{2-[(diethylamino)methyl]piperidin-1-yl}-1-methyl-2-oxoethyl)-2-oxopyrrolidin-3-yl]naphthalene-2-sulfonamide;

6-Chloro-N-((3S)-1-{(1S)-1-methyl-2-oxo-2-[2-(pyrrolidin-1-ylmethyl)piperidin-1-yl]ethyl}-2-oxopyrrolidin-3-yl)naphthalene-2-sulfonamide formate;

1-[(2S)-2-((3S)-3-{[(6-Chloro-2-naphthyl)sulfonyl]amino}-2-oxopyrrolidin-1-yl)propanoyl]piperidine-3-carboxamide;

6-Chloro-N-{(3S)-1-[(1S)-1-methyl-2-oxo-2-(3-{[(trifluoromethyl)sulfonyl]amino}piperidin-1-yl)ethyl]-2-oxopyrrolidin-3-yl}naphthalene-2-sulfonamide;

1-[(2S)-2-((3S)-3-{[(6-Chloro-2-naphthyl)sulfonyl]amino}-2-oxopyrrolidin-1-yl)propanoyl]piperidine-2-carboxamide;

1-[(2S)-2-((3S)-3-{[(6-Chloro-2-naphthyl)sulfonyl]amino}-2-oxopyrrolidin-1-yl)propanoyl]piperidine-4-carboxamide;

5'-Chloro-N-{(3S)-1-[(1S)-1-methyl-2-morpholin-4-yl-2-oxoethyl]-2-oxopyrrolidin-3-yl}-2,2'-bithiophene-5-sulfonamide;

5'-Chloro-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)-2,2'-bithiophene-5-sulfonamide;

(E)-2-(4-Chlorophenyl)-N-{(3S)-1-[(1S)-1-methyl-2-morpholin-4-yl-2-oxoethyl]-2-oxopyrrolidin-3-yl}ethenesulfonamide;

(E)-2-(4-Chlorophenyl)-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)ethenesulfonamide;

5'-Chloro-N-(cyanomethyl)-N-{(3S)-1-[(1S)-1-methyl-2-morpholin-4-yl-2-oxoethyl]-2-oxopyrrolidin-3-yl}-2,2'-bithiophene-5-sulfonamide;

Methyl N-[(5'-chloro-2,2'-bithien-5-yl)sulfonyl]-N-{(3S)-1-[(1S)-1-methyl-2-morpholin-4-yl-2-oxoethyl]-2-oxopyrrolidin-3-yl}glycinate;

5'-Chloro-N-{(3S)-1-[(1S)-1-methyl-2-morpholin-4-yl-2-oxoethyl]-2-oxopyrrolidin-3-yl}-N-(2-oxobutyl)-2,2'-bithiophene-5-sulfonamide;

N-{(3S)-1-[(1S)-2-(3-Aminopiperidin-1-yl)-1-methyl-2-oxoethyl]-2-oxopyrrolidin-3-yl}-6-chloronaphthalene-2-sulfonamide;

(E)-2-(4-Chlorophenyl)-N-{(3S)-1-[(1S)-1-methyl-2-oxo-2-piperidin-1-ylethyl]-2-oxopyrrolidin-3-yl}ethenesulfonamide;

Methyl N-{[(E)-2-(4-chlorophenyl)ethenyl]sulfonyl}-N-{(3S)-1-[(1S)-1-methyl-2-oxo-2-piperidin-1-ylethyl]-2-oxopyrrolidin-3-yl}glycinate;

(E)-2-(4-Chlorophenyl)-N-(cyanomethyl)-N-{(3S)-1-[(1S)-1-methyl-2-oxo-2-piperidin-1-ylethyl]-2-oxopyrrolidin-3-yl}ethenesulfonamide;

6-Chloro-N-{(3S)-1-[(1S)-1-methyl-2-(3-methylpiperidin-1-yl)-2-oxoethyl]-2-oxopyrrolidin-3-yl}naphthalene-2-sulfonamide;

6-Chloro-N-((3S)-1-{(1S)-2-[3-(hydroxymethyl)piperidin-1-yl]-1-methyl-2-oxoethyl}-2-oxopyrrolidin-3-yl)naphthalene-2-sulfonamide;

N-{1-[(2S)-2-((3S)-3-{[(6-Chloro-2-naphthyl)sulfonyl]amino}-2-oxopyrrolidin-1-yl)propanoyl]piperidin-3-yl}acetamide;

6-Chloro-N-((3S)-1-{(1S)-1-methyl-2-oxo-2-[3-(1H-pyrrol-1-ylmethyl)piperidin-1-yl]ethyl}-2-oxopyrrolidin-3-yl)naphthalene-2-sulfonamide;

6-Chloro-N-{(3S)-1-[(1S)-2-(3,3-dimethylpiperidin-1-yl)-1-methyl-2-oxoethyl]-2-oxopyrrolidin-3-yl}naphthalene-2-sulfonamide;

6-Chloro-N-{(3S)-1-[(1S)-1-methyl-2-(2-methylpiperidin-1-yl)-2-oxoethyl]-2-oxopyrrolidin-3-yl}naphthalene-2-sulfonamide;

6-Chloro-N-((3S)-1-{(1S)-1-methyl-2-oxo-2-[3-(trifluoromethyl)piperidin-1-yl]ethyl}-2-oxopyrrolidin-3-yl)naphthalene-2-sulfonamide;

6-Chloro-N-((3S)-1-{(1S)-1-methyl-2-oxo-2-[2-(2-pyrrolidin-1-ylethyl)piperidin-1-yl]ethyl}-2-oxopyrrolidin-3-yl)naphthalene-2-sulfonamide formate;

6-Chloro-N-{(3S)-1-[(1S)-2-(3-methoxypiperidin-1-yl)-1-methyl-2-oxoethyl]-2-oxopyrrolidin-3-yl}naphthalene-2-sulfonamide;

6-Chloro-N-{(3S)-1-[(1S)-1-methyl-2-(4-methylpiperidin-1-yl)-2-oxoethyl]-2-oxopyrrolidin-3-yl}naphthalene-2-sulfonamide;

6-Chloro-N-{(3S)-1-[(1S)-2-(3-hydroxypiperidin-1-yl)-1-methyl-2-oxoethyl]-2-oxopyrrolidin-3-yl}naphthalene-2-sulfonamide;

6-Chloro-N-{(3S)-1-[(1S)-1-methyl-2-octahydroquinolin-1(2H)-yl-2-oxoethyl]-2-oxopyrrolidin-3-yl}naphthalene-2-sulfonamide;

6-Chloro-N-{(3S)-1-[(1S)-2-(4-hydroxypiperidin-1-yl)-1-methyl-2-oxoethyl]-2-oxopyrrolidin-3-yl}naphthalene-2-sulfonamide;

5'-Chloro-N-{(3R)-1-[(1S)-1-methyl-2-oxo-2-piperidin-1-ylethyl]-2-oxopyrrolidin-3-yl}-2,2'-bithiophene-5-sulfonamide;

(E)-2-(4-Chlorophenyl)-N-{(3R)-1-[(1S)-1-methyl-2-oxo-2-piperidin-1-ylethyl]-2-oxopyrrolidin-3-yl}ethenesulfonamide;

N-{1-[(2S)-2-((3S)-3-{[(6-Chloro-2-naphthyl)sulfonyl]amino}-2-oxopyrrolidin-1-yl)propanoyl]piperidin-3-yl}prop-2-ynamide;

N-{1-[(2S)-2-((3S)-3-{[(6-Chloro-2-naphthyl)sulfonyl]amino}-2-oxopyrrolidin-1-yl)propanoyl]piperidin-3-yl}-1-methyl-1H-pyrrole-3-carboxamide;

tert-Butyl 1-[(2S)-2-((3S)-3-{[(6-chloro-2-naphthyl)sulfonyl]amino}-2-oxopyrrolidin-1-yl)propanoyl]piperidin-3-ylcarbamate;

Methyl 4-({1-[(2S)-2-((3S)-3-{[(6-chloro-2-naphthyl)sulfonyl]amino}-2-oxopyrrolidin-1-yl)propanoyl]piperidin-3-yl}amino)-4-oxobutanoate;

4-({1-[(2S)-2-((3S)-3-{[(6-Chloro-2-naphthyl)sulfonyl]amino}-2-oxopyrrolidin-1-yl)propanoyl]piperidin-3-yl}amino)-4-oxobutanoic acid;

N-{1-[(2S)-2-((3S)-3-{[(6-Chloro-2-naphthyl)sulfonyl]amino}-2-oxopyrrolidin-1-yl)propanoyl]piperidin-3-yl}-1H-1,2,4-triazole-3-carboxamide;

N-{1-[(2S)-2-((3S)-3-{[(6-Chloro-2-naphthyl)sulfonyl]amino}-2-oxopyrrolidin-1-yl)propanoyl]piperidin-3-yl}-1-methyl-1H-pyrrole-2-carboxamide;

N-{1-[(2S)-2-((3S)-3-{[(6-Chloro-2-naphthyl)sulfonyl]amino}-2-oxopyrrolidin-1-yl)propanoyl]piperidin-3-yl}propanamide;

N-{1-[(2S)-2-((3S)-3-{[(6-Chloro-2-naphthyl)sulfonyl]amino}-2-oxopyrrolidin-1-yl)propanoyl]piperidin-3-yl}-1H-pyrazole-3-carboxamide;

N-{1-[(2S)-2-((3S)-3-{[(6-Chloro-2-naphthyl)sulfonyl]amino}-2-oxopyrrolidin-1-yl)propanoyl]piperidin-3-yl}-2-ethylbutanamide;

N-{1-[(2S)-2-((3S)-3-{[(6-Chloro-2-naphthyl)sulfonyl]amino}-2-oxopyrrolidin-1-yl)propanoyl]piperidin-3-yl}cyclopentanecarboxamide;

N-{1-[(2S)-2-((3S)-3-{[(6-Chloro-2-naphthyl)sulfonyl]amino}-2-oxopyrrolidin-1-yl)propanoyl]piperidin-3-yl}pentanediamide;

N-{1-[(2S)-2-((3S)-3-{[(6-Chloro-2-naphthyl)sulfonyl]amino}-2-oxopyrrolidin-1-yl)propanoyl]piperidin-3-yl}pyrazine-2-carboxamide;

N-{1-[(2S)-2-((3S)-3-{[(6-Chloro-2-naphthyl)sulfonyl]amino}-2-oxopyrrolidin-1-yl)propanoyl]piperidin-3-yl}-1H-pyrazole-4-carboxamide;

N-{1-[(2S)-2-((3S)-3-{[(6-chloro-2-naphthyl)sulfonyl]amino}-2-oxopyrrolidin-1-yl)propanoyl]piperidin-3-yl}malonamide;

N-{1-[(2S)-2-((3S)-3-{[(6-Chloro-2-naphthyl)sulfonyl]amino}-2-oxopyrrolidin-1-yl)propanoyl]piperidin-3-yl}-2-methylpropanamide;

N-1-{1-[(2S)-2-((3S)-3-{[(6-Chloro-2-naphthyl)sulfonyl]amino}-2-oxopyrrolidin-1-yl)propanoyl]piperidin-3-yl}-N-3-,N-3-dimethyl-beta-alaninamide;

N-{1-[(2S)-2-((3S)-3-{[(6-Chloro-2-naphthyl)sulfonyl]amino}-2-oxopyrrolidin-1-yl)propanoyl]piperidin-3-yl}succinamide;

N-{(3S)-1-[(2S)-2-((3S)-3-{[(6-Chloro-2-naphthyl)sulfonyl]amino}-2-oxopyrrolidin-1-yl)propanoyl]piperidin-3-yl}nicotinamide;

N-{(3S)-1-[(2S)-2-((3S)-3-{[(6-Chloro-2-naphthyl)sulfonyl]amino}-2-oxopyrrolidin-1-yl)propanoyl]piperidin-3-yl}pyridine-2-carboxamide;

N-{(3S)-1-[(2S)-2-((3S)-3-{[(6-Chloro-2-naphthyl)sulfonyl]amino}-2-oxopyrrolidin-1-yl)propanoyl]piperidin-3-yl}isonicotinamide;

Methyl 3-({(3S)-1-[(2S)-2-((3S)-3-{[(6-chloro-2-naphthyl)sulfonyl]amino}-2-oxopyrrolidin-1-yl)propanoyl]piperidin-3-yl}amino)-3-oxopropanoate;

N-1-{(3S)-1-[(2S)-2-((3S )-3-{[(6-Chloro-2-naphthyl)sulfonyl]amino}-2-oxopyrrolidin-1-yl)propanoyl]piperidin-3-yl}-N-2-,N-2-dimethylglycinamide;

Benzyl (3R)-1-[(2S)-2-((3S)-3-{[(6-chloro-2-naphthyl)sulfonyl]amino}-2-oxopyrrolidin-1-yl)propanoyl]piperidin-3-ylcarbamate;

N-{(3R)-1-[(2S)-2-((3S)-3-{[(6-Chloro-2-naphthyl)sulfonyl]amino}-2-oxopyrrolidin-1-yl)propanoyl]piperidin-3-yl}nicotinamide;

N-{(3R)-1-[(2S)-2-((3S)-3-{[(6-Chloro-2-naphthyl)sulfonyl]amino}-2-oxopyrrolidin-1-yl)propanoyl]piperidin-3-yl}pyridine-2-carboxamide;

N-{(3R)-1-[(2S)-2-((3S)-3-{[(6-Chloro-2-naphthyl)sulfonyl]amino}-2-oxopyrrolidin-1-yl)propanoyl]piperidin-3-yl}isonicotinamide;

Methyl 3-({(3R)-1-[(2S)-2-((3S)-3-{[(6-chloro-2-naphthyl)sulfonyl]amino}-2-oxopyrrolidin-1-yl)propanoyl]piperidin-3-yl}amino)-3-oxopropanoate;

N-1-{(3R)-1-[(2S)-2-((3S)-3-{[(6-Chloro-2-naphthyl)sulfonyl]amino}-2-oxopyrrolidin-1-yl)propanoyl]piperidin-3-yl}N-2-N-2-dimethylglycinamide;

5'-Chloro-N-{(3S)-1-[(1S)-1-methyl-2-oxo-2-piperidin-1-ylethyl]-2-oxopyrrolidin-3-yl}-2,2'-bithiophene-5-sulfonamide;

4'-Fluoro-N-{(3S)-1-[(1S)-1-methyl-2oxo-2-piperidin-1-ylethyl]-2-oxopyrrolidin-3-yl}-1,1'-biphenyl-4-sulfonamide;

6-Chloro-N-{(3S)-1-[(1S)-1-methyl-2-oxo-2-piperidin-1-ylethyl]-2-oxopyrrolidin-3-yl}-1-benzothiophene-2-sulfonamide;

(E)-2-(4-Chlorophenyl)-N-{(3S)-1-[(1S)-1-methyl-2-oxo-2-piperidin-1-ylethyl]-2-oxopyrrolidin-3-yl}ethenesulfonamide;

6-Chloro-N-{(3S)-1-[(1S)-1-methyl-2-oxo-2-piperidin-1-ylethyl]-2-oxopyrrolidin-3-yl}-1-benzothiophene-2-sulfonamide compound with 4-chloro-N-{(3S)-1-[(1S)-1-methyl-2-oxo-2-piperidin-1-ylethyl]-2-oxopyrrolidin-3-yl}-1-benzothiophene-2-sulfonamide (1:1);

6-Fluoro-N-{(3S)-1-[(1S)-1-methyl-2-oxo-2-piperidin-1-ylethyl]-2-oxopyrrolidin-3-yl}naphthalene-2-sulfonamide;

6-Chloro-N-(3-furylmethyl)-N-{(3S)-1-[(1S)-1-methyl-2-morpholin-4-yl-2-oxoethyl]-2-oxopyrrolidin-3-yl}naphthalene-2-sulfonamide;

6-Chloro-N-{(3S)-1-[(1S)-1-methyl-2-morpholin-4-yl-2-oxoethyl]-2-oxopyrrolidin-3-yl}-N-(pyridin-3-ylmethyl)naphthalene-2-sulfonamide formate;

N-{1-[(2R)-2-((3S)-3-{[(6-Chloro-2-naphthyl)sulfonyl]amino}-2-oxopyrrolidin-1-yl)propanoyl]piperidin-3-yl}benzamide;

6-Chloro-N-{(3S)-1-[(1S)-1-methyl-2-morpholin-4-yl-2-oxoethyl]-2-oxopyrrolidin-3-yl}-N-(2-oxobutyl)naphthalene-2-sulfonamide;

N-2-[(6-Chloro-2-naphthyl)sulfonyl]-N-2-{(3S)-1-[(1S)-1-methyl-2-morpholin-4-yl-2-oxoethyl]-2-oxopyrrolidin-3-yl}glycinamide;

6-Chloro-N-(2-furylmethyl)-N-{(3S)-1-[(1S)-1-methyl-2-morpholin-4-yl-2-oxoethyl]-2-oxopyrrolidin-3-yl}naphthalene-2-sulfonamide;

6-Chloro-N-{(3S)-1-[(1S)-1-methyl-2-morpholin-4-yl-2-oxoethyl]-2-oxopyrrolidin-3-yl}-N-(1,3-thiazol-2-ylmethyl)naphthalene-2-sulfonamide;

Methyl N-[(5'-chloro-2,2'-bithien-5-yl)sulfonyl]-N-{(3S)-1-[(1S)-1-methyl-2-oxo-2-piperidin-1-ylethyl]-2-oxopyrrolidin-3-yl}glycinate;

5'-Chloro-N-(cyanomethyl)-N-{(3S)-1-[(1S)-1-methyl-2-oxo-2-piperidin-1-ylethyl]-2-oxopyrrolidin-3-yl}-2,2'-bithiophene-5-sulfonamide;

6-Chloro-N-{(3S)-1-[(1R)-1-methyl-2-(3-methylpiperidin-1-yl)-2-oxoethyl]-2-oxopyrrolidin-3-yl}naphthalene-2-sulfonamide;

N-{1-[(2R)-2-((3S)-3-{[(6-Chloro-2-naphthyl)sulfonyl]amino}-2-oxopyrrolidin-1-yl)propanoyl]piperidin-3-yl}acetamide;

6-Chloro-N-methyl-N-{(3R)-1-[(1S)-1-methyl-2-oxo-2-piperidin-1-ylethyl]-2-oxopyrrolidin-1-yl}naphthalene-2-sulfonamide;

6-Chloro-N-methyl-N-{(3S)-1-[(1R)-1-methyl-2-(3-methylpiperidin-1-yl)-2-oxoethyl]-2-oxopyrrolidin-3-yl}naphthalene-2-sulfonamide;

N-[1-((2R)-2-{(3S)-3-[[(6-chloro-2-naphthyl)sulfonyl](methyl)amino]-2-oxopyrrolidin-1-yl}propanoyl)piperidin-3-yl]acetamide;

6-Chloro-N-methyl-N-{(3S)-1-[(1R)-1-methyl-2-oxo-2-(3-{[(phenylsulfonyl)amino]methyl}piperidin-1-yl)ethyl]-2-oxopyrrolidin-3-yl}naphthalene-2-sulfonamide;

6-Chloro-N-((3S)-1-{(1R)-2-[3-(hydroxymethyl)piperidin-1-yl]-1-methyl-2-oxoethyl}-2-oxopyrrolidin-3-yl)-N-methylnaphthalene-2-sulfonamide;

6-Chloro-N-((3S)-1-{(1R)-2-[2-(hydroxymethyl)piperidin-1-yl]-1-methyl-2-oxoethyl}-2-oxopyrrolidin-3-yl)-N-methylnaphthalene-2-sulfonamide;

6-Chloro-N-(cyanomethyl)-N-{(3S)-1-[(1S)-1-methyl-2-morpholin-4-yl-2-oxoethyl-2-oxopyrrolidin-3-yl}naphthalene-2-sulfonamide;

6-Chloro-N-methyl-N-{(3S)-1-[(1S)-1-methyl-2-morpholin-4-yl-2-oxoethyl]-2-oxopyrrolidin-3-yl}naphthalene-2-sulfonamide;

N-Allyl-6-chloro-N-{(3S)-1-[(1S)-1-methyl-2-morpholin-4-yl-2-oxoethyl]-2-oxopyrrolidin-3-yl}naphthalene-2-sulfonamide;

Methyl N-[(6-chloro-2-naphthyl)sulfonyl]-N-{(3S)-1-[(1S)-1-methyl-2-morpholin-4-yl-2-oxoethyl]-2-oxopyrrolidin-3-yl}glycinate;

N-[(6-Chloro-2-naphthyl)sulfonyl]-N-{(3S)-1-[(1S)-1-methyl-2-morpholin-4-yl-2-oxoethyl]-2-oxopyrrolidin-3-yl}glycine;

1-[(2S)-2-((3S)-3-{[(6-Chloro-2-naphthyl)sulfonyl]amino}-2-oxopyrrolidin-1-yl)propanoyl]piperidine-2-carboxylic acid;

6-Chloro-N-{(3S)-1-[(1R)-1-methyl-2-oxo-2-piperidin-1-ylethyl]-2-oxopyrrolidin-3-yl}naphthalene-2-sulfonamide;

6-Chloro-N-methyl-N-{(3S)-1-[(1S)-1-methyl-2-oxo-2-piperidin-1-ylethyl]-2-oxopyrrolidin-3-yl}naphthalene-2-sulfonamide;

6-Chloro-N-methyl-N-((3S)-1-{(1S)-1-methyl-2-[(2R)-2-methylpiperidin-1-yl]-2-oxoethyl}-2-oxopyrrolidin-3-yl)naphthalene-2-sulfonamide;

6-Chloro-N-[(3S)-1-((1S)-2-{2-[(diethylamino)methyl]piperidin-1-yl}-1-methyl-2-oxoethyl)-2-oxopyrrolidin-3-yl]-N-methylnaphthalene-2-sulfonamide;
Methyl N-[(6-chloro-2-naphthyl)sulfonyl]-N-{(3S)-1-[(1S)-1-methyl-2-oxo-2-piperidin-1-ylethyl]-2-oxopyrrolidin-3-yl}glycinate;
N-[(6-Chloro-2-naphthyl)sulfonyl]-N-{(3S)-1-[(1S)-1-methyl-2-oxo-2-piperidin-1-ylethyl]-2-oxopyrrolidin-3-yl}glycine;
6-Chloro-N-(cyanomethyl)-N-{(3S)-1-[(1S)-1-methyl-2-oxo-2-piperidin-1-ylethyl]-2-oxopyrrolidin-3-yl}naphthalene-2-sulfonamide;
N-2-[(6-Chloro-2-naphthyl)sulfonyl]-N-2-{(3S)-1-[(1S)-1-methyl-2-oxo-2-piperidin-1-ylethyl]-2-oxopyrrolidin-3-yl}glycinamide;
6-Chloro-N-{(3S)-1-[(1S)-1-methyl-2-oxo-2-piperidin-1-ylethyl]-2-oxopyrrolidin-3-yl}-N-(2-oxobutyl)naphthalene-2-sulfonamide;
N-2-[(6-Chloro-2-naphthyl)sulfonyl]-N-2-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)glycinamide;
Methyl N-[(6-chloro-2-naphthyl)sulfonyl]-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)glycinate formate;
6-Chloro-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)-N-(2-oxobutyl)naphthalene-2-sulfonamide;
N-[1-((2R)-2-{(3S)-3-[[(6-Chloro-2-naphthyl)sulfonyl](methyl)amino]-2-oxopyrrolidin-1-yl}propanoyl)piperidin-3-yl]benzamide;
6-Chloro-N-methyl-N-{(3R)-1-[(1R)-1-methyl-2-oxo-2-piperidin-1-ylethyl]-2-oxopyrrolidin-3-yl}naphthalene-2-sulfonamide;
6-Chloro-N-methyl-N-((3S)-1-{(1R)-1-methyl-2-[(2R)-2-methylpiperidin-1-yl]-2-oxoethyl}-2-oxopyrrolidin-3-yl)naphthalene-2-sulfonamide;
N-((3S)-1-{(1R)-2-[((1R,4S)-2-Azabicyclo[2.2.1]hept-2-yl]-1-methyl-2-oxoethyl}-2-oxopyrrolidin-3-yl)-6-chloro-N-methylnaphthalene-2-sulfonamide;
6-Chloro-N-((3S)-1-{(1S)-2-[3-(ethylamino)piperidin-1-yl]-1-methyl-2-oxoethyl}-2-oxopyrrolidin-3-yl)naphthalene-2-sulfonamide;
6-Chloro-N-[(3S)-1-((1S)-1-methyl-2-oxo-2-{3-[(1H-pyrrol-2-ylmethyl)amino]piperidin-1-yl}ethyl)-2-oxopyrrolidin-3-yl]naphthalene-2-sulfonamide;
6-Chloro-N-[(3S)-1-((1S)-1-methyl-2-oxo-2-{3-[(pyridin-3-ylmethyl)amino]piperidin-1-yl}ethyl)-2-oxopyrrolidin-3-yl]naphthalene-2-sulfonamide;
6-Chloro-N-[(3S)-1-((1S)-2-{3-[(3-hydroxybutyl)amino]piperidin-1-yl}-1-methyl-2-oxoethyl)-2-oxopyrrolidin-3-yl]naphthalene-2-sulfonamide;
6-Chloro-N-[(3S)-1-((1S)-1-methyl-2-oxo-2-{3-[(pyridin-4-ylmethyl)amino]piperidin-1-yl}ethyl)-2-oxopyrrolidin-3-yl]naphthalene-2-sulfonamide;
N-{(3S)-1-[(1S)-2-(3-{[(2-Aminopyrimidin-5-yl)methyl]amino}piperidin-1-yl)-1-methyl-2-oxoethyl]-2-oxopyrrolidin-3-yl}-6-chloronaphthalene-2-sulfonamide;
6-Chloro-N-[(3S)-1-((1S)-1-methyl-2-oxo-2-{3-[(pyridin-2-ylmethyl)amino]piperidin-1-yl}-ethyl)-2-oxopyrrolidin-3-yl]naphthalene-2-sulfonamide;
6-Chloro-N-[(3S)-1-((1S)-1-methyl-2-oxo-2-{3-[(1H-pyrazol-3-ylmethyl)amino]piperidin-1-yl}ethyl)-2-oxopyrrolidin-3-yl]naphthalene-2-sulfonamide;
6-Chloro-N-[(3S)-1-((1S)-1-methyl-2-oxo-2-{3-[(pyridin-4-ylmethyl)amino]piperidin-1-yl}ethyl)-2-oxopyrrolidin-3-yl]naphthalene-2-sulfonamide;
6-Chloro-N-((3S)-1-{(1S)-2-[3-({[5-(hydroxymethyl)-2-furyl]methyl}amino)piperidin-1-yl]-1-methyl-2-oxoethyl}-2-oxopyrrolidin-3-yl)naphthalene-2-sulfonamide;
6-Chloro-N-[(3S)-1-((1S)-1-methyl-2-oxo-2-{3-[(1,3-thiazol-2-ylmethyl)amino]piperidin-1-yl}ethyl)-2-oxopyrrolidin-3-yl]naphthalene-2-sulfonamide;
6-Chloro-N-{(3S)-1-[(1S)-1-methyl-2-(3{[(1-methyl-1H-imidazol-2-yl)methyl]amino}piperidin-1-yl)-2-oxoethyl]-2-oxopyrrolidin-3-yl}naphthalene-2-sulfonamide;
6-Chloro-N-[(3S)-1-((1S)-2-{3-[(3-hydroxy-2,2-dimethylpropyl)amino]piperidin-1-yl}-1-methyl-2-oxoethyl)-2-oxopyrrolidin-3-yl]naphthalene-2-sulfonamide;
6-Chloro-N-[(3S)-1-((1S)-2-{3-[(1H-imidazolylmethyl)amino]piperidin-1-yl}-1-methyl-2-oxoethyl)-2-oxopyrrolidin-3-yl]naphthalene-2-sulfonamide;
Benzyl (3S)-1-(2S)-2-((3S)-3-{[(6-chloro-2-naphthyl)sulfonyl]amino}-2-oxopyrrolidin-1-yl)propanoyl]piperidin-3-ylcarbamate;
N-((3S)-1-{(1S)-2-[(3S)-3-Aminopiperidin-1-yl]-1-methyl-2-oxoethyl}-2-oxopyrrolidin-3-yl)-6-chloronaphthalene-2-sulfonamide;
N-((3S)-1-{(1S)-2-[(3R)-3-Aminopiperidin-1-yl]-1-methyl-2-oxoethyl}-2-oxopyrrolidin-3-yl)-6-chloronaphthalene-2-sulfonamide.

More preferred compounds of the invention also include:
6-Chloro-N-{(3S)-1-[(1S)-1-methyl-2-morpholin-4-yl-2-oxoethyl]-2-oxopyrrolidin-3-yl}naphthalene-2-sulfonamide;
6-Chloro-N-{(3S)-1-[(1S)-1-methyl-2-oxo-2-piperidin-1-ylethyl]-2-oxopyrrolidin-3-yl}naphthalene-2-sulfonamide;
6-Chloro-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)naphthalene-2-sulfonamide formate;
6-Chloro-N-((3S)-1-{(1S)-1-methyl-2-[(2R)-2-methylpiperidin-1-yl]-2-oxoethyl}-2-oxopyrrolidin-3-yl)naphthalene-2-sulfonamide;
6-Chloro-N-[(3S)-1-((1S)-2-{2-[(diethylamino)methyl]piperidin-1-yl}-1-methyl-2-oxoethyl)-2-oxopyrrolidin-3-yl]naphthalene-2-sulfonamide;
6-Chloro-N-((3S)-1-{(1S)-1-methyl-2-oxo-2-[2-(pyrrolidin-1-ylmethyl)piperidin-1-yl]ethyl}-2-oxopyrrolidin-3-yl)naphthalene-2-sulfonamide formate;
5'-Chloro-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)-2,2'-bithiophene-5-sulfonamide;
(E)-2-(4-Chlorophenyl)-N-{(3S)-1-[(1S)-1-methyl-2-morpholin-4-yl-2-oxoethyl]-2-oxopyrrolidin-3-yl}ethenesulfonamide;
(E)-2-(4-Chlorophenyl)-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)ethenesulfonamide;
5'-Chloro-N-(cyanomethyl)-N-{(3S)-1-[(1S)-1-methyl-2-morpholin-4-yl-2-oxoethyl]-2-oxopyrrolidin-3-yl}-2,2'-bithiophene-5-sulfonamide;
Methyl N-[(5'-chloro-2,2'-bithien-5-yl)sulfonyl]-N-{(3S)-1-[(1S)-1-methyl-2-morpholin-4-yl-2-oxoethyl]-2-oxopyrrolidin-3-yl}glycinate;
5'-Chloro-N-{(3S)-1-[(1S)-1-methyl-2-morpholin-4-yl-2-oxoethyl]-2-oxopyrrolidin-3-yl}-N-(2-oxobutyl)-2,2'-bithiophene-5-sulfonamide;
N-{(3S)-1-[(1S)-2-(3-Aminopiperidin-1-yl)-1-methyl-2-oxoethyl]-2-oxopyrrolidin-3-yl}-6-chloronaphthalene-2-sulfonamide;
(E)-2-(4-Chlorophenyl)-N-{(3S)-1-[(1S)-1-methyl-2-oxo-2-piperidin-1-ylethyl]-2-oxopyrrolidin-3-yl}ethenesulfonamide;

Methyl N-{[(E)-2-(4-chlorophenyl)ethenyl]sulfonyl}-N-{(3S)-1-[(1S)-1-methyl-2-oxo-2-piperidin-1-ylethyl]-2-oxopyrrolidin-3-yl}glycinate;

(E)-2-(4-Chlorophenyl)-N-(cyanomethyl)-N-{(3S)-1-[(1S)-1-methyl-2-oxo-2-piperidin-1-ylethyl]-2-oxopyrrolidin-3-yl}ethenesulfonamide;

6-Chloro-N-{(3S)-1-[(1S)-1-methyl-2-(3-methylpiperidin-1-yl)-2-oxoethyl]-2-oxopyrrolidin-3-yl}naphthalene-2-sulfonamide;

6-Chloro-N-{(3S)-1-[(1S)-2-[3-(hydroxymethyl)piperidin-1-yl]-1-methyl-2-oxoethyl]-2-oxopyrrolidin-3-yl)naphthalene-2-sulfonamide;

N-{1-[(2S)-2-((3S)-3-{[(6-Chloro-2-naphthyl)sulfonyl]amino}-2-oxopyrrolidin-1-yl)propanoyl]piperidin-3-yl}acetamide;

6-Chloro-N-((3S)-1-{(1S)-1-methyl-2-oxo-2-[3-(1H-pyrrol-1-ylmethyl)piperidin-1-yl]ethyl}-2-oxopyrrolidin-3-yl)naphthalene-2-sulfonamide;

6-Chloro-N-{(3S)-1-[(1S)-2-(3,3-dimethylpiperidin-1-yl)-1-methyl-2-oxoethyl]-2-oxopyrrolidin-3-yl}naphthalene-2-sulfonamide;

6-Chloro-N-((3S)-1-{(1S)-1-methyl-2-oxo-2-[2-(2-pyrrolidin-1-ylethyl)piperidin-1-yl]ethyl}-2-oxopyrrolidin-3-yl)naphthalene-2-sulfonamide formate;

(E)-2-(4-Chlorophenyl)-N-{(3R)-1-[(1S)-1-methyl-2-oxo-2-piperidin-1-ylethyl]-2-oxopyrrolidin-3-yl}ethenesulfonamide;

N-{1-[(2S)-2-((3S)-3-{[(6-Chloro-2-naphthyl)sulfonyl]amino}-2-oxopyrrolidin-1-yl)propanoyl]piperidin-3-yl}prop-2-ynamide;

N-{1-[(2S)-2-((3S)-3-{[(6-Chloro-2-naphthyl)sulfonyl]amino}-2-oxopyrrolidin-1-yl)propanoyl]piperidin-3-yl}-1-methyl-1H-pyrrole-3-carboxamide;

Methyl 4-({1-[(2S)-2-((3S)-3-{[(6-chloro-2-naphthyl)sulfonyl]amino}-2-oxopyrrolidin-1-yl)propanoyl]piperidin-3-yl}amino)-4-oxobutanoate;

4-({1-[(2S)-2-((3S)-3-{[(6-Chloro-2-naphthyl)sulfonyl]amino}-2-oxopyrrolidin-1-yl)propanoyl]piperidin-3-yl}amino)-4-oxobutanoic acid;

N-{1-[(2S)-2-((3S)-3-{[(6-Chloro-2-naphthyl)sulfonyl]amino}-2-oxopyrrolidin-1-yl)propanoyl]piperidin-3-yl}-1H-1,2,4-triazole-3-carboxamide;

N-{1-[(2S)-2-((3S)-3-{[(6-Chloro-2-naphthyl)sulfonyl]amino}-2-oxopyrrolidin-1-yl)propanoyl]piperidin-3-yl}-1-methyl-1H-pyrrole-2-carboxamide;

N-{1-[(2S)-2-((3S)-3-{[(6-Chloro-2-naphthyl)sulfonyl]amino}-2-oxopyrrolidin-1-yl)propanoyl]piperidin-3-yl}-2-ethylbutanamide;

N-{1-[(2S)-2-((3S)-3-{[(6-Chloro-2-naphthyl)sulfonyl]amino}-2-oxopyrrolidin-1-yl)propanoyl]piperidin-3-yl}pyrazine-2-carboxamide;

N-{(3S)-1-[(2S)-2-((3S)-3-{[(6-Chloro-2-naphthyl)sulfonyl]amino}-2-oxopyrrolidin-1-yl)propanoyl]piperidin-3-yl}nicotinamide;

N-{(3S)-1-[(2S)-2-((3S)-3-{[(6-Chloro-2-naphthyl)sulfonyl]amino}-2-oxopyrrolidin-1-yl)propanoyl]piperidin-3-yl}pyridine-2-carboxamide;

N-{(3S)-1-[(2S)-2-((3S)-3-{[(6-Chloro-2-naphthyl)sulfonyl]amino}-2-oxopyrrolidin-1-yl)propanoyl]piperidin-3-yl}isonicotinamide;

Methyl 3-({(3S)-1-[(2S)-2-((3S)-3-{[(6-chloro-2-naphthyl)sulfonyl]amino}-2-oxopyrrolidin-1-yl)propanoyl]piperidin-3-yl}amino)-3-oxopropanoate;

N-1-{(3S)-1-[(2S)-2-((3S)-3-{[(6-Chloro-2-naphthyl)sulfonyl]amino}-2oxopyrrolidin-1-yl)propanoyl]piperidin-3-yl}-N-2-,N-2-dimethylglycinamide;

Benzyl (3R)-1-[(2S)-2-((3S)-3-{[(6-chloro-2-naphthyl)sulfonyl]amino}-2-oxopyrrolidin-1-yl)propanoyl]piperidin-3-ylcarbamate;

N-{(3R)-1-[(2S)-2-((3S)-3-{[(6-Chloro-2-naphthyl)sulfonyl]amino}-2-oxopyrrolidin-1-yl)propanoyl]piperidin-3-yl}nicotinamide;

N-{(3R)-1-[(2S)-2-((3S)-3-{[(6-Chloro-2-naphthyl)sulfonyl]amino}-2-oxopyrrolidin-1-yl)propanoyl]piperidin-3-yl}pyridine-2-carboxamide;

N-{(3R)-1-[(2S)-2-((3S)-3-{[(Chloro-2-naphthyl)sulfonyl]amino}-2-oxopyrrolidin-1-yl)propanoyl]piperidin-3-yl}isonicotinamide;

5'-Chloro-N-{(3S)-1-[(1S)-1-methyl-2-oxo-2-piperidin-1-ylethyl]-2-oxopyrrolidin-3-yl}-2,2'-bithiophene-5-sulfonamide;

6-Chloro-N-{(3S)-1-((1S)-1-methyl-2-oxo-2-piperidin-1-ylethyl]-2-oxopyrrolidin-3-yl}-1-benzothiophene-2-sulfonamide;

(E)-2-(4Chlorophenyl)-N-{(3S)-1-[(1S)-1-methyl-2-oxo-2-piperidin-1-ylethyl]-2-oxopyrrolidin-3-yl}ethenesulfonamide;

6-Chloro-N-{(3S)-1-[(1S)-1-methyl-2-oxo-2-piperidin-1-ylethyl]-2-oxopyrrolidin-3-yl}-1-benzothiophene-2-sulfonamide compound with 4-chloro-N-{(3S)-1-[(1S)-1-methyl-2-oxo-2-piperidin-1-ylethyl]-2-oxopyrrolidin-3-yl}-1-benzothiophene-2-sulfonamide (1:1);

6-Chloro-N-(3-furylmethyl)-N-{(3S)-1-[(1S)-1-methyl-2-morpholin-4-yl-2-oxoethyl]-2-oxopyrrolidin-3-yl}naphthalene-2-sulfonamide;

6-Chloro-N-{(3S)-1-[(1S)-1-methyl-2-morpholin-4-yl-2-oxoethyl]-2-oxopyrrolidin-3-yl}-N-(pyridin-3-ylmethyl)naphthalene-2-sulfonamide formate;

6-Chloro-N-{(3S)-1-[(1S)-1-methyl-2-morpholin-4-yl-2-oxoethyl]-2-oxopyrrolidin-3-yl}-N-(2-oxobutyl)naphthalene-2-sulfonamide;

N-2-[(6-Chloro-2-naphthyl)sulfonyl]-N-2-{(3S)-1-[(1S)-1-methyl-2-morpholin-4-yl-2-oxoethyl]-2-oxopyrrolidin-3-yl}glycinamide;

6-Chloro-N-(2-furylmethyl)-N-{(3S)-1-[(1S)-1-methyl-2-morpholin-4-yl-2-oxoethyl]-2-oxopyrrolidin-3-yl}naphthalene-2-sulfonamide;

6-Chloro-N-{(3S)-1-[(1S)-1-methyl-2-morpholin-4-yl-2-oxoethyl]-2-oxopyrrolidin-3-yl}-N-(1,3-thiazol-2-ylmethyl)naphthalene-2-sulfonamide;

Methyl N-[(5'-chloro-2,2'-bithien-5-yl)sulfonyl]-N-{(3S)-1-[(1S)-1-methyl-2-oxo-2-piperidin-1-ylethyl]-2-oxopyrrolidin-3-yl}glycinate;

5'-Chloro-N-(cyanomethyl)-N-{(3S)-1-[(1S)-1-methyl-2-oxo-2-piperidin-1-ylethyl]-2-oxopyrrolidin-3-yl}-2,2'-bithiophene-5-sulfonamide;

6-Chloro-N-{(3S)-1-[(1R)-1-methyl-2-(3-methylpiperidin-1-yl)-2-oxoethyl]-2-oxopyrrolidin-3-yl}naphthalene-2-sulfonamide;

6-Chloro-N-methyl-N-{(3R)-1-[(1S)-1-methyl-2-oxo-2-piperidin-1-ylethyl]-2-oxopyrrolidin-3-yl}naphthalene-2-sulfonamide;

6-Chloro-N-methyl-N-{(3S)-1-[(1R)-1-methyl-2-(3-methylpiperidin-1-yl)-2-oxoethyl]-2-oxopyrrolidin-3-yl}naphthalene-2-sulfonamide;

N-[1-((2R)-2-{(3S)-3-[[(6-chloro-2-naphthyl)sulfonyl](methyl)amino]-2-oxopyrrolidin-1-yl}propanoyl)piperidin-3-yl]acetamide;

6-Chloro-N-(cyanomethyl)-N-{(3S)-1-[(1S)-1-methyl-2-morpholin-4-yl-2-oxoethyl]-2-oxopyrrolidin-3-yl}naphthalene-2-sulfonamide;

6-Chloro-N-methyl-N-{(3S)-1-[(1S)-1-methyl-2-morpholin-4-yl-2-oxoethyl]-2-oxopyrrolidin-3-yl}naphthalene-2-sulfonamide;

N-Allyl-6-chloro-N-{(3S)-1-[(1S)-1-methyl-2-morpholin-4-yl-2-oxoethyl]-2-oxopyrrolidin-3-yl}naphthalene-2-sulfonamide;

Methyl N-[(6-chloro-2-naphthyl)sulfonyl]-N-{(3S)-1-[(1S)-1-methyl-2-morpholin-4-yl-2-oxoethyl]-2-oxopyrrolidin-3-yl}glycinate;

N-[(6-Chloro-2-naphthyl)sulfonyl]-N-{(3S)-1-[(1S)-1-methyl-2-morpholin-4-yl-2-oxoethyl]-2-oxopyrrolidin-3-yl}glycine;

6-Chloro-N-methyl-N-{(3S)-1-[(1S)-1-methyl-2-oxo-2-piperidin-1-ylethyl]-2-oxopyrrolidin-3-yl}naphthalene-2-sulfonamide;

6-Chloro-N-methyl-N-((3S)-1-{(1S)-1-methyl-2-[(2R)-2-methylpiperidin-1-yl]-2-oxoethyl}-2-oxopyrrolidin-3-yl)naphthalene-2-sulfonamide;

6-Chloro-N-[(3S)-1-((1S)-2-{2-[(diethylamino)methyl]piperidin-1-yl}-1-methyl-2-oxoethyl)-2-oxopyrrolidin-3-yl]-N-methylnaphthalene-2-sulfonamide;

Methyl N-[(6-chloro-2-naphthyl)sulfonyl]-N-{(3S)-1-[(1S)-1-methyl-2-oxo-2-piperidin-1-ylethyl]-2-oxopyrrolidin-3-yl}glycinate;

N-[(6-Chloro-2-naphthyl)sulfonyl]-N-{(3S)-1-[(1S)-1-methyl-2-oxo-2-piperidin-1-oxopyrrolidin-3-yl]glycine;

6-Chloro-N-(cyanomethyl)-N-{(3S)-1-[(1S)-1-methyl-2-oxo-2-piperidin-1-ylethyl]-2-oxopyrrolidin-3-yl}naphthalene-2-sulfonamide;

N-2-[(6-Chloro-2-naphthyl)sulfonyl]-N-2-{(3S)-1-[(1S)-1-methyl-2-oxo-2-piperidin-1-ylethyl]-2-oxopyrrolidin-3-yl}glycinamide;

6-Chloro-N-{(3S)-1-[(1S)-1-methyl-2-oxo-2-piperidin-1-ylethyl]-2-oxopyrrolidin-3-yl}-N-2-oxobutyl)naphthalene-2-sulfonamide;

N-2-[(6-Chloro-2-naphthyl)sulfonyl]-N-2-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)glycinamide;

Methyl N-[(6-chloro-2-naphthyl)sulfonyl]-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)glycinate formate;

6-Chloro-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)-N-(2-oxobutyl)naphthalene-2-sulfonamide;

N-[1-((2R)-2-{(3S)-3-[[(6-Chloro-2-naphthyl)sulfonyl](methyl)amino]-2-oxopyrrolidin-1-yl}propanoyl)piperidin-3-yl]benzamide;

6-Chloro-N-methyl-N-{(3R)-1-[(1R)-1-methyl-2-oxo-2-piperidin-1-ylethyl]-2-oxopyrrolidin-3-yl}naphthalene-2-sulfonamide;

6-Chloro-N-methyl-N-((3S)-1-{(1R)-1-methyl-2-[(2R)-2-methylpiperidin-1-yl]-2-oxoethyl}-2-oxopyrrolidin-3-yl)naphthalene-2-sulfonamide;

6-Chloro-N-((3S)-1-{(1S)-2-[3-(ethylamino)piperidin-1-yl]-1-methyl-2-oxoethyl}-2-oxopyrrolidin-3-yl)naphthalene-2-sulfonamide;

6-Chloro-N-((3S)-1-((1S)-1-methyl-2-oxo-2-{3-[(1H-pyrrol-2-ylmethyl)amino]piperidin-1-yl}ethyl)-2-oxopyrrolidin-3-yl)naphthalene-2-sulfonamide;

6-Chloro-N-[(3S)-1-((1S)-1-methyl-2-oxo-2-{3-[(pyridin-3-ylmethyl)amino]piperidin-1-yl}ethyl)-2-oxopyrrolidin-3-yl]naphthalene-2-sulfonamide;

6-Chloro-N-[(3S)-1-((1S)-2-{3-[(3-hydroxybutyl)amino]piperidin-1-yl}-1-methyl-2-oxoethyl)-2-oxopyrrolidin-3-yl]naphthalene-2-sulfonamide;

N-{(3S)-1-[(1S)-2-(3-{[(2-Aminopyrimidin-5-yl)methyl]amino}piperidin-1-yl)-1-methyl-2-oxoethyl]-2-oxopyrrolidin-3-yl}-6-chloronaphthalene-2-sulfonamide;

6-Chloro-N-[(3S)-1-((1S)-1-methyl-2-oxo-2-{3-[(1H-pyrazol-3-ylmethyl)amino]piperidin-1-yl}ethyl)-2-oxopyrrolidin-3-yl]naphthalene-2-sulfonamide;

6-Chloro-N-[(3S)-1-((1S)-2-{3-[(3-hydroxy-2,2-dimethylpropyl)amino]piperidin-1-yl}-1-methyl-2-oxoethyl)-2-oxopyrrolidin-3-yl]naphthalene-2-sulfonamide;

N-((3S)-1-{(1S)-2-[(3S)-3-Aminopiperidin-1-yl]-1-methyl-2-oxoethyl}-2-oxopyrrolidin-3-yl)-6-chloronaphthalene-2-sulfonamide;

N-((3S)-1-{(1S)-2-[(3R)-3-Aminopiperidin-1-yl]-1-methyl-2-oxoethyl}-2-oxopyrrolidin-3-yl)-6-chloronaphthalene-2-sulfonamide.

The compounds of formula (I), (Ia), (Ib), or (Ic), including pharmaceutically acceptable derivatives thereof, are Factor Xa inhibitors and as such are useful in the treatment of clinical conditions susceptible to amelioration by administration of a Factor Xa inhibitor. Such conditions include acute vascular diseases such as coronary thrombosis (for example myocardial infarction and unstable angina), thromboembolism, acute vessel closure associated with thrombolytic therapy and percutaneous transluminal coronary angioplasty (PTCA), transient ischemic attacks, pulmonary embolism, deep vein thrombosis, peripheral arterial occlusion, prevention of vessel luminal narrowing (restenosis), and the prevention of thromboembolic events associated with atrial fibrillation, e.g. stroke; in oedema and PAF mediated inflammatory diseases such as adult respiratory shock syndrome, septic shock and reperfusion damage; the treatment of pulmonary fibrosis; the treatment of tumour metastasis; neurogenerative disease such as Parkinson's and Alzheimer's diseases; viral infection; Kasabach Merritt Syndrome; Haemolytic uremic syndrome; arthritis; osteoporosis; as anti-coagulants for extracorporeal blood in for example, dialysis, blood filtration, bypass, and blood product storage; and in the coating of invasive devices such as prostheses, artificial valves and catheters in reducing the risk of thrombus formation.

Preferably, the condition susceptible to amelioration by a Factor Xa inhibitor is selected from coronary thrombosis (for example myocardial infarction and unstable angina), pulmonary embolism, deep vein thrombosis and the prevention of thromboembolic events associated with atrial fibrillation, e.g. stroke.

Accordingly, one aspect of present invention provides a compound of formula (I), (Ia), (Ib), or (Ic) or a pharmaceutically acceptable derivative thereof for use in medical therapy, particularly for use in the amelioration of a clinical condition in a mammal, including a human, for which a Factor Xa inhibitor is indicated.

In another aspect, the invention provides a method for the treatment and/or prophylaxis of a mammal, including a human, suffering from a condition susceptible to amelioration by a Factor Xa inhibitor which method comprises administering to the subject an effective amount of a compound of formula (I), (Ia), (Ib), or (Ic) or a pharmaceutically acceptable derivative thereof.

In another aspect, the present invention provides the use of a compound of formula (I), (Ia), (Ib), or (Ic) or a pharmaceutically acceptable derivative thereof, for the manufacture of a medicament for the treatment and/or prophylaxis of a condition susceptible to amelioration by a Factor Xa inhibitor.

It will be appreciated that reference to treatment includes acute treatment or prophylaxis as well as the alleviation of established symptoms.

While it is possible that, for use in therapy, a compound of the present invention may be administered as the raw chemical, it is preferable to present the active ingredient as a pharmaceutical formulation.

In a further aspect, the invention provides a pharmaceutical composition comprising at least one compound of formula (I), (Ia), (Ib), or (Ic) or a pharmaceutically acceptable derivative thereof in association with a pharmaceutically acceptable carrier and/or excipient. The carrier and/or excipient must be "acceptable" in the sense of being compatible with the other ingredients of the formulation and not deletrious to the receipient thereof.

Accordingly, the present invention further provides a pharmaceutical formulation comprising at least one compound of formula (I), (Ia), (Ib), or (Ic) or a pharmaceutically acceptable derivative thereof, thereof in association with a pharmaceutically acceptable carrier and/or excipient. The carrier and/or excipient must be "acceptable" in the sense of being compatible with the other ingredients of the formulation and not deletrious to the receipient thereof.

In another aspect, the invention provides a pharmaceutical composition comprising, as active ingredient, at least one compound of formula (I), (Ia), (Ib), or (Ic) or a pharmaceutically acceptable derivative thereof in association with a pharmaceutically acceptable carrier and/or excipient for use in therapy, and in particular in the treatment of human or animal subjects suffering from a condition susceptible to amelioration by a Factor Xa inhibitor.

There is further provided by the present invention a process of preparing a pharmaceutical composition, which process comprises mixing at least one compound of formula (I), (Ia), (Ib), or (Ic) or a pharmaceutically acceptable derivative thereof, together with a pharmaceutically acceptable carrier and/or excipient.

The compounds for use according to the present invention may be formulated for oral, buccal, parenteral, topical, rectal or transdermal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions or they may be presented as a dry product for constitution with water or other suitable vehicles before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in a conventional manner.

The compounds according to the present invention may be formulated for parenteral administration by injection, e.g. by bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds according to the present invention may be formulated for topical administration by insufflation and inhalation. Examples of types of preparation for topical administration include sprays and aerosols for use in an inhaler or insufflator.

Powders for external application may be formed with the aid of any suitable powder base, for example, lactose, talc or starch. Spray compositions may be formulated as aqueous solutions or suspensions or as aerosols delivered from pressurised packs, such as metered dose inhalers, with the use of a suitable propellant.

The compounds according to the present invention may also be formulated in rectal compositions such as suppositories or retention enemas, e.g. containing conventional suppository bases such as cocoa butter or other glycerides.

In addition to the formulations described previously, the compounds may also be formulated as a depot preparation. Such long acting formulations may be administered by implantation (for example subcutaneously, transcutaneously or intramuscularly) or by intramuscular injection. Thus, for example, the compounds according to the present invention may be formulated with suitable polymeric or hydrophobic materials (for example as an emulsion in an acceptable oil) or ion exchange resins or as sparingly soluble derivatives, for example, as a sparingly soluble salt.

A proposed dose of the compounds according to the present invention for administration to a human (of approximately 70 kg body weight) is 0.1 mg to 1 g, preferably to 1 mg to 500 mg of the active ingredient per unit dose, expressed as the weight of free base. The unit dose may be administered, for example, 1 to 4 times per day. The dose will depend on the route of administration. It will be appreciated that it may be necessary to make routine variations to the dosage depending on the age and weight of the patient as well as the severity of the condition to be treated. The dosage will also depend on the route of administration. The precise dose and route of administration will ultimately be at the discretion of the attendant physician or veterinarian.

The compounds of formula (I), (Ia), (Ib), or (Ic) may also be used in combination with other therapeutic agents. The invention thus provides, in a further aspect, a combination comprising a compound of formula (I), (Ia), (Ib), or (Ic) or a pharmaceutically acceptable derivative thereof together with a further therapeutic agent.

When a compound of formula (I), (Ia), (Ib), or (Ic) or a pharmaceutically acceptable derivative thereof is used in combination with a second therapeutic agent active against the same disease state the dose of each compound may differ from that when the compound is used alone. The compounds of the present invention may be used in combination with other antithrombotic drugs such as thrombin inhibitors, thromboxane receptor antagonists, prostacyclin mimetics, phosphodiesterase inhibitors, fibrinogen antagonists, thrombolytic drugs such as tissue plaminogen activator and streptokinase, non-steroidal anti-inflammatory drugs such as aspirin, and the like.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations by any convenient route.

When administration is sequential, either the Factor Xa inhibitor or the second therapeutic agent may be administered first. When administration is simultaneous, the combination may be administered either in the same or different pharmaceutical composition.

When combined In the same formulation it will be appreciated that the two compounds must be stable and compatible with each other and the other components of the formulation. When formulated separately they may be provided in any convenient formulation, conveniently in such manner as are known for such compounds in the art.

When a compound of formula (I), (Ia), (Ib), or (Ic) or a pharmaceutically acceptable derivative thereof is used in combination with a second therapeutic agent active against the same disease state the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian.

The compounds of formula (I), (Ia), (Ib), or (Ic) and physiologically acceptable salts or solvates thereof may be prepared by the processes described hereinafter, said processes constituting a further aspect of the invention. In the following description, the groups are as defined above for compounds of formula (I), (Ia), (Ib), or (Ic) unless otherwise stated.

According to a further aspect of the present invention, there is provided a process (A) for preparing a compound of formula (I), (Ia), (Ib), or (Ic), which process comprises reacting a compound of formula (II) with a compound of formula (III).

Suitably, the reaction may be carried out in the presence of a coupling agent, for example 1-[3-(dimethylamino)propyl]-3-ethyl carbodiimide hydrochloride, HOBt (1-hydroxybenzotriazole), a base, e.g. Et$_3$N (triethylamine), and an organic solvent, e.g. DCM (dichloromethane), suitably at room temperature.

It will be appreciated by persons skilled in the art that compounds of formula (I), (Ia), (Ib), or (Ic) may be prepared by interconversion, utilising other compounds of formula (I), (Ia), (Ib), or (Ic), which are optionally protected by standard protecting groups, as precursors. For instance, compounds of formula (I) or (Ib) where $R^4$ and $R^5$ together with the N atom to which they are bonded, form a 5-, 6- or 7-membered non-aromatic heterocyclic ring substituted by —NH$_2$, may be converted into compounds of formula (I) or (Ib) possessing alternative substituents on the heterocyclic ring, e.g. —NHCOR$^d$, —NR$^b$R$^d$, —NHCOR$^e$ and/or —NHC$_{1-3}$alkylene-R$^e$, by methods well known in the art (see for example March, J., Advanced Organic Chemistry, John Wiley & Sons). Similarly, compounds of formula (Ia) where B represents —C$_{1-3}$alkylNH$_2$, may be converted into compounds of formula (Ia) possessing alternative substituents on the heterocyclic ring, e.g. —C$_{1-3}$alkylNH$^b$R$^c$, by methods well known in the art.

Compounds of formula (II) may be prepared from compounds of formula (IV):

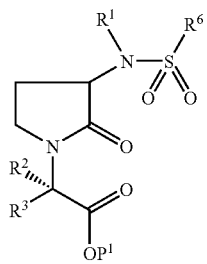

(IV)

wherein P$^1$ is a suitable carboxylic acid protecting group, e.g. t-Butyl, by removal of the protecting group under standard conditions. For example, when P$^1$ represents t-Butyl, removal of the protecting group may be effected under acidic conditions, using for example TFA (trifluoroacetic acid) in a solvent such as DCM.

A compound of formula (IV) may be prepared by reacting a compound of formula (V) with a compound of formula (VI) where P$^1$ is as described above:

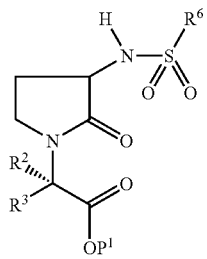

(V)

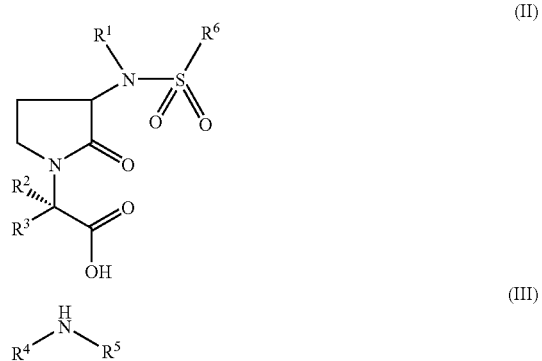

R$^1$—X (VI)

Suitably, where X is a leaving group such as a halogen atom, e.g. bromine, the reaction is carried out in the presence of a base, e.g. LiHMDS (lithium hexamethyidisilylamide), potassium carbonate or sodium carbonate. Preferably, the reaction is effected in a suitable organic solvent, e.g. THF, DMF, at a temperature from −78° C. to +50° C., preferably −78° C. to +20° C.

Alternatively, where X is hydroxy, the coupling reaction is carried out using standard reagents such as DIAD (diisopropyl azodicarboxylate) and n-Bu₃P (tri n-butyl phosphine) in a solvent such as tetrahydrofuran, suitably at room temperature:

A compound of formula (V) may be prepared by reacting a compound of formula (VII) with a compound of formula (VIII):

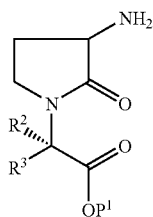

(VII)

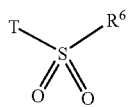

(VIII)

wherein T is a reactive group, such as a halide, preferably chloride, and P¹ is as described above. The reaction is conveniently carried out in the presence of a base, e.g. pyridine, and in a suitable solvent, e.g. DCM, suitably at room temperature.

A compound of formula (VII) may be prepared from a compound of formula (IX)

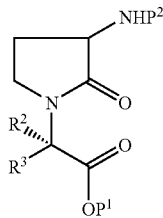

(IX)

where P¹ is as described above and P² represents a suitable amine protecting group, e.g. Cbz (benzyloxycarbonyl), by removal of the protecting group under standard conditions. For example, the protecting group may be removed by reaction with hydrogen in the presence of a metal catalyst, e.g. palladium/charcoal at atmospheric pressure. Suitably, the reaction is carried out in an alcoholic solvent, e.g. ethanol, suitably at room temperature.

A compound of formula (IX) may be prepared from a compound of formula (X)

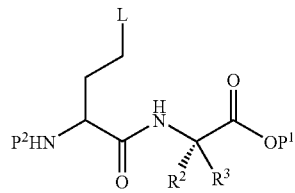

(X)

by cyclisation, wherein P¹ and P² are as described above and L represents a leaving group, e.g. SMeRX. The ring closure may be performed by treatment with Dowex 2×8 400 mesh OH⁻ resin in a suitable solvent, e.g. MeCN (acetonitrile). Attentively, the ring closure may be performed by treatment with potassium carbonate in a suitable solvent, e.g. MeCN. Generally R will represent alkyl or aralkyl and X will represent halide, especially iodide or sulphate.

Alternatively, a compound of formula (IX) may be prepared from a compound of formula (Xb):

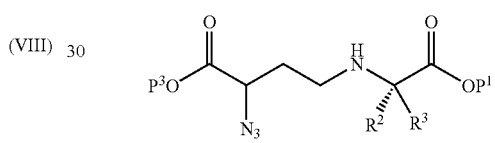

(Xb)

where P¹ and P³ are protecting groups, by reaction with LiOH in a suitable solvent e.g. THF followed by reaction with DPPA (diphenylphosphoryl azide), a base e.g. Et₃N (triethylamine) in a suitable solvent e.g. DMF, suitably at room temperature to 70° C.

A compound of formula (Xb) may be prepared by reacting a compound of formula (Xb-1) with a compound of formula (Xb-2)

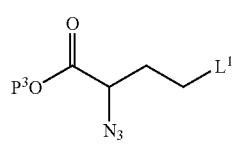

(Xb-1)

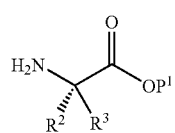

(Xb-2)

where L¹ is a leaving group e.g. bromine, in the presence of a base e.g. Et₃N in a suitable solvent e.g. MeCN.

A compound of formula (X) in which L represents SMeRX may be formed from a compound of formula (XI)

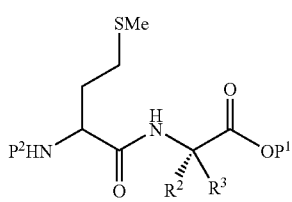

(XI)

by treatment with RX, where $P^1$ and $P^2$ are as described above and RX is a compound (e.g. MeI, benzyl iodide or $Me_2SO_4$) capable of converting sulphur in the SMe moiety to a sulphonium salt, in a suitable solvent, e.g. propanone or acetonitrile.

A compound of formula (XI) may be prepared by reacting a compound of formula (XII) with a compound of formula (XIII):

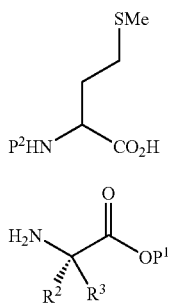

(XII)

(XIII)

Suitably, the reaction may be carried out in the presence of a coupling agent, for example 1-[3-(dimethylamino)propyl]-3-ethyl carbodiimide hydrochloride, HOBt, a base, e.g. $Et_3N$, and an organic solvent, e.g. DCM, suitably at room temperature.

There is provided a further process (B) for preparing compounds of formula (IV) from compounds of formula (VII). According to process (B), a compound of formula (IV) may be prepared by reductive amination of a compound of formula (VII) with $R^{1a}CHO$ (where $R^{1a}$ is $R^1$ without a $CH_2$ linker directly attached to the N) using a suitable selective reducing agent to produce a compound of formula (XIV), followed by reaction with a compound of formula (VIII) in the presence of a base, e.g. pyridine, and in a solvent, e.g. DCM, suitably at room temperature.

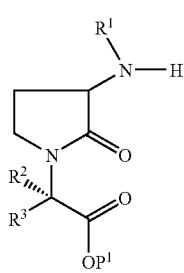

(XIV)

The reductive amination is conveniently carried out by treatment with sodium triacetoxyborohydride in the presence of an acid such as acetic acid, in a solvent such as DCM, suitably at room temperature.

Compounds of formulae (III), (VI), (VIII), (Xb-1), (Xb-2), (X), (XI), (XII) and (XIII) are known compounds and/or can be prepared by processes well known in the art.

The various general methods described above may be useful for the introduction of the desired groups at any stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product. For example, those skilled in the art will appreciate that, with the use of appropriate protecting groups, the coupling to any of groups —$R^1$, —$SO_2R^6$ or —$NR^4R^5$ can be the final step in the preparation of a compound of formula (I), (Ia), (Ib), or (Ic). Hence, in another aspect of the invention, the final step in the preparation of a compound of formula (I), (Ia), (Ib), or (Ic) may comprise the coupling to group —$R^1$ by reacting a compound of formula (XV) with a compound of formula (VI):

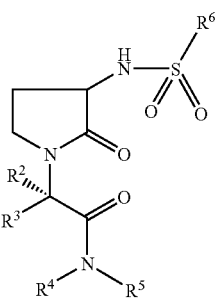

(XV)

Suitably, where X is a leaving group such as a halogen atom, e.g. bromine, the reaction is carried out in the presence of a base, e.g. LiHMDS (lithium hexamethyldisilylamide), potassium carbonate or sodium carbonate. Preferably, the reaction is effected in a suitable organic solvent, e.g. THF, DMF, at a temperature from −78° C. to +50° C., preferably −78° C. to +20° C.

In a further aspect of the present invention, the final step in the preparation of a compound of formula (I), (Ia), (Ib), or (Ic) may comprise the coupling to group —$SO_2R^6$ by reacting a compound of formula (XVI) with a compound of formula (VIII):

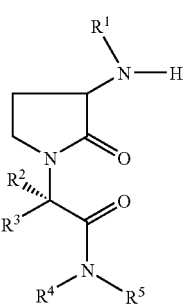

(XVI)

The reaction is conveniently carried out in the presence of a base, e.g. pyridine, and in a suitable solvent, e.g. DCM, suitably at room temperature.

In a further aspect of the present invention, a compound of formula (I) where $R^1$ is an aryl or heteroaryl group may be prepared from a compound of formula (XV) by reaction with a compound of formula (XVII):

$$R^1-C^1 \qquad (XVII)$$

where $C^1$ is a suitable coupling group e.g. boronate. [B(OH)$_2$] under metal catalysis, for example, with a copper salt such as copper(II) acetate, in the presence of an organic solvent e.g. DCM and a base, e.g. pyridine and optionally in the presence of molecular sieves.

In a further aspect of the present invention, a compound of formula (I) where $R^6$ is —SO$_2$—CH=CH-aryl, SO$_2$—CH=CH-heteroaryl, SO$_2$—C(CH$_3$)=CH-aryl or SO$_2$—C(CH$_3$)=CH-heteroaryl may be prepared from a compound of formula (XVI) where $R^1$ is hydrogen, by reaction with a compound of formula (XVIII), or alternatively with a compound of formula (XIX):

$$T^1-SO_2-C(R)=CH_2 \qquad (XVIII)$$

$$T^1-SO_2-C(R)-CH_2-T^2 \qquad (XIX)$$

where $T^1$ and $T^2$ are independently reactive groups, such as a halide, preferably chloride, in the presence of a base e.g. N,N-diisopropylethylamine and a suitable solvent e.g. MeCN, suitably at room temperature, to provide a compound of formula (XV) where $R^6$ is C(R)=CH$_2$, followed by reaction with a compound of formula (XX):

$$\text{L-R}^h \qquad (XX)$$

Where $R^h$ is aryl or heteroaryl and L is a leaving group, e.g. bromine, in the presence of a base e.g. N,N-diisopropylethylamine, and a suitable solvent e.g. dioxane and a suitable transition metal catalyst e.g. di(palladium)tris(dibenzylideneacetone) and a suitable ligand e.g. 2-(di-t-butylphosphino)biphenyl under an inert atmosphere e.g. nitrogen, at a temperature 20–100° C. preferably 40° C.

In a further aspect of the present invention, a compound of formula (I) where $R^6$ is a biaryl group may be prepared from a compound of formula (XVI) where $R^1$ is hydrogen and the amino group is optionally protected, for example, as a solid supported derivative derived from reductive amination under standard conditions, by reaction with a compound of formula of formula (XXI):

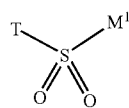

(XXI)

wherein T is a reactive group, such as a halide, preferably chloride, and $M^1$ is an aryl or heteroaryl group with a suitable coupling group e.g. halogen, preferably bromide or iodide, in the presence of a suitable solvent e.g. DMF and a suitable base, e.g. N,N-diisopropylethylamine, followed by reaction with a compound of formula (XXII):

$$M^2\text{-}C^2 \qquad (XXII)$$

wherein $M^2$ is an aryl or heteroaryl group and $C^2$ is a suitable coupling group e.g. boronate [B(OH)$_2$], in the presence of a metal catalyst e.g. tetrakis(triphenylphosphine)palladium (0), a base e.g. sodium carbonate, a suitable solvent e.g. THF and optionally in the presence of a cosolvent e.g. H$_2$O, followed by removal of any protecting groups under standard conditions, e.g. under standard conditions.

Those skilled in the art will appreciate that in the preparation of the compound of formula (I), (Ia), (Ib), or (Ic) or a solvate thereof it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate.

Various intermediate compounds used in the above-mentioned process, including but not limited to certain compounds of formulae formulae (II), (IV), (V), (VII), (IX), (XIV), (XV) and (XVI) are novel and accordingly constitute a further aspect of the present invention.

The present invention will now be further illustrated by the accompanying examples which should not be construed as limiting the scope of the invention in any way.

EXAMPLES

| Abbreviations | |
|---|---|
| Boc | t-Butyloxycarbonyl |
| Cbz | Benzyloxycarbonyl |
| THF | Tetrahydrofuran |
| DCM | Dichloromethane |
| DMF | N,N-Dimethylformamide |
| HOBT | 1-Hydroxybenzotriazole |
| br | broad |
| m | multiplet |
| q | quartet |
| s | singlet |
| t | triplet |
| d | doublet |

Intermediate 1 tert-Butyl N-[(benzyloxy)carbonyl]-L-methionyl-L-alaninate

Z-Protected L-methionine (10 g) was dissolved in DMF (200 ml) and 1-[3-(dimethylamino)propyl]-3-ethylcarbodiimide hydrochloride (8.13 g) was added followed by HOBT (5.72 g) and triethylamine (19.7 ml). The mixture was stirred for 1 h then L-alanine tert-butyl ester (7.7 g) was added and stirring continued for 18 h. The mixture was concentrated under reduced pressure and partitioned between diethyl ether and water. The separated organic phase was washed with hydrochloric acid (1M), saturated sodium bicarbonate solution and brine, dried (over magnesium sulphate) and concentrated under reduced pressure to give the title compound (11.9 g) as an orange oil which crystallised on standing.

Mass spectrum: Found: MH$^+$ 411.

Intermediate 2 tert-Butyl N-[(benzyloxy)carbonyl]-D-methionyl-L-alaninate

Using Z-protected D-methionine, L-alanine tert-butyl ester, and the procedure described for Intermediate 1, the title compound was prepared.

Mass spectrum: Found: MH$^+$ 411.

Intermediate 3 (RR)

tert-Butyl N-[(benzyloxy)carbonyl]-D-methionyl-D-alaninate

Using Z-protected D-methionine, D-alanine tert-butyl ester and the procedure described for Intermediate 1, the title compound was prepared.

Mass spectrum: Found: MH$^+$ 411.

Intermediate 4 (SR)

tert-Butyl N-[(benzyloxy)carbonyl]-L-methionyl-D-alaninate

Using Z-protected L-methionine, D-alanine tert-butyl ester and the procedure described for Intermediate 1, the title compound was prepared.

Mass spectrum: Found: MH$^+$ 411.

Intermediate 5 tert-Butyl (2S)-2-((3S)-3-{[(benzyloxy)carbonyl]amino}-2-oxopyrrolidin-1-yl)propanoate A solution of Intermediate 1 (11.9 g) in acetone (75 ml) was treated with methyl iodide (18 ml) and stirred at room temperature for 72 h. The reaction mixture was then concentrated under reduced pressure to give an orange solid which was dissolved in acetonitrile (200 ml). Dowex (OH$^-$ form) resin (19.42 g) was added and the mixture stirred for 18 h at room temperature. The mixture was filtered and the resin washed with ethyl acetate. The filtrate was concentrated under reduced pressure to afford a yellow oil which was purified by Biotage™ chromatography (eluting with cyclohexane:ethyl acetate 3:2) to give the title compound (2.92 g) as a colourless oil.

Mass spectrum: Found: MH$^+$ 363.

Intermediate 6 tert-Butyl (2S)-2-((3R)-3-{[(benzyloxy)carbonyl]amino}-2-oxopyrrolidin-1-yl)propanoate Using Intermediate 2 and the procedure described for Intermediate 5, the title compound was prepared.

Mass spectrum: Found: MH$^+$ 363.

Intermediate 7 tert-Butyl (2R)-2-((3R)-3-{[(benzyloxy)carbonyl]amino}-2-oxopyrrolidin-1-yl)propanoate Using Intermediate 3 and the procedure described for Intermediate 5, the title compound was prepared.

Mass spectrum: Found: MH$^+$ 363.

Intermediate 8 tert-Butyl (2R)-2-((3S)-3-{[(benzyloxy)carbonyl]amino}-2-oxopyrrolidin-1-yl)propanoate Using Intermediate 4 and the procedure described for Intermediate 5, the title compound was prepared.

Mass spectrum: Found: MH$^+$ 363.

Intermediate 9 tert-Butyl (2S)-2-[(3S)-3-amino-2-oxopyrrolidin-1-yl]propanoate

A mixture of tera-butyl (2S)-2-((3S)-3-{[(benzyloxy)carbonyl]amino}-2-oxopyrrolidin-1-yl)propanoate (2.82 g), 10% palladium on carbon (0.3 g) and ethanol (150 ml) was stirred under an atmosphere of hydrogen for 18 h. The reaction mixture was filtered through Harbolite™ and the filtrate was concentrated under reduced pressure to give the title compound (1.8 g) as a pale yellow oil.

$^1$H NMR (D$_4$MeOH): δ 4.56(1H, q), 3.57(1H, dd), 3.49–3.35(2H, 2×m), 2.48–2.39(1H, m), 1.88–1.77(1H, m), 1.47(9H, s), 1.40 (3H, d) ppm.

Intermediate 10 tert-Butyl (2S)-2-[(3R)-3-amino-2-oxopyrrolidin-1-yl]propanoate

Using Intermediate 6 and the procedure described for Intermediate 9, the title compound was prepared.

$^1$H NMR (D$_4$MeOH): δ 4.60(1H, q), 3.58(1H, dd), 3.46 (1H, dt), 3.41–3.33(1H, m), 2.48–2.40(1H, m), 1.82–1.70 (1H, m), 1.45(9H, s), 1.40(3H, d) ppm.

Intermediate 11 tert-Butyl (2R)-2-[(3R)-3-amino-2-oxopyrrolidin-1-yl]propanoate

Using Intermediate 7 and the procedure described for Intermediate 9, the title compound was prepared.

$^1$H NMR (D$_4$MeOH): δ 4.58(1H, q), 3.75(1H, dd), 3.55–3.41(2H, 2×m), 2.50(1H, m), 1.90(1H, m), 1.49(9H, s), 1.42(3H, d) ppm.

Intermediate 12 tert-Butyl (2R)-2-[(3S)-3-amino-2-oxopyrrolidin-1-yl]propanoate

Using Intermediate 8 and the procedure described for Intermediate 9, the title compound was prepared.

$^1$H NMR (D$_4$MeOH): δ 4.68(1H, q), 3.78(1H, t), 3.56–3.40(2H, 2×m), 2.52(1H, m), 1.90(1H, m), 1.48(9H, s), 1.42(3H, d) ppm.

Intermediate 13

(2S)-2-((3S)-3-{[(Benzyloxy)carbonyl]amino}-2-oxopyrrolidin-1-yl)propanoic acid tert-Butyl (2S)-2-((3S)-3-{[(benzyloxy)carbonyl]amino}-2-oxopyrrolidin-1-yl)propanoate (0.5 g) was dissolved in DCM (7 ml), and trifluoroacetic acid (4.7 ml) was added. The mixture was stirred at room temperature for 1.5 h and then concentrated under reduced pressure to give the title compound (0.423 g) as a colourless oil which after azeotroping with toluene, crystallised.

Mass spectrum: Found: MH$^+$ 307.

Intermediate 14

(2R)-2-((3R)-3-{[(Benzyloxy)carbonyl]amino}-2-oxopyrrolidin-1-yl)propanoic acid

Using Intermediate 7 and the procedure described for Intermediate 13, the title compound was prepared.

Mass spectrum: Found: MH$^+$ 307.

Intermediate 15

(2S)-2-((3R)-3-{[(Benzyloxy)carbonyl]amino}-2-oxopyrrolidin-1-yl)propanoic acid

Using Intermediate 6 and the procedure described for Intermediate 13, the title compound was prepared.

Mass spectrum: Found: MH$^+$ 307.

Intermediate 16

(2R)-2-((3S)-3-{[(Benzyloxy)carbonyl]amino}-2-oxopyrrolidin-1-yl)propanoic acid

Using Intermediate 8 and the procedure described for Intermediate 13, the title compound was prepared.

Mass spectrum: Found: MH$^+$ 307.

Intermediate 17

Benzyl (3S)-1-[(1S)-1-methyl-2-oxo-2-piperidin-1-ylethyl]-2-oxopyrrolidin-3-ylcarbamate To a solution of (2S)-2-((3S)-3-{[(benzyloxy)carbonyl]amino}-2-oxopyrrolidin-1-yl)propanoic acid (3.1 g) in DCM (30 ml) were added 1-[3-(dimethylamino)propyl]-3-ethylcarbodiimide hydrochloride (4.6 g), HOBT (3.2 g) and triethylamine (2.5 ml) and the mixture was stirred at room temperature for 5 min. Piperidine (2.9 ml) was added and the resultant mixture stirred at room temperature for 72 h. The mixture was washed with potassium carbonate (2M), dried (over magnesium sulphate) and concentrated under reduced pressure. The residue was purified using Biotage™ chromatography (silica, eluting with cyclohexane:ethyl acetate 3:1 and then ethyl acetate) to give the title compound (2.6 g) as a white solid.

Mass spectrum: Found: MH$^+$ 374.

Intermediate 18

Benzyl (3R)-1-[(1R)-1-methyl-2-oxo-2-piperidin-1-ylethyl]-2-oxopyrrolidin-3-ylcarbamate Using Intermediate 14 and the procedure described for Intermediate 17, the title compound was prepared.

Mass spectrum: Found: MH$^+$ 374.

Intermediate 19

Benzyl (3R)-1-[(1S)-1-methyl-2-oxo-2-piperidin-1-ylethyl]-2-oxopyrrolidin-3-ylcarbamate Using Intermediate 15 and the procedure described for Intermediate 17, the title compound was prepared.

Mass spectrum: Found: MH$^+$ 374.

Intermediate 20

Benzyl (3S)-1-[(1R)-1-methyl-2-oxo-2-piperidin-1-ylethyl]-2-oxopyrrolidin-3-ylcarbamate Using Intermediate 16 and the procedure described for Intermediate 17, the title compound was prepared.

Mass spectrum: Found: MH$^+$ 374.

Intermediate 21

(3R)-3-Amino-1-[(1S)-1-methyl-2-oxo-2-piperidin-1-ylethyl]pyrrolidin-2-one

Using Intermediate 19 and the procedure described for Intermediate 9, the title compound was prepared.

Mass spectrum: Found: MH$^+$ 240.

Intermediate 22

(3R)-3-Amino-1-[(1R)-1-methyl-2-oxo-2-piperidin-1-ylethyl]pyrrolidin-2-one

Using Intermediate 18 and the procedure described for Intermediate 9, the title compound was prepared.

Mass spectrum: Found: MH$^+$ 240.

Intermediate 23

(3S)-3-Amino-1-[(1S)-1-methyl-2-oxo-2-piperidin-1-ylethyl]pyrrolidin-2-one

Using Intermediate 17 and the procedure described for Intermediate 9, the title compound was prepared.

Mass spectrum: Found: MH$^+$ 240.

Intermediate 24

(3S)-3-Amino-1-[(1R)-1-methyl-2-oxo-2-piperidin-1-ylethyl]pyrrolidin-2-one

Using Intermediate 20 and the procedure described for Intermediate 9, the title compound was prepared.

Mass spectrum: Found: MH$^+$ 240.

Intermediate 25 tert-Butyl (2S)-2-((3S)-3-{[(6-chloro-2-naphthyl)
sulfonyl]amino}-2-oxopyrrolidin-1-yl)propanoate A solution of tert-butyl (2S)-2-[(3S)-3-amino-2-oxopyrrolidin-1-yl]propanoate (1.8 g) in DCM (75 ml) was treated with 6-chloronaphthylsulphonyl chloride[1] (2.28 g) and pyridine (0.705 ml) and stirred at room temperature for 72 h. The mixture was washed with water and concentrated under reduced pressure to yield an oil which was purified by Biotage™ chromatography (eluting with cyclohexane:ethyl acetate 3:1) to give the title compound (2.31 g), as a white solid.
Mass spectrum: Found: MH+ 453.

Intermediate 26 tert-Butyl (2S)-2-((3R)-3-{[(6-chloro-2-naphthyl)
sulfonyl]amino}-2-oxopyrrolidin-1-yl)propanoate Using Intermediate 10 and the procedure described for Intermediate 25, the title compound was prepared.
$^1$H NMR (CDCl$_3$): δ 8.45(1H, br.s), 7.96–7.83(4H, m), 7.56 (1H, dd), 5.41(1H, br.s), 4.66 (1H, q), 3.73(1H, dt), 3.42–3.34(2H, m), 2.62(1H, m), 2.01(1H, m), 1.38–1.32 (12H, s+d) ppm.

Intermediate 27 tert-Butyl (2R)-2-((3R)-3-{[(6-chloro-2-naphthyl)
sulfonyl]amino}-2-oxopyrrolidin-1-yl)propanoate Using Intermediate 11 and the procedure described for Intermediate 25, the title compound was prepared.
Mass spectrum: Found: MH+ 453.

Intermediate 28 tert-Butyl (2S)-2-{(3R)-3-[[(6-chloro-2-naphthyl)
sulfonyl](methyl)amino[-2-oxopyrrolidin-1-
yl}propanoate Using Intermediate 26 and methyl tosylate, and the procedure described for Intermediate 52, the title compound was prepared.
Mass spectrum: Found: MH+ 467.

Intermediate 29

(2S)-2-((3S)-3-{[(6-Chloro-2-naphthyl)sulfonyl]
amino}-2-oxopyrrolidin-1-yl)propanoic acid tert-Butyl (2S)-2-((3S)-3-{[(6-chloro-2-naphthyl)sulfonyl]amino}-2-oxopyrrolidin-1-yl)propanoate (0.643 g) was dissolved in DCM (19 ml), and trifluoroacetic acid (19 ml) was added. The mixture was stirred at room temperature for 2.5 h and then concentrated under reduced pressure. Anhydrous DCM (4 ml) was added and the solution concentrated under reduced pressure. Repetitive addition of DCM and concentration under reduced pressure provided the title compound (0.56 g) as a white foam.
Mass spectrum: Found: MH+ 397.

Intermediate 30

(2S)-2-{(3R)-3-[[(6-Chloro-2-naphthyl)sulfonyl]
(methyl)amino]-2-oxopyrrolidin-1-yl}propanoic
acid Using Intermediate 28 and the procedure described for Intermediate 29, the title compound was prepared.
Mass spectrum: Found: MH+ 411.

Intermediate 31

(2S)-2-((3R)-3-{[(6-Chloro-2-naphthyl)sulfonyl]
amino}-2-oxopyrrolidin-1-yl)propanoic acid Using Intermediate 26 and the procedure described for Intermediate 29, the title compound was prepared.
Mass spectrum: Found: MH+ 397.

Intermediate 32

(2R)-2-((3R)-3-{[(6-Chloro-2-naphthyl)sulfonyl]
amino}-2-oxopyrrolidin-1-yl)propanoic acid Using Intermediate 27 and the procedure described for Intermediate 29, the title compound was prepared.
Mass spectrum: Found: MH+ 397.

Intermediate 33 tert-Butyl (2R)-2-(3-azido-2-oxopyrrolidin-1-yl)
propanoate

To a solution of D-alanine tert-butylester (1.28 g) and N,N-diisopropylethyamine (1.22 ml) in acetonitrile (15 ml), was added a solution of ethyl 2-azido-4-bromobutanoate (1 g) and sodium iodide (0.02 g) in acetonitrile (5 ml). The mixture was heated at 60° C. for 60 h and then concentrated under pressure to give a brown oil. This oil was partitioned between DCM and water. The separated organic layer was washed further with water and dried (over magnesium sulphate), and concentrated under reduced pressure. The residual brown oil was purified using Biotage™ chromatography (silica, eluting with cyclohexane;ethyl acetate 3:1) to give the title compound (0.204 g) as a mixture of two diastereoisomers.
T.l.c. (cyclohexane:ethyl acetate, 2:1) R$_f$ 0.20

Intermediate 34 tert-Butyl (2S)-2-(3-azido-2-oxopyrrolidin-1-yl)
propanoate

Using ethyl 2-azido-4-iodobutanoate and L-alanine tert-butyl ester, and the procedure described for Intermediate 33, the title compound was prepared as a mixture of two diastereoisomers.
T.l.c. (cyclohexane:ethyl acetate, 3:1) R$_f$ 0.15

Intermediate 35 tert-Butyl (2R)-2-(3-{[(6chloro-2-naphthyl)sulfonyl]
amino}-2-oxopyrrolidin-1-yl)propanoate A mixture of tert-butyl (2R)-2-(3-azido-2-oxopyrrolidin-1-yl)propanoate (0.035 g), 10% palladium on carbon (0.003 g) and ethanol (2 ml) was stirred under an atmosphere of hydrogen for 16 h. The reaction mixture was filtered through Harbolite™ and the filtrate was concentrated under reduced pressure to give a yellow gum. The gum (0.026 g) in DCM (2 ml) was treated with 6-chloronaphthylsulphonyl chloride[1] (0.03 g) and pyridine (0.02 ml) and stirred at room temperature for 42 h. The mixture was washed with water and concentrated under reduced pressure to yield an oil which was partially purified using SPE (aminopropyl, eluting with methanol). The organic washings were concentrated under reduced pressure and the residue dissolved in DCM. The organic solution was purified by SPE (aminopropyl, eluting with methanol containing 10% v/v 2N HCl) to give the title compound (0.012 g) as a white solid.

Mass spectrum: Found: MH+ 453.

Intermediate 36 tert-Butyl (2S)-2-(3-{[(6-chloro-2-naphthyl)sulfonyl]amino}-2-oxopyrrolidin-1-yl)propanoate Using Intermediate 34 and the synthetic procedure described for Intermediate 35, the title compound was prepared.

Mass spectrum: Found: MH+ 453.

Intermediate 37

(2R)-2-(3-{[(6-Chloro-2-naphthyl)sulfonyl]amino}-2-oxopyrrolidin-1-yl)propanoic acid Using Intermediate 35, and the synthetic procedure for Intermediate 13, the title compound was prepared.

Mass spectrum: Found: MH+ 411.

Intermediate 38

(2S)-2-(3-{[(6-Chloro-2-naphthyl)sulfonyl]amino}-2-oxopyrrolidin-1-yl)propanoic acid Using Intermediate 36, and the synthetic procedure for Intermediate 13, the title compound was prepared.

Mass spectrum: Found: MH+ 411.

Intermediate 39

(2R)-2-(3-{[(3'-Chloro-1,1'-biphenyl-4-yl)sulfonyl]amino}-2-oxopyrrolidin-1-yl)propanoic acid Using Intermediate 33 and (3'-chloro-1,1'-biphenyl-4-yl)sulfonyl chloride and similar chemistry to that described for Intermediates 35 and 37, the title compound was prepared.

Mass spectrum: Found: MH+ 424.

Intermediate 40

(2R)-2-(3-{[(3-Chloroisoquinolin-7-yl)sulfonyl]amino}-2-oxopyrrolidin-1-yl)propanoic acid Using Intermediate 33 and (3-chloroisoquinolin-7-yl)sulfonyl chloride and similar chemistry to that described for Intermediates 35 and 37, the title compound was prepared.

Mass spectrum: Found: MH+ 398.

Intermediates 41* and 42 tert-Butyl(2R)-2-((3R)-3-{[(6-chloro-2-naphthyl)sulfonyl]amino}-2-oxopyrrolidin-1-yl)propanoate
(1)

tert-Butyl(2R)-2-((3S)-3-{[(6-chloro-2-naphthyl)sulfonyl]amino}-2-oxopyrrolidin-1-yl)propanoate
(2)

A mixture of tert-butyl (2R)-2-(3-azido-2-oxopyrrolidin-1-yl)propanoate (0.204 g), 10% palladium on carbon (0.02 g) and ethanol (10 ml) was stirred under an atmosphere of hydrogen for 5 h. The reaction mixture was filtered through Harbolite™ and the filtrate was concentrated under reduced pressure to give a yellow oil. The oil (0.150 g) in DCM (10 ml) was treated with 6-chloronaphthylsulphonyl chloride[1] (0.188 g) and pyridine (0.058 ml) and stirred at room temperature for 72 h. The mixture was washed with water and concentrated under reduced pressure to yield an oil which was purified by Biotage™ chromatography (eluting with cyclohexane:ethyl acetate 2:1) to give the title compounds [(1)—0.067 g and (2)—0.060 g], both as white solids.

*Intermediate 41=Intermediate 27

(1) Mass spectrum: Found: MH+ 453.

(2) Mass spectrum: Found: MH+ 453.

Using Intermediates 41 and 42 and the synthetic procedure described for Intermediate 52, the following compounds were similarly prepared:

Intermediate 43 tert-Butyl(2R)-2-{(3R)-3-[[(6-chloro-2-naphthyl)sulfonyl](methyl)amino]-2-oxopyrrolidin-1-yl}propanoate Mass spectrum: Found: MH+ 467.

Intermediate 44 tert-Butyl(2R)-2-{(3S)-3-[[(6-chloro-2-naphthyl)sulfonyl](methyl)amino]-2-oxopyrrolidin-1-yl}propanoate Mass spectrum: Found: MH+ 467.

Intermediate 45 tert-Butyl (2S)-2-{(3S)-3-[[(6-chloro-2-naphthyl)sulfonyl](2-oxobutyl)amino]-2-oxopyrrolidin-1-yl}propanoate A solution of tert-butyl (2S)-2-((3S)-3-{[(6-chloro-2-naphthyl)sulfonyl]amino}-2-oxopyrrolidin-1-yl)propanoate (0.07 g) in THF (2 ml) was cooled to −78° C. under nitrogen, and treated with lithium bis(trimethylsilyl) amide (1.0M solution in THF; 0.186 ml), followed by 1-bromo-2-butanone (0.08 ml). The resultant solution was allowed to reach room temperature and stirred for a further 72 h. Methanol (1 ml) was added and the resultant solution concentrated under reduced pressure. The residue was purified using SPE (silica, eluting with cyclohexane:ethyl acetate 10:1, 5:1, 3:1, 2:1, 1:1, 1:2, 1:3, 1:5, ethyl acetate and methanol:ethyl acetate 1:9) to give the title compound (0.07 g) as a gum.

Mass spectrum: Found: MH+ 523.

Similarly prepared using other commercially available alkyl halides, were:

Intermediate 46 tert-Butyl (2S)-2-((3S)-3-{(2-amino-2-oxoethyl)[(6-chloro-2-naphthyl)sulfonyl]amino}-2-oxopyrrolidin-1-yl)propanoate Mass spectrum: Found: MH$^+$ 510.

Intermediate 47 tert-Butyl (2S)-2-{(3S)-3-[[(6-chloro-2-naphthyl)sulfonyl](2-methoxy-2-oxoethyl)amino]-2-oxopyrrolidin-1-yl}propanoate Mass spectrum: Found: MH$^+$ 525.

Intermediate 48

(2S)-2-{(3S)-3-[[(6-Chloro-2-naphthyl)sulfonyl](2-oxobutyl)amino]-2-oxopyrrolidin-1-yl}propanoic acid tert-Butyl (2S)-2-{(3S)-3-[[(6-chloro-2-naphthyl)sulfonyl](2-oxobutyl)amino]-2-oxopyrrolidin-1-yl}propanoate (0.07 g) was dissolved in DCM (2 ml), and trifluoroacetic acid (2 ml) was added. The mixture was stirred at room temperature for 1.5 h and then partitioned between water and DCM. The organic layer was separated, dried (over magnesium sulphate) and concentrated under reduced pressure to give the title compound (0.063 g) as an orange gum.
Mass spectrum: Found: MH$^+$ 467.
Using similar chemistry, the following were prepared:

Intermediate 49

(2S)-2-{(3S)-3-((2-Amino-2-oxoethyl)[(6-chloro-2-naphthyl)sulfonyl]amino}-2-oxopyrrolidin-1-yl)propanoic acid Using Intermediate 46 and similar chemistry to that described for Intermediate 48, the title compound was prepared.
Mass spectrum: Found: MH$^+$ 454.

Intermediate 50

(2S)-2-{(3S)-3-[[(6-Chloro-2-naphthyl)sulfonyl](2-methoxy-2-oxoethyl)amino]-2-oxopyrrolidin-1-yl}propanoic acid Using Intermediate 47 and similar chemistry to that described for Intermediate 48, the title compound was prepared.
Mass spectrum: Found: MH$^+$ 469.

Intermediate 51

7-[({(3S)-1-[(1S)-1-Methyl-2-oxo-2-piperidin-1-ylethyl]-2-oxopyrrolidin-3-yl}amino)sulfonyl]-2-naphthyl benzoate The title compound was prepared using Intermediate 23, 7-(chlorosulfonyl)-2-naphthyl benzoate, and the synthetic procedure described for Intermediate 25.
M ass spectrum: Found: MH$^+$ 446.

Intermediate 52 tert-Butyl (2S)-2-{(3S)-3-[[(6-chloro-2-naphthyl)sulfonyl](methyl)amino]-2-oxopyrrolidin-1-yl}propanoate A solution of tert-butyl (2S)-2-((3S)-3-{[(6-chloro-2-naphthyl)sulfonyl]amino}-2-oxopyrrolidin-1-yl)propanoate (0.1 g) in THF (5 ml) was cooled to −78° C. under nitrogen, and treated with lithium bis(trimethylsilyl) amide (1.0M solution in THF; 0.23 ml), followed by methyl tosylate (0.206 g). The resultant solution was allowed to reach room temperature and stirred for a further 16 h. The mixture was quenched with sodium acetate (0.074 g), stirred for 1 h and partitioned between water and ethyl acetate. The separated organic layer was washed with water, dried (over magnesium sulphate), and concentrated under reduced pressure. The residue was purified using SPE (silica, eluting with cyclohexane:ethyl acetate 10:1, 8:1, 5:1, 3:1, 2:1,1:1) to give the title compound (0.101 g) as a colourless gum.
Mass spectrum: Found: MH$^+$ 467.

Intermediate 53

(2S)-2-{(3S)-3-[[(6-Chloro-2-naphthyl)sulfonyl](methyl)amino]-2-oxopyrrolidin-1-yl}propanoic acid tert-Butyl (2S)-2-{(3S)-3-[[(6-chloro-2-naphthyl)sulfonyl](methyl)amino]-2-oxopyrrolidin-1-yl}propanoate (0.1 g) was dissolved in DCM (2 ml), and trifluoroacetic acid (2 ml) was added. The mixture was stirred at room temperature for 1.5 h and then partitioned between water and DCM. The organic layer was separated, dried (over magnesium sulphate) and concentrated under reduced pressure to give the title compound (0.09 g) as an colourless gum.
Mass spectrum: Found: MH$^+$ 411.

Intermediate 54

(2R)-2-((3S)-3-{[(6-Chloro-2-naphthyl)sulfonyl]amino]-2-oxopyrrolidin-1-yl)propanoic acid Using Intermediate 42 and the procedure described for Intermediate 53, the title compound was similarly prepared.
Mass spectrum: Found: MH$^+$ 397.

Intermediate 55

(2R)-2-{(3S)-3-[[(6-Chloro-2-naphthyl)sulfonyl](methyl)amino]-2-oxopyrrolidin-1-yl}propanoic acid Using Intermediate 44 and the procedure described for Intermediate 53, the title compound was similarly prepared.
Mass spectrum: Found: MH$^+$ 411.

Intermediate 56

(2R)-2-{(3R)-3-[[(6-Chloro-2-naphthyl)sulfonyl](methyl)amino]-2-oxopyrrolidin-1-yl}propanoic acid Using Intermediate 43 and the procedure described for Intermediate 53, the title compound was similarly prepared.
Mass spectrum: Found: MH$^+$ 411.

Intermediate 57

5-Chlorothieno[2,3-b]pyridine-2-sulfonyl chloride n-Butyl lithium (1.6M in hexanes, 0.37 ml) was added to a cooled (−78° C.) solution of 5-chlorothieno[2,3-b]pyridine* (0.100 g) in anhydrous THF (5 ml) over 15 min. The reaction was stirred for a further 5 min, warmed to −45° C. and stirred for 40 min. The mixture was cooled to −70° C. and sulphur dioxide gas was bubbled into the vessel over 10 min. The reaction was allowed to reach room temperature over 45 min, and then concentrated under reduced pressure. The residue was dissolved in anhydrous DCM (5 ml), treated with N-chlorosuccinimide (0.097 g) and stirred at room temperature for 75 min. The solution was filtered, and the filtrate concentrated under reduced pressure to give the title compound (0.198 g) as a yellow solid.

*Klemm. L. H. et.al., J. Heterocycl. Chem. (1968), 5(6), 773–8.

Mass Spectrum: Found: $MH^+$ 277 for dimethylamine quenched mass spectrum sample.

Intermediate 58 tert-Butyl 3-(benzoylamino)piperidine-1-carboxylate

A solution of benzoic add (0.123 g) in DMF (5 ml) was treated with 1-[3-(dimethylamino)propyl]-3-ethylcarbodiimide hydrochloride (0.231 g), HOBT (0.163 g) and triethylamine (0.56 ml) and stirred at room temperature for 1 h. A solution of 3-amino-1-N-Boc-piperidine (0.3 g) in DMF (1 ml) was then added and stirring continued for 18 h. The solution was concentrated under reduced pressure to give an oil which was partitioned between ethyl acetate and water. The separated organic extracts were washed with water, hydrochloric acid (2N), saturated sodium bicarbonate solution and brine, dried (over magnesium sulphate) and concentrated under reduced pressure to give the title compound (0.120 g) as a yellow solid.

Mass spectrum: Found: $MH^+$ 305.

Intermediate 59

N-Piperidin-3-ylbenzamide

A solution of tert-butyl 3-(benzoylamino)piperidine-1-carboxylate (0.120 g) in DCM (5 ml) was treated with trifluoroacetic acid (5 ml) and stirred at room temperature for 6 h. The mixture was concentrated under reduced pressure to give a yellow oil which following neutralisation with aqueous ammonia solution, was purified using SPE (silica, eluting with methanol and 5% aqueous ammonia in methanol) to give the title compound (0.085 g) as an off-white solid.

$^1$H NMR (D$_4$MeOH): δ 7.82(2H, br.d), 7.53(1H, tt), 7.45(2H, t), 4.27(1H, tt), 3.50(1H, br.dd), 3.34(1H, br.dt), 2.96(2H, m), 2.08(2H, m), 1.90–1.68(2H, m) ppm.

Intermediate 60 tert-Butyl (2S)-2-{(3S)-3-[[(6-chloro-2-naphthyl)sulfonyl](2-furylmethyl)amino]-2-oxopyrrolidin-1-yl}propanoate A solution of tert-butyl (2S)-2-((3S)-3-{[(6-chloro-2-naphthyl)sulfonyl]amino}-2-oxopyrrolidin-1-yl)propanoate (0.07 g) in THF (0.5 ml) was treated with diisopropyl azodicarboxylate (0.06 ml), 3-furfuryl alcohol (0.030 g) and tributylphosphine (0.075 ml) and shaken at room temperature for 18 h. The mixture was concentrated under reduced pressure and the residue purified by Biotage™ chromatography (eluting with cyclohexane:ethyl acetate 3:1) to give the title compound (0.015 g) as a colourless gum.

Mass spectrum: Found: $MH^+$ 533.

Using similar chemistry, the following was prepared:

Intermediate 61 tert-Butyl (2S)-2-{(3S)-3-[[(6-chloro-2-naphthyl)sulfonyl](1,3-thiazol-2-ylmethyl)amino]-2-oxopyrrolidin-1-yl}propanoate Mass spectrum: Found: $MH^+$ 550.

Intermediate 62

(2S)-2-{(3S)-3-[[(6-Chloro-2-naphthyl)sulfonyl](1,3-thiazol-2-ylmethyl)amino]-2-oxopyrrolidin-1-yl}propanoic acid A solution of tert-butyl (2S)-2-{(3S)-3-[[(6-chloro-2-naphthyl)sulfonyl](1,3-thiazol-2-ylmethyl)amino]-2-oxopyrrolidin-1-yl}propanoate (0.03 g) in DCM (1 ml) was treated with trifluoroacetic acid (1 ml) and stirred at room temperature for 1 h. The solution was then concentrated under reduced pressure to give the title compound (0.019 g) as a colourless solid.

Mass spectrum: Found: $MH^+$ 494.

Using Intermediate 60 and similar chemistry to that described for Intermediate 62, the following was prepared:

Intermediate 63

(2S)-2-{(3S)-3-[[(6-Chloro-2-naphthyl)sulfonyl](2-furylmethyl)amino]-2-oxopyrrolidin-1-yl}propanoic acid mixture with (2S)-2-((3S)-3-{[(6-chloro-2-naphthyl)sulfonyl]amino}-2-oxopyrrolidin-1-yl)propanoic acid (56:44)

Mass spectrum: Found: $MH^+$ 478.

Intermediate 64 tert-Butyl 5-chloro-2-[({(3S)-1-[(1S)-1-methyl-2-morpholin-4-yl-2-oxoethyl]-2-oxopyrrolidin-3-yl}amino)sulfonyl]-1H-indole-1-carboxylate 1-tert-Butoxycarbonyl-5-chloroindole (0.1 g) was dissolved in anhydrous THF (2 ml) under nitrogen and cooled to −78° C. n-Butyllithium (1.6M in hexanes, 0.273 ml) was added dropwise over 10 min. After stirring at −78° C. for 45 min, sulphur dioxide gas was bubbled through the reaction for 5 min. The reaction mixture was allowed to reach room temperature over 2 h and concentrated under reduced pressure to give an off-white solid. The solid was re-suspended in anhydrous DCM (2 ml) and treated with N-chlorosuccinimide (0.0584 g). The mixture was then stirred for 1 h at room temperature and any remaining white solid removed by filtration. Half of this filtrate was treated with pyridine (0.017 ml) and Intermediate 87 (0.022 g). The reaction mixture was stirred at 40° C. for 5 h and then 72 h at 30° C. in a sealed vessel. The reaction mixture was washed with water, the organic phase separated and dried (over magne-

Intermediate 65

N-{(3S)-1-[(1S)-1-Methyl-2-morpholin-4-2-oxoethyl]-2-oxopyrrolidin-3-yl}ethenesulfonamide 2-Chloroethanesulfonyl chloride (0.284 ml) was added dropwise to a mixture of Intermediate 87 (0.436 g) and N,N-di-isopropylethylamine (0.938 ml) in dry acetonitrile (6 ml) at 0° C. over 2 min. The mixture was allowed to reach room temperature and stirred for 3 days, after which the reaction was quenched with water and concentrated under reduced pressure to give a brown residue. This residue was partitioned between ethyl acetate and water. The combined organic extracts were dried (over magnesium sulphate) and concentrated under reduced pressure to give a brown foam which was purified by SPE (silica, eluting with ethyl acetate: cyclohexane 1:1, ethyl acetate and then ethyl acetate:methanol 19:1) to give the title compound (0.227 g) as a clear film.
Mass Spectrum: Found: $MH^+$ 332.

Intermediate 66

(3S)-3-{[(6-Chloro-1,3-benzothiazol-2-yl)thio]amino}-1-[(1S)-1-methyl-2-morpholin-4-2-oxoethyl]pyrrolidin-2-one N-Chlorosuccinimide (0.37 g) was added to 4-chloro-2-mercaptobenzothiazole (0.5 g) in DCM (15 ml) under nitrogen, and stirred at room temperature for 3 h. A solution of Intermediate 87 (0.569 g) and triethylamine (1.04 ml) in anhydrous DCM (5 ml) were added and the resulting mixture stirred at room temperature under nitrogen for 2 h. The solution was filtered and the filtrate was diluted with DCM. The organic solution was washed with water and brine, dried (over magnesium sulphate) and concentrated under reduced pressure. The residue was purified by SPE (silica, eluting with cyclohexane:ethyl acetate 1:1 increasing polarity to ethyl acetate:methanol 19:1) to give the title compound (0.3 g) as a white solid.
Mass spectrum: Found: $MH^+$ 441.

Intermediate 67 tert-Butyl (2S)-2-((3S)-3-{[(5'-chloro-2,2'-bithien-5-yl)sulfonyl]amino}-2-oxopyrrolidin-1-yl)propanoate A solution of tert-butyl (2S)-2-[(3S)-3-amino-2-oxopyrrolidin-1-yl]propanoate (0.337 g) in acetonitrile (20 ml) was treated with triethylamine (0.41 ml) and 5'-chloro-2,2'-bithiophene-5-sulfonyl chloride[2] (0.372 g) and stirred at room temperature for 17 h. The mixture was concentrated under reduced pressure and the residue purified using SPE (aminopropyl, eluting with methanol) to give the title compound (0.651 g) as a brown oil.
Mass spectrum: Found: $MH^+$ 491.
Using similar chemistry and Intermediate 9, the following were prepared:

Intermediate 68 teat-Butyl (2S)-2-[(3S)-3-({[(E)-2-(4-chlorophenyl)ethenyl]sulfonyl}amino)-2-oxopyrrolidin-1-yl]propanoate Mass spectrum: Found: $MH^+$ 429.

Intermediate 69 tert-Butyl (2S)-2-((3S)-3-{[(6-chloro-1-benzothien-2-yl)sulfonyl]amino}-2-oxopyrrolidin-1-yl)propanoate Mass spectrum: Found: $MH^+$ 459.

Intermediate 70 tert-Butyl (2S)-2-((3S)-3-{[(5-chloro-1-benzothien-2-yl)sulfonyl]amino}-2-oxopyrrolidin-1-yl)propanoate Mass spectrum: Found: $MH^+$ 459.

Intermediate 71 tert-Butyl (2S)-2-{(3S)-3-[[(5'-chloro-2,2'-bithien-5-yl)sulfonyl](2-oxobutyl)amino]-2-oxopyrrolidin-1-yl}propanoate Using Intermediate 67, and the synthetic procedure described for Intermediate 45, the title compound was similarly prepared.
Mass spectrum: Found: $MH^+$ 561.

Intermediate 72 tert-Butyl (2S)-2-{(3S)-3-[{[(E)-2-(4-chlorophenyl)ethenyl]sulfonyl}(2-oxobutyl)amino]-2-oxopyrrolidin-1-yl}propanoate Using Intermediate 68, and the synthetic procedure described for Intermediate 45, the title compound was similarly prepared.
Mass spectrum: Found: $MH^+$ 499.

Intermediate 73 tert-Butyl (2S)-2-{(3S)-3-[[(6-chloro-1-benzothien-2-yl)sulfonyl](2-oxobutyl)amino]-2-oxopyrrolidin-1-yl}propanoate Using Intermediate 69, and the synthetic procedure described for Intermediate 45, the title compound was similarly prepared.
Mass spectrum: Found: $MH^+$ 529.

Intermediate 74 tert-Butyl (2S)-2-{(3S)-3-[[(5-chloro-1-benzothien-2-yl)sulfonyl](2-oxobutyl)amino]-2-oxopyrrolidin-1-yl}propanoate Using Intermediate 70, and the synthetic procedure described for Intermediate 45, the title compound was similarly prepared.
Mass spectrum: Found: $MH^+$ 529.

sium sulphate), and concentrated under a stream of nitrogen to give a residue which was purified by mass directed preparative h. p.l.c. to give the title compound (0.011 g) as a colourless glass.
Mass spectrum: Found: $MH^+$ 555.

Intermediate 75 tert-Butyl (2S)-2-[(3S)-3-{(2-amino-2-oxoethyl)[(E)-2-(4-chlorophenyl)ethenyl]sulfonyl}amino)-2-oxopyrrolidin-1-yl]propanoate Using Intermediate 68, and the synthetic procedure described for Intermediate 45, the title compound was similarly prepared.

Mass spectrum: Found: MH$^+$ 487.

Intermediate 76 tert-Butyl (2S)-2-((3S)-3-{(2-amino-2-oxoethyl){[(5'-chloro-2,2'-bithien-5-yl)sulfonyl]amino}-2-oxopyrrolidin-1-yl)propanoate Using Intermediate 67, and the synthetic procedure described for Intermediate 45, the title compound was similarly prepared.

Mass spectrum: Found: MH$^+$ 548.

Intermediate 77

Dimethyl (2R)-2-{[(benzyloxy)carbonyl]amino}pentanedioate

Thionyl chloride (30 ml) was added to a cooled solution of D-glutamic acid (33.2 g) in methanol (250 ml) and the mixture subsequently heated under reflux for 16 h. On cooling, the mixture was concentrated under reduced pressure and the residue azeotroped with toluene to give a white solid. This was stirred with ethyl acetate, water and potassium hydrogen carbonate at 0° C. while benzyl chloroformate (30 ml) was added. The mixture was warmed to room temperature and stirred for 5 h. The separated organic phase was washed with water, dried (over magnesium sulphate) and concentrated under reduced pressure to provide a yellow oil. This oil was purified using flash column chromatography (silica, eluting with cyclohexane:ethyl acetate 2:1) to give the title compound (22.45 g) as an oil.

$^1$H NMR (CDCl$_3$): δ 7.40–7.30(5H, m), 5.50(1H, br.d), 5.10(2H, s), 4.40(1H, m), 3.73(3H, s), 3.64(3H, s), 2.50–2.35(2H, m), 2.30–1.90(2H, 2×m) ppm.

Intermediate 78

Benzyl (1S)-4-hydroxy-1-(hydroxymethyl)butylcarbamate

A solution of Z-glutamic acid (10 g) in THF (50 ml) was added portionwise to a stirred solution of lithium aluminium hydride in THF (1M, 100 ml) under nitrogen at 0° C., and the resultant mixture stirred at room temperature for 24 h. Wet ether was added and the mixture was diluted with water and ethyl acetate. The mixture was filtered through Harbolite™ and the filtrate diluted further with water. The separated organic phase was washed with water, dried (over magnesium sulphate) and concentrated under reduced pressure to give solid which was purified by flash column chromatography (silica, eluting with ethyl acetate) to give the title compound (2.74 g) as a white solid.

$^1$H NMR (D$_6$DMSO): δ 7.40–7.30(5H, m), 6.95(1H, br.d), 5.00(2H, s), 4.65(1H, br.t), 4.40(1H, br.t), 3.50–3.20 (5H, m), 1.65–1.15(4H, m) ppm.

Intermediate 79

Benzyl (1R)-4-hydroxy-1-(hydroxymethyl)butylcarbamate

A solution of dimethyl (2R)-2-{[((benzyloxy)carbonyl]amino}pentanedioate (22.4 g) in dry THF (74 ml) was added dropwise over 1 h to a stirred mixture of lithium borohydride (4.5 g) in THF (200 ml) at room temperature, under nitrogen. Stirring at room temperature was continued for 3 days. The reaction mixture was diluted with brine and water, and extracted with ethyl acetate. The combined organic extracts were washed with brine, dried (over magnesium sulphate) and concentrated under reduced pressure to give the title compound (16.5 g) as a white solid.

$^1$H NMR (D$_6$DMSO): δ 7.41–7.30(5H, m), 7.00(1H, br.d), 5.02(2H, s), 4.65(1H, br.t), 4.40(1H, br.t), 3.50–3.20 (5H, m), 1.63–1.20(4H, m) ppm.

Intermediate 80

(2R)-2-{[(Benzyloxy)carbonyl]amino}-5-[(methylsulfonyl)oxy]pentyl methanesulfonate A solution of benzyl (1R)-4-hydroxy-1-(hydroxymethyl)butylcarbamate (1.5 g) in DCM (60 ml) was treated with triethylamine (3.3 ml) and stirred at room temperature for 10 min. Methanesulphonyl chloride (1.34 ml) was then added dropwise and the resultant mixture stirred at 0° C. for 75 min. Sodium bicarbonate solution was added and the reaction mixture allowed to reach room temperature over 1 h. The organic layer was separated, washed with brine, dried (over magnesium sulphate) and concentrated under reduced pressure to give a yellow oil. The oil was purified using Biotage™ chromatography (eluting with hexane:ethyl acetate 1:2, 1:3) to give the title compound (1.924 g) as a yellow oil Mass spectrum: Found: MH$^+$ 410.

Similarly prepared using Intermediate 80 was:

Intermediate 81

(2S)-2-{[(Benzyloxy)carbonyl]amino}-5-[(methylsulfonyl)oxy]pentyl methanesulfonate Mass spectrum: Found: MH$^+$ 410.

Intermediate 82

Benzyl (3R)-piperidin-3-ylcarbamate

Liquid ammonia (ca. 30 ml) was added to a solution of (2R)-2-{[(benzyloxy)carbonyl]amino}-5-[(methylsulfonyl)oxy]pentyl methanesulfonate (1 g) in THF (15 ml) at −78° C. in a bomb reaction vessel and then the resultant mixture was allowed to reach room temperature. After 46 h, the solution was concentrated under reduced pressure to give an off-white solid which was purified using SPE (silica, eluting with methanol, methanol:aqueous ammonia 95:5, 9:1) to give the title compound (0.587 g) as an off white solid.

Mass spectrum: Found: MH$^+$ 235.

Similarly prepared using Intermediate 81 was:

Intermediate 83

Benzyl (3S)-piperidin-3-ylcarbamate

Mass spectrum: Found: MH+ 235.

Intermediate 84

Benzyl (3S)-1-[(2S)-2-((3S)-3-{[(6-chloro-2-naphthyl)sulfonyl]amino}-2-oxopyrrolidin-1-yl)propanoyl]piperidin-3-ylcarbamate A solution of (2S)-2-((3S)-3-{[(6-chloro-2-naphthyl)sulfonyl]amino}-2-oxopyrrolidin-1-yl)propanoic acid (0.408 g) in DCM (21 ml) was treated with 1-[3-(dimethylamino)propyl]-3-ethylcarbodiimide hydrochloride (0.394 g), HOBT (0.278 g) and triethylamine (0.286 ml) and stirred at room temperature for 1 h. A solution of benzyl (3S)-piperidin-3-ylcarbamate (0.361 g) in DCM (1 ml) was then added and stirring continued for 72 h. The mixture was partitioned between DCM and water. The separated organic extracts were washed with water and brine, dried (over magnesium sulphate), and concentrated under reduced pressure. The residue was purified using Biotage™ chromatography (eluting with hexane:ethyl acetate 1:7→1:10) to give the title compound (0.268 g) as an oil.

Mass spectrum: Found: MH+ 614.

Intermediate 85

Benzyl (3R)-1-[(2S)-2-((3S)-3-{[(6-chloro-2-naphthyl)sulfonyl]amino}-2-oxopyrrolidin-1-yl)propanoyl]piperidin-3-ylcarbamate Using benzyl (3R)-piperidin-3-ylcarbamate and the procedure described for Intermediate 84, the title compound was prepared.

Mass spectrum: Found: MH+ 614.

Intermediate 86

Benzyl (3S)-1-[(1S)-1-methyl-2-morpholin-4-yl-2-oxoethyl]-2-oxopyrrolidin-3-ylcarbamate (2S)-2-((3S)-3-{[(Benzyloxy)carbonyl]amino}-2-oxopyrrolidin-1-yl)propanoic acid (84.5 g) was dissolved in DMF (2l) and O-(benzotriazol-1-yl)-N,N,N',N'-tetramethyluronium tetrafluoroborate (161 g) was added, followed by N,N-diisopropylethylamine (92 ml) and morpholine (46 ml). The mixture was stirred under nitrogen for 2.5 h, and saturated aqueous ammonium chloride was added. The mixture was stirred for 15 min then partitioned between water and ethyl acetate. The separated organic phase was washed with lithium chloride (10% by weight), followed by saturated sodium bicarbonate and brine. The organic layer was dried (over sodium sulphate) and concentrated under reduced pressure to give the title compound (65 g) as a yellow solid.

Mass spectrum: Found: MH+ 376.

Intermediate 87

(3S)-3-Amino-1-[(1S)-1-methyl-2-morpholin-4-yl-2-oxoethyl]pyrrolidin-2-one

A mixture of benzyl (3S)-1-[(1S)-1-methyl-2-morpholin-4-yl-2-oxoethyl]-2-oxopyrrolidin-3-ylcarbamate (20 g), 10% palladium on carbon (2 g) and ethanol (1.3 l) was stirred under an atmosphere of hydrogen for 16 h. The reaction mixture was filtered through Celite™ and the filtrate was concentrated under reduced pressure to give the title compound (12.3 g) as a pale white oil.

$^1$H NMR (D$_4$MeOH): δ 5.05(1H, dd), 3.59(9H, m), 3.37 (2H, m), 2.42(1H, m), 1.75(1H, m), 1.30(3H, d) ppm.

Intermediate 88

6-Chloro-N-((3S)-1-{(1S)-2-[(1R,5S)-3-(tert-butyloxycarbonyl)-7-diazabicyclo[3.3.1]non-3-yl]-1-methyl-2-oxoethyl}-2-oxopyrrolidin-3-yl)naphthalene-2-sulfonamide Using Example 408 and N-Boc-sarcosine, and the synthetic procedure described for Example 409, the title compound was prepared.

Mass spectrum: Found: MH+ 676.

Intermediate 89 tert-Butyl (2S)-2-((3S)-3-{[(2-methyl-1,3-thiazolyl)methyl]amino}-2-oxopyrrolidin-1-yl)propanoate A solution of 2-methyl-1,3-thiazole4-carbaldehyde (0.028 g) in DCM (2 ml) was treated with Intermediate 9 (0.05 g) followed by acetic acid (0.013 ml) and tetramethylammonium triacetoxyborohydride (0.116 g), and the resultant mixture stirred at room temperature for 66 h. The reaction mixture was partitioned between water and DCM. The organic layer was separated, dried (over magnesium sulphate) and concentrated under reduced pressure to give the title compound (0.07 g) as an oil.

Mass spectrum: Found: MH+ 340.

Using similar chemistry, the following were prepared:

Intermediate 90 tert-Butyl (2S)-2-{(3S)-2-oxo-3-[(pyridin-4-ylmethyl)amino]pyrrolidin-1-yl}propanoate Mass spectrum: Found: MH+ 320.

Intermediate 91 tert-Butyl (2S)-2-{(3S)-2-oxo-3-[(pyridin-2-ylmethyl)amino]pyrrolidin-1-yl}propanoate Mass spectrum: Found: MH+ 320.

Intermediate 92 tert-Butyl (2S)-2-((3S)-3-{[(6-chloro-2-naphthyl)sulfonyl][(2-methyl-1,3-thiazol-4-yl)methyl]amino}-2-oxopyrrolidin-1-yl)propanoate Using Intermediate 89 and the synthetic procedure described for Intermediate 25, the title compound was similarly prepared.

Mass spectrum: Found: MH+ 564.

Intermediate 93 tert-Butyl (2S)-2-{(3S)-3-[[(6-chloro-2-naphthyl)sulfonyl](pyridin-4-ylmethyl)amino]-2-oxopyrrolidin-1-yl}propanoate Using Intermediate 90 and the synthetic procedure described for Intermediate 25, the title compound was similarly prepared.
Mass spectrum: Found: MH+ 544.

Intermediate 94 tert-Butyl (2S)-2-{(3S)-3-[[(6-chloro-2-naphthyl)sulfonyl](pyridin-2-ylmethyl)amino]-2-oxopyrrolidin-1-yl}propanoate Using Intermediate 91 and the synthetic procedure described for Intermediate 25, the title compound was similarly prepared.
Mass spectrum: Found: MH+ 544.

Intermediate 95

(2S)-2-((3S)-3-{[(6-Chloro-2-naphthyl)sulfonyl][(2-methyl-1,3-thiazol-4-yl)methyl]amino}-2-oxopyrrolidin-1-yl)propanoic acid Using Intermediate 92 and the synthetic procedure described for Intermediate 13, the title compound was similarly prepared.
Mass spectrum: Found: MH+ 508.

Intermediate 96

(2S)-2-{(3S)-3-[[(6-Chloro-2-naphthyl)sulfonyl](pyridin-4-ylmethyl)amino}-2-oxopyrrolidin-1-yl}propanoic acid hydrochloride Using Intermediate 93 and the synthetic procedure described for Intermediate 13, the title compound was similarly prepared.
Mass spectrum: Found: MH+ 488.

Intermediate 97

(2S)-2-{(3S)-3-[[(6-Chloro-2-naphthyl)sulfonyl](pyridin-2-ylmethyl)amino]-2-oxopyrrolidin-1-yl}propanoic acid hydrochloride Using Intermediate 94 and the synthetic procedure described for Intermediate 13, the title compound was similarly prepared.
Mass spectrum: Found: MH+ 488.

Intermediate 98

(3S)-3-{[2-Methoxy-4-(2-polystyrylethoxy)benzyl]amino}-1-[(1S)-1-methyl-2-oxo-2-(1-piperidinyl)ethyl]-2-pyrrolidinone A solution of (3S)-3-amino-1-[(1S)-1-methyl-2-oxo-2-(1-piperidinyl)ethyl]-2-pyrrolidine (0.795 g) in anhydrous DMF (ca. 8 ml) was added to pre-swollen 2-(3-methoxy-4-formylphenoxy)ethoxymethyl polystryene resin (1.45 g) followed by the N,N-diisopropylethylamine (0.58 ml) and acetic acid (0.19 ml). The mixture was shaken at room temperature for 2 h, after which time a solution of tetra n-butylammonium borohydride (0.856 g) and acetic acid (0.19 ml) in anhydrous DMF (ca. 5 ml) was added. The mixture was shaken for 20 h at room temperature, filtered and washed with DMF, 10% ethanolamine in DMF, DMF, DCM, methanol and diethyl ether. The resultant resin was dried in vacuo to give the title compound (1.53 g) as pale yellow beads.
IR: $v_{max}$ 2890, 2327, 2282, 1749, 1715 and 1643 cm$^{-1}$

Intermediate 99

5-Bromo-N-[2-methoxy-4-(2-polystyrylethoxy)benzyl]-N-{(3S)-1-[(1S)-1-methyl-2-oxo-2-(1-piperidinyl)ethyl]-2-oxopyrrolidinyl}-2-thiophenesulfonamide Intermediate 98 pre-swollen with DCM (ca. 15 ml) and then filtered, was treated with a solution of 5-bromothiophene-2-sulfonyl chloride (0.85g) in DMF (15 ml), followed by N,N-diisopropylethylamine (1.14 ml). The mixture was shaken for 20 h at room temperature, filtered, washed with DMF, DCM and diethyl ether. The resultant solid was dried in vacuo to give the title compound (1.59 g) as an orange/brown resin.
0.025 g of this resin was treated with trifluoroacetic acid-DCM (1:1, 1 ml) and shaken for 2 h and filtered. The filtrate was concentrated under a stream of nitrogen to give Example 367 (0.0025 g) as an off-white glass.
Mass spectrum: Found: MH+ 465.

Intermediate 100 tert-butyl (2S)-2-((3S)-3-{[(6-chloro-2-naphthyl)sulfonyl](2-benzyloxy-2-oxoethyl)amino}-2-oxopyrrolidin-1-yl)propanoate To a solution of tert-butyl (2S)-2-((3S)-3-{[(6-chloro-2-naphthyl)sulfonyl]amino}-2-oxopyrrolidin-1-yl)propanoate (1 g) in DMF (20 ml) was added potassium carbonate (0.92 g) and benzyl-2-bromoacetate (0.33 g), and the mixture was stirred under nitrogen at room temperature for 72 h. The reaction mixture was filtered, concentrated under reduced pressure, and the residue partitioned between water and DCM. The organic layer was isolated, dried (over magnesium sulphate and purified by SPE (silica, cyclohexane:ethyl acetate 2:1) to give the title compound (1.0 g) as a white solid.
Mass spectrum: Found: MH+ 601.

Intermediate 101

Benzyl N-[(6-chloro-2-naphthyl)sulfonyl]-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)glycinate formate A mixture of Intermediate 100 (0.5 g) was dissolved in DCM (10 ml) and cooled to 0° C., using an ice bath. Trifluoroacetic acid (10 ml) was added dropwise, and the solution left to warm to room temperature over 2 h. The reaction mixture was concentrated under reduced pressure to give a clear residue (0.45 g) that was dissolved in DCM (20 ml). 1-Hydroxybenzotriazole hydrate (0.34 g), 1-[3-(dimethylamino)propyl]-3-ethylcarbodiimide hydrochloride (0.48 g) and (S)-(+)-1-(2-pyrrolidinylmethyl)pyrrolidine (0.39 g) were added, and the resultant solution was stirred at room temperature for 0.5 h. Triethylamine (0.5 ml) was added, and the resultant mixture stirred under nitrogen for 72 h. The mixture was washed with water and the aqueous layer re-extracted with DCM. The combined organic layers were dried (over magnesium sulfate), filtered and concentrated under reduced pressure. The residue was purified by mass directed preparative h.p.l.c. to give the title compound (0.18 g) as a white solid.

Mass spectrum: Found: $MH^+$ 681.

Intermediate 102

5-Chloro-1-benzofuran

To a solution of 5-chloro-1-benzofuran-2-carboxylic acid (0.2 g) in 1-methyl-2-pyrrolidinone (2 ml) was added copper granules (0.2 g). The reaction mixture was heated at 250° C. for 3.5 min in a microwave. The reaction vessel was cooled to room temperature and the mixture combined with four other similar mixtures and the combined mixtures partitioned between water and diethyl ether. The organic layer was washed with water and brine, dried (over magnesium sulphate) and concentrated under reduced pressure to give the title compound (0.65 g) as a yellow oil.

Gas-chromatography electron-ionisation spectrum: Found: $M^+$ 152, Rt 5.72 min.

Intermediate 103

5-Chloro-1-benzofuran-2-sulfonyl chloride n-Butyl lithium (1.6M in hexanes, 0.45 ml) was added to a cooled (−78° C.) solution of Intermediate 102 (0.11 g) in anhydrous THF (5 ml) over 5 min. The reaction was stirred for a further 5 min, warmed to −45° C. and stirred for 40 min. The mixture was cooled to −70° C. and sulphur dioxide gas bubbled into the vessel over 7 min. The solution was allowed to warm to room temperature over 45 min, and then concentrated under reduced pressure to give a yellow gum. To a suspension of the gum in anhydrous DCM (4 ml) was added N-chlorosuccinimide (0.118 g) and the mixture stirred at room temperature for 75 min. The solution was filtered, and the filtrate concentrated under reduced pressure to give the title compound (0.093 g) as a yellow solid.

Mass Spectrum: Found: $MH^+$ 260 for dimethylamine quenched sample.

Intermediate 104

2-Chloro-4-ethenylphenol

To a slurry of methyltriphenylphosphonium bromide (0.23 g) in dry THF (5 ml) under nitrogen at −78° C., n-butyl lithium (1.6M in hexanes, 0.37 ml) was added dropwise over 2 min. The mixture was allowed to warm to 0° C., stirred for 20 min, cooled to −78° C. and a solution of 3-chloro-4-[[(1, 1-dimethylethyl)dimethylsilyl]oxy]benzaldehyde* (0.134 g) in dry THF (5 ml) added. The reaction mixture was allowed to reach room temperature overnight and quenched with saturated aqueous ammonium chloride. The resultant mixture was extracted with diethyl ether and the combined organic extracts were concentrated under reduced pressure. The residue was purified using SPE (silica, eluting with cyclohexane, followed by 5% to 25% ethyl acetate:cyclohexane) to give the title compound (0.049 g) as an oil.

*Boukouvalas, J; Maltais, F; Lachance, N., Tetrahedron Lett. (1994), 35(43), 7897–900.

H.p.l.c. (1) Rt 3.26 min.

Intermediate 105 tert-Butyl(2-chloro-4-vinylphenoxy)diphenylsilane

A mixture of Intermediate 104 (0.038 g), imidazole (0.042 g) and tert-butyldiphenylsilyl chloride (0.083 ml) was stirred in dry DMF (0.5 ml) at room temperature under nitrogen for 20 h. The mixture was quenched with water, extracted with diethyl ether, dried (over magnesium sulphate), filtered and concentrated under reduced pressure. The resultant oil was purified using SPE (silica, eluting with cyclohexane followed by 5% to 20% ethyl acetate:cyclohexane) to give the title compound (0.102 g) as an oil.

H.p.l.c. (1) Rt 4.71 min.

Intermediate 106

3-{[tert-Butyl(dimethyl)silyl]oxy}-4-chlorobenzaldehyde

A mixture of 4-chloro-3-hydroxy-benzaldehyde* (0.354 g), 4-N,N-dimethylaminopyridine (0.028 g), tert-butyldimethylsilyl chloride (0.409 g) and triethylamine (0.473 ml) in DCM (15 ml) was stirred at room temperature under nitrogen for 19 h. The mixture was quenched with saturated aqueous sodium bicarbonate and extracted with diethyl ether. The combined organic extracts were concentrated under reduced pressure to give an oil which was purified using SPE (silica, eluting with cyclohexane followed by 10% to 30% ethyl acetate-cyclohexane) to give the title compound (0.42 g) as an oil.

*Kelley, J; Linn, J; Selway, J. W. T., J. Med. Chem. (1989), 32(8), 1757–63.

H.p.l.c. (1) Rt 4.11 min.

Intermediate 107

2-Chloro-5-vinylphenol

The title compound was prepared using Intermediate 106, and the synthetic procedure described for Intermediate 104.

H.p.l.c. (1) Rt 3.22 min.

Intermediate 108 tert-Butyl(2chloro-5-vinylphenoxy)diphenylsilane

The title compound was prepared using Intermediate 107, and the synthetic procedure described for Intermediate 105.

H.p.l.c. (1) Rt 4.68 min.

Intermediate 109

(E)-2-(3-{[tert-Butyl(diphenyl)silyl]oxy}-4-chlorophenyl)-N-{(3S)-1-[(1S)-1-methyl-2-morpholin-4-yl-2-oxoethyl]-2-oxopyrrolidin-3-yl}ethenesulfonamide Sulphuryl chloride (0.103 ml) was added dropwise to DMF (0.116 ml) at 0° C. under nitrogen, over 5 min. The mixture was allowed to reach room temperature and stirred for 30 min. Intermediate 108 (0.293 g) in cyclohexane (0.2 ml) was added in one portion and the resultant mixture was heated at 90° C. for 6 h. The cooled mixture was poured onto crushed ice, extracted with diethyl ether, dried (over sodium sulphate) and concentrated under reduced pressure. This crude sulfonyl chloride was treated with Intermediate 87 (0.134 g), 4-dimethylaminopyridine (0.0068 g), di-isopropylethylamine (0.192 ml) in dry DCM (5 ml), and after stirring for 3 days at room temperature under nitrogen, the mixture was concentrated under reduced pressure. The resultant solution was washed with water and filtered through a hydrophobic frit. The filtrate was concentrated under reduced pressure, and the remaining oil purified by SPE (silica, eluting with cyclohexane/ethyl acetate 19:1 and then 10:1) followed by mass directed preparative h.p.l.c. to give the title compound (0.0078 g) as a colourless gum.

Mass spectrum: Found: $MH^+$ 696.

Intermediate 110

Ethyl 2-azido-4-{[1-(tert-butoxycarbonyl)propyl]amino}butanoate

To a solution of tert-butyl 2-amino-butanoate (0.397 g) and ethyl 2-azido-4-bromo-butanoate (0.286 g) in acetonitrile (5 ml) was added triethylamine (0.347 ml). The mixture was heated at 50° C. for 18 h, cooled and evaporated onto silica gel (Merck.7734). The pre-absorbed material was purified by flash column chromatography (Merck. 9385, eluting with cyclohexane:ethyl acetate 6:1) to give the title compound (0.200 g) as a mixture of four diastereomers.

Mass spectrum: Found: $MH^+$ 315.

Intermediate 111

2-Azido-4-{[1-(tert-butoxycarbonyl)propyl]amino}butanoic acid

To a solution of Intermediate 110 (0.2 g) in THF (3 ml) and water (3 ml) was added lithium hydroxide (0.038 g) and the resultant solution was stirred at room temperature for 18 h. The pH of the reaction mixture was adjusted to pH5 with 2N aqueous HCl. The mixture was then concentrated under reduced pressure to give the title compound (0.187 g) as a mixture of four diastereomers.

Mass spectrum: Found: $MH^+$ 287.

Intermediate 112 and Intermediate 113 tert-Butyl 2-(3-azido-2-oxopyrrolidin-1-yl)butanoate [Mixture 1 and Mixture 2]

A solution of Intermediate 111 (0.187 g), diphenylphosphoryl azide (0.281 ml) and triethylamine (0.364 ml) in DMF (5 ml) was stirred at room temperature for 48 h and then concentrated under reduced pressure. The mixture was partitioned between ethyl acetate and water and the organic extract was concentrated under reduced pressure. The resultant oil was purified by flash chromatography (Merck. 9385, eluting with cyclohexane:ethyl acetate 1:1) to give the title diastereomeric compounds as two enantiomeric pairs (0.051 g and 0.039 g).

Mass Spectrum: Found: $MH^+$ 269 for both Mixture 1 and Mixture 2.

Intermediate 114 tert-Butyl 2-(3-{[(6-chloro-2-naphthyl)sulfonyl]amino}-2-oxopyrrolidin-1-yl)butanoate [Isomer 1 and Isomer 2]

A mixture of Intermediate 112 [Mixture 1] (0.051 g), 10% palladium on carbon (0.01 g) and ethanol (5 ml) was stirred under an atmosphere of hydrogen for 18 h. The reaction mixture was filtered through Celite™ and the filtrate was concentrated under reduced pressure to give a yellow gum. The gum (0.034 g) in DCM (2 ml) was treated with 6-chloronaphthylsulphonyl chloride[1] (0.04 g) and N,N-di-isopropylamine (0.073 ml) and stirred at room temperature for 24 h. The mixture was washed with water and concentrated under reduced pressure to yield an oil which was partially purified using SPE (silica, eluting with cyclohexane:ethyl acetate 1:1) to give the title compound (0.043 g) as a white solid.

Mass spectrum: Found: $MH^+$ 467.

Using Intermediate 113 and similar chemistry to that described above, the following was prepared:

Intermediate 115 tert-Butyl 2-(3-{[(6-chloro-2-naphthyl)sulfonyl]amino}-2-oxopyrrolidin-1-yl)butanoate [Isomer 3 and Isomer 4]

Mass spectrum: Found: $MH^+$ 467.

Intermediate 116

2-(3-{[(6-Chloro-2-naphthyl)sulfonyl[amino}-2-oxopyrrolidin-1-yl)butanoic acid [Isomer 1 and Isomer 2]

Using Intermediate 114 and the synthetic procedure described for Intermediate 13, the title compound was prepared.

H.p.l.c. (1) Rt 3.11 min.

Intermediate 117

2-(3-{[(6-Chloro-2-naphthyl)sulfonyl]amino}-2-oxopyrrolidin-1-yl)butanoic acid [Isomer 3 and Isomer 4]

Using Intermediate 115 and the synthetic procedure described for Intermediate 13, the title compound was prepared.

H.p.l.c. (1) Rt 3.20 min.

Intermediate 118

5-Chlorothieno[3,2-b]pyridine-2-sulfonyl chloride

5-Chlorothieno[3,2-b]pyridine* (0.2 g) was dissolved in anhydrous THF (10 ml) under nitrogen and cooled to −70° C. n-Butyllithium (1.6M in hexanes, 0.780 ml) was added dropwise over 10 min and the mixture stirred for a further 5 min. The mixture was warmed to −50° C. and stirred for 55 min. The reaction was cooled to −70° C., and sulphur dioxide gas was bubbled through the reaction for 10 min. The reaction was allowed to warm to room temperature and concentrated under reduced pressure to give a yellow residue which was re-suspended in anhydrous DCM (6 ml) and treated with N-chlorosuccinimide (0.189 g). The mixture was stirred for 2 h at room temperature and any remaining solid removed by filtration. The filtrate was concentrated under reduced pressure to give the title compound (0.153 g) as a white solid.

*Barker. J. N, et.al., J. Chem. Res. (1984), (3), 771–795.

Mass Spectrum: Found: $MH^+$ 277 for dimethylamine quenched mass spectrum sample.

Intermediate 119

(2R)-2-(3-{[(6-Bromo-2-naphthyl)sulfonyl]amino}-2-oxopyrrolidin-1-yl)propanoic acid Using Intermediate 33 and 6-bromo-2-naphthalenesulfonyl chloride and similar chemistry to that described for Intermediates 35 and 37, the title compound was prepared.
Mass spectrum: Found: MH+ 442.

Intermediate 120

(2R)-2-(3-{[(5-Chloro-3-methyl-1-benzothien-2-yl)sulfonyl]amino}-2-oxopyrrolidin-1-yl)propanoic acid Using Intermediate 33 and 5-chloro-3-methylbenzo[b]thiophene-2-sulphonyl chloride and similar chemistry to that described for Intermediates 35 and 37, the title compound was prepared.
Mass spectrum: Found: MH+ 417.

Example 1

6-Chloro-N-{(3S)-1-[(1S)-1-methyl-2-morpholin-4-yl-2-oxoethyl]-2-oxopyrrolidin-3-yl}naphthalene-2-sulfonamide To a solution of (2S)-2-((3S)-3-{[(6-chloro-2-naphthyl)sulfonyl]amino}-2-oxopyrrolidin-1-yl)propanoic acid [Intermediate 29] (0.105 g) in DCM (10 ml) were added 1-[3-(dimethylamino)propyl]-3-ethylcarbodiimide hydrochloride (0.152 g), HOBT (0.107 g) and triethylamine (0.222 ml) and the mixture was stirred at room temperature for 30 min. Morpholine (0.07 ml) was added and the resultant mixture stirred at room temperature for 16 h. The mixture was partitioned between DCM and water. The aqueous layer was re-extracted with DCM and the combined, dried (over magnesium sulphate) organic extracts were concentrated under reduced pressure. The residue was purified using SPE (silica, eluting with cyclohexane:ethyl acetate 5:1, and ethyl acetate) to give the title compound (0.1 g) as a white solid.
Mass spectrum: Found: MH+ 466 H.p.l.c. (1) Rt 3.13 min
1H NMR (D4MeOH): δ 3 8.54(1H, br.s), 8.08–7.96(4H, m), 7.63(1H, dd), 5.00(1 H, q), 4.18(1H, dd), 3.69–3.46(9H, m), 3.31–3.29(1H, m), 2.27(1H, m), 1.77(1H, m), 1.26(3H, d) ppm.

The title compound could also be prepared using Intermediate 87 and 6-chloronaphthalene sulphonyl chloride[1], and the chemistry described for the preparation of Example 386 (Route 1).

Using similar chemistry to that described for Example 1, the following were prepared:

Example 2

6-Chloro-N-{(3S)-1-[(1S)-1-methyl-2-oxo-2-piperidin-1-ylethyl]-2-oxopyrrolidin-3-yl}naphthalene-2-sulfonamide Mass spectrum: Found: MH+ 464 H.p.l.c. (1) Rt 3.22 min.

Example 3

6-Chloro-N-{(3S)-1-{(1S)-1-methyl-2-oxo-2-[(2S)-2-(pyrrolidin-1-ylmethyl)pyrrolidin-1-yl]ethyl}-2-oxopyrrolidin-3-yl)naphthalene-2-sulfonamide formate The title compound was isolated from a crude reaction mixture using mass directed preparative h.p.l.c.
Mass spectrum: Found: MH+ 533 H.p.l.c. (1) Rt 2.64 min.

Example 4

6-Chloro-N-((3S)-1-{(1S)-1-methyl-2-[(2R)-2-methylpiperidin-1-yl]-2-oxoethyl}-2-oxopyrrolidin-3-yl)naphthalene-2-sulfonamide Mass spectrum: Found: MH+ 478 H.p.l.c. (1) Rt 3.1 min.

Example 5

6-Chloro-N-[(3S)-1-((1S)-2-{-2-[(diethylamino)methyl]piperidin-1-yl}-1-methyl-2-oxoethyl}-2-oxopyrrolidin-3-yl]naphthalene-2-sulfonamide Mass spectrum: Found: MH+ 549 H.p.l.c. (1) Rt 2.5 min.

Example 6

6-Chloro-N-((3S)-1-{(1S)-1-methyl-2-oxo-2-[2-(pyrrolidin-1-ylmethyl)piperidin-1-yl]ethyl}-2-oxopyrrolidin-3-yl)naphthalene-2-sulfonamide formate Mass spectrum: Found: MH+ 547 H.p.l.c. (1) Rt 2.76 min.

Example 7

1-[(2S)-2-((3S)-3-{[(6-Chloro-2-naphthyl)sulfonyl]amino}-2-oxopyrrolidin-1-yl)propanoyl]piperidine-3-carboxamide Mass spectrum: Found: MH+ 507 H.p.l.c. (1) Rt 3.06 min.

Example 8

6-Chloro-N-{(3S)-1-[(1S)-1-methyl-2-oxo-2-(3-{[(trifluoromethyl)sulfonyl]amino)piperidin-1-yl)ethyl]-2-oxopyrrolidin-3-yl}naphthalene-2-sulfonamide Mass spectrum: Found: MH+ 612 H.p.l.c. (1) Rt 3.59 min.

Example 9

1-[(2S)-2-((3S)-3-{[(6-Chloro-2-naphthyl)sulfonyl]amino}-2-oxopyrrolidin-1-yl)propanoyl]piperidine-2-carboxamide Mass spectrum: Found: MH+ 507 H.p.l.c. (1) Rt 3.16 min.

Example 10

1-[(2S)-2-((3S)-3-{[(6-Chloro-2-naphthyl)sulfonyl]amino}-2-oxopyrrolidin-1-yl)propanoyl]piperidine-4-carboxamide Mass spectrum: Found: MH+ 507 H.p.l.c. (1) Rt 3.04 min.

Example 11

6-Chloro-N-{(3S)-1-[(1S)-1-methyl-2-oxo-2-piperazin-1-ylethyl]-2-oxopyrrolidin-3-yl}naphthalene-2-sulfonamide trifluoroacetate tert-Butyl 4-[(2S)-2-((3S)-3-{[(6-chloro-2-naphthyl)sulfonyl]amino}-2-oxopyrrolidin-1-yl)propanoyl]piperazine-1-carboxylate was prepared using the generic method as described for Example 1. The title compound was prepared using the synthetic procedure as described for Intermediate 13.

Mass spectrum: Found: MH+ 465 H.p.l.c. (1) Rt 2.48 min.

Example 12

6-Chloro-N-{(3S)-1-[(1S)-1-methyl-2oxo-2-(5-oxo-1,4-diazepan-1-yl)ethyl]-2-oxopyrrolidin-3-yl}naphthalene-2-sulfonamide Mass spectrum: Found: MH+ 493 H.p.l.c. (1) Rt 2.74 min.

Example 13

6-Chloro-N-{(3S)-1-[(1S)-1-methyl-2-(4-methyl-5-oxo-1,4-diazepan-1-yl)-2-oxoethyl]-2-oxopyrrolidin-3-yl}naphthalene-2-sulfonamide Mass spectrum: Found: MH+ 507 H.p.l.c. (1) Rt 2.81 min.

Example 14

6-Chloro-N-[(3S)-1-((1S)-1-methyl-2-{2-[(4-methylpiperazin-1-yl)methyl]pyrrolidin-1-yl}-2-oxoethyl)-2-oxopyrrolidin-3-yl]naphthalene-2-sulfonamide formate Mass spectrum: Found: MH+ 562 H.p.l.c. (1) Rt 2.53 min.

Example 15

6-Chloro-N-((3S)-1-(1S)-1-methyl-2-[2-(morpholin-4-ylmethyl)pyrrolidin-1-yl]-2-oxoethyl}-2-oxopyrrolidin-3-yl)naphthalene-2-sulfonamide formate Mass spectrum: Found: MH+ 549 H.p.l.c. (1) Rt 2.56 min.

Example 16

6-Chloro-N-{(3S)-1-[(1S)-1-methyl-2-oxo-2-pyrrolidin-1-ylethyl]-2-oxopyrrolidin-3-yl}naphthalene-2-sulfonamide Mass spectrum: Found: MH+ 450 H.p.l.c. (1) Rt 3.0 min.

Example 17

6-Chloro-N-{(3S)-1-[(1S)-2-(2,6-dimethylmorpholin-4-yl)-1-methyl-2-oxoethyl]-2-oxopyrrolidin-3-yl}naphthalene-2-sulfonamide Mass spectrum: Found: MH+ 494 H.p.l.c. (1) Rt 3.16 min.

Example 18

6-Chloro-N-((3S)-1-{(1S)-1-methyl-2-[(1S,4S)-2-oxa-5-azabicyclo[2.2.1]hept-5-yl]-2-oxoethyl}-2-oxopyrrolidin-3-yl)naphthalene-2-sulfonamide Mass spectrum: Found: MH+ 478 H.p.l.c. (1) Rt 2.93 min.

Example 19

6-Chloro-N-{(3S)-1-(1S)-1-methyl-2-(3-methylmorpholin-4-yl)-2-oxoethyl]-2-oxopyrrolidin-3-yl}naphthalene-2-sulfonamide Mass spectrum: Found: MH+ 480 H.p.l.c. (1) Rt 3.23 min.

Example 20

6-Chloro-N-((3S)-1-{(1S)-1-methyl-2-oxo-2-[2-(2-pyrrolidin-1-ylethyl)piperidin-1-yl]ethyl}-2-oxopyrrolidin-3-yl)naphthalene-2-sulfonamide [Isomer 1]

Mass spectrum: Found: MH+ 561 H.p.l.c. (1) Rt 2.73 min.

Example 21

6-Chloro-N-((3S)-1-{(1S)-1-methyl-2-oxo-2-[2-(2-pyrrolidin-1-ylethyl)piperidin-1-yl]ethyl)-2-oxopyrrolidin-3-yl)naphthalene-2-sulfonamide [Isomer 2]

Mass spectrum: Found: MH+ 561 H.p.l.c. (1) Rt 2.74 min.

Example 22

Methyl 1-(2S)-2-((3S)-3-{[(6-chloro-2-naphthyl)sulfonyl]amino}-2-oxopyrrolidin-1-yl)propanoyl]piperidine-2-carboxylate Mass spectrum: Found: MH+ 522 H.p.l.c. (1) Rt 3.57 min.

Example 23

6-Chloro-N-((3S)-1-{(1S)-1-methyl-2-oxo-2-[3-(pyrrolidin-1-ylcarbonyl)morpholin-4-yl]ethyl}-2-oxopyrrolidin-3-yl)naphthalene-2-sulfonamide Mass spectrum: Found: MH+ 563 H.p.l.c. (1) Rt 3.08 min.

Example 24

6-Chloro-N-[(3S)-1-((1S)-1-methyl-2-{2-[(methylsulfonyl)methyl]morpholin-4-yl-}2-oxoethyl)-2-oxopyrrolidin-3-yl]naphthalene-2-sulfonamide Mass spectrum: Found: MH+ 558 H.p.l.c. (1) Rt 3.17 min.

Example 25

6-Chloro-N-((3S)-1-(1S)-2-[2-(methoxymethyl)morpholin-4-yl]-1-methyl-2-oxoethyl}-2-oxopyrrolidin-3-yl)naphthalene-2-sulfonamide Mass spectrum: Found: MH+ 510 H.p.l.c. (1) Rt 3.02 min.

Example 26 and Example 27

4-[(2S)-2-((3S)-3-{[(6-Chloro-2-naphthyl)sulfonyl]amino}-2-oxopyrrolidin-1-yl)propanoyl]-N-methylmorpholine-2-carboxamide [Isomer 1 and Isomer 2]

Isomer 1
Mass spectrum: Found: MH+ 523 H.p.l.c. (1) Rt 2.93 min.

Isomer 2
Mass spectrum: Found: MH+ 523 H.p.l.c. (1) Rt 2.96 min.

Example 28

6-Chloro-N-((3S)-1-(1S)-1-methyl-2-oxo-2-[2-(pyrrolidin-1-ylcarbonyl)morpholin-4-yl]ethyl}-2-oxopyrrolidin-3-yl)naphthalene-2-sulfonamide Mass spectrum: Found: MH+ 563 H.p.l.c. (1) Rt 3.04 min.

Example 29

4-[(2S)-2-((3S)-3-{[(6-Chloro-2-naphthyl)sulfonyl]amino-}2-oxopyrrolidin-1-yl)propanoyl]-N,N-dimethylmorpholine-2-carboxamide Mass spectrum: Found: MH+ 537 H.p.l.c. (1) Rt 2.96 min.

Example 30 Example 31 and Example 32

4-[(2S)-2-((3S)-3-{[(6-Chloro-2-naphthyl)sulfonyl]amino}-2-oxopyrrolidin-1-yl)propanoyl]-N-(2-hydroxypropyl)morpholine-2-carboxamide [Isomer 1, Isomer 2 and Isomer 3]

Isomer 1
Mass spectrum: Found: MH+ 567. H.p.l.c. (1) Rt 2.92 min.

Isomer 2
Mass spectrum: Found: MH+ 567. H.p.l.c. (1) Rt 2.91 min.

Isomer 3
Mass spectrum: Found: MH+ 567. H.p.l.c. (1) Rt 2.92 min.

Example 33

4-[(2S)-2-((3S)-3-{[(6-Chloro-2-naphthyl)sulfonyl]amino}-2-oxopyrrolidin-1-yl)propanoyl]-N,N-diisopropylmorpholine-2-carboxamide Mass spectrum: Found: MH+ 593. H.p.l.c. (1) Rt 3.4 min.

Example 34

6-Chloro-N-((3S)-1-{(1S)-1-methyl-2-oxo-2-[2-(piperidin-1-ylcarbonyl)morpholin-4-yl]ethyl}-2-oxopyrrolidin-3-yl)naphthalene-2-sulfonamide Mass spectrum: Found: MH+ 577. H.p.l.c. (1) Rt 3.21 min.

Example 35

6-Chloro-N-[(3S)-1-((1S)-1-methyl-2-{2-[(methylamino)methyl]morpholin-4-yl}-2-oxoethyl)-2-oxopyrrolidin-3-yl]naphthalene-2-sulfonamide formate Mass spectrum: Found: MH+ 509. H.p.l.c. (1) Rt 2.58 min.

Example 36

6-Chloro-N-((3S)-1-{(1S)-1-methyl-2-oxo-2-[2-(pyrrolidin-1-ylmethyl)morpholin-4-yl]ethyl}-2-oxopyrrolidin-3-yl)naphthalene-2-sulfonamide formate Mass spectrum: Found: MH+ 549. H.p.l.c. (1) Rt 2.58 min.

Example 37

6-Chloro-N-{(3S)-1-[(1S)-2-(2-{[(2-hydroxypropyl)amino]methyl}morpholin-4-yl)-1-methyl-2-oxoethyl]-2-oxopyrrolidin-3-yl}naphthalene-2-sulfonamide formate Mass spectrum: Found: MH+ 553. H.p.l.c. (1) Rt 2.55 min.

Example 38 and Example 39

6-Chloro-N-{(3S)-1-((1S)-2-{2-[(dimethylamino)methyl]morpholin-4-yl}-1-methyl-2-oxoethyl]-2-oxopyrrolidin-3-yl}naphthalene-2-sulfonamide formate (Isomer 1 and Isomer 2]

Isomer 1
Mass spectrum: Found: MH+ 523. H.p.l.c. (1) Rt 2.54 min.

Isomer 2
Mass spectrum: Found: MH+ 523. H.p.l.c. (1) Rt 2.55 min.

Example 40

6-Chloro-N-[(3S)-1-((1S)-2-{2-[(diisopropylamino)methyl]morpholin-4-yl}-1-methyl-2-oxoethyl)-2-oxopyrrolidin-3-yl]naphthalene-2-sulfonamide formate Mass spectrum: Found: MH+ 579. H.p.l.c. (1) Rt 2.67 min.

Example 41

6-Chloro-N-((3S)-1-{(1S)-1-methyl-2-oxo-2-[2-(piperidin-1-ylmethyl)morpholin-4-yl]ethyl}-2-oxopyrrolidin-3-yl)naphthalene-2-sulfonamide formate Mass spectrum: Found: MH+ 563. H.p.l.c. (1) Rt 2.62 min.

Example 42 and Example 43

6-Chloro-N-{(3S)-1-[(1S)-1-methyl-2-oxo-2-(2-pyridin-3-ylpyrrolidin-1-yl)ethyl]-2-oxopyrrolidin-3-yl}naphthalene-2-sulfonamide [Isomer 1 and Isomer 2]

Isomer 1
Mass spectrum: Found: MH$^+$ 528. H.p.l.c. (1) Rt 2.78 min.

Isomer 2
Mass spectrum: Found: MH$^+$ 528. H.p.l.c. (1) Rt 2.81 min.

Example 44

6-Chloro-N-{(3S)-1-[(1S)-2-(3,3-difluoropiperidin-1-yl)-1-methyl-2-oxoethyl]-2-oxopyrrolidin-3-yl}naphthalene-2-sulfonamide Mass spectrum: Found: MH$^+$ 500. H.p.l.c. (1) Rt 3.34 min.

Example 45

6-Chloro-N-{(3S)-1-[(1S)-2-(4,4-difluoropiperidin-1-yl)-1-methyl-2-oxoethyl]-2-oxopyrrolidin-3-yl}naphthalene-2-sulfonamide Mass spectrum: Found: MH$^+$ 500. H.p.l.c. (1) Rt 3.33 min.

Example 46

N-{(3S)-1-[(1S)-2-Azetidin-1-yl-1-methyl-2-oxoethyl]-2-oxopyrrolidin-3-yl}-6-chloronaphthalene-2-sulfonamide Mass spectrum: Found: MH$^+$ 436. H.p.l.c. (1) Rt 2.99 min.

Example 47

6-Chloro-N-{(3S)-1-[(1S)-2-(3-hydroxyazetidin-1-yl)-1-methyl-2-oxoethyl]-2-oxopyrrolidin-3-yl}naphthalene-2-sulfonamide Mass spectrum: Found: MH$^+$ 452. H.p.l.c. (1) Rt 2.99 min.

Example 48

6-Chloro-N-((3S)-1-{(1S)-2-[(2R,6S)-2,6-dimethylmorpholin-4-yl]-1-methyl-2-oxoethyl}-2-oxopyrrolidin-3-yl)naphthalene-2-sulfonamide Mass spectrum: Found: MH$^+$ 494. H.p.l.c. (1) Rt 3.15 min.

Example 49

6-Chloro-N-{(3S)-1-[(1S)-2-(3,4-dihydro-1,6-naphthyridin-1(2H)-yl)-1-methyl-2-oxoethyl]-2-oxopyrrolidin-3-yl}naphthalene-2-sulfonamide Mass spectrum: Found: MH$^+$ 513. H.p.l.c. (1) Rt 2.66 min.

Example 50

6-Chloro-N-((3S)-1-{(1S)-1-methyl-2-[(1 S,4S)-2-oxa-5-azabicyclo[2.2.1]hept-5-yl]-2-oxoethyl}-2-oxopyrrolidin-3-yl)naphthalene-2-sulfonamide Mass spectrum: Found: MH$^+$ 478. H.p.l.c. (1) Rt 2.93 min.

Example 51

N-((3S)-1-{(1S)-2-[(1R,4S)-2-Azabicyclo[2.2.1]hept-2-yl]-1-methyl-2-oxoethyl}-2-oxopyrrolidin-3-yl)-6-chloronaphthalene-2-sulfonamide Mass spectrum: Found: MH$^+$ 476. H.p.l.c. (1) Rt 3.17 min.

Example 52

6-Chloro-N-{(3S)-1-[(1S)-1-methyl-2-oxo-2-(2-pyridin-4-ylpyrrolidin-1-yl)ethyl]-2-oxopyrrolidin-3-yl}naphthalene-2-sulfonamide formate Mass spectrum: Found: MH$^+$ 527. H.p.l.c. (1) Rt 2.67 min.

Example 53

6-Chloro-N-{(3S)-1-[(1S)-1-methyl-2-oxo-2-(2-pyridin-4-ylpyrrolidin-1-yl)ethyl]-2-oxopyrrolidin-3-yl}naphthalene-2-sulfonamide formate Mass spectrum: Found: MH$^+$ 527. H.p.l.c. (1) Rt 2.66 min.

Example 54

6-Chloro-N-{1-[(1S)-1-methyl-2-(4-methylpiperazin-1-yl)-2-oxoethyl-1-2-oxopyrrolidin-3-yl}naphthalene-2-sulfonamide Using Intermediate 38, and the synthetic procedure described for Example 1, the title compound was prepared.
Mass spectrum: Found: MH$^+$ 479. H.p.l.c. (1) Rt 2.93 min.

Using similar chemistry, the following was prepared:

Example 55

N-{1[(1S)-2-Azepan-1-yl-1-methyl-2-oxoethyl]-2-oxopyrrolidin-3-yl}-6-chloronaphthalene-2-sulfonamide Mass spectrum: Found: MH$^+$ 478. H.p.l.c. (1) Rt 2.93 min.

Example 56

N-{(3S)-1-[(1S)-2-(2-Azabicyclo[2.2.2]oct-2-yl)-1-methyl-2-oxoethyl]-2-oxopyrrolidin-3-yl}-6-chloronaphthalene-2-sulfonamide Mass spectrum: Found: MH$^+$ 490. H.p.l.c. (1) Rt 3.28 min.

Example 57

6-Chloro-N-{(3R)-1-[(1S)-1-methyl-2-oxo-2-piperidin-1-ylethyl]-2-oxopyrrolidin-3-yl}naphthalene-2-sulfonamide Using Intermediate 31, and the synthetic procedure described for Example 1, the title compound was prepared.
Mass spectrum: Found: MH$^+$ 464. H.p.l.c. (1) Rt 3.28 min.
Using similar chemistry, the following were prepared:

Example 58

6-Chloro-N-{(3R)-1-[(1S)-1-methyl-2-morpholin-4-yl-2-oxoethyl]-2-oxopyrrolidin-3-yl}naphthalene-2-sulfonamide Mass spectrum: Found: MH$^+$ 466. H.p.l.c. (1) Rt 2.96 min.

Example 59

6-Chloro-N-{(3R)-1-[(1S)-1-methyl-2-oxo-2-pyrrolidin-1-ylethyl]-2-oxopyrrolidin-3-yl}naphthalene-2-sulfonamide Mass spectrum: Found: MH$^+$ 450. H.p.l.c. (1) Rt 3.12 min.

Example 60

6-Chloro-N-((3R)-1-{(1S)-1-methyl-2-[(2R)-2-methylpiperidin-1-yl]-2-oxoethyl}-2-oxopyrrolidin-3-yl)naphthalene-2-sulfonamide Mass spectrum: Found: MH$^+$ 478. H.p.l.c. (1) Rt 3.38 min.

Example 61

6-Chloro-N-[(3R)-1-((1S)-2-{2-[(diethylamino)methyl]piperidin-1-yl}-1-methyl-2-oxoethyl)-2-oxopyrrolidin-3-yl]naphthalene-2-sulfonamide Mass spectrum: Found: MH$^+$ 549. H.p.l.c. (1) Rt 2.67 min.

Example 62

5'-Chloro-N-{(3S)-1-[(1S)-1-methyl-2-morpholin-4-yl-2-oxoethyl]-2-oxopyrrolidin-3-yl}-2,2'-bithiophene-5-sulfonamide tert-Butyl (2S)-2-((3S)-3-{[(5'-chloro-2,2'-bithien-5-yl)sulfonyl]amino}-2-oxopyrrolidin-1-yl)propanoate (0.217 g) was dissolved in DCM (2 ml) and treated with trifluoroacetic acid (2 ml) and stirred at room temperature for 2 h. The mixture was then concentrated under reduced pressure to give an oil which was subsequently dissolved in DCM (5 ml) and treated with 1-[3-(dimethylamino)propyl]-3-ethylcarbodiimide hydrochloride (0.256 g), HOBT (0.184 g) and triethylamine (0.375 ml). After the solution had been stirred at room temperature for 30 min., morpholine (0.117 ml) was added and the resultant mixture stirred for a further 20 h. The mixture was concentrated under reduced pressure and the residue partitioned between DCM and water. The organic component was washed with water and brine, and concentrated under reduced pressure. The residue was purified using SPE (silica, eluting with cyclohexane; cyclohexane: ethyl acetate 4:1, 1:1, 1:4; ethyl acetate; methanol:ethyl acetate 1:10; methanol) to give the title compound (0.078 g) as a white solid.

Mass spectrum: Found: MH$^+$ 504. H.p.l.c. (1) Rt 3.17 min
$^1$H NMR (D$_4$MeOH): δ 7.61(1H, d), 7.23(1H, d), 7.22(1H, d), 7.03(1H, d), 5.04(1H, q), 4.21(1H, dd), 3.69–3.46(9H, m), 3.39–3.35(1H, m), 2.39(1H, m), 1.86(1H, m), 1.30(3H, d) ppm.

Example 63

5'-Chloro-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)-N-(2-oxobutyl)-2,2'-bithiophene-5-sulfonamide Using Intermediate 71 and the synthetic procedure described for Example 62, the title compound was prepared.
Mass spectrum: Found: MH$^+$ 641. H.p.l.c. (1) Rt 2.98 min.

Example 64

(E)-2-(4-Chlorophenyl)-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)-N-(2-oxobutyl)ethenesulfonamide formate Using Intermediate 72 and the synthetic procedure described for Example 62, the title compound was prepared.
Mass spectrum: Found: MH$^+$ 579. H.p.l.c. (1) Rt 2.75 min.

Example 65

6-Chloro-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)-N-(2-oxobutyl)-1-benzothiophene-2-sulfonamide Using Intermediate 73 and the synthetic procedure described for Example 62, the title compound was prepared.
Mass spectrum: Found: MH$^+$ 609. H.p.l.c. (1) Rt 2.77 min.

Example 66

5-Chloro-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)-N-(2-oxobutyl)-1-benzothiophene-2-sulfonamide Using Intermediate 74 and the synthetic procedure described for Example 62, the title compound was prepared.
Mass spectrum: Found: MH$^+$ 609. H.p.l.c. (1) Rt 2.77 min.

Example 67

5'-Chloro-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)-2,2'-bithiophene-5-sulfonamide tert-Butyl (2S)-2-((3S)-3-{[(5'-chloro-2,2'-bithien-5-yl)sulfonyl]amino}-2-oxopyrrolidin-1-yl)propanoate (0.217 g) was dissolved in DCM (2 ml) and treated with trifluoroacetic acid (2 ml) and stirred at room temperature for 2 h. The mixture was then concentrated under reduced pressure to give an oil which was subsequently dissolved in DCM (5 ml) and treated with 1-[3-(dimethylamino)propyl]-3-ethylcarbodiimide hydrochloride (0.256 g), HOBT (0.184 g) and triethylamine (0.375 ml). After the solution had been stirred at room temperature for 30 min, (S)-(+)-1-(2-pyrrolidinylmethyl)pyrrolidine (0.219 ml) was added and the resultant mixture stirred for a further 20 h. The mixture was concentrated under reduced pressure and the residue partitioned between DCM and water. The organic component was washed with water and brine, and concentrated under reduced pressure. The residue was purified using SPE (silica, eluting with cyclohexane; cyclohexane:ethyl acetate 4:1, 1:1, 1:4; ethyl acetate; methanol:ethyl acetate 1:10; methanol) to give the title compound (0.042 g) as a white solid.

Mass spectrum: Found: MH$^+$ 571. H.p.l.c. (1) Rt 2.77 min.

Example 68

(E)-2-(4-Chlorophenyl)-N-{(3S)-1-[(1S)-1-methyl-2-morpholin-4-yl-2-oxoethyl]-2-oxopyrrolidin-3-yl}ethenesulfonamide Using Intermediate 68 and the synthetic procedure described for Example 62, the title compound was prepared.

Mass spectrum: Found: MH$^+$ 442. H.p.l.c. (1) Rt 2.86 min
$^1$H NMR (CDCl$_3$):δ 7.46(1H, d), 7.44(2H, d), 7.38(2H, d), 6.89(1H, d), 5.35(1H, br.d), 5.05(1H, q), 4.00(1H, m), 3.69–3.48(9H, m), 3.35(1H, m), 2.62(1H, m), 2.06(1H, m), 1.33(3H, d) ppm.

Example 69

N2-{[(E)-2-(4-Chlorophenyl)ethenyl]sulfonyl}-N2-{(3S)-1-[(1S)-1-methyl-2-morpholin-4-yl-2-oxoethyl]-2-oxopyrrolidin-3-yl}glycinamide Using Intermediate 75 and the synthetic procedure described for Example 62, the title compound was prepared.

Mass spectrum: Found: MH$^+$ 499. H.p.l.c. (1) Rt 2.81 min.

Example 70

(E)-2-(4-Chlorophenyl)-N-((3S)-1-(1S)-1-methyl-2-oxo-2-[(2S)-2-(pyrrolidin-1-ylmethyl)pyrrolidin-1-yl]ethyl}-2-oxopyrrolidin-3-yl)ethenesulfonamide Using Intermediate 68 and the synthetic procedure described for Example 67, the title compound was prepared.

Mass spectrum: Found: MH$^+$ 509. H.p.l.c. (1) Rt 2.5 min.

Example 71

N2-[(5'-Chloro-2,2'-bithien-5-yl)sulfonyl]-N2-{(3S)-1-[(1S)-1-methyl-2-morpholin-4-yl-2-oxoethyl]-2-oxopyrrolidin-3-yl}glycinamide Using Intermediate 76 and the synthetic procedure described for Example 62, the title compound was prepared.

Mass spectrum: Found: MH$^+$ 561. H.p.l.c. (1) Rt 2.96 min.

Example 72

5'-Chloro-N-(cyanomethyl)-N-{(3S)-1-[(1S)-1-methyl-2-morpholin-4-yl-2-oxoethyl]-2-oxopyrrolidin-3-yl}-2,2'-bithiophene-5-sulfonamide Using Example 62 and the synthetic procedure described for Example 293, the title compound was prepared.

Mass spectrum: Found: MH$^+$ 543. H.p.l.c. (1) Rt 3.34 min.

Using similar chemistry, the following were prepared:

Example 73

Methyl N-[(5'-chloro-2,2'-bithien-5-yl)sulfonyl]-N-{(3S)-1-[(1S)-1-methyl-2-morpholin-4-yl-2-oxoethyl]-2-oxopyrrolidin-3-yl}glycinate Mass spectrum: Found: MH$^+$ 576. H.p.l.c. (1) Rt 3.34 min.

Example 74

5'-Chloro-N-{(3S)-1-[(1S)-1-methyl-2-morpholin-4-yl-2-oxoethyl]-2-oxopyrrolidin-3-yl}-N-(2-oxobutyl)-2,2'-bithiophene-5-sulfonamide Mass spectrum: Found: MH$^+$ 574. H.p.l.c. (1) Rt 3.4 min.

Example 75

N-[(5'-Chloro-2,2'-bithien-5-yl)sulfonyl]-N-{(3S)-1-[(1S)-1-methyl-2-morpholin-4-yl-2-oxoethyl]-2-oxopyrrolidin-3-yl}glycine Using standard alkaline hydrolysis conditions, the title compound was prepared from Example 73.

Mass spectrum: Found: MH$^+$ 562. H.p.l.c. (1) Rt 3.21 min.

Example 76

(E)-2-(4-Chlorophenyl)-N-(cyanomethyl)-N-{(3S)-1-1-(1S)-1-methyl-2-morpholin-4-yl-2-oxoethyl]-2-oxopyrrolidin-3-yl}ethenesulfonamide Using Example 68 and bromoacetonitrile, and the synthetic procedure described for Example 293, the title compound was prepared.

Mass spectrum: Found: MH$^+$ 481. H.p.l.c. (1) Rt 3.05 min.

Using similar chemistry, the following were prepared:

Example 77

(E)-2-(4-Chlorophenyl)-N-{(3S)-1-[(1S)-1-methyl-2-morpholin-4-yl-2-oxoethyl]-2-oxopyrrolidin-3-yl}-N-(2-oxobutyl)ethenesulfonamide Mass spectrum: Found: MH$^+$ 512. H.p.l.c. (1) Rt 3.11 min.

Example 78

Methyl N-{[(E)-2-(4-chlorophenyl)ethenyl]sulfonyl}-N-{(3S)-1-[(1S)-1-methyl-2-morpholin-4-yl-2-oxoethyl]-2-oxopyrrolidin-3-yl}glycinate Mass spectrum: Found: MH$^+$ 514. H.p.l.c. (1) Rt 3.05 min.

Example 79

N-{[(E)-2-(4-Chlorophenyl)ethenyl]sulfonyl}-N-{(3S)-1-[(1S)-1-methyl-2-morpholin-4-yl-2-oxoethyl]-2-oxopyrrolidin-3-yl}glycine Using standard alkaline hydrolysis conditions, the title compound was prepared from Example 78.

Mass spectrum: Found: MH$^+$ 500. H.p.l.c. (1) Rt 2.9 min.

Example 80

(E)-2-(4-Chlorophenyl)-N-{(3S)-1-[(1S)-1-methyl-2-oxo-2-piperidin-1-ylethyl]-2-oxopyrrolidin-3-yl}ethenesulfonamide tert-Butyl (2S)-2-[(3S)-3-({[(E)-2-(4-chlorophenyl)ethenyl]sulfonyl}amino)-2-oxopyrrolidin-1-yl]propanoate (0.192 g) was dissolved in DCM (2 ml) and treated with trifluoroacetic acid (2 ml) and stirred at room temperature for 2 h. The mixture was then concentrated under reduced pressure to give an oil which was subsequently dissolved in DCM (5 ml) and treated with 1-[3-(dimethylamino)propyl]-3-ethylcarbodiimide hydrochloride (0.256 g), HOBT (0.184 g) and triethylamine (0.375 ml). After the solution had been stirred at room temperature for 30 min, piperidine (0.133 ml) was added and the resultant mixture stirred for a further 20 h. The mixture was concentrated under reduced pressure and the residue partitioned between DCM and water. The organic component was washed with water and brine, and concentrated under reduced pressure. The residue was purified using SPE (silica, eluting with cyclohexane; cyclohexane:ethyl acetate 4:1, 1:1, 1:4; ethyl acetate; methanol:ethyl acetate 1:10; methanol) to give the title compound (0.042 g) as a white solid.

Mass spectrum: Found: MH$^+$ 440. H.p.l.c. (1) Rt 3.1 min.

Example 81

Methyl N-{[(E)-2-(4-chlorophenyl)ethenyl]sulfonyl}-N-{(3S)-1-[(1S)-1-methyl-2-oxo-2-piperidin-1-ylethyl]-2-oxopyrrolidin-3-yl}glycinate Using Example 80 and methyl bromoacetate, and the synthetic procedure described for Example 293, the title compound was prepared.

Mass spectrum: Found: MH$^+$ 512. H.p.l.c. (1) Rt 3.3 min.

Using similar chemistry, the following was prepared:

Example 82

(E)-2-(4-Chlorophenyl)-N-(cyanomethyl)-N-{(3S)-1-[(1S)-1-methyl-2-oxo-2-piperidin-1-ylethyl]-2-oxopyrrolidin-3-yl}ethenesulfonamide Mass spectrum: Found: MH$^+$ 479. H.p.l.c. (1) Rt 3.31 min.

Example 83

N-{[(E)-2-(4-Chlorophenyl)ethenyl]sulfonyl}-N-{(3S)-1-[(1S)-1-methyl-2-oxo-2-piperidin-1-ylethyl]-1-2-oxopyrrolidin-3-yl}glycine Using standard alkaline hydrolysis conditions, the title compound was prepared from Example 81.

Mass spectrum: Found: MH$^+$ 498. H.p.l.c. (1) Rt 3.16 min.

Example 84

N-{(3S)-1-[(1S)-2-(3-Aminopiperidin-1-yl)-1-methyl-2-oxoethyl]-2-oxopyrrolidin-3-yl}-6-chloronaphthalene-2-sulfonamide tert-Butyl 1-[(2S)-2-((3S)-3-{[(6-chloro-2-naphthyl)sulfonyl]amino}-2-oxopyrrolidin-1-yl)propanoyl]piperidin-3-ylcarbamate (0.6 g) was dissolved in DCM (11 ml) and trifluoroacetic acid (11 ml) was added. The mixture was stirred at room temperature for 2 h and then concentrated under reduced pressure. The residue was dissolved in water (5 ml) and ammonia solution (0.88%; 1 ml) added. The resultant aqueous mixture was extracted with DCM. The combined organic extracts were dried (over magnesium sulphate), filtered and concentrated under reduced pressure to give the title compound (0.38 g) as a white foam.

Mass spectrum: Found: MH$^+$ 479. H.p.l.c. (1) Rt 2.71 min.

Example 85

6-Chloro-N-{(3S)-1-[(1S)-1-methyl-2-(3-methylpiperidin-1-yl)-2-oxoethyl]-2-oxopyrrolidin-3-yl}naphthalene-2-sulfonamide To polymer N-cyclohexylcarbodiimide-N'-propyloxymethyl polystyrene (0.038 g) in an Alltech™ tube was added a solution of (2S)-2-((3S)-3-{[(6-chloro-2-naphthyl)sulfonyl]amino}-2-oxopyrrolidin-1-yl)propanoic acid (0.007 g) in DCM (0.9 ml) followed by 3-methylpiperidine (0.0025 g) in DMF (0.1 ml) and N,N-diisopropylethylamine (0.006 ml). The mixture was shaken at room temperature for 4 days. The tube was drained, the filtrate collected and the resin washed with DCM. The combined DCM solutions were concentrated under reduced pressure and the residue purified by mass directed preparative h.p.l.c. to give the title compound (0.0023 g) as a white solid.

Mass spectrum: Found: MH$^+$ 478. H.p.l.c. (1) Rt 3.25 min.

Using similar chemistry, the following were prepared:

Example 86

6-Chloro-N-((3S)-1-{(1S)-2-[3-(hydroxymethyl)piperidin-1-yl]-1-methyl-2-oxoethyl}-2-oxopyrrolidin-3-yl)naphthalene-2-sulfonamide Mass spectrum: Found: $MH^+$ 494. H.p.l.c. (1) Rt 2.93 min.

Example 87

N-{1-[(2S)-2-((3S)-3-{[(6-Chloro-2-naphthyl)sulfonyl]amino}-2-oxopyrrolidin-1-yl)propanoyl]piperidin-3-yl}acetamide Mass spectrum: Found: $MH^+$ 521. H.p.l.c. (1) Rt 2.86 and 2.97 min (two diastereoisomers).

Example 88

6-Chloro-N-((3S)-1-{(1S)-1-methyl-2-oxo-2-[3-(1H-pyrrol-1-ylmethyl)piperidin-1-yl]ethyl}-2-oxopyrrolidin-3-yl)naphthalene-2-sulfonamide Mass spectrum: Found: $MH^+$ 543. H.p.l.c. (1) Rt 3.57 min.

Example 89

6-Chloro-N-{(3S)-1-[(1S)-2-(3,3-dimethylpiperidine-1-yl)-1-methyl-2-oxoethyl]-2-oxopyrrolidin-3-yl}naphthalene-2-sulfonamide Mass spectrum: Found: $MH^+$ 492. H.p.l.c. (1) Rt 3.51 min.

Example 90

6-Chloro-N-{(3S)-1-[(1S)-1-methyl-2-(2-methylpiperidin-1-yl)-2-oxoethyl]-2-oxopyrrolidin-3-yl}naphthalene-2-sulfonamide Mass spectrum: Found: $MH^+$ 478. H.p.l.c. (1) Rt 3.21 min.

Example 91

6-Chloro-N-((3S)-1-{(1S)-1-methyl-2-oxo-2-[3-(trifluoromethyl)piperidin-1-yl]ethyl}-2-oxopyrrolidin-3-yl)naphthalene-2-sulfonamide Mass spectrum: Found: $MH^+$ 532. H.p.l.c. (1) Rt 3.52 min.

Example 92

6-Chloro-N-((3S)-1-{(1S)-1-methyl-2-oxo-2-[2-(2-pyrrolidin-1-ylethyl)piperidin-1-yl]ethyl}-2-oxopyrrolidin-3-yl)naphthalene-2-sulfonamide formate The title compound was isolated from a crude reaction mixture using mass directed preparative h.p.l.c.
Mass spectrum: Found: $MH^+$ 561. H.p.l.c. (1) Rt 2.8 min.

Example 93

6-Chloro-N-{(3S)-1-[(1S)-2-(3-methoxypiperidin-1-yl)-1-methyl-2-oxoethyl]-2-oxopyrrolidin-3-yl}naphthalene-2-sulfonamide Mass spectrum: Found: $MH^+$ 494. H.p.l.c. (1) Rt 3.04 min.

Example 94

6-Chloro-N-{(3S)-1-[(1S)-1-methyl-2-(4-methylpiperidin-1-yl)-2-oxoethyl]-2-oxopyrrolidin-3-yl}naphthalene-2-sulfonamide Mass spectrum: Found: $MH^+$ 478. H.p.l.c. (1) Rt 3.43 min.

Example 95

6-Chloro-N-{(3S)-1-[(1S)-2-(3-hydroxypiperidin-1-yl)-1-methyl-2-oxoethyl]-2-oxopyrrolidin-3-yl}naphthalene-2-sulfonamide Mass spectrum: Found: $MH^+$ 480. H.p.l.c. (1) Rt 3.05 min.

Example 96

6-Chloro-N-{(3S)-1-[(1S)-1-methyl-2-octahydroquinolin-1(2H)-yl-2-oxoethyl]-2-oxopyrrolidin-3-yl}naphthalene-2-sulfonamide Mass spectrum: Found: $MH^+$ 518. H.p.l.c. (1) Rt 3.55 min.

Example 97

6-Chloro-N-{(3S)-1-[(1S)-2-(4-hydroxypiperidin-1-yl)-1-methyl-2-oxoethyl]-2-oxopyrrolidin-3-yl}naphthalene-2-sulfonamide Mass spectrum: Found: $MH^+$ 480. H.p.l.c. (1) Rt 3.00 min.

Example 98

6-Chloro-N-{(3S)-1-[(1S)-2-[2-(hydroxymethyl)piperidin-1-yl]-1-methyl-2-oxoethyl}-2-oxopyrrolidin-3-yl)naphthalene-2-sulfonamide Mass spectrum: Found: $MH^+$ 494. H.p.l.c. (1) Rt 3.16 min.

Example 99

1-[(2S)-2-((3S)-3-{[(6-Chloro-2-naphthyl)sulfonyl]amino}-2-oxopyrrolidin-1-yl)propanoyl]-N,N-diethylpiperidine-3-carboxamide Mass spectrum: Found: $MH^+$ 563. H.p.l.c. (1) Rt 3.27 min.

Example 100

6-Chloro-N-{(3S)-1-[(1S)-1-methyl-2-oxo-2-(2-phenylpiperidin-1-yl)ethyl]-2-oxopyrrolidin-3-yl}naphthalene-2-sulfonamide Mass spectrum: Found: MH$^+$ 530. H.p.l.c. (1) Rt 3.68 min.

Example 101

6-Chloro-N-{(3S)-1-[(1S)-1-methyl-2-oxo-2-(3-phenylpiperidin-1-yl)ethyl]-2-oxopyrrolidin-3-yl}naphthalene-2-sulfonamide Mass spectrum: Found: MH$^+$ 540. H.p.l.c. (1) Rt 3.66 min.

Example 102

6-Chloro-N-((3S)-1-{(1S)-1-methyl-2-oxo-2-[2-(pyrrolidin-1-ylcarbonyl)piperidin-1-yl]ethyl}-2-oxopyrrolidin-3-yl)naphthalene-2-sulfonamide Mass spectrum: Found: MH$^+$ 561. H.p.l.c. (1) Rt 3.32 min.

Example 103

6-Chloro-N-((3S)-1-{(1S)-2-[4-(dimethylamino)piperidin-1-yl[-1-methyl-2-oxoethyl}-2-oxopyrrolidin-3-yl)naphthalene-2-sulfonamide formate Mass spectrum: Found: MH$^+$ 508. H.p.l.c. (1) Rt 2.64 min.

Example 104

1-[(2S)-2-((3S)-3-{[(6-Chloro-2-naphthyl)sulfonyl]amino}-2-oxopyrrolidin-1-yl)propanoyl]-N,N-dimethylprolinamide Mass spectrum: Found: MH$^+$ 521. H.p.l.c. (1) Rt 3.05 min.

Example 105

N-{1-[(2S)-2-((3S)-3-{[(6-Chloro-2-naphthyl)sulfonyl]amino}-2-oxopyrrolidin-1-yl)propanoyl]pyrrolidin-3-yl}acetamide Mass spectrum: Found: MH$^+$ 507. H.p.l.c. (1) Rt 2.96 min.

Example 106

6-Chloro-N-{(3S)-1-[(1S)-2-(3-hydroxypyrrolidin-1-yl)-1-methyl-2-oxoethyl]-2-oxopyrrolidin-3-yl}naphthalene-2-sulfonamide Mass spectrum: Found: MH$^+$ 466. H.p.l.c. (1) Rt 2.95 min.

Example 107

Methyl 1-[(2S)-2-((3S)-3-{[(6-chloro-2-naphthyl)sulfonyl]amino}-2-oxopyrrolidin-1-yl)propanoyl]-L-prolinate Mass spectrum: Found: MH$^+$ 508. H.p.l.c. (1) Rt 3.2 min.

Example 108

6-Chloro-N-{(3S)-1-[(1S)-2-(4-methoxypiperidin-1-yl)-1-methyl-2-oxoethyl]-2-oxopyrrolidin-3-yl}naphthalene-2-sulfonamide Mass spectrum: Found: MH$^+$ 494. H.p.l.c. (1) Rt 3.17 min.

Example 109

6-Chloro-N-((3S)-1-{(1S)-2-[4-(hydroxymethyl)piperidin-1-yl]-1-methyl-2-oxoethyl}-2-oxopyrrolidin-3-yl)naphthalene-2-sulfonamide Mass spectrum: Found: MH$^+$ 494. H.p.l.c. (1) Rt 3.06 min.

Example 110

Methyl 1-[(2S)-2-((3S)-3-{[(6-chloro-2-naphthyl)sulfonyl]amino}-2-oxopyrrolidin-1-yl)propanoyl]piperidine-4-carboxylate Mass spectrum: Found: MH$^+$ 522. H.p.l.c. (1) Rt 3.32 min.

Example 111

Methyl 1-[(2S)-2-((3S)-3-{[(6-chloro-2-naphthyl)sulfonyl]amino}-2-oxopyrrolidin-1-yl)propanoyl]piperidine-3-carboxylate Mass spectrum: Found: MH$^+$ 522. H.p.l.c. (1) Rt 3.32 min.

Example 112

2-{1-[(2S)-2-((3S)-3-{[(6-Chloro-2-naphthyl)sulfonyl]amino}-2-oxopyrrolidin-1-yl)propanoyl]pyrrolidin-2-yl}acetamide Mass spectrum: Found: MH$^+$ 507. H.p.l.c. (1) Rt 2.98 min.

Example 113

N-{1-[(2S)-2-((3S)-3-{[(6-Chloro-2-naphthyl)sulfonyl]amino}-2-oxopyrrolidin-1-yl)propanoyl]piperidin-4-yl}acetamide Mass spectrum: Found: MH$^+$ 521. H.p.l.c. (1) Rt 2.98 min.

Example 114

6-Chloro-N-{(3S)-1-[(1S)-1-methyl-2-oxo-2-(3-oxopiperazin-1-yl)ethyl]-2-oxopyrrolidin-3-yl}naphthalene-2-sulfonamide Mass spectrum: Found: MH$^+$ 479. H.p.l.c. (1) Rt 2.94 min.

Example 115

6-Chloro-N-[(3S)-1-((1S)-1-methyl-2-{3-[(methylamino)methyl]pyrrolidin-1-yl}-2-oxoethyl)-2-oxopyrrolidin-3-yl]naphthalene-2-sulfonamide formate Mass spectrum: Found: MH$^+$ 493. H.p.l.c. (1) Rt 2.65 min.

Example 116

6-Chloro-N-{(3S)-1-[(1S)-1-methyl-2-oxo-2-(4-phenylpiperidin-1-yl)ethyl]-2-oxopyrrolidin-3-yl}naphthalene-2-sulfonamide Mass spectrum: Found: M$^+$ 540. H.p.l.c. (1) Rt 3.64 min.

Example 117

N-{(3S)-1-[(1S)-2-(4-Acetylpiperidin-1-yl)-1-methyl-2-oxoethyl]-2-oxopyrrolidin-3-yl}-6-chloronaphthalene-2-sulfonamide Mass spectrum: Found: MH$^+$ 506. H.p.l.c. (1) Rt 3.16 min.

Example 118

N-{1-[(2S)-2-((3S)-3-{[(6-Chloro-2-naphthyl)sulfonyl]amino}-2-oxopyrrolidin-1-yl)propanoyl]pyrrolidin-3-yl}benzamide Mass spectrum: Found: MH$^+$ 569. H.p.l.c. (1) Rt 3.28 min.

Example 119

6-Chloro-N-((3S)-1-{(1S)-2-[(2R)-2-(methoxymethyl)pyrrolidin-1-yl]-1-methyl-2-oxoethyl}-2-oxopyrrolidin-3-yl)naphthalene-2-sulfonamide Mass spectrum: Found: MH$^+$ 494. H.p.l.c. (1) Rt 3.24 min.

Example 120

Ethyl 1-[(2S)-2-((3S)-3-{[(6-chloro-2-naphthyl)sulfonyl]amino}-2-oxopyrrolidin-1-yl)propanoyl]piperidine-2-carboxylate Mass spectrum: Found: MH$^+$ 536. H.p.l.c. (1) Rt 3.49 min.

Example 121

6-Chloro-N-{(3S)-1-[(1S)-1-methyl-2-(2-methylpyrrolidin-1-yl)-2-oxoethyl]-2-oxopyrrolidin-3-yl}naphthalene-2-sulfonamide Mass spectrum: Found: MH$^+$ 464. H.p.l.c. (1) Rt 3.27 min.

Example 122

6-Chloro-N-{(3S)-1-[(1S)-1-methyl-2-oxo-2-(4-pyrrolidin-1-ylpiperidin-1-yl)ethyl]-2-oxopyrrolidin-3-yl}naphthalene-2-sulfonamide Mass spectrum: Found: MH$^+$ 533. H.p.l.c. (1) Rt 2.65 min.

Example 123

1-[(2S)-2-((3S)-3-{[(6-Chloro-2-naphthyl)sulfonyl]amino}-2-oxopyrrolidin-1-yl)propanoyl]prolinamide Mass spectrum: Found: MH$^+$ 493. H.p.l.c. (1) Rt 2.95 min.

Example 124

6-Chloro-N-((3S)-1-{(1S)-1-methyl-2-[2-(4-methylpyridin-2-yl)pyrrolidin-1-yl]-2-oxoethyl}-2-oxopyrrolidin-3-yl)naphthalene-2-sulfonamide Mass spectrum: Found: MH$^+$ 541. H.p.l.c. (1) Rt 3.0 min.

Example 125

6-Chloro-N-{(3S)-1-[(1S)-2-(3-isopropyltetrahydropyrimidin-1(2H)-yl)-1-methyl-2-oxoethyl]-2-oxopyrrolidin-3-yl}naphthalene-2-sulfonamide Mass spectrum: Found: MH$^+$ 507. H.p.l.c. (1) Rt 2.69 min.

Example 126

6-Chloro-N-((3S)-1-{(1S)-1-methyl-2-[(2S)-2-(morpholin-4-ylmethyl)pyrrolidin-1-yl]-2-oxoethyl}-2-oxopyrrolidin-3-yl)naphthalene-2-sulfonamide Mass spectrum: Found: MH$^+$ 549. H.p.l.c. (1) Rt 2.68 min.

Example 127

6-Chloro-N-{(3S)-1-[(1S)-1-methyl-2oxo-2-(4,6,7,8-tetrahydro-5H-thieno[3,2-c]azepin-5-yl)ethyl]-2-oxopyrrolidin-3-yl}naphthalene-2-sulfonamide Mass spectrum: Found: MH$^+$ 532. H.p.l.c. (1) Rt 3.54 min.

Example 128

6-Chloro-N-{(3S)-1-[(1S)-1-methyl-2-oxo-2-(3,4,6,7-tetrahydro-5H-imidazo[4,5-c]pyridin-5-yl)ethyl]-2-oxopyrrolidin-3-yl}naphthalene-2-sulfonamide Mass spectrum: Found: MH$^+$ 502. H.p.l.c. (1) Rt 2.67 min.

Example 129

6-Chloro-N-{(3S)-1-[(1S)-1-methyl-2-oxo-2-(3,5,6,7-tetrahydro-4H-[1,2,3]triazolo[4,5-b]pyridin-4-yl)ethyl]-2-oxopyrrolidin-3-yl}naphthalene-2-sulfonamide Mass spectrum: Found: MH$^+$ 503. H.p.l.c. (1) Rt 3.33 min.

Example 130

6-Chloro-N-{(3S)-1-[(1S)-2-(3,4-dihydroquinolin-1(2H)-yl)-1-methyl-2-oxoethyl]-2-oxopyrrolidin-3-yl}naphthalene-2-sulfonamide Mass spectrum: Found: MH$^+$ 512. H.p.l.c. (1) Rt 3.59 min.

Example 131

6-Chloro-N-{(3S)-1-[(1S)-2-(3,4-dihydroisoquinolin-2(1H)-yl)-1-methyl-2-oxoethyl]-2-oxopyrrolidin-3-yl}naphthalene-2-sulfonamide Mass spectrum: Found: MH$^+$ 512. H.p.l.c. (1) Rt 3.52 min.

Example 132

6-Chloro-N-{(3S)-1-[(1S)-2-(2,3-dihydro-1H-indol-1-yl)-1-methyl-2-oxoethyl]-2-oxopyrrolidin-3-yl}naphthalene-2-sulfonamide Mass spectrum: Found: MH$^+$ 498. H.p.l.c. (1) Rt 3.58 min.

Example 133

6-Chloro-N-{(3S)-1-[(1S)-2-(1,3-dihydro-2H-isoindol-2-yl)-1-methyl-2-oxoethyl]-2-oxopyrrolidin-3-yl}naphthalene-2-sulfonamide Mass spectrum: Found: MH$^+$ 498. H.p.l.c. (1) Rt 3.44 min.

Example 134

6-Chloro-N-{(3S)-1-[(1S)-1-methyl-2-oxo-2-(1,3,4,5-tetrahydro-2H-2-benzazepin-2-yl)ethyl]-2-oxopyrrolidin-3-yl}naphthalene-2-sulfonamide Mass spectrum: Found: MH$^+$ 526. H.p.l.c. (1) Rt 3.57 min.

Example 135

1-[(2S)-2-((3S)-3-{[(6-Chloro-2-naphthyl)sulfonyl]amino}-2-oxopyrrolidin-1-yl)propanoyl]-L-proline The title compound was prepared by alkaline hydroysis (lithium hydroxide) of the corresponding methyl ester, Example 107.

Mass spectrum: Found: MH$^+$ 494. H.p.l.c. (1) Rt 3.03 min.

Example 136

1-[(2S)-2-((3S)-3-{[(6-Chloro-2-naphthyl)sulfonyl]amino}-2-oxopyrrolidin-1-yl)propanoyl]piperidine-3-carboxylic acid The title compound was prepared by alkaline hydrolysis (lithium hydroxide) of the corresponding methyl ester, Example 111.

Mass spectrum: Found: MH$^+$ 508. H.p.l.c. (1) Rt 3.0 min.

Example 137

1-[(2S)-2-((3S)-3-{[(6-Chloro-2-naphthyl)sulfonyl]amino}-2-oxopyrrolidin-1-yl)propanoyl]piperidine-4-carboxylic acid Mass spectrum: Found: MH$^+$ 508. H.p.l.c. (1) Rt 3.01 min.

Example 138

6-Chloro-N-{(3S)-1-[(1S)-1-methyl-2-(4-methyl-5-oxo-1,4-diazepan-1-yl)-2-oxoethyl]-2-oxopyrrolidin-3-yl}naphthalene-2-sulfonamide Mass spectrum: Found: MH$^+$ 507. H.p.l.c. (1) Rt 3.01 min.

Example 139

6-Chloro-N-{(3S)-1-[(1S)-1-methyl-2-oxo-2-(5-oxo-1,4-diazepan-1-yl)ethyl]-2-oxopyrrolidin-3-yl}naphthalene-2-sulfonamide Mass spectrum: Found: MH$^+$ 493. H.p.l.c. (1) Rt 2.95 min.

Example 140

6-Chloro-N-{(3S)-1-[(1S)-1-methyl-2-oxo-2-thiomorpholin-4-ylethyl]-2-oxopyrrolidin-3-yl}naphthalene-2-sulfonamide Mass spectrum: Found: MH$^+$ 482. H.p.l.c. (1) Rt 3.34 min.

Example 141

6-Chloro-N-{(3S)-1-[(1S)-2-(2,5-dihydro-1H-pyrrol-1-yl)-1-methyl-2-oxoethyl]-2-oxopyrrolidin-3-yl}naphthalene-2-sulfonamide Mass spectrum: Found: MH$^+$ 448. H.p.l.c. (1) Rt 3.08 min.

Example 142

6-Chloro-N-{(3S)-1-[(1S)-1-methyl-2-(2-methylmorpholin-4-yl)-2-oxoethyl]-2-oxopyrrolidin-3-yl}naphthalene-2-sulfonamide Mass spectrum: Found: MH$^+$ 480. H.p.l.c. (1) Rt 3.17 min.

Example 143

6-Chloro-N-{(3S)-1-[(1S)-1-methyl-2-(4-methyl-1,4-diazepan-1-yl)-2-oxoethyl]-2-oxopyrrolidin-3-yl}naphthalene-2-sulfonamide Mass spectrum: Found: MH$^+$ 493. H.p.l.c. (1) Rt 2.64 min.

Example 144

6-Chloro-N-{(3S)-1-[(1S)-2-(3,6-dihydropyridin-1-(2H)-yl)-1-methyl-2-oxoethyl]-2-oxopyrrolidin-3-yl}naphthalene-2-sulfonamide Mass spectrum: Found: MH$^+$ 462. H.p.l.c. (1) Rt 3.3 min.

Example 145

6-Chloro-N-{(3S)-1-[(1S)-2-(1,1-dioxidothiomorpholin-4-yl)-1-methyl-2-oxoethyl]-2-oxopyrrolidin-3-yl}naphthalene-2-sulfonamide Mass spectrum: Found: MH$^+$ 514. H.p.l.c. (1) Rt 3.12 min.

Example 146

6-Chloro-N-{(3S)-1-[(1S)-2-(3-hydroxyquinoxalin-1(2H)-yl)-1-methyl-2-oxoethyl]-2-oxopyrrolidin-3-yl}naphthalene-2-sulfonamide Mass spectrum: Found: MH$^+$ 527. H.p.l.c. (1) Rt 3.23 min.

Example 147

5'-Chloro-N-{(3R)-1-[(1S)-1-methyl-2-oxo-2-piperidin-1-ylethyl]-2-oxopyrrolidin-3-yl}-2,2'-bithiophene-5-sulfonamide To a solution of (3R)-3-amino-1-[(1S)-1-methyl-2-oxo-2-piperidin-1-ylethyl]pyrrolidin-2-one (0.01 g) in acetonitrile (1 ml) was added triethylamine (0.008 ml) and 5'-chloro-2,2'-bithiophene-5-sulfonyl chloride$^2$ (0.013 g) and the mixture stirred at room temperature for 24 h. The mixture was concentrated under reduced pressure and the residue purified by mass directed preparative h.p.l.c. to give the title compound (0.004 g) as a white solid.

Mass spectrum: Found: MH$^+$ 502. H.p.l.c. (1) Rt 3.43 min.

Using similar chemistry, the following was prepared:

Example 148

(E)-2-(4Chlorophenyl)-N-{(3R)-1-[(1S)-1-methyl-2-oxo-2-piperidin-1-ylethyl]-2-oxopyrrolidin-3-yl}ethenesulfonamide Mass spectrum: Found: MH$^+$ 440. H.p.l.c. (1) Rt 3.11 min.

Example 149 tert-Butyl 1-[(2S)-2-((3S)-3-{[(6-chloro-2-naphthyl)sulfonyl]amino}-2-oxopyrrolidin-1-yl)propanoyl]piperidin-3-ylcarbamate The title compound was prepared using Intermediate 29 and tert-butyl piperidin-3-ylcarbamate, and the synthetic procedure described for Example 1.

Mass spectrum: Found: MH$^+$ 579. H.p.l.c. (1) Rt 3.53 min.

Example 150

N-{1-[(2S)-2-((3S)-3-{[(6-Chloro-2-naphthyl)sulfonyl]amino}-2-oxopyrrolidin-1-yl)propanoyl]piperidin-3-yl}prop-2-ynamide To a solution of N-{(3S)-1-[(1S)-2-(3-aminopiperidin-1-yl)-1-methyl-2-oxoethyl]-2-oxopyrrolidin-3-yl}-6-chloronaphthalene-2-sulfonamide (0.005 g) in DMF (0.5 ml) were added propiolic acid (0.001 g), N,N-diisopropylethylamine (0.0044 ml) and o-(7-azabenzotriazol-1-yl)-N,N,N',N'-tetramethyluronium hexafluorophosphate (0.004 g). The mixture was stirred at room temperature for 18 h and then concentrated under reduced pressure. The residue was partitioned between DCM and saturated sodium bicarbonate solution and then passed through a hydrophobic frit. The separated organic fraction was concentrated under reduced pressure to give the title compound (0.0064 g) as an oil.

Mass spectrum: Found: MH$^+$ 531. H.p.l.c. (1) Rt 3.42 min.

Using similar chemistry, the following were prepared:

Example 151

N-{1-[(2S)-2-((3S)-3-{[(6-Chloro-2-naphthyl)sulfonyl]amino}-2-oxopyrrolidin-1-yl)propanoyl]piperidin-3-yl)-1-methyl-1H-pyrrole-3-carboxamide Mass spectrum: Found: MH$^+$ 586. H.p.l.c. (1) Rt 3.32 min.

Example 152

Methyl 4-({1-[(2S)-2-((3S)-3-{[(6-chloro-2-naphthyl)sulfonyl]amino}-2-oxopyrrolidin-1-yl)propanoyl]piperidin-3-yl}amino)-4-oxobutanoate Mass spectrum: Found: MH$^+$ 593. H.p.l.c. (1) Rt 3.31 min.

Example 153

4-({1-[(2S)-2-((3S)-3-{[(6-Chloro-2-naphthyl)sulfonyl]amino}-2-oxopyrrolidin-1-yl)propanoyl]piperidin-3-yl}amino)-4-oxobutanoic acid Using standard alkaline hydrolysis conditions, the title compound was prepared from Example 152.

Mass spectrum: Found: MH$^+$ 579. H.p.l.c. (1) Rt 3.02 min.

Example 154

N-{1-[(2S)-2-((3S)-3-{[(6-Chloro-2-naphthyl)sulfonyl]amino}-2-oxopyrrolidin-1-yl)propanoyl]piperidin-3-yl-1H-1,2,4-triazole-3-carboxamide Mass spectrum: Found: MH⁺ 574. H.p.l.c. (1) Rt 3.16 min.

Example 155

N-{1-[(2S)-2-((3S)-3-{[(6-Chloro-2-naphthyl)sulfonyl]amino}-2-oxopyrrolidin-1-yl)propanoyl]piperidin-3-yl}-1-methyl-1H-Pyrrole-2-carboxamide Mass spectrum: Found: MH⁺ 586. H.p.l.c. (1) Rt 3.33 min.

Example 156

N-{1-[(2S)-2-((3S)-3-{[(6-Chloro-2-naphthyl)sulfonyl]amino}-2-oxopyrrolidin-1-yl)propanoyl]piperidin-3-yl}propanamide Mass spectrum: Found: MH⁺ 536. H.p.l.c. (1) Rt 3.18 min.

Example 157

N-{1-[(2S)-2-((3S)-3-{[(6-Chloro-2-naphthyl)sulfonyl]amino}-2-oxopyrrolidin-1-yl)propanoyl]piperidin-3-yl}-1H-pyrazole-3-carboxamide Mass spectrum: Found: MH⁺ 573. H.p.l.c. (1) Rt 3.29 min.

Example 158

N-{1-[(2S)-2-((3S)-3-{[(6-Chloro-2-naphthyl)sulfonyl]amino}-2-oxopyrrolidin-1-yl)propanoyl]piperidin-3-yl}-2-ethylbutanamide Mass spectrum: Found: MH⁺ 577. H.p.l.c. (1) Rt 2.71 min.

Example 159

N-{1-[(2S)-2-((3S)-3-{[(6-Chloro-2-naphthyl)sulfonyl]amino}-2-oxopyrrolidin-1-yl)propanoyl]piperidin-3-yl}cyclopentanecarboxamide Mass spectrum: Found: MH⁺ 575. H.p.l.c. (1) Rt 3.55 min.

Example 160

N-{1-[(2S)-2-((3S)-3-{[(6-Chloro-2-naphthyl )sulfonyl]amino}-2-oxopyrrolidin-1-yl)propanoyl]piperidin-3-yl}pentanediamide Mass spectrum: Found: MH⁺ 592. H.p.l.c. (1) Rt 3.12 min.

Example 161

N-{1-[(2S)-2-((3S)-3-{[(6-Chloro-2-naphthyl)sulfonyl]amino}-2-oxopyrrolidin-1-yl)propanoyl]piperidin-3-yl}pyrazine-2-carboxamide Mass spectrum: Found: MH⁺ 584. H.p.l.c. (1) Rt 3.48 min.

Example 162

N-{1-[(2S)-2-((3S)-3-{[(6-Chloro-2-naphthyl)sulfonyl]amino}-2-oxopyrrolidin-1-yl)propanoyl]piperidin-3-yl}-1H-pyrazole-4carboxamide Mass spectrum: Found: MH⁺ 573. H.p.l.c. (1) Rt 3.2 min.

Example 163

N-{1-[(2S)-2-((3S)-3-{[(6-Chloro-2-naphthyl)sulfonyl]amino}-2-oxopyrrolidin-1-yl)propanoyl]piperidin-3-yl}malonamide Mass spectrum: Found: MH⁺ 564. H.p.l.c. (1) Rt 3.11 min.

Example 164

N-{1-[(2S)-2-((3S)-3-{[(6-Chloro-2-naphthyl)sulfonyl]amino}-2-oxopyrrolidin-1-yl)propanoyl]piperidin-3-yl}-2-methylpropanamide Mass spectrum: Found: MH⁺ 549. H.p.l.c. (1) Rt 3.27 min.

Example 165

N-1-{1-[(2S)-2-((3S)-3-{[(6-Chloro-2-naphthyl)sulfonyl]amino}-2-oxopyrrolidin-1-yl)propanoyl]piperidin-3-yl}-N-3-,N-3-dimethyl-beta-alaninamide Mass spectrum: Found: MH⁺ 578. H.p.l.c. (1) Rt 3.4 min.

Example 166

N-{1-[(2S)-2-((3S)-3-{[(6-Chloro-2-naphthyl)sulfonyl]amino}-2-oxopyrrolidin-1-yl)propanoyl]piperidin-3-yl}succinamide Mass spectrum: Found: MH⁺ 578. H.p.l.c. (1) Rt 3.09 min.

Example 167

N-{1-[(2S)-2-((3S)-3-{[(6-Chloro-2-naphthyl)sulfonyl]amino}-2-oxopyrrolidin-1-yl)propanoyl]piperidin-3-yl}prop-2-ynamide Mass spectrum: Found: MH⁺ 531. H.p.l.c. (1) Rt 3.36 min.

Example 168

N-{1-[(2S)-2-((3S)-3-}[(6-Chloro-2-naphthyl)sulfonyl]amino}-2-oxopyrrolidin-1-yl)propanoyl]piperidin-3-yl}-1H-pyrrole-2-carboxamide Mass spectrum: Found: MH⁺ 572. H.p.l.c. (1) Rt 3.5 min.

Example 169

N-{1-[(2S)-2-((3S)-3-{[(6-Chloro-2-naphthyl)sulfonyl]amino}-2-oxopyrrolidin-1-yl)propanoyl]piperidin-3-yl}-1-methyl-1H-1,2,3-triazole-4-carboxamide Mass spectrum: Found: MH$^+$ 588. H.p.l.c. (1) Rt 3.4 min.

Example 170

N-{1-[(2S)-2-((3S)-3-{[(6-Chloro-2-naphthyl)sulfonyl]amino}-2-oxopyrrolidin-1-yl)propanoyl]piperidin-3-yl}-1,3-thiazole-2-carboxamide Mass spectrum: Found: MH$^+$ 590. H.p.l.c. (1) Rt 3.3 min.

Example 171

6-Chloro-N-{(3S)-1-[(1S)-1-methyl-2-oxo-2-(3-{[(trifluoromethyl)sulfonyl]amino}piperidin-1-yl)ethyl]-2-oxopyrrolidin-3-yl}naphthalene-2-sulfonamide Using triflic anhydride and Example 84, the title compound was prepared as described for Example 150.

Mass spectrum: Found: MH$^+$ 611. H.p.l.c. (1) Rt 3.53 min.

Example 172

N-{1-[(2S)-2-((3S)-3-{[(6-Chloro-2-naphthyl)sulfonyl]amino}-2-oxopyrrolidin-1-yl)propanoyl]piperidin-3-yl}-N2,N2-dimethylglycinamide Mass spectrum: Found: MH$^+$ 565. H.p.l.c. (1) Rt 2.63 min.

Example 173

Methyl 3-({1-[(2S)-2-((3S)-3-{[(6-chloro-2-naphthyl)sulfonyl]amino}-2-oxopyrrolidin-1-yl)propanoyl]piperidin-3-yl}amino)-3-oxopropanoate Mass spectrum: Found: MH$^+$ 579. H.p.l.c. (1) Rt 2.7 min.

Example 174

N-{1-[(2S)-2-((3S)-3-{[(6-Chloro-2-naphthyl)sulfonyl]amino}-2-oxopyrrolidin-1-yl)propanoyl]piperidin-3-yl}nicotinamide Mass spectrum: Found: MH$^+$ 584. H.p.l.c. (1) Rt 3.17 min.

Example 175 and Example 176

N-{1-[(2S)-2-((3S)-3-{[(6-Chloro-2-naphthyl)sulfonyl]amino}-2-oxopyrrolidin-1-yl)propanoyl]piperidin-3-yl}pyridine-2-carboxamide [Isomer 1 and Iosmer 2]

Isomer 1
Mass spectrum: Found: MH$^+$ 584. H.p.l.c. (1) Rt 3.48 min.

Isomer 2
Mass spectrum: Found: MH$^+$ 584. H.p.l.c. (1) Rt 3.6 min.

Example 177

N-{1-[(2S)-2-((3S)-3-{[(6-Chloro-2-naphthyl)sulfonyl]amino}-2-oxopyrrolidin-1-yl)propanoyl]piperidin-3-yl}-4H-1,2,4-triazole-3-carboxamide Mass spectrum: Found: MH$^+$ 574. H.p.l.c. (1) Rt 3.23 min.

Example 178 and Example 179

N-{1-[(2S)-2-((3S)-3-{[(6-Chloro-2-naphthyl)sulfonyl]amino}-2-oxopyrrolidin-1-yl)propanoyl]piperidin-3-yl}-2-ethylbutanamide [Isomer 1 and Isomer 2]

Isomer 1
Mass spectrum: Found: MH$^+$ 578. H.p.l.c. (1) Rt 2.71 min.

Isomer 2
Mass spectrum: Found: MH$^+$ 578. H.p.l.c. (1) Rt 3.58 min.

Example 180

N-{1-[(2S)-2-((3S)-3-{[(6-Chloro-2-naphthyl)sulfonyl]amino}-2-oxopyrrolidin-1-yl)propanoyl]piperidin-3-yl}prop-2-ynamide Mass spectrum: Found: MH$^+$ 531. H.p.l.c. (1) Rt 3.36 min.

Example 181

N-{(3S)-1-[(2S)-2-((3S)-3-{[(6-Chloro-2-naphthyl)sulfonyl]amino}-2-oxopyrrolidin-1-yl)propanoyl]piperidin-3-yl}nicotinamide To a solution of nicotinic acid (0.006 g) in DCM (0.5 ml) were added 1-[3-(dimethylamino)propyl]-3-ethylcarbodiimide hydrochloride (0.018 g), HOBT (0.013 g) and triethylamine 0.017 ml) and the mixture was stirred at room temperature for 1 h. Example 365 (0.015 g) was added and the resultant mixture stirred at room temperature for 21 h. The mixture was partitioned between DCM and water. The aqueous layer was re-extracted with DCM and the combined, dried (over magnesium sulphate) organic extracts were concentrated under reduced pressure. The residue was purified using SPE (silica, eluting with cyclohexane:ethyl acetate 5:1, 1:1, 1:5, and DCM:methanol 25:1, 15:1, 5:1) to give the title compound (0.01 g) as a white solid.

Mass spectrum: Found: MH$^+$ 584. H.p.l.c. (1) Rt 3.24 min.

Using similar chemistry, the following were prepared:

Example 182

N-{(3S)-1-[(2S)-2-((3S)-3-{[(6-Chloro-2-naphthyl)sulfonyl]amino}-2-oxopyrrolidin-1-yl)propanoyl]piperidin-3-yl}pyridine-2-carboxamide Mass spectrum: Found: MH$^+$ 584. H.p.l.c: (1) Rt 3.54 min.

Example 183

N-{(3S)-1-[(2S)-2-((3S)-3-{[(6-Chloro-2-naphthyl)sulfonyl]amino}-2-oxopyrrolidin-1-yl)propanoyl]piperidin-3-yl}isonicotinamide Mass spectrum: Found: MH$^+$ 584. H.p.l.c. (1) Rt 3.18 min.

Example 184

Methyl 3-({(3S)-1-[(2S)-2-((3S)-3-{[(6-chloro-2-naphthyl)sulfonyl]amino}-2-oxopyrrolidin-1-yl)propanoyl]piperidin-3-yl}amino)-3-oxopropanoate Mass spectrum: Found: MH$^+$ 579. H.p.l.c. (1) Rt 3.11 min.

Example 185

N-1-{(3S)-1-[(2S)-2-((3S)-3-{[(6-Chloro-2-naphthyl)sulfonyl]amino}-2-oxopyrrolidin-1-yl)propanoyl]piperidin-3-yl}-N-2-,N-2-dimethylglycinamide Mass spectrum: Found: MH$^+$ 564. H.p.l.c. (1) Rt 2.63 min.

Example 186

Benzyl (3R)-1-[(2S)-2-((3S)-3-{[(6-chloro-2-naphthyl)sulfonyl]amino}-2-oxopyrrolidin-1-yl)propanoyl]piperidin-3-ylcarbamate Using Example 366 and the synthetic procedure described in Example 181, the title compound was prepared.

Mass spectrum: Found: MH$^+$ 613. H.p.l.c. (1) Rt 3.46 min.

Using similar chemistry, the following were prepared:

Example 187

N-{(3R)-1-[(2S)-2-((3S)-3-{[(6-Chloro-2-naphthyl)sulfonyl]amino}-2-oxopyrrolidin-1-yl)propanoyl]piperidin-3-yl}nicotinamide Mass spectrum: Found: MH$^+$ 584. H.p.l.c. (1) Rt 3.07 min.

Example 188

N-{(3R)-1[(2S)-2-((3S)-3-{[(6-Chloro-2-naphthyl)sulfonyl]amino}-2-oxopyrrolidin-1-yl)propanoyl]piperidin-3-yl}pyridine-2-carboxamide Mass spectrum: Found: MH$^+$ 584. H.p.l.c. (1) Rt 3.38 min.

Example 189

N-{(3R)-1-[(2S)-2-((3S)-3-{[(6-Chloro-2-naphthyl)sulfonyl]amino}-2-oxopyrrolidin-1-yl)propanoyl]piperidin-3-yl}isonicotinamide Mass spectrum: Found: MH$^+$ 584. H.p.l.c. (1) Rt 3.01 min.

Example 190

Methyl 3-({(3R)-1-[(2S)-2-((3S)-3-{[(6-chloro-2-naphthyl)sulfonyl]amino}-2-oxopyrrolidin-1-yl)propanoyl]piperidin-3-yl}amino)-3-oxopropanoate Mass spectrum: Found: MH$^+$ 579. H.p.l.c. (1) Rt 3.01 min.

Example 191

N-1-{(3R)-1-[(2S)-2-((3S)-3-{[(6-Chloro-2-naphthyl)sulfonyl]amino}-2-oxopyrrolidin-1-yl)propanoyl]piperidin-3-yl}-N-2-N-2-dimethylglycinamide Mass spectrum: Found: MH$^{30}$ 564. H.p.l.c. (1) Rt 2.59 min.

Example 192

5'-Chloro-N-{(3S)-1-[(1S)-1-methyl-2-oxo-2-piperidin-1-ylethyl]-2-oxopyrrolidin-3-yl}-2,2'-bithiophene-5-sulfonamide A solution of the (3S)-3-amino-1-[(1S)-1-methyl-2-oxo-2-piperidin-1-ylethyl]pyrrolidin-2-one (0.007 g) in DCM (0.5 ml) was treated with 5'-chloro-2,2'-bithiophene-5-sulfonyl chloride$^2$ (0.009 g) and triethylamine (0.0054 ml) and stirred at room temperature for 48 h. The mixture was concentrated under reduced pressure and the residue purified using SPE (silica, eluting with methanol) to give the title compound (0.009 g) as an off-white solid.

Mass spectrum: Found: MH$^+$ 502. H.p.l.c. (1) Rt 3.39 min.

Using Intermediates 21, 22, 23 and 24, and chemistry to that described for the preparation of Example 192, the following were prepared:

Example 193

4'-Fluoro-N-{(3S)-1-[(1S)-1-methyl-2oxo-2-piperidin-1-ylethyl]-2-oxopyrrolidin-3-yl}-1,1'-biphenyl-4-sulfonamide Mass spectrum: Found: MH$^+$ 472. H.p.l.c. (1) Rt 3.17 min.

Example 194

6-Chloro-N-{(3S)-1-[(1S)-1-methyl-2-oxo-2-piperidin-1-ylethyl]-2-oxopyrrolidin-3-yl}-1-benzothiophene-2-sulfonamide Mass spectrum: Found: MH$^+$ 470. H.p.l.c. (1) Rt 3.22 min.

Example 195

(E)-2-(4-Chlorophenyl)-N-{(3S)-1-[(1S)-1-methyl-2-oxo-2-piperidin-1-ylethyl]-2-oxopyrrolidin-3-yl}ethenesulfonamide Mass spectrum: Found: MH$^+$ 439. H.p.l.c. (2) Rt 5.93 min.

Example 196

6-Chloro-N-{(3S)-1-[(1S)-1-methyl-2-oxo-2-piperidin-1-ylethyl]-2-oxopyrrolidin-3-yl}-1-benzothiophene-2-sulfonamide compound with 4-chloro-N-{(3S)-1-[(1S)-1-methyl-2-oxo-2-piperidin-1-ylethyl]-2-oxopyrrolidin-3-yl}-1-benzothiophene-2-sulfonamide (1:1)

Mass spectrum: Found: MH$^+$ 469. H.p.l.c. (2) Rt 6.83 min.

Example 197

6-Fluoro-N-{(3S)-1-[(1S)-1-methyl-2-oxo2-piperidin-1-ylethyl]-2-oxopyrrolidin-3-yl}naphthalene-2-sulfonamide Mass spectrum: Found: MH$^+$ 448. H.p.l.c. (1) Rt 3.03 min.

Example 198

5-Isoxazol-3-yl-N-{(3S)-1-[(1R)-1-methyl-2-oxo-2-piperidin-1-ylethyl]-2-oxopyrrolidin-3-yl}thiophene-2-sulfonamide Mass spectrum: Found: MH$^+$ 453. H.p.l.c. (1) Rt 2.84 min.

Example 199

5-(5-Chloro-1,3,4-thiadiazol-2-yl)-N-{(3S)-1-[(1R)-1-methyl-2oxo-2-piperidin-1-ylethyl]-2-oxopyrrolidin-3-yl}thiophene-2-sulfonamide Mass spectrum: Found: MH$^+$ 504. H.p.l.c. (1) Rt 3.06 min.

Example 200

6-Chloro-N-{(3S)-1-[(1R)-1-methyl-2-oxo-2-piperidin-1-ylethyl]-2-oxopyrrolidin-3-yl}-1-benzothiophene-2-sulfonamide compound with 4-chloro-N-{(3S)-1-[(1R)-1-methyl-2-oxo-2-piperidin-1-ylethyl]-2-oxopyrrolidin-3-yl}-1-benzothiophene-2-sulphonamide Mass spectrum: Found: MH$^+$ 470. H.p.l.c. (1) Rt 3.27 min.

Example 201

5'-Chloro-N-{(3S)-1-[(1R)-1-methyl-2-oxo-2-piperidin-1-ylethyl]-2-oxopyrrolidin-3-yl}-2,2'-bithiophene-5-sulfonamide Mass spectrum: Found: MH$^+$ 502. H.p.l.c. (1) Rt 3.46 min.

Example 202

N-{(3S)-1-[(1R)-1-Methyl-2-oxo-2-piperidin-1-ylethyl]-2-oxopyrrolidin-3-yl}thieno[2,3-c]pyridine-2-sulfonamide Mass spectrum: Found: MH$^+$ 437. H.p.l.c. (1) Rt 2.49 min.

Example 203

(E)-2-(4-Chlorophenyl)-N-{(3S)-1-[(1R)-1-methyl-2-oxo-2-piperidin-1-ylethyl]-2-oxopyrrolidin-3-yl}ethenesulfonamide Mass spectrum: Found: MH$^+$ 440. H.p.l.c. (1) Rt 3.14 min.

Example 204

5-Chloro-N-{(3S)-1-[(1R)-1-methyl-2-oxo-2-piperidin-1-ylethyl]-2-oxopyrrolidin-3-yl}-1-benzothiophene-2-sulfonamide Mass spectrum: Found: MH$^+$ 470. H.p.l.c. (1) Rt 3.28 min.

Example 205

3-Chloro-N-{(3S)-1-[(1R)-1-methyl-2-oxo-2-piperidin-1-ylethyl]-2-oxopyrrolidin-3-yl}isoquinoline-7-sulfonamide Mass spectrum: Found: MH$^+$ 465. H.p.l.c. (1) Rt 2.90 min.

Example 206

4-Methoxy-N-{(3S)-1-[(1S)-1-methyl-2-oxo-2-piperidin-1-ylethyl]-2-oxopyrrolidin-3-yl}benzenesulfonamide Mass spectrum: Found: MH$^+$ 409. H.p.l.c. (1) Rt 2.74 min.

Example 207

3-Chloro-N-{(3S)-1-[(1S)-1-methyl-2oxo-2-piperidin-1-ylethyl]-2-oxopyrrolidin-3-yl}isoquinoline-7-sulfonamide Mass spectrum: Found: MH$^+$ 464. H.p.l.c. (1) Rt 2.95 min.

Example 208

N-{(3S)-1-[(1S)-1-Methyl-2-oxo-2-piperidin-1-ylethyl]-2-oxopyrrolidin-3-yl}-5-pyridin-2-ylthiophene-2-sulfonamide Mass spectrum: Found: MH$^+$ 463. H.p.l.c. (1) Rt 2.79 min.

Example 209

N-{(3S)-1-[(1S)-1-Methyl-2-oxo-2-piperidin-1-yl-ethyl]-2-oxopyrrolidin-3-yl}-3-(1H-tetraazol-5-yl)benzenesulfonamide Mass spectrum: Found: MH$^+$ 448. H.p.l.c. (1) Rt 2.66 min.

Example 210

N-{(3S)-1-[(1S)-1-Methyl-2-oxo-2-piperidin-1-yl-ethyl]-2-oxopyrrolidin-3-yl}naphthalene-2-sulfonamide Mass spectrum: Found: MH$^+$ 430. H.p.l.c. (1) Rt 2.97 min.

Example 211

N-{(3S)-1-[(1S)-1-Methyl-2-oxo-2-piperidin-1-yl-ethyl]-2-oxopyrrolidin-3-yl}-1-benzothiophene-2-sulfonamide Mass spectrum: Found: MH$^+$ 436. H.p.l.c. (1) Rt 2.99 min.

Example 212

4-Chloro-N-{(3S)-1-[(1S)-1-methyl-2-oxo-2-piperidin-1-ylethyl]-2-oxopyrrolidin-3-yl}-1-benzothiophene-2-sulfonamide Mass spectrum: Found: MH$^+$ 470. H.p.l.c. (1) Rt 3.19 min.

Example 213

N-{(3S)-1-[(1S)-1-Methyl-2-oxo-2-piperidin-1-yl-ethyl]-2-oxopyrrolidin-3-yl}-5-(1,2,3-thiadiazol-4-yl)thiophene-2-sulfonamide Mass spectrum: Found: MH$^+$ 470. H.p.l.c. (1) Rt 2.8 min.

Example 214

4-Methoxy-N-{(3R)-1-[(1R)-1-methyl-2-oxo-2-piperidin-1-ylethyl-2-oxopyrrolidin-3-yl}benzenesulfonamide Mass spectrum: Found: MH$^+$ 410. H.p.l.c. (1) Rt 2.7 min.

Example 215

4'-Chloro-N-{(3R)-1-[(1R)-1-methyl-2-oxo-2-piperidin-1-ylethyl]-2-oxopyrrolidin-3-yl}-1,1'-biphenyl-4-sulfonamide Mass spectrum: Found: MH$^+$ 490. H.p.l.c. (1) Rt 3.42 min.

Example 216

4-Chloro-N-{(3R)-1-[(1R)-1-methyl-2-oxo-2-piperidin-1-ylethyl]-2-oxopyrrolidin-3-yl}benzenesulfonamide Mass spectrum: Found: MH$^+$ 414. H.p.l.c. (1) Rt 2.91 min.

Example 217

6-Chloro-N-{(3R)-1-[(1R)-1-methyl-2-oxo-2-piperidin-1-ylethyl]-2-oxopyrrolidin-3-yl}-1-benzothiophene-2-sulfonamide compound with 4-chloro-N-{(3R)-1-[(1R)-1-methyl-2-oxo-2-piperidin-1-ylethyl]-2-oxopyrrolidin-3-yl}-1-benzothiophene-2-sulfonamide Mass spectrum: Found: MH$^+$ 470. H.p.l.c. (1) Rt 3.28 min.

Example 218

(E)-2-(4-Chlorophenyl)-N-{(3R)-1-[(1R)-1-methyl-2-oxo-2-piperidin-1-ylethyl]-2-oxopyrrolidin-3-yl}ethenesulfonamide Mass spectrum: Found: MH$^+$ 440. H.p.l.c. (1) Rt 3.14 min.

Example 219

6-Chloro-N-{(3R)-1-[(1R)-1-methyl-2-oxo-2-piperidin-1-ylethyl]-2-oxopyrrolidin-1-yl}-1H-benzimidazole-2-sulfonamide Mass spectrum: Found: MH$^+$ 454. H.p.l.c. (1) Rt 2.55 min.

Example 220

5-Chloro-N-{(3R)-1-[(1R)-1-methyl-2-oxo-2-piperidin-1-ylethyl]-2-oxopyrrolidin-3-yl}-1-benzothiophene-2-sulfonamide Mass spectrum: Found: MH$^+$ 470. H.p.l.c. (1) Rt 3.29 min.

Example 221

5'-Chloro-N-{(3R)-1-[(1R)-1-methyl-2-oxo-2-piperidin-1-ylethyl]-2-oxopyrrolidin-3-yl}-2,2'-bithiophene-5-sulfonamide Mass spectrum: Found: MH$^+$ 502. H.p.l.c. (1) Rt 3.46 min.

Example 222

3-Chloro-N-{(3R)-1-[(1R)-1-methyl-2oxo-2-piperidin-1-ylethyl]-2-oxopyrrolidin-3-yl}isoquinoline-7-sulfonamide Mass spectrum: Found: MH$^+$ 469. H.p.l.c. (1) Rt 3.37 min.

Example 223

5-Chloro-N-{(3S)-1-[(1S)-1-methyl-2-oxo-2-piperidin-1-ylethyl]-2-oxopyrrolidin-3-yl}-1-benzothiophene-2-sulfonamide Mass spectrum: Found: MH$^+$ 470. H.p.l.c. (1) Rt 3.19 min.

Example 224

5-Chloro-N-{(3R)-1-[(1S)-1-methyl-2-oxo-2-piperidin-1-ylethyl]-2-oxopyrrolidin-3-yl}-1-benzothiophene-2-sulfonamide Mass spectrum: Found: MH$^+$ 469. H.p.l.c. (1) Rt 3.37 min.

Example 225

3-Chloro-N-{(3R)-1-[(1S)-1-methyl-2-oxo-2-piperidin-1-ylethyl]-2-oxopyrrolidin-3-yl}isoquinoline-7-sulfonamide Mass spectrum: Found: MH$^+$ 465. H.p.l.c. (1) Rt 2.87 min.

Example 226

6-Fluoro-N-{(3S)-1[-(1S)-1-methyl-2-oxo-2-piperidin-1-ylethyl]-2-oxopyrrolidin-3-yl}naphthalene-2-sulfonamide Mass spectrum: Found: MH$^+$ 448. H.p.l.c. (1) Rt 2.4 min.

Example 227

5-Chloro-3-methyl-N-{(3S)-1-[(1S)-1-methyl-2-oxo-2-piperidin-1-ylethyl]-2-oxopyrrolidin-3-yl}-1-benzothiophene-2-sulfonamide Mass spectrum: Found: MH$^+$ 484. H.p.l.c. (1) Rt 3.38 min.

Example 228

6-Chloro-N-(3-furylmethyl)-N-{(3S)-1-[(1S)-1-methyl-2-morpholin-4-yl-2-oxoethyl]-2-oxopyrrolidin-3-yl}naphthalene-2-sulfonamide A solution of 6-chloro-N-{(3S)-1-[(1S)-1-methyl-2-morpholin-4-yl-2-oxoethyl]-2-oxopyrrolidin-3-yl}naphthalene-2-sulfonamide (0.015 g) in THF (0.5 ml) was treated with diisopropyl azodicarboxylate (0.01 ml), 3-furanmethanol (0.004 ml) and tri-n-butylphosphine (0.008 ml) and shaken at room temperature for 60 h. The mixture was concentrated under reduced pressure and the residue purified by mass directed preparative h.p.l.c. to give the title compound (0.015 g) as a colourless gum.

Mass spectrum: Found: MH$^+$ 546. H.p.l.c. (1) Rt 3.33 min.

Using similar chemistry, the following were prepared:

Example 229

6-Chloro-N-{(3S)-1-[(1S)-1-methyl-2-morpholin-4-yl-2-oxoethyl]-2-oxopyrrolidin-3-yl}-N-(pyridin-3-ylmethyl)naphthalene-2-sulfonamide formate The title compound was isolated from a crude reaction mixture using mass directed preparative h.p.l.c.

Mass spectrum: Found: MH$^+$ 557. H.p.l.c. (1) Rt 2.9 min.

Example 230

6-Chloro-N-ethyl-N-{(3S)-1-[(1S)-1-methyl-2-morpholin-4-yl-2-oxoethyl]-2-oxopyrrolidin-3-yl}naphthalene-2-sulfonamide Mass spectrum: Found: MH$^+$ 494. H.p.l.c. (1) Rt 3.32 min.

Example 231

N-{1-[(2R)-2-((3S)-3-{[(6-Chloro-2-naphthyl)sulfonyl]amino}-2-oxopyrrolidin-1-yl)propanoyl]piperidin-3-yl}benzamide A solution of tert-butyl (2R)-2-((3S)-3-{[(6-chloro-2-naphthyl)sulfonyl]amino}-2-oxopyrrolidin-1-yl)propanoate (0.025 g) in DCM (1 ml) was treated with trifluoroacetic acid (1 ml) and stirred at room temperature for 2 h. The mixture was then concentrated under reduced pressure to give an oil which was subsequently treated with 1-[3-(dimethylamino)propyl]-3-ethylcarbodiimide hydrochloride (0.013 g), HOBT (0.009 g) and triethylamine (0.023 ml). After stirring at room temperature for 1 h, N-piperidin-3-ylbenzamide (0.015 g) was added and stirring was continued for 48 h. The reaction mixture was partitioned between DCM and water. The organic extract was concentrated under reduced pressure and the residue purified using SPE (silica, eluting with cyclohexane:ethyl acetate 5:1, 3:1, 1:1, 1:3 and ethyl acetate) to give the title compound (0.012 g) as a colourless gum.

Mass spectrum: Found: MH$^+$ 583. H.p.l.c. (1) Rt 3.32 min.

Example 232

6-Chloro-N-{(3S)-1-[(1S)-1-methyl-2-morpholin-4-yl-2-oxoethyl]-2-oxopyrrolidin-3-yl}-N-(2-oxobutyl)naphthalene-2-sulfonamide To a solution of (2S)-2-{(3S)-3-[[(6-chloro-2-naphthyl)sulfonyl](2-oxobutyl)amino]-2-oxopyrrolidin-1-yl}propanoic acid (0.035 g) in DCM (2 ml) were added 1-[3-(dimethylamino)propyl]-3-ethylcarbodiimide hydrochloride (0.044 g), HOBT (0.031 g) and triethylamine (0.064 ml) and the mixture was stirred at room temperature for 30 min. Morpholine (0.02 ml) was added and the resultant mixture stirred at room temperature for 16 h. The mixture was partitioned between DCM and water. The aqueous layer was re-extracted with DCM and the combined, dried (over magnesium sulphate) organic extracts were concentrated under reduced pressure. The residue was purified using mass directed preparative h.p.l.c. to give the title compound (0.008 g) as a white solid.

Mass spectrum: Found: MH$^+$ 536. H.p.l.c. (1) Rt 3.20 min.

Using similar chemistry, the following were prepared:

Example 233

N-2-[(6-Chloro-2-naphthyl)sulfonyl]-N-2-{(3S)-1-(1S)-1-methyl-2-morpholin-4-yl-2-oxoethyl]-2-oxopyrrolidin-3-yl}glycinamide The title compound was prepared from Intermediate 49
Mass spectrum: Found: MH$^+$ 523. H.p.l.c. (1) Rt 2.87 min.

Example 234

6-Chloro-N-(2-furylmethyl)-N-{(3S)-1-[(1S)-1-methyl-2-morpholin-4-yl-2-oxoethyl]-2-oxopyrrolidin-3-yl}naphthalene-2-sulfonamide The title compound was prepared from Intermediate 63
Mass spectrum: Found: MH$^+$ 546. H.p.l.c. (1) Rt 3.33 min.

Example 235

6-Chloro-N-{(3S)-1-[(1S)-1-methyl-2-morpholin-4-yl-2-oxoethyl]-2-oxopyrrolidin-3-yl}-N-(1,3-thiazol-2-ylmethyl)naphthalene-2-sulfonamide The title compound was prepared from Intermediate 62.
Mass spectrum: Found: MH$^+$ 563. H.p.l.c. (1) Rt 3.18 min.

Example 236

N2-[(6-Chloro-2-naphthyl)sulfonyl]-N2-{(3S)-1-[(1S)-1-methyl-2-oxo-2-(5-oxo-1,4-diazepan-1-yl)ethyl]-2-oxopyrrolidin-3-yl}glycinamide The title compound was prepared from Intermediate 49.
Mass spectrum: Found: MH$^+$ 550. H.p.l.c. (1) Rt 2.66 min.

Example 237

N2-[(6-Chloro-2-naphthyl)sulfonyl]-N2-{(3S)-1-[(1S)-1-methyl-2-(4-methyl-5-oxo-1,4-diazepan-1-yl)-2oxoethyl]-2-oxopyrrolidin-3-yl}glycinamide The title compound was prepared from Intermediate 49.
Mass spectrum: Found: MH$^+$ 564. H.p.l.c. (1) Rt 2.7 min.

Example 238

N2-[(6-Chloro-2-naphthyl)sulfonyl]-N2-{(3S)-1-[(1S)-1-methyl-2-oxo-2-(2-pyridin-3-ylpyrrolidin-1-yl)ethyl]-2-oxopyrrolidin-3-yl}glycinamide The title compound was prepared from Intermediate 49.
Mass spectrum: Found: MH$^+$ 584. H.p.l.c. (3).Rt 10.85 min.

Example 239

N2-[(6-Chloro-2-naphthyl)sulfonyl]-N2-{(3S)-1-[(1S)-1-methyl-2-oxo-2-(2-pyridin-3-ylpiperidin-1-yl)ethyl]-2-oxopyrrolidin-3-yl}glycinamide The title compound was prepared from Intermediate 49.
Mass spectrum: Found: MH$^+$ 598. H.p.l.c. (3) Rt 11.3 min.

Example 240

N2-[(6-Chloro-2-naphthyl)sulfonyl]-N2-{(3S)-1-[(1S)-1-methyl-2-oxo-2-(2-pyridin-4-ylpyrrolidin-1-yl)ethyl]-2-oxopyrrolidin-3-yl}glycinamide The title compound was prepared from Intermediate 49.
Mass spectrum: Found: MH$^+$ 584. H.p.l.c. (3) Rt 10.7 min.

Example 241

N2-[(6-Chloro-2-naphthyl)sulfonyl]-N2-((3S)-1-{(1S)-2-[(1S,4S)-2,5-diazabicyclo[2,2,1]hept-2-yl]-1-methyl-2-oxoethyl}-2-oxopyrrolidin-3-yl)glycinamide The title compound was prepared from Intermediate 49.
Mass spectrum: Found: MH$^+$ 534. H.p.l.c. (1) Rt 2.37 min.

Example 242

N2-[(6-Chloro-2-naphthyl)sulfonyl]-N2-((3S)-1-{(1S)-1-methyl-2-[(1S,4S)-5-methyl-2,5-diazabicyclo[2.2.1]hept-2-yl]-2-oxoethyl}-2-oxopyrrolidin-3-yl)glycinamide hydrobromide The title compound was prepared from Intermediate 49.
Mass spectrum: Found: MH$^+$ 548. H.p.l.c. (3) Rt 10.3 min.

Example 243

N2-[(6-Chloro-2-naphthyl)sulfonyl]-1-N2-(3S)-1-[(1S)-1-methyl-2-(4-methyl-1,4-diazepan-1-yl)-2-oxoethyl]-2-oxopyrrolidin-3-yl}glycinamide The title compound was prepared from Intermediate 49.
Mass spectrum: Found: MH$^+$ 550. H.p.l.c. (3) Rt 10.4 min.

Example 244

N2-[(6-Chloro-2-naphthyl)sulfonyl]-N2-{(3S)-1-[(1S)-2-(1,4-diazepan-1-yl)-1-methyl-2-oxoethyl]-2-oxopyrrolidin-3-yl}glycinamide The title compound was prepared from Intermediate 49.
Mass spectrum: Found: MH$^+$ 536. H.p.l.c. (3) Rt 14.5 min.

Example 245

N2-[(6-Chloro-2-naphthyl)sulfonyl]-N2-((3S)-1-{(1S)-2-[(2R,6S)-2,6-dimethylmorpholin-4-yl]-1-methyl-2-oxoethyl}-2-oxopyrrolidin-3-yl)glycinamide The title compound was prepared from Intermediate 49.
Mass spectrum: Found: MH$^+$ 551. H.p.l.c. (3) Rt 13.4 min.

Example 246

N2-[(6-Chloro-2-naphthyl)sulfonyl]-N2-((3S)-1-
((1S)-1-methyl-2-[(1S,4S)-2-oxa-5-azabicyclo[2.2.1]
hept-5yl]-2-oxoethyl]-2-oxopyrrolidin-3-yl)glycinamide The title compound was prepared from Intermediate 49.
Mass spectrum: Found: MH$^+$ 535. H.p.l.c. (3) Rt 12.7 min.

Example 247

6-Chloro-N-{(3S)-1-[(1S)-1-methyl-2-morpholin-4-
yl-2-oxoethyl]-2-oxopyrrolidin-3yl}-N-[(2-methyl-1,
3-thiazol-4-yl)methyl]naphthalene-2-sulfonamide The title compound was prepared from Intermediate 95.
Mass spectrum: Found: MH$^+$ 577. H.p.l.c. (1) Rt 3.24 min.

Example 248

6-Chloro-N-{(3S)-1-[(1S)-1-methyl-2-morpholin-4-
yl-2-oxoethyl]-2-oxopyrrolidin-3-yl}-N-(pyridin-2-
ylmethyl)naphthalene-2-sulfonamide formate The title compound was prepared from Intermediate 97.
Mass spectrum: Found: MH$^+$ 563. H.p.l.c. (1) Rt 3.62 min.

Example 249

6-Chloro-N-{(3S)-1-[(1S)-1-methyl-2-morpholin-4-
yl-2-oxoethyl]-2-oxopyrrolidin-3-yl}-N-(pyridin-4-
ylmethyl)naphthalene-2-sulfonamide formate The title compound was prepared from Intermediate 96.
Mass spectrum: Found: MH$^+$ 557. H.p.l.c. (1) Rt 2.83 min.

Example 250

6-Chloro-N-((3S)-1-{(1S)-1-methyl-2-oxo-2-[(2S)-
2-(pyrrolidin-1-ylmethyl)pyrrolidin-1-yl]ethyl}-2-
oxopyrrolidin-3-yl)-N-[(2-methyl-1,3-thiazol-4-yl)
methyl]naphthalene-2-sulfonamide formate The title compound was prepared from Intermediate 95.
Mass spectrum: Found: MH$^+$ 644. H.p.l.c. (1) Rt 2.83 min.

Example 251

6-Chloro-N-((3S)-1-{(1S)-1-methyl-2-oxo-2-[(2S)-
2-(pyrrolidin-1-yl]methyl)pyrrolidin-1-yl]ethyl}-2-
oxopyrrolidin-3-yl)-N-(pyridin-4-ylmethyl)naphtha-
lene-2-sulfonamide formate The title compound was prepared from Intermediate 96.
Mass spectrum: Found: MH$^+$ 624. H.p.l.c. (1) Rt 2.74 min.

Example 252

Methyl N-[(5'-chloro-2,2'-bithien-5-yl)sulfonyl]-N-{
(3S)-1-[(1S)-1-methyl-2-oxo-2-piperidin-1-ylethyl]-
2-oxopyrrolidin-3-yl}glycinate A solution of 5'-chloro-N-{(3S)-1-[(1S)-1-methyl-2-oxo-
2-piperidin-1-ylethyl]-2-oxopyrrolidin-3-yl}-2,2'-
bithiophene-5sulfonamide (0.025 g) in THF (3 ml) was
cooled to −78° C. under nitrogen, and treated with lithium
bis(trimethylsilyl) amide (1.0M solution in THF; 0.092 ml),
followed by methyl bromoacetate (0.026 ml). The resultant
solution was allowed to reach room temperature and stirred
for a further 22 h. Methanol was added and the mixture was
concentrated under reduced pressure. The residue was partitioned between DCM and water and then passed through a
hydrophobic frit. The organic extract was concentrated
under reduced pressure and the residue purified by mass
directed preparative h.p.l.c. to give the title compound
(0.006 g) as a white solid.
Mass spectrum: Found: MH$^+$ 574. H.p.l.c. (1) Rt 3.57 min.

Similarly prepared using the commercially available alkyl halide, was:

Example 253

5'-Chloro-N-(cyanomethyl)-N-{(3S)-1-[(1S)-1-me-
thyl-2-oxo-2-piperidin-1-ylethyl]-2-oxopyrrolidin-3-
yl}-2,2'-bithiophene-5-sulfonamide Mass spectrum: Found: MH$^+$ 541. H.p.l.c. (1) Rt 3.56 min.

Example 254

N-[(5'-Chloro-2,2'-bithien-5yl)sulfonyl]-N-{(3S)-1-
[(1S)-1-methyl-2-oxo-2-piperidin-1-ylethyl]-2-ox-
opyrrolidin-3-yl}glycine Using standard alkaline hydrolysis conditions, the title compound was prepared from Example 252.
Mass spectrum: Found: MH$^+$ 560. H.p.l.c. (1) Rt 3.47 min.

Example 255

6-Chloro-N-{(3S)-1-[(1R)-1-methyl-2-(3-methylpip-
eridin-1-yl)-2-oxoethyl]-2-oxopyrrolidin-3-
yl}naphthalene-2-sulfonamide To a solution of (2R)-2-((3S)-3-{[(6-chloro-2-naphthyl)
sulfonyl]amino}-2-oxopyrrolidin-1-yl)propanoic acid
(0.018 g) in DCM (0.5 ml) were added 1-[3-(dimethy-
lamino)propyl]-3-ethylcarbodiimide hydrochloride (0.018
g), HOBT (0.013 g) and triethylamine (0.039 ml) and the
mixture was stirred at room temperature for 75 min. 3-Me-
thylpiperidine (0.010 ml) was added and the resultant mixture stirred at room temperature for 48 h. The mixture was
partitioned between DCM and saturated sodium bicarbonate
solution and then passed through a hydrophobic frit. The
organic extract concentrated under reduced pressure and the
residue was purified using SPE (silica, eluting with cyclo-
hexane:ethyl acetate 2:1, 1:1; ethyl acetate; ethyl acetate:
methanol 2:1, 1:1) to give the title compound (0.007 g) as a
white solid.
Mass spectrum: Found: MH$^+$ 478. H.p.l.c. (1) Rt 3.4 min.

Using similar chemistry, the following were prepared:

Example 256

N-{1-[(2R)-2-((3S)-3-{[(6-Chloro-2-naphthyl)sulfonyl]amino}-2-oxopyrrolidin-1-yl)propanoyl]piperidin-3-yl}acetamide Mass spectrum: Found: MH$^+$ 521. H.p.l.c. (1) Rt 3.14 min.

Example 257

6-Chloro-N-((3S)-1-{(1R)-1-methyl-2-[(2R)-2-methylpiperidin-1-yl]-2-oxoethyl}-2-oxopyrrolidin-3-yl)naphthalene-2-sulfonamide Mass spectrum: Found: MH$^+$ 478. H.p.l.c. (1) Rt 3.36 min.

Example 258

6-Chloro-N-((3S)-1-{(1R)-1-methyl-2-[(2S)-2-methylpiperidin-1-yl]-2-oxoethyl}-2-oxopyrrolidin-3-yl)naphthalene-2-sulfonamide Mass spectrum: Found: MH$^+$ 478. H.p.l.c. (1) Rt 3.36 min.

Example 259

6-Chloro-N-[(3S)-1-((1R)-2-{2-[(diethylamino)methyl]piperidin-1-yl}-1-methyl-2-oxoethyl)-2-oxopyrrolidin-3-yl]naphthalene-2-sulfonamide Mass spectrum: Found: MH$^+$ 549. H.p.l.c. (1) Rt 2.59 min.

Example 260

6-Chloro-N-{(3S)-1-[(1R)-1-methyl-2-oxo-2-pyrrolidin-1-ylethyl]-2-oxopyrrolidin-3-yl}naphthalene-2-sulfonamide Mass spectrum: Found: MH$^+$ 450. H.p.l.c. (1) Rt 3.03 min.

Example 261

6-Chloro-N-{(3S)-1-[(1R)-1-methyl-2-morpholin-4-yl-2-oxoethyl]-2-oxopyrrolidin-3-yl}naphthalene-2-sulfonamide Mass spectrum: Found: MH$^+$ 466. H.p.l.c. (1) Rt 2.95 min.

Example 262

6-Chloro-N-((3S)-1-{(1R)-2-[3-(hydroxymethyl)piperidin-1-yl]-1-methyl-2-oxoethyl}-2-oxopyrrolidin-3-yl)naphthalene-2-sulfonamide Mass spectrum: Found: MH$^+$ 521. H.p.l.c. (1) Rt 2.98 min.

Example 263

6-Chloro-N-methyl-N-{(3R)-1-[(1S)-1-methyl-2-oxo-2-piperidin-1-ylethyl]-2-oxopyrrolidin-3-yl}naphthalene-2-sulfonamide Using Intermediate 30 and piperidine, and the chemistry described for Example 255, the title compound was prepared.

Mass spectrum: Found: MH$^+$ 478. H.p.l.c. (1) Rt 3.4 min.

Example 264

6-Chloro-N-methyl-N-{(3S)-1-[(1R)-1-methyl-2-(3-methylpiperidin-1-yl)-2-oxoethyl]-2-oxopyrrolidin-3-yl}naphthalene-2-sulfonamide Using Intermediate 55 and 3-methylpiperidine and chemistry described for Example 255, the title compound was prepared.

Mass spectrum: Found: MH$^+$ 494. H.p.l.c. (1) Rt 3.03 min.

Using similar chemistry, the following were prepared:

Example 265

N-[1-((2R)-2-{(3S)-3-[[(6-chloro-2-naphthyl)sulfonyl](methyl)amino]-2-oxopyrrolidin-1-yl}propanoyl)piperidin-3-yl]acetamide Mass spectrum: Found: MH$^+$ 535. H.p.l.c. (1) Rt 3.1 min.

Example 266

6-Chloro-N-methyl-N-{(3S)-1-[(1R)-1-methyl-2-oxo-2-(3-{[(phenylsulfonyl)amino]methyl}piperidin-1-yl)ethyl]-2-oxopyrrolidin-3-yl}naphthalene-2-sulfonamide Mass spectrum: Found: MH$^+$ 647. H.p.l.c. (1) Rt 3.55 min.

Example 267

6-Chloro-N-((3S)-1-{(1R)-2-[3-(hydroxymethyl)piperidin-1-yl]-1-methyl-2-oxoethyl}-2-oxopyrrolidin-3-yl)-N-methylnaphthalene-2-sulfonamide Mass spectrum: Found: MH$^+$ 508. H.p.l.c. (1) Rt 3.1 min.

Example 268

6-Chloro-N-((3S)-1-{(1R)-2-[2-(hydroxymethyl)piperidin-1-yl]-1-methyl-2-oxoethyl}-2-oxopyrrolidin-3-yl)-N-methylnaphthalene-2-sulfonamide Mass spectrum: Found: MH$^+$ 508. H.p.l.c. (1) Rt 3.23 min.

Example 269

6-Chloro-N-methyl-N-{(3S)-1-[(1R)-1-methyl-2-oxo-2-piperidin-1-ylethyl]-2-oxopyrrolidin-3-yl}naphthalene-2-sulfonamide Mass spectrum: Found: MH$^+$ 478. H.p.l.c. (1) Rt 3.49 min.

Example 270

N-[1-((2R)-2-{(3S)-3-[[(6-Chloro-2-naphthyl)sulfonyl](methyl)amino]-2-oxopyrrolidin-1-yl}propanoyl)piperidin-3-yl]benzamide Mass spectrum: Found: MH⁺ 597. H.p.l.c. (1) Rt 3.41 min.

Example 271

6-Chloro-N-[(3S)-1-((1R)-2-{2-[(diethylamino)methyl]piperidin-1-yl}-1-methyl-2-oxoethyl]-2-oxopyrrolidin-3-yl]-N-methylnaphthalene-2-sulfonamide Mass spectrum: Found: MH⁺ 563. H.p.l.c. (1) Rt 2.65 min.

Example 272

6-Chloro-N-methyl-N-{(3S)-1-[(1R)-1-methyl-2-oxo-2-pyrrolidin-1-ylethyl]-2-oxopyrrolidin-3-yl}naphthalene-2-sulfonamide Mass spectrum: Found: MH⁺ 464. H.p.l.c. (1) Rt 3.21 min.

Example 273

6-Chloro-N-methyl-N-((3S)-1-{(1R)-1-methyl-2-[(2S)-2-methylpiperidin-1-yl]-2-oxoethyl}-2-oxopyrrolidin-3-yl)naphthalene-2-sulfonamide Mass spectrum: Found: MH⁺ 492. H.p.l.c. (1) Rt 3.49 min.

Example 274

N-{(3S)-1-[(1R)-2-Azepan-1-yl-1-methyl-2oxoethyl]-2-oxopyrrolidin-3-yl}-6-chloro-N-methylnaphthalene-2-sulfonamide Mass spectrum: Found: MH⁺ 492. H.p.l.c. (1) Rt 3.41 min.

Example 275

6-Chloro-N-methyl-N-{(3S)-1-[(1R)-1-methyl-2-oxo-2-(4pyrrolidin-1-ylpiperidin-1-yl)ethyl]-2-oxopyrrolidin-3-yl}naphthalene-2-sulfonamide Mass spectrum: Found: MH⁺ 547. H.p.l.c. (1) Rt 2.68 min.

Example 276

6-Chloro-N-methyl-N-((3S)-1-{(1R)-1-methyl-2-oxo-2-[2-(pyrrolidin-1-ylmethyl)piperidin-1-yl]ethyl}-2-oxopyrrolidin-3-yl)naphthalene-2-sulfonamide Mass spectrum: Found: MH⁺ 561. H.p.l.c. (1) Rt 2.77 min.

Example 277

6-Chloro-N-methyl-N-{(3S)-1-[(1R)-1-methyl-2-(4-methylpiperidin-1-yl)-2-oxoethyl]-2-oxopyrrolidin-3-yl}naphthalene-2-sulfonamide Mass spectrum: Found: MH⁺ 492. H.p.l.c. (1) Rt 3.58 min.

Example 278

N-{(3S)-1-[(1R)-2-(4-{[(Benzylsulfonyl)amino]methyl}piperidin-1-yl)-1-methyl-2-oxoethyl]-2-oxopyrrolidin-3-yl}-6-chloro-N-methylnaphthalene-2-sulfonamide Mass spectrum: Found: MH⁺ 661. H.p.l.c. (1) Rt 3.52 min.

Example 279

N-[1-((2R)-2-{(3S)-3-[[(6-Chloro-2-naphthyl)sulfonyl](methyl)amino]-2-oxopyrrolidin-1-yl}propanoyl)piperidin-4-yl]benzamide Mass spectrum: Found: MH⁺ 597. H.p.l.c. (1) Rt 3.38 min.

Example 280

N-[1-((2R)-2-{(3S)-3-[[(6-Chloro-2-naphthyl)sulfonyl](methyl)amino]-2-oxopyrrolidin-1-yl}propanoyl)pyrrolidin-3-yl]benzamide Mass spectrum: Found: MH⁺ 583. H.p.l.c. (1) Rt 3.32 min.

Example 281

N-{[1-((2R)-2-{(3S)-3-[[(6-Chloro-2-naphthyl)sulfonyl](methyl)amino]-2-oxopyrrolidin-1-yl}propanoyl)piperidin-2-yl]methyl}benzamide Mass spectrum: Found: MH⁺ 611. H.p.l.c. (1) Rt 3.52 min.

Example 282

N-[1-((2R)-2-{(3S)-3-[[(6-Chloro-2-naphthyl)sulfonyl](methyl)amino]-2-oxopyrrolidin-1-yl}propanoyl)piperidin-4-yl]acetamide Mass spectrum: Found: MH⁺ 535. H.p.l.c. (1) Rt 3.04 min.

Example 283

N-[1-((2R)-2-{(3S)-3-[[(6-Chloro-2-naphthyl)sulfonyl](methyl)amino]-2-oxopyrrolidin-1-yl}propanoyl)pyrrolidin-3-yl]acetamide Mass spectrum: Found: MH⁺ 521. H.p.l.c. (1) Rt 2.99 min.

Example 284

6-Chloro-N-methyl-N-((3S)-1-{(1R)-1-methyl-2-oxo-2-[2-(pyrrolidin-1-ylcarbonyl)piperidin-1-yl]ethyl}-2-oxopyrrolidin-3-yl)naphthalene-2-sulfonamide Mass spectrum: Found: MH$^+$ 575. H.p.l.c. (1) Rt 3.42 min.

Example 285

6-Chloro-N-((3S)-1-{(1R)-2-[4(dimethylamino)piperidin-1-yl]-1-methyl-2-oxoethyl-}2-oxopyrrolidin-3-yl)-N-methylnaphthalene-2-sulfonamide Mass spectrum: Found: MH$^+$ 521. H.p.l.c. (1) Rt 2.65 min.

Example 286

6-Chloro-N-((3S)-1-{(1R)-2-[4-(hydroxymethyl)piperidin-1-yl]-1-methyl-2-oxoethyl}-2-oxopyrrolidin-3-yl)-N-methylnaphthalene-2-sulfonamide Mass spectrum: Found: MH$^+$ 508. H.p.l.c. (1) Rt 3.11 min.

Example 287

6-Chloro-N-{(3S)-1-[(1R)-2-(4-methoxypiperidin-1-yl)-1-methyl-2-oxoethyl]-2-oxopyrrolidin-3-yl}-N-methylnaphthalene-2-sulfonamide Mass spectrum: Found: MH$^+$ 508. H.p.l.c. (1) Rt 3.29 min.

Example 288

6-Chloro-N-{(3S)-1-[(1R)-2-(3-methoxypiperidin-1-yl)-1-methyl-2-oxoethyl]-2-oxopyrrolidin-3-yl}-N-methylnaphthalene-2-sulfonamide Mass spectrum: Found: MH$^+$ 508. H.p.l.c. (1) Rt 3.35 min.

Example 289

6-Chloro-N-methyl-N-{(3S)-1-[(1R)-1-methyl-2-morpholin-4-yl-2-oxoethyl]-2-oxopyrrolidin-3-yl}naphthalene-2-sulfonamide Mass spectrum: Found: MH$^+$ 479. H.p.l.c. (1) Rt 3.18 min.

Example 290

6-Chloro-N-methyl-N-{(3R)-1-[(1S)-1-methyl-2-oxo-2-pyrrolidin-1-ylethyl]-2-oxopyrrolidin-3-yl}naphthalene-2-sulfonamide The title compound was prepared from Intermediate 30.
Mass spectrum: Found: MH$^+$ 464. H.p.l.c. (1) Rt 3.25 min.

Example 291

6-Chloro-N-methyl-N-((3R)-1-{(1S)-1-methyl-2-[(2R)-2-methylpiperidin-1-yl]-2-oxoethyl}-2-oxopyrrolidin-3-yl)naphthalene-2-sulfonamide The title compound was prepared from Intermediate 30.
Mass spectrum: Found: MH$^+$ 492. H.p.l.c. (1) Rt 3.51 min.

Example 292

6-Chloro-N-[(3R)-1-((1S)-2-{2-[(diethylamino)methyl]piperidin-1-yl}-methyl-2-oxoethyl)-2-oxopyrrolidin-3-yl]-N-methylnaphthalene-2-sulfonamide The title compound was prepared from Intermediate 30.
Mass spectrum: Found: MH$^+$ 563. H.p.l.c. (1) Rt 2.82 min.

Example 293

6-Chloro-N-(cyanomethyl)-N-{(3S)-1-[(1S)-1-methyl-2-morpholin-4-yl-2-oxoethyl]-2-oxopyrrolidin-3-yl}naphthalene-2-sulfonamide A solution of 6-chloro-N-{(3S)-1-[(1S)-1-methyl-2-morpholin-4-yl-2-oxoethyl]-2-oxopyrrolidin-3-yl}naphthalene-2-sulfonamide (0.01 g) in THF (2 ml) was cooled to –78° C. under nitrogen, and treated with lithium bis(trimethylsilyl)amide (1.0M solution in THF; 0.026 ml), followed by bromoacetonitrile (0.013 g). The resultant solution was allowed to reach room temperature and stirred for a further 16 h. The mixture was then cooled to –78° C. and further lithium bis(trimethylsilyl) amide (0.026 ml) added. After reaching room temperature, the reaction mixture was stirred for a further 18 h and then quenched by the addition of methanol (1 ml). The resultant solution was concentrated under reduced pressure and the residue purified by mass directed preparative h.p.l.c. to give the title compound (0.003 g) as a white solid.

Mass spectrum: Found: MH$^+$ 505. H.p.l.c. (1) Rt 3.16 min.

Similarly prepared using commercially available alkyl halides, were:

Example 294

6-Chloro-N-methyl-N-{(3S)-1-[(1S)-1-methyl-2-morpholin-4-yl-2-oxoethyl]-2-oxopyrrolidin-3-yl}naphthalene-2-sulfonamide Mass spectrum: Found: MH$^+$ 480. H.p.l.c. (1) Rt 3.11 min.

Example 295

6-Chloro-N-(3,3-dimethyl-2-oxobutyl)-N-{(3S)-1-1-[(1S)-1-methyl-2-morpholin-4-yl-2-oxoethyl]-2-oxopyrrolidin-3-yl}naphthalene-2-sulfonamide Mass spectrum: Found: MH$^+$ 564. H.p.l.c. (1) Rt 3.39 min.

Example 296

N2-[(6-Chloro-2-naphthyl)sulfonyl]-N1-methyl-N2-{(3S)-1-[(1S)-1-methyl-2-morpholin-4-yl-2-oxoethyl]-2-oxopyrrolidin-3-yl}glycinamide Mass spectrum: Found: MH$^+$ 537. H.p.l.c. (1) Rt 2.98 min.

Example 297

N-Allyl-6-chloro-N-{(3S)-1-[(1S)-1-methyl-2-morpholin-4-yl-2-oxoethyl]-2-oxopyrrolidin-3-yl}naphthalene-2-sulfonamide Mass spectrum: Found: MH$^+$ 506. H.p.l.c. (1) Rt 3.26 min.

Example 298

Methyl N-[(6-chloro-2-naphthyl)sulfonyl]-N-{(3S)-1-[(1S)-1-methyl-2-morpholin-4-yl-2-oxoethyl]-2-oxopyrrolidin-3-yl}glycinate Mass spectrum: Found: MH$^+$ 538. H.p.l.c. (1) Rt 3.12 min.

Example 299

Ethyl N-[(6-chloro-2-naphthyl)sulfonyl]-N-{(3S)-1-[(1S)-1-methyl-2-morpholin-4-yl-2-oxoethyl]-2-oxopyrrolidin-3-yl}glycinate Mass spectrum: Found: MH$^+$ 552. H.p.l.c. (1) Rt 3.36 min.

Example 300 tert-Butyl N-[(6-chloro-2-naphthyl)sulfonyl]-N-{(3S)-1-[(1S)-1-methyl-2-morpholin-4-yl-2-oxoethyl]-2-oxopyrrolidin-3-yl}glycinate Mass spectrum: Found: MH$^+$ 580. H.p.l.c. (1) Rt 3.45 min.

Example 301

N-[1-((2R)-2-{(3R)-3-[[(6-Chloro-2-naphthyl)sulfonyl](methyl)amino]-2-oxopyrrolidin-1-yl}propanoyl)piperidin-3-yl]benzamide Using Example 327 and the synthetic procedure described for Intermediate 52, the title compound was prepared.
Mass spectrum: Found: MH$^+$ 597. H.p.l.c. (1) Rt 3.37 min.

Example 302

N-{(3R)-1-[(1R)-2-Azepan-1-yl-1-methyl-2-oxoethyl]-2-oxopyrrolidin-3-yl}-6-chloro-N-methylnaphthalene-2-sulfonamide Using Example 328 and the synthetic procedure described for Intermediate 52, the title compound was prepared.
Mass spectrum: Found: MH$^+$ 491. H.p.l.c. (1) Rt 3.4 min.

Example 303

N-[(6-Chloro-2-naphthyl)sulfonyl]-N-{(3S)-1-[(1S)-1-methyl-2-morpholin-4-yl-2-oxoethyl]-2-oxopyrrolidin-3-yl}glycine To a solution of methyl N-[(6-chloro-2-naphthyl)sulfonyl]-N-{(3S)-1-[(1S)-1-methyl-2-morpholin-4-yl-2-oxoethyl]-2-oxopyrrolidin-3-yl}glycinate (0.010 g) in THF (2 ml) was added lithium hydroxide (0.003 g) in water (2 ml), and the resultant solution stirred for 16 h. The mixture was acidified to pH5 using hydrochloric acid (2N), and then concentrated under reduced pressure. The residue was purified using mass directed preparative h.p.l.c. to give the title compound (0.006 g) as a white solid.
Mass spectrum: Found: MH$^+$ 524. H.p.l.c. (1) Rt 3.00 min.

Example 304

1-[(2S)-2-((3S)-3-{[(6-Chloro-2-naphthyl)sulfonyl]amino}-2-oxopyrrolidin-1-yl)propanoyl]piperidine-2-carboxylic acid To a solution of (2S)-2-((3S)-3-{[(6-chloro-2-naphthyl)sulfonyl]amino}-2-oxopyrrolidin-1-yl)propanoic acid (0.025 g) in DCM (10 ml) were added 1-[3-(dimethylamino)propyl]-3-ethylcarbodiimide hydrochloride (0.036 g), HOBT (0.026 g) and triethylamine (0.026 ml) and the mixture was stirred at room temperature for 30 min. Ethyl pipecolinate (0.030 g) was added and the resultant mixture stirred at room temperature for 16 h. The mixture was partitioned between DCM and water. The aqueous layer was re-extracted with DCM and the combined, dried (over magnesium sulphate) organic extracts were concentrated under reduced pressure. The residue was then dissolved in a mixture of THF (1 ml) and water (1 ml), treated with lithium hydroxide (0.005 g) and stirred at room temperature for 18 h. The reaction mixture was acidified to pH5 using hydrochloric acid (2N) and concentrated under reduced pressure. The residue was purified using SPE (aminopropyl stationary phase, washed with methanol and eluted with 10% hydrochloric acid in methanol) to give the title compound (0.007 g) as white solid.
Mass spectrum: Found: MH$^+$ 508. H.p.l.c. (1) Rt 3.09 min.

Example 305

6-Chloro-N-{(3S)-1-[(1R)-1-methyl-2-oxo-2-piperidin-1-ylethyl]-2-oxopyrrolidin-3-yl}naphthalene-2-sulfonamide A solution of tert-butyl (2R)-2-((3S)-3-{[(6-chloro-2-naphthyl)sulfonyl]amino}-2-oxopyrrolidin-1-yl)propanoate (0.025 g) in DCM (3 ml) was treated with trifluoroacetic acid (3 ml) and stirred at room temperature for 2 h. The mixture was then concentrated under reduced pressure to give an oil which was subsequently treated with 1-[3-(dimethylamino)propyl]-3-ethylcarbodiimide hydrochloride (0.013 g), HOBT (0.009 g) and triethylamine (0.023 ml). After stirring at room temperature for 1 h, piperidine (0.007 ml) was added and stirring was continued for 48 h. The reaction mixture was partitioned between DCM and water. The organic extract was concentrated under reduced pressure and the residue purified using SPE (silica, eluting with cyclohexane:ethyl acetate 5:1, 3:1, 1:1, 1:3 and ethyl acetate) to give the title compound (0.021 g) as a colourless gum.

Mass spectrum: Found: MH$^+$ 464. H.p.l.c. (1) Rt 3.27 min.

Example 306

6-Chloro-N-methyl-N-{(3S)-1-[(1S)-1-methyl-2-oxo-2-piperidin-1-ylethyl]-2-oxopyrrolidin-3-yl}naphthalene-2-sulfonamide To a solution of (2S)-2{(3S)-3-[[(6-chloro-2-naphthyl)sulfonyl](methyl)amino]-2-oxopyrrolidin-1-yl}propanoic acid (0.020 g) in DCM (2 ml) were added 1-[3-(dimethylamino)propyl]-3-ethylcarbodiimide hydrochloride (0.011 g), HOBT (0.007 g) and triethylamine (0.020 ml) and the mixture was stirred at room temperature for 30 min. Piperidine (0.006 ml) was added and the resultant mixture stirred at room temperature for 16 h. The mixture was partitioned between DCM and water. The aqueous layer was re-extracted with DCM and the combined, dried (over magnesium sulphate) organic extracts were concentrated under reduced pressure. The residue was purified using mass directed preparative h.p.l.c. to give the title compound (0.002 g) as a colourless gum.

Mass spectrum: Found: MH$^+$ 478. H.p.l.c. (1) Rt 3.51 min.

Using similar chemistry, the following were prepared:

Example 307

6-Chloro-N-methyl-N-((3S)-1-{(1S)-1-methyl-2-[(2R)-2-methylpiperidin-1-yl]-2oxoethyl}-2-oxopyrrolidin-3-yl)naphthalene-2-sulfonamide Mass spectrum: Found: MH$^+$ 492. H.p.l.c. (1) Rt3.61 min.

Example 308

6-Chloro-N-[(3S)-1-((1S)-2-{2-[(diethylamino)methyl]piperidin-1-yl}-1-methyl-2-oxoethyl)-2-oxopyrrolidin-3-yl]-N-methylnaphthalene-2-sulfonamide Mass spectrum: Found: MH$^+$ 563. H.p.l.c. (1) Rt 2.88 min.

Example 309

6-Chloro-N-methyl-N-{(3S)-1-[(1S)-1-methyl-2-oxo-2-pyrrolidin-1-ylethyl]-2-oxopyrrolidin-3-yl}naphthalene-2-sulfonamide Mass spectrum: Found: MH$^+$ 464. H.p.l.c. (1) Rt 3.48 min.

Example 310

Methyl N-[(6-chloro-2-naphthyl)sulfonyl]-N-{(3S)-1-[(1S)-1-methyl-2-oxo-2-piperidin-1-ylethyl]-2-oxopyrrolidin-3-yl}glycinate To a solution of (2S)-2-{(3S)-3-[[(6-chloro-2-naphthyl)sulfonyl](2-methoxy-2-oxoethyl)amino]-2-oxopyrrolidin-1-yl}propanoic acid (0.032 g) in DCM (5 ml) were added 1-[3-(dimethylamino)propyl]-3-ethylcarbodiimide hydrochloride (0.02 g), HOBT (0.014 g) and triethylamine (0.034 ml) and the mixture was stirred at room temperature for 1 h. Piperidine (0.01 ml) was added and the resultant mixture stirred at room temperature for 72 h. The mixture was concentrated under reduced pressure and the residue purified using mass directed preparative h.p.l.c. to give the title compound (0.017 g) as a white solid.

Mass spectrum: Found: MH$^+$ 536. H.p.l.c. (1) Rt 3.54 min.

Example 311

N-[(6-Chloro-2-naphthyl)sulfonyl]-N-{(3S)-1-[(1S)-1-methyl-2-oxo-2-piperidin-1-ylethyl]-2-oxopyrrolidin-3-yl}glycine To a solution of methyl N-[(6-chloro-2-naphthyl)sulfonyl]-N-{(3S)-1-[(1S)-1-methyl-2-oxo-2-piperidin-1-ylethyl]-2-oxopyrrolidin-3-yl}glycinate (0.010 g) in THF (1 ml) was added lithium hydroxide (0.005 g) in water (1 ml), and the resultant solution stirred for 16 h. The mixture was acidified to pH5 using hydrochloric acid (2N), and then concentrated under reduced pressure. The residue was purified using SPE (eluting with methanol and then 10% HCl/methanol) to give the title compound (0.01 g) as a white solid.

Mass spectrum: Found: MH$^+$ 522. H.p.l.c. (1) Rt 3.29 min.

Example 312

6-Chloro-N-(cyanomethyl)-N-{(3S)-1-[(1S)-1-methyl-2-oxo-2-piperidin-1-ylethyl]-2-oxopyrrolidin-3-yl}naphthalene-2-sulfonamide A solution of 6-chloro-N-{(3S)-1-[(1S)-1-methyl-2-oxo-2-piperidin-1-ylethyl]-2-oxopyrrolidin-3-yl}naphthalene-2-sulfonamide (0.015 g) in THF (2 ml) was cooled to −78° C. under nitrogen, and treated with lithium bis(trimethylsilyl) amide (1.0M solution in THF; 0.042 ml), followed by bromoacetonitrile (0.019 g). The resultant solution was allowed to reach room temperature and stirred for a further 16 h. The mixture was then cooled to −78° C. and further lithium bis(trimethylsilyl) amide (0.042 ml) added. After reaching room temperature, the reaction mixture was stirred for a further 18 h and then quenched by the addition of methanol (1 ml). The resultant solution was concentrated under reduced pressure and the residue partitioned between water and DCM. The organic layer was separated, dried (over magnesium sulphate) and concentrated under reduced pressure. The residue was purified by mass directed preparative h.p.l.c to give the title compound (0.007 g) as a colourless gum.

Mass spectrum: Found: MH$^+$ 503. H.p.l.c. (1) Rt 3.35 min.

Similarly prepared using commercially available alkyl halides, were:

Example 313

N-2-[(6-Chloro-2-naphthyl)sulfonyl]-N-2-{(3S)-1-[(1S)-1-methyl-2-oxo-2-piperidin-1-ylethyl]-2-oxopyrrolidin-3-yl}glycinamide Mass spectrum: Found: MH$^+$ 521. H.p.l.c. (1) Rt 3.07 min.

Example 314

6-Chloro-N-{(3S)-1-[(1S)-1-methyl-2-oxo-2-piperidin-1-ylethyl]-2-oxopyrrolidin-3-yl}-N-(2-oxobutyl)naphthalene-2-sulfonamide Mass spectrum: Found: MH$^+$ 534. H.p.l.c. (1) Rt 3.39 min.

Example 315 and Example 316

N-Allyl-6-chloro-N-{1-[(1S)-1-methyl-2-oxo-2-piperidin-1-ylethyl]-2-oxopyrrolidin-3-yl}naphthalene-2-sulfonamide [Isomer 1 and Isomer 2]

The title compounds were prepared by alkylation of Example 2 with allyl iodide, followed by purification using mass directed preparative h.p.l.c.

Isomer 1

Mass spectrum: Found: MH$^+$ 504. H.p.l.c. (1) Rt 3.5 min.

Isomer 1

Mass spectrum: Found: MH$^+$ 504. H.p.l.c. (1) Rt 3.52 min.

Example 317

N-2-[(6-Chloro-2-naphthyl)sulfonyl]-N-2-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)glycinamide A solution of 6-chloro-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)naphthalene-2-sulfonamide (0.01 g) in THF (2 ml) was cooled to −78° C. under nitrogen, and treated with lithium bis(trimethylsilyl) amide (1.0M solution in THF; 0.023 ml), followed by 2-bromoacteamide (0.012 g). The resultant solution was allowed to reach room temperature and stirred for a further 16 h. The mixture was then cooled to −78° C. and further lithium bis(trimethylsilyl) amide (0.023 ml) added. After reaching room temperature, the reaction mixture was stirred for a further 16 h and then quenched by the addition of methanol (1 ml). The resultant solution was concentrated under reduced pressure and the residue partitioned between water and DCM. The organic layer was separated, dried (over magnesium sulphate) and concentrated under reduced pressure. The residue was purified by mass directed preparative h.p.l.c. to give the title compound (0.001 g) as a white solid.

Mass spectrum: Found: MH$^+$ 590. H.p.l.c. (1) Rt 2.77 min.

Similarly prepared using commercially available alkyl halides, were:

Example 318

Methyl N-[(6-chloro-2-naphthyl)sulfonyl]-N-((3S)-1-{(1S)-1l-methyl-2-oxo-2-[(2S)-2-(pyrrolidin-1-ylmethyl)pyrrolidin-1-yl]ethyl}-2-oxopyrrolidin-3-yl)glycinate formate Mass spectrum: Found: MH$^+$ 605. H.p.l.c. (1) Rt 2.62 min.

Example 319

6-Chloro-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)-N-(2-oxobutyl)naphthalene-2-sulfonamide Mass spectrum: Found: MH$^+$ 603. H.p.l.c. (1) Rt 2.81 min.

Example 320 and Example 321

N-[(6-Chloro-2-naphthyl)sulfonyl]-N-(1-{1-methyl-2-oxo-2-[2-(pyrrolidin-1-ylmethyl)pyrrolidin-1-yl]ethyl}-2-oxopyrrolidin-3-yl)glycine formate [Isomer 1 and Isomer 2]

The title compounds were prepared by alkaline hydrolysis (LiOH) of Example 318, followed by purification using mass directed preparative h.p.l.c.

Isomer 1

Mass spectrum: Found: MH$^+$ 591. H.p.l.c. (1) Rt 2.6 min.

Isomer 1

Mass spectrum: Found: MH$^+$ 591. H.p.l.c. (1) Rt 2.63 min.

Example 322

N-[(6-Chloro-2-naphthyl)sulfonyl]-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)glycine The title compound was prepared by trifluoroacetic acid hydrolysis of Intermediate 88, followed by purification using mass directed preparative h.p.l.c.

Mass spectrum: Found: MH$^+$ 591. H.p.l.c. (1) Rt 2.85 min.

Example 323

N-[1-((2R)-2-{(3S)-3-[[(6-Chloro-2-naphthyl)sulfonyl](methyl)amino]-2-oxopyrrolidin-1-yl}propanoyl)piperidin-3-yl]benzamide A solution of tert-butyl (2R)-2-{(3S)-3-[[(6-chloro-2-naphthyl)sulfonyl](methyl)amino]-2-oxopyrrolidin-1-yl}propanoate (0.017 g) in DCM (0.5 ml) was treated with trifluoroacetic acid (0.5 ml) and stirred at room temperature for 2 h. The mixture was then concentrated under reduced pressure to give an oil which was subsequently treated with 1-[3-(dimethylamino)propyl]-3-ethylcarbodiimide hydrochloride (0.01 g), HOBT (0.007 g) and triethylamine (0.020 ml). After stirring at room temperature for 1 h, N-piperidin-3-ylbenzamide (0.010 g) was added and stirring was continued for 16 h. The reaction mixture was partitioned between DCM and water. The organic extract was concentrated under reduced pressure and the residue purified using SPE (silica, eluting with cyclohexane:ethyl acetate 3:1, 1:1, 1:3, ethyl acetate) to give the title compound (0.012 g) as a pale yellow gum.

Mass spectrum: Found: MH$^+$ 597. H.p.l.c. (1) Rt 3.35 min.

Note: Example 323=Example 270.

Using the procedure described above, the following compounds were also prepared:

Example 324

6-Chloro-N-methyl-N-((3S)-1-{(1R)-1-methyl-2-[(2R)-2-methylpiperidin-1-yl]-2-oxoethyl}-2-oxopyrrolidin-3-yl)naphthalene-2-sulfonamide Mass spectrum: Found: MH$^+$ 492. H.p.l.c. (1) Rt 3.57 min.

Example 325

N-((3S)-1-{(1R)-2-[(1R,4S)-2-Azabicyclo[2.2.1]hept-2-yl]-1-1-methyl-2-oxoethyl}-2-oxopyrrolidin-3-yl)-6-chloro-N-methylnaphthalene-2-sulfonamide Mass spectrum: Found: MH$^+$ 490. H.p.l.c. (1) Rt 3.18 min.

Example 326

6-Chloro-N-{(3R)-1-[(1R)-1-methyl-2-oxo-2-piperidin-1-ylethyl]-2-oxopyrrolidin-3-yl}naphthalene-2-sulfonamide Using Intermediate 32 and the procedure described for Example 1, the title compound was prepared.
Mass spectrum: Found: MH$^+$ 464. H.p.l.c. (1) Rt 3.35 min.
Using similar chemistry, the following were prepared:

Example 327

N-{1-[(2R)-2-((3R)-3-{[(6-Chloro-2-naphthyl)sulfonyl]amino}-2-oxopyrrolidin-1-yl)propanoyl]piperidin-3-yl}benzamide (two diastereoisomers)

Mass spectrum: Found: MH$^+$ 583. H.p.l.c. (1) Rt 3.26 & 3.44 min.

Example 328

N-{(3R)-1-[(1R)-2-Azepan-1-yl-1-methyl-2-oxoethyl]-2-oxopyrrolidin-3-yl}-6-chloronaphthalene-2-sulfonamide Mass spectrum: Found: MH$^+$ 478. H.p.l.c. (1) Rt 3.29 min.

Example 329

6-Chloro-N-{(3R)-1-[(1R)-1-methyl-2-morpholin-4-yl-2-oxoethyl]-2-oxopyrrolidin-3-yl}naphthalene-2-sulfonamide Mass spectrum: Found: MH$^+$ 466. H.p.l.c. (1) Rt 2.95 min.

Example 330

6-Chloro-N-{(3R)-1-[(1R)-1-methyl-2-oxo-2-pyrrolidin-1-ylethyl]-2-oxopyrrolidin-3-yl}naphthalene-2-sulfonamide Mass spectrum: Found: MH$^+$ 450. H.p.l.c. (1) Rt 3.05 min.

Example 331

6-Chloro-N-((3R)-1-{(1R)-1-methyl-2-[(2R)-2-methylpiperidin-1-yl]-2-oxoethyl}-2-oxopyrrolidin-3-yl)naphthalene-2-sulfonamide Mass spectrum: Found: MH$^+$ 478. H.p.l.c. (1) Rt 3.29 min.

Example 332

6-Chloro-N-((3R)-1-{(1R)-1-methyl-2-[(2S)-2-methylpiperidin-1-yl]-2-oxoethyl}-2-oxopyrrolidin-3-yl)naphthalene-2-sulfonamide Mass spectrum: Found: MH$^+$ 478. H.p.l.c. (1) Rt 3.29 min.

Example 333

6-Chloro-N-[(3R)-1-((1R)-2-{-2-[(diethylamino)methyl]piperidin-1-yl}-1-methyl-2-oxoethyl)-2-oxopyrrolidin-3-yl]naphthalene-2-sulfonamide Mass spectrum: Found: MH$^+$ 549. H.p.l.c. (1) Rt 2.66 min.

Example 334

N-((3R)-1-{(1R)-2-[(1R,4S)-2-Azabicyclo[2.2.1]hept-2-yl]-1-methyl-2-oxoethyl}-2-oxopyrrolidin-3-yl)-6-chloronaphthalene-2-sulfonamide Mass spectrum: Found: MH$^+$ 476. H.p.l.c. (1) Rt 3.15 min.

Example 335

6-Chloro-N-{1-[(1R)-1-methyl-2-(4-methylpiperazin-1-yl)-2-oxoethyl]-2-oxopyrrolidin-3-yl}naphthalene-2-sulfonamide Using Intermediate 37, and the synthetic procedure described for Example 1, the title compound was prepared.
Mass spectrum: Found: MH$^+$ 479. H.p.l.c. (1) Rt 2.92 min.
Using similar chemistry, the following were prepared:

Example 336

6-Bromo-N-{1-[(1R)-1-methyl-2-oxo-2-piperidin-1-ylethyl]-2-oxopyrrolidin-3-yl}naphthalene-2-sulfonamide The title compound was prepared using Intermediate 119.
Mass spectrum: Found: MH$^+$ 509. H.p.l.c. (1) Rt 3.26 min.

Example 337

5-Chloro-3-methyl-N-{1-[(1R)-1-methyl-2-oxo-2-piperidin-1-ylethyl]-2-oxopyrrolidin-3-yl}-1-benzothiophene-2-sulfonamide The title compound was prepared using Intermediate 120.
Mass spectrum: Found: MH$^+$ 484. H.p.l.c. (1) Rt 3.31 min.

Example 338

3-Chloro-N-{1-[(1R)-1-methyl-2-oxo-2-piperidin-1-ylethyl]-2-oxopyrrolidin-3-yl}isoquinoline-7-sulfonamide Using Intermediate 40, and the synthetic procedure described for Example 1, the title compound was prepared.
Mass spectrum: Found: MH+ 465. H.p.l.c. (1) Rt 2.84 min.

Example 339

3'-Chloro-N-{1-[(1R)-1-methyl-2-oxo-2-piperidin-1-ylethyl]-2-oxopyrrolidin-3-yl}-1,1'-biphenyl-4-sulfonamide Using Intermediate 39, and the synthetic procedure described for Example 1, the title compound was prepared.
Mass spectrum: Found: MH+ 490. H.p.l.c. (1) Rt 3.34 min.

Example 340

7-Hydroxy-N-{(3S)-1-[(1S)-1-methyl-2-oxo-2-piperidin-1-ylethyl]-2-oxopyrrolidin-3-yl}naphthalene-2-sulfonamide n-Butylamine (1 ml) was added to a suspension of Intermediate 51 (0.015 g) in dry THF (1 ml), stirred at room temperature for 5 h and concentrated under reduced pressure. The residue was partitioned between DCM and water. The separated organic extract was passed through a hydrophobic frit and the filtrate concentrated under reduced pressure to give the title compound (0.0035 g) as an oil.
Mass spectrum: Found: MH+ 446. H.p.l.c. (1) Rt 3.05 min.

Example 341

6-Chloro-N-methyl-N-{(3R)-1-[(1R)-1-methyl-2-oxo-2-piperidin-1-ylethyl]-2-oxopyrrolidin-3-yl}naphthalene-2-sulfonamide Using Intermediate 56 and the procedure described for Example 1, the title compound was prepared.
Mass spectrum: Found: MH+ 478. H.p.l.c. (1) Rt 3.49 min.
Using similar chemistry, the following were prepared:

Example 342

6-Chloro-N-methyl-N-{(3R)-1-[(1R)-1-methyl-2-oxo-2-pyrrolidin-1-ylethyl]-2-oxopyrrolidin-3-yl}naphthalene-2-sulfonamide Mass spectrum: Found: MH+ 464. H.p.l.c. (1) Rt 3.25 min.

Example 343

6-Chloro-N-[(3R)-1-((1R)-2-{2-[(diethylamino)methyl]piperidin-1-yl}-1-methyl-2-oxoethyl)-2-oxopyrrolidin-3-yl]-N-methylnaphthalene-2-sulfonamide Mass spectrum: Found: MH+ 563. H.p.l.c. (1) Rt 2.74 min.

Example 344

N-((3R)-1-{(1R)-2-[(1R,4S)-2-Azabicyclo[2.2.1]hept-2-yl]-1-methyl-2-oxoethyl}-2-oxopyrrolidin-3-yl)-6-chloro-N-methylnaphthalene-2-sulfonamide Mass spectrum: Found: MH+ 490. H.p.l.c. (1) Rt 3.29 min.

Example 345

6-Chloro-N-methyl-N-((3R)-1-{(1R)-1-methyl-2-[(2R)-2-methylpiperidin-1-yl]-2-oxoethyl}-2-oxopyrrolidin-3-yl)naphthalene-2-sulfonamide Mass spectrum: Found: MH+ 492. H.p.l.c. (1) Rt 3.43 min.

Example 346

6-Chloro-N-((3S)-1-{(1S)-2-[3-(ethylamino)piperidin-1-yl]-1-methyl-2-oxoethyl}-2-oxopyrrolidin-3-yl)naphthalene-2-sulfonamide To a solution of acetaldehyde (0.041 ml from a stock solution made up from 0.0127 l acetaldehyde dissolved in 1 ml DCM)) in dry DCM (0.4 ml) treated with acetic acid (0.1 ml from a stock solution made up from 0.0054 ml acetic acid dissolved in 1 ml DCM) was added N-{(3S)-1-[(1S)-2-(3-aminopiperidin-1-yl)-1-methyl-2-oxoethyl]-2-oxopyrrolidin-3-yl }-6-chloronaphthalene-2-sulfonamide [Example 365] (0.045 g) followed by tetraethylammonium triacetoxyborohydride (0.005 g). The mixture was stirred at room temperature, under nitrogen, for 60 h. DCM (1 ml) was added and the resultant solution washed with saturated sodium bicarbonate (1 ml) in a hydrophobic frit. The solvent was concentrated under reduced pressure and the residue purified by mass directed preparative h.p.l.c. to give the title compound (0.8 mg) as an oil.
Mass spectrum: Found: MH+ 507. H.p.l.c. (2) Rt 6.22 min.
Similarly prepared using commercially available aldehydes, were:

Example 347

6-Chloro-N-[(3S)-1-((1S)-1-methyl-2-oxo-2-{3-[(1H-pyrrol-2-ylmethyl)amino]piperidin-1-yl}ethyl)-2-oxopyrrolidin-3-yl]naphthalene-2-sulfonamide Mass spectrum: Found: MH+ 558. H.p.l.c. (2) Rt 5.21 min.

Example 348

6-Chloro-N-[(3S)-1-((1S)-1-methyl-2-oxo-2-{3-[(pyridin-3-ylmethyl)amino]piperidin-1-yl}ethyl)-2-oxopyrrolidin-3-yl]naphthalene-2-sulfonamide Mass spectrum: Found: MH+ 570. H.p.l.c. (2) Rt 5.18 min.

Example 349

6-Chloro-N-[(3S)-1-((1S)-2-{3-[(3-hydroxybutyl)amino]piperidin-1-yl}-1-methyl-2-oxoethyl)-2-oxopyrrolidin-3-yl]naphthalene-2-sulfonamide Mass spectrum: Found: MH+ 551. H.p.l.c. (2) Rt 6.9 min.

Example 350

6-Chloro-N-[(3S)-1-((1S)-1-methyl-2-oxo-2-{3-[(pyridin-4-ylmethyl)amino]piperidin-1-yl}ethyl)-2-oxopyrrolidin-3-yl]naphthalene-2-sulfonamide Mass spectrum: Found: MH+ 570. H.p.l.c. (2) Rt 5.76 min.

Example 351

N-{(3S)-1-[(1S)-2-(3-{[(2-Aminopyrimidin-5-yl)methyl]amino}piperidin-1-yl)-1-methyl-2-oxoethyl]-2-oxopyrrolidin-3-yl}-6-chloronaphthalene-2-sulfonamide Mass spectrum: Found: MH+ 586. H.p.l.c. (2) Rt 6.42 min.

Example 352

6-Chloro-N-[(3S)-1-((1S)-1-methyl-2-oxo-2-{3-[(pyridin-2-ylmethyl)amino]piperidin-1-yl}ethyl)-2-oxopyrrolidin-3-yl]naphthalene-2-sulfonamide Mass spectrum: Found: MH+ 570. H.p.l.c. (2) Rt 5.89 min.

Example 353

6-Chloro-N-[(3S)-1-((1S)-1-methyl-2-oxo-2-{3-[(1H-pyrazol-3-ylmethyl)amino]piperidin-1-yl}ethyl)-2-oxopyrrolidin-3-yl]naphthalene-2-sulfonamide Mass spectrum: Found: MH+ 559. H.p.l.c. (2) Rt 7.3 min.

Example 354

6-Chloro-N-[(3S)-1-((1S)-1-methyl-2-oxo-2-{3-[(pyridin-4-ylmethyl)amino]piperidin-1-}ethyl)-2-oxopyrrolidin-3-yl]naphthalene-2-sulfonamide Mass spectrum: Found: MH+ 570. H.p.l.c. (2) Rt 5.69 min.

Example 355

6-Chloro-N-((3S)-1-{(1S)-2-[3-({[5-(hydroxymethyl)-2-furyl]methyl}amino)piperidin-1-yl]-1-methyl-2-oxoethyl}-2-oxopyrrolidin-3-yl)naphthalene-2-sulfonamide Mass spectrum: Found: MH+ 589. H.p.l.c. (2) Rt 7.1 min.

Example 356

6-Chloro-N-[(3S)-1-((1S)-1-methyl-2-oxo-2-{3-[(1,3-thiazol-2-ylmethyl)amino]piperidin-1-yl}ethyl)-2-oxopyrrolidin-3-yl]naphthalene-2-sulfonamide Mass spectrum: Found: MH+ 576. H.p.l.c. (2) Rt 5.89 min.

Example 357

6-Chloro-N-{(3S)-1-[(1S)-1-methyl-2-(3-{[(1-methyl-1H-imidazol-2-yl)methyl]amino}piperidin-1-yl)-2-oxoethyl]-2-oxopyrrolidin-3-yl}naphthalene-2-sulfonamide Mass spectrum: Found: MH+ 573. H.p.l.c. (2) Rt 4.22 min.

Example 358

6-Chloro-N-[(3S)-1-((1S)-2-{3-[(3-hydroxy-2,2-dimethylpropyl)amino]piperidin-1-yl}-1-methyl-2-oxoethyl)-2-oxopyrrolidin-3-yl]naphthalene-2-sulfonamide Mass spectrum: Found: MH+ 565. H.p.l.c. (2) Rt 7.4 min.

Example 359

6-Chloro-N-[(3S)-1-((1S)-2-{3-[(1H-imidazol-4-ylmethyl)amino]piperidin-1-yl}-1-methyl-2-oxoethyl)-2-oxopyrrolidin-3-yl]naphthalene-2-sulfonamide Mass spectrum: Found: MH+ 559. H.p.l.c. (2) Rt 9.42 min.

Example 360

6-Chloro-N-[(3S)-1-((1S)-2-{3-[(3-ethoxy-2-oxopropyl)amino]piperidin-1-yl}-1-methyl-2-oxoethyl)-2-oxopyrrolidin-3-yl]naphthalene-2-sulfonamide Mass spectrum: Found: MH+ 581. H.p.l.c. (2) Rt 6.21 min.

Example 361

6-Chloro-N-[(3S)-1-((1S)-2-{3-[(3-methoxypropyl)amino]piperidin-1-yl}-1-methyl-2-oxoethyl)-2-oxopyrrolidin-3-yl]naphthalene-2-sulfonamide Mass spectrum: Found: MH+ 551. H.p.l.c. (2) Rt 7.75 min.

Example 362

4-[({1-[(2S)-2-((3S)-3-{[(6-Chloro-2-naphthyl)sulfonyl]amino}-2-oxopyrrolidin-1-yl)propanoyl]piperidin-3-yl}amino)methyl]-1-methylpyridinium iodide Mass spectrum: Found: MH+ 588. H.p.l.c. (2) Rt 4.75 min.

Example 363

6-Chloro-N-{(3S)-1-[(1S)-1-methyl-2-(3-{[(5-methyl-1H-imidazol-4-yl)methyl]amino}piperidin-1-yl)-2-oxoethyl]-2-oxopyrrolidin-3-yl}naphthalene-2-sulfonamide Mass spectrum: Found: MH+ 573. H.p.l.c. (2) Rt 5.03 min.

Example 364

Benzyl (3S)-1-[(2S)-2-((3S)-3-{[(6-chloro-2-naphthyl)sulfonyl]amino}-2-oxopyrrolidin-1-yl)propanoyl]piperidin-3-ylcarbamate A solution of (2S)-2-((3S)-3-{[(6-chloro-2-naphthyl)sulfonyl]amino}-2-oxopyrrolidin-1-yl)propanoic acid (0.408 g) in DCM (21 ml) was treated with 1-[3-(dimethylamino)propyl]-3-ethylcarbodiimide hydrochloride (0.394 g), HOBT (0.278 g) and triethylamine (0.286 ml) and stirred at room temperature for 1 h. A solution of benzyl (3S)-piperidin-3-ylcarbamate (0.361 g) in DCM (1 ml) was then added and stirring continued for 72 h. The mixture was partitioned between DCM and water. The separated organic extracts were washed with water and brine, dried (over magnesium sulphate), and concentrated under reduced pressure. The residue was purified using Biotage™ chromatography (eluting with hexane:ethyl acetate 1:7→1:10) to give the title compound (0.268 g) as an oil.

Mass spectrum: Found: MH+ 613. H.p.l.c. (1) Rt 3.59 min.

Example 365

N-((3S)-1-{(1S)-2-[(3S)-3-Aminopiperidin-1-yl]-1-methyl-2-oxoethyl}-2-oxopyrrolidin-3-yl )-6-chloronaphthalene-2-sulfonamide Benzyl (3S)-1-[(2S)-2-((3S)-3-{[(6-chloro-2-naphthyl)sulfonyl]amino}-2-oxopyrrolidin-1-yl)propanoyl]piperidin-3-ylcarbamate (0.128 g) was dissolved in DCM (3.5 ml) and treated with trifluoroacetic acid (10.5 ml) and stirred at room temperature for 6 h. The mixture was concentrated under reduced pressure and the residue purified by SPE (acid ion-exchange, eluting with ethyl acetate:methanol 9:1) to give the title compound (0.093 g) as a colourless oil.

Mass spectrum: Found: MH+ 480. H.p.l.c. (1) Rt 2.75 min.

Example 366

N-((3S)-1-{(1S)-2-[(3R)-3-Aminopiperidin-1-yl]-1-methyl-2-oxoethyl}-2-oxopyrrolidin-3-yl)-6-chloronaphthalene-2-sulfonamide Using benzyl (3R)-1-[(2S)-2-((3S)-3-{[(6-chloro-2-naphthyl)sulfonyl]amino}-2-oxopyrrolidin-1-yl)propanoyl]piperidin-3-ylcarbamate and the synthetic procedure described for Example 365, the title compound was prepared.

Mass spectrum: Found: MH+ 480. H.p.l.c. (1) Rt 2.55 min.

Example 367

5-(4-Chlorophenyl)-N-{(3S)-1-[(1S)-1-methyl-2-oxo-2-(1-piperidinyl)ethyl]-2-oxopyrrolidinyl}-2-thiophenesulfonamide A mixture of 5-bromo-N-[2-methoxy-4-(2-polystyrylethoxy)benzyl]-N-{(3S)-1-[(1S)-1-methyl-2-oxo-2-(1-piperidinyl)ethyl]-2-oxopyrrolidinyl}-2-thiophenesulfonamide (0.025 g), sodium carbonate (0.0017 g), 4-chlorobenzeneboronic acid (0.0042 g), tetrakis(triphenylphosphine) palladium(0) (0.0015 g) and tetrahydrofuran-water (4:1, 0.5 ml) was stirred gently at in a sealed vessel at 78° C. for 72 h. The resin was filtered, washed with DMF, 0.2N HCl, methanol and then DCM. The dried resin was then treated with trifluoroacetic acid-DCM (1:1, 0.5 ml), shaken at room temperature for 1 h and filtered. The resultant filtrate was concentrated under reduced pressure to give the title compound (0.0026 g) as an off-white glass.

Mass spectrum: Found: MH+ 496. H.p.l.c. (1) Rt 3.39 min.

Using similar chemistry, the following were prepared:

Example 368

N-{(3S)-1-[(1S)-1-Methyl-2-oxo-2-piperidin-1-ylethyl]-2-oxopyrrolidin-3-yl}-5-phenylthiophene-2-sulfonamide Mass spectrum: Found: MH+ 462. H.p.l.c. (1) Rt 3.2 min.

Example 369

5-(4-Hydroxyphenyl)-N-{(3S)-1-[(1S)-1-methyl-2-oxo-2-piperidin-1-ylethyl]-2-oxopyrrolidin-3-yl}thiophene-2-sulfonamide Mass spectrum: Found: MH+ 478. H.p.l.c. (1) Rt 2.98 min.

Example 370

5-(3-Methoxyphenyl)-N-{(3S)-1-[(1S)-1-methyl-2-oxo-2-piperidin-1-ylethyl]-2-oxopyrrolidin-3-yl}thiophene-2-sulfonamide Mass spectrum: Found: MH+ 492. H.p.l.c. (1) Rt 3.23 min.

Example 371

N-{(3S)-1-[(1S)-1-Methyl-2-oxo-2-piperidin-1-ylethyl]-2-oxopyrrolidin-3-yl}-5-(4-methylphenyl)thiophene-2-sulfonamide Mass spectrum: Found: MH+ 476. H.p.l.c. (1) Rt 3.35 min.

Example 372

5-(3-Chlorophenyl)-N-{(3S)-1-[(1S)-1-methyl-2-oxo-2-piperidin-1-ylethyl]-2-oxopyrrolidin-3-yl}thiophene-2-sulfonamide Mass spectrum: Found: MH+ 487. H.p.l.c. (1) Rt 3.46 min.

Example 373

5-(2-Chlorophenyl)-N-{(3S)-1-[(1S)-1-methyl-2-oxo-2-piperidin-1-ylethyl]-2-oxopyrrolidin-3-yl}thiophene-2-sulfonamide Mass spectrum: Found: $MH^+$ 496. H.p.l.c. (1) Rt 3.31 min.

Example 374

5-(2,3-Dichlorophenyl)-N-{(3S)-1-[(1S)-1-methyl-2-oxo-2-piperidin-1-ylethyl]-2-oxopyrrolidin-3-yl}thiophene-2-sulfonamide Mass spectrum: Found: $MH^+$ 530. H.p.l.c. (1) Rt 3.47 min.

Example 375

5-(2-Fluoro-4-methylphenyl)-N-{(3S)-1-[(1S)-1-methyl-2-oxo-2-piperidin-1-ylethyl]-2-oxopyrrolidin-3-yl}thiophene-2-sulfonamide Mass spectrum: Found: $MH^+$ 492. H.p.l.c. (1) Rt 3.35 min.

Example 376

5-(6-Amino-5-methylpyridin-3-yl)-N-{(3S)-1-[(1S)-1-methyl-2-oxo-2-piperidin-1-ylethyl]-2-oxopyrrolidin-3-yl}thiophene-2-sulfonamide Mass spectrum: Found: $MH^+$ 492. H.p.l.c. (1) Rt 2.13 min.

Example 377

N-{(3S)-1-[(1S)-1-Methyl-2-oxo-2-piperidin-1-ylethyl]-2-oxopyrrolidin-3-yl}-2,2'-bithiophene-5-sulfonamide Mass spectrum: Found: $MH^+$ 464. H.p.l.c. (1) Rt 3.26 min.

Example 378

5-(3-Furyl)-N-{(3S)-1-[(1S)-1-methyl-2-oxo-2-piperidin-1-ylethyl]-2-oxopyrrolidin-3-yl}thiophene-2-sulfonamide Mass spectrum: Found: $MH^+$ 451. H.p.l.c. (1) Rt 3.35 min.

Example 379

N-{(3S)-1-[(1S)-1-Methyl-2-oxo-2-piperidin-1-ylethyl]-2-oxopyrrolidin-3-yl}-2,3'-bithiophene-5-sulfonamide Mass spectrum: Found: $MH^+$ 468. H.p.l.c. (1) Rt 3.47 min.

Example 380

5-(3-Aminophenyl)-N-{(3S)-1-[(1S)-1-methyl-2-oxo-2-piperidin-1-ylethyl]-2-oxopyrrolidin-3-yl}thiophene-2-sulfonamide Mass spectrum: Found: $MH^+$ 477. H.p.l.c. (1) Rt 3.01 min.

Example 381

5-(2-Fluorophenyl)-N-{(3S)-1-[(1S)-1-methyl-2-oxo-2-piperidin-1-ylethyl]-2-oxopyrrolidin-3-yl}thiophene-2-sulfonamide Mass spectrum: Found: $MH^+$ 480. H.p.l.c. (1) Rt 3.56 min.

Example 382

5-(2-Hydroxyphenyl)-N-{(3S)-1-[(1S)-1-methyl-2-oxo-2-piperidin-1-ylethyl]-2-oxopyrrolidin-3-yl}thiophene-2-sulfonamide Mass spectrum: Found: $MH^+$ 478. H.p.l.c. (1) Rt 3.41 min.

Example 383 and Example 384

N-[(6-Chloro-2-naphthyl)sulfonyl]-N-(1-{1-methyl-2-oxo-2-[2-(pyrrolidin-1-ylmethyl)pyrrolidin-1-yl]ethyl}-2-oxopyrrolidin-3-yl)glycine formate [Isomer 1 and Isomer 2]

To a solution of benzyl N-[(6-chloro-2-naphthyl)sulfonyl]-N-((3S)-1-{(1S)-1-methyl-2-oxo-2-[(2S)-2-(pyrrolidin-1-ylmethyl)pyrrolidin-1-yl]ethyl}-2-oxopyrrolidin-3-yl)glycinate compound with formic acid (1:1) (0.060 g) in methanol (4 ml) were added potassium carbonate (0.3 g) and water (2 ml) and the mixture left to stir for 5 h. The mixture was concentrated under reduced pressure and the inorganics removed using SPE (6 g OASIS™ HLB Extraction Cartridge, eluting with water and then methanol) to give a clear gum, which was purified by mass directed preparative h.p.l.c. to give the title compounds (Isomer 1, 0.011 g; Isomer 2, 0.016 g) as white solids.

Isomer 1
Mass spectrum: Found: $MH^+$ 591. H.p.l.c. (1) Rt 2.42 min.

Isomer 2
Mass spectrum: Found: $MH^+$ 591. H.p.l.c. (1) Rt 2.46 min.

Example 385

5-Chloro-N-{(3S)-1-[(1S)-1-methyl-2-morpholin-4-yl-2-oxoethyl]-2-oxopyrrolidin-3-yl}-1-benzofuran-2-sulfonamide To a solution of (3S)-3-amino-1-[(1S)-1-methyl-2-morpholin-4-yl-2-oxoethyl]pyrrolidin-2-one (0.077 g) in anhydrous acetonitrile (2ml) were added 5-chloro-1-benzofuran-2-sulfonyl chloride (0.043 g) in acetonitrile (2 ml) and pyridine (0.057 ml), and the mixture was stirred at room temperature for 72 h. Saturated ammonium chloride solution (2 ml) was added and the resultant mixture stirred at room temperature for 20 min. The mixture was concentrated under reduced pressure and the residue partitioned between chloroform and hydrochloric acid (2M). The organic layer was washed with saturated sodium bicarbonate and brine. The organic layer was isolated, dried (over magnesium sulphate) and concentrated under reduced pressure to give the title compound (0.043 g) as a white solid.

Mass spectrum: Found: $MH^+$ 456. H.p.l.c. (1) Rt 2.78 min.

Example 386

(E)-2-(5-Chlorothien-2-yl)-N-{(3S)-1-[(1S)-1-methyl-2-morpholin-4-yl-2-oxoethyl]-2-oxopyrrolidin-3-yl}ethenesulfonamide Route 1

To a solution of (3S)-3-amino-1-[(1S)-1-methyl-2-morpholin-4-yl-2-oxoethyl]pyrrolidin-2-one (14.9 g) in anhydrous acetonitrile (750 ml) were added (E)-2-(5-chlorothien-2-yl)ethenesulfonyl chloride (16.5 g) in acetonitrile (250 ml) and pyridine (11 ml), and the mixture was stirred at room temperature for 72 h. Saturated ammonium chloride solution was added and the resultant mixture stirred at room temperature for 30 min. The mixture was concentrated under reduced pressure and the residue partitioned between chloroform and a 1:1 mixture of hydrochloric acid (2M) and water. The organic layer was washed with a 1:1 mixture of saturated sodium bicarbonate and water, and brine. The organic layer was isolated, dried (over magnesium sulphate) and concentrated under reduced pressure to give the title compound (19.3 g) as a white solid.

Mass spectrum: Found: $MH^+$ 448. H.p.l.c. (1) Rt 2.99 min $^1$H NMR (CDCl$_3$): δ 7.48(1H, d), 7.08(1H, d), 6.90(1H, d), 6.55(1H, d), 5.12(1H, br.d), 5.06(1H, q), 3.96(1H, m), 3.70–3.48(9H, m), 3.35(1H, m), 2.62(1H, m), 2.05(1H, m), 1.34(3H, d) ppm.

Route 2

To a mixture of N-{(3S)-1-[(1S)-1-methyl-2-morpholin-4-yl-2-oxoethyl]-2-oxopyrrolidin-3-yl}ethenesulfonamide (0.028 g), tris(dibenzylideneacetone)dipalladium (0) (0.0028 g) and 2-(di-t-butylphosphino)biphenyl (0.0037 g) under nitrogen, was added dry dioxan (0.25 ml) and the mixture was stirred for 5 min. at room temperature. N,N-Di-isopropylethylamine (0.02 ml) followed by 2-bromo-5-chlorothiophene (0.016 ml) in dry dioxan (0.25 ml) were then added and the resultant solution was stirred at room temperature for 19 h and then heated at 80° C. for 1 h. The reaction was lowered to 60° C. and maintained at this temperature for 20 h. Evaporation of the cooled reaction mixture under a stream of nitrogen gave a residue that was purified by SPE (silica; using an OPTIX. Gradient elution (flow rate 10 ml/min; fraction size 10 ml; UV detector set at λ$_{max}$ 254 nm; 0 to 50% ethyl acetate-cyclohexane over 5 min, followed by 50% to 100% ethyl acetate-cyclohexane for 11 min and then 100% ethyl acetate for 4 min]) gave the title compound (0.0187 g) as a clear oil.

Using similar chemistry to that described for Example 386Route 1, the following were prepared:

Example 387

5-Chloro-N-{(3S)-1-[(1S)-1-methyl-2-morpholin-4-yl-2-oxoethyl]-2-oxopyrrolidin-3-yl}-1-benzothiophene-2-sulfonamide Mass spectrum: Found: $MH^+$ 472. H.p.l.c. (1) Rt 2.9 min $^1$H NMR (CDCl$_3$): δ 7.87(1H, d), 7.86(1H, m), 7.78(1H, dm), 7.46(1H, dd), 5.58(1H, br.d), 5.02(1 H, q), 3.91(1H, m), 3.69–3.44(9H, m), 3.34(1H, m), 2.65(1H, m), 2.10(1H, m), 1.31(3H, d) ppm.

Example 388

6-Chloro-N-{(3S)-1-[(1S)-1-methyl-2-morpholin-4-yl-2-oxoethyl]-2-oxopyrrolidin-3-yl}-1-benzothiophene-2-sulfonamide Mass spectrum: Found: $MH^+$ 472. H.p.l.c. (1) Rt 2.96 min $^1$H NMR (CDCl$_3$): δ 7.89(1H, s), 7.85(1H, br.m), 7.81(1H, d), 7.44(1H, dd), 5.46(1H, br.d), 5.01(1H, q), 3.90(1H, m), 3.73–3.48(9H, m), 3.34(1H, m), 2.67(1H, m), 2.10(1H, m), 1.31(3H, d) ppm.

Example 389

5-Chloro-3-methyl-N-{(3S)-1-[(1S)-1-methyl-2-morpholin-4-yl-2-oxoethyl]-2-oxopyrrolidin-3-yl}-1-benzothiophene-2-sulfonamide Mass spectrum: Found: $MH^+$ 486. H.p.l.c. (1) Rt 3.11 min.

Example 390

3-Cyano-N-{(3S)-1-[(1S)-1-methyl-2-morpholin-4-yl-2-oxoethyl]-2-oxopyrrolidin-3-yl}benzenesulfonamide Mass spectrum: Found: $MH^+$ 407. H.p.l.c. (1) Rt 2.4 min.

Example 391

4-Cyano-N-{(3S)-1-[(1S)-1-methyl-2-morpholin-4-yl-2-oxoethyl]-2-oxopyrrolidin-3-yl}benzenesulfonamide Mass spectrum: Found: $MH^+$ 407. H.p.l.c. (1) Rt 2.4 min.

Example 392

5-(5-Chloro-1,3,4-thiadiazol-2-yl)-N-{(3S)-1-[(1S)-1-methyl-2-morpholin-4-yl-2-oxoethyl]-2-oxopyrrolidin-3-yl}thiophene-2-sulfonamide Mass spectrum: Found: $MH^+$ 506. H.p.l.c. (1) Rt 2.82 min.

Two additional compounds, Examples 440 and 441 were prepared using similar chemistry.

Example 393

6-Chloro-N-{(3S)-1-[(1S)-1-methyl-2-morpholin-4-yl-2-oxoethyl]-2-oxopyrrolidin-3-yl}-N-(2-oxobutyl)-1-benzothiophene-2-sulfonamide Using Example 388 and 1-bromo-2-butanone, and the synthetic procedure described for Example 293, the title compound was prepared.

Mass spectrum: Found: $MH^+$ 542. H.p.l.c. (1) Rt 3.28 min.

Using similar chemistry, the following was prepared:

Example 394

N2-[(6-Chloro-1-benzothien-2-yl)sulfonyl]-N2-{(3S)-1-[(1S)-1-methyl-2-morpholin-4-yl-2-oxoethyl]-2-oxopyrrolidin-3-yl}glycinamide Mass spectrum: Found: MH$^+$ 529. H.p.l.c. (1) Rt 2.86 min.

Example 395

5-Chloro-N-{(3S)-1-[(1S)-1-methyl-2-morpholin-4-yl-2-oxoethyl]-2-oxopyrrolidin-3-yl}-N-(2-oxobutyl)-1-benzothiophene-2-sulfonamide Using Example 387 and 1-bromo-2-butanone, and the synthetic procedure described for Example 293, the title compound was prepared.
Mass spectrum: Found: MH$^+$ 542. H.p.l.c. (1) Rt 3.27 min.
Using similar chemistry, the following was prepared:

Example 396

N2-[(5-Chloro-1-benzothien-2-yl)sulfonyl]-N2-{(3S)-1-[(1S)-1-methyl-2-morpholin-4-yl-2-oxoethyl]-2-oxopyrrolidin-3-yl}glycinamide Mass spectrum: Found: MH$^+$ 529. H.p.l.c. (1) Rt 2.85 min.

Example 397

6-Chloro-N-{(3S)-1-[(1S)-1-methyl-2-morpholin-4-yl-2-oxoethyl]-2-oxopyrrolidin-3-yl}-N-phenylnaphthalene-2-sulfonamide A mixture of Example 1 (0.0206 g), phenylboronic acid (0.0162 mg), copper (II) acetate (0.016 g), triethylamine 0.123 ml) and powered 4 Å molecular sieves (dried, 0.1 g) in dry DCM (0.5 ml) was stirred at room temperature for 6 days. The reaction mixture was filtered using SPE (silica, eluting with 30% methanol in ethyl acetate). The organic fraction was concentrated under reduced pressure to give a brown residue that was purified by mass directed preparative h.p.l.c. to give the title compound (0.0062 g) as a gum.
Mass spectrum: Found: MH$^+$ 542. H.p.l.c. (1) Rt 3.38 min.
Using similar chemistry, the following were prepared:

Example 398

6-Chloro-N-(4-fluorophenyl)-N-{(3S)-1-[(1S)-1-methyl-2-morpholin-4-yl-2-oxoethyl]-2-oxopyrrolidin-3-yl}naphthalene-2-sulfonamide Mass spectrum: Found: MH$^+$ 560. H.p.l.c. (1) Rt 3.43 min.

Example 399

6-Chloro-N-{(3S)-1-[(1S)-1-methyl-2-morpholin-4-yl-2-oxoethyl]-2-oxopyrrolidin-3-yl}-N-pyridin-4-ylnaphthalene-2-sulfonamide Mass spectrum: Found: MH$^+$ 543. H.p.l.c. (1) Rt 3.06 min.

Example 400

6-Chloro-N-{(3S)-1-[(1S)-1-methyl-2-morpholin-4-yl-2-oxoethyl]-2-oxopyrrolidin-3-yl}-N-pyridin-3-ylnaphthalene-2-sulfonamide Mass spectrum: Found: MH$^+$ 543. H.p.l.c. (1) Rt 3.10 min.

Example 401

6-Chloro-N-{(3S)-1-[(1S)-1-methyl-2-morpholin-4-yl-2-oxoethyl]-2-oxopyrrolidin-3-yl}-N-thien-3-ylnaphthalene-2-sulfonamide Mass spectrum: Found: MH$^+$ 548. H.p.l.c. (1) Rt 3.38 min.

Example 402

5-Bromo-N-{(3S)-1-[(1S)-1-methyl-2-oxo-2-piperidin-1-ylethyl]-2-oxopyrrolidin-3-yl}thiophene-2-sulfonamide Intermediate 99 (0.025 g of resin) was treated with trifluoroacetic acid-DCM (1:1, 1 ml) and shaken for 2 h and filtered. The filtrate was concentrated under a stream of nitrogen to give the title compound (0.0025 g) as an off-white glass.
Mass spectrum: Found: MH$^+$ 465. H.p.l.c. (1) Rt 3.09 min.

Example 403

N-((3S)-1-{(1S)-2-[(3R)-3-Aminopiperidin-1-yl]-1-methyl-2-oxoethyl}-2-oxopyrrolidin-3-yl)naphthalene-2-sulfonamide formate and Example 404

Benzyl (3R)-1-((2S)-2-{(3S)-3-[(2-naphthylsulfonyl)amino]-2-oxopyrrolidin-1-yl}propanoyl)piperidin-3-ylcarbamate A mixture of benzyl (3R)-1-[(2S)-2-((3S)-3-{[(6-chloro-2-naphthyl)sulfonyl]amino}-2-oxopyrrolidin-1-yl)propanoyl]piperidin-3-ylcarbamate (0.350 g), 10% palladium on carbon (0.035 g) and ethanol (1000 ml) was stirred under an atmosphere of hydrogen for 17 h. The reaction mixture was filtered through Harbolite™ and the filtrate was concentrated under reduced pressure to give an oil. The oil was partially purified using SPE (silica, eluting with methanol and then 10% aqueous ammonia in methanol) and then fully purified using mass directed preparative h.p.l.c. to give the title compounds (Example 403, 0.01 g; Example 404, 0.028 g), both as oils.

Example 403

Mass spectrum: Found: MH$^+$ 445. H.p.l.c. (1) Rt 2.37 min.

Example 404

Mass spectrum: Found: MH⁻ 577. H.p.l.c. (1) Rt 3.27 min.

Example 405

N-((3S)-1-{(1S)-2-[(3S)-3-Aminopiperidin-1-yl]-1-methyl-2-oxoethyl}-2-oxopyrrolidin-3-yl)naphthalene-2-sulfonamide formate and

Example 406

Benzyl (3S)-1-((2S)-2-{(3S)-3-[(2-naphthylsulfonyl)amino]-2-oxopyrrolidin-1-yl}propanoyl)piperidin-3-ylcarbamate Using benzyl (3S)-1-[(2S)-2-((3S)-3-{[(6-chloro-2-naphthyl)sulfonyl]amino}-2-oxopyrrolidin-1-yl)propanoyl]piperidin-3-ylcarbamate and the synthetic procedure described for Examples 403 and 404, the title compounds were prepared.

Example 405

Mass spectrum: Found: MH⁺ 445. H.p.l.c. (1) Rt 2.55 min.

Example 406

Mass spectrum: Found: MH⁻ 577. H.p.l.c. (1) Rt 3.37 min.

Example 407 tert-Butyl (1R,5S)-7-[(2S)-2-((3S)-3-{[(6-chloro-2-naphthyl)sulfonyl]amino}-2-oxopyrrolidin-1-yl)propanoyl]-3,7-diazabicyclo[3.3.1]nonane-3-carboxylate Using (2S)-2-((3S)-3-{[(6-chloro-2-naphthyl)sulfonyl]amino}-2-oxopyrrolidin-1-yl)propanoic acid and 3,7-diazabicyclo[3.3.1]nonane-3-carboxylic acid, 1,1-dimethylethyl ester* and the synthetic procedure described in Example 1, the title compound was prepared.

* Reference for 3,7-Diazabicyclo[3.3.1]nonane-3-carboxylic acid, 1,1-dimethylethyl ester: Alstermark, C; Andersson, K; Bjore, A; Bjorsne, M; Lindstedt, A. E; Nilsson, G; Polla, M; Strandlund, G; Ortengren, Y. PCT Int. Appl. (2000), WO 0077000.

Mass spectrum: Found: MH⁺ 605. H.p.l.c. (1) Rt 3.44 min.

Example 408

6-Chloro-N-((3S)-1{(1S)-2-[(1R,5S)-3,7-diazabicyclo[3.3.1]non-3-yl]-1-methyl-2-oxoethyl}-2-oxopyrrolidin-3-yl)naphthalene-2-sulfonamide A mixture of Example 407 (0.199 g) and trifluoroacetic acid (2 ml) in DCM (6 ml) was stirred at room temperature for 2 h and then concentrated under reduced pressure to give an oil. Saturated aqueous sodium bicarbonate (10 ml) was added and the resultant mixture extracted with DCM. The combined organic extracts were dried (over magnesium sulphate) and concentrated under reduced pressure to give the title compound (0.173 g) as a light brown foam.

Mass spectrum: Found: MH⁺ 505. H.p.l.c. (1) Rt 2.60 min.

Example 409

N1-[(1R,5S)-7-[(2S)-2-((3S)-3-{[(6-Chloro-2-naphthyl)sulfonyl]amino}-2-oxopyrrolidin-1-yl)propanoyl]-3-(N,N-dimethylglycyl)-3,7-diazabicyclo[3.3.1]non-2-yl]-N1-[(1S,5R)-7-[(2S)-2-((3S)-3-{[(6-chloro-2-naphthyl)sulfonamide A mixture of N,N-dimethylglycine (0.0062 g), HOBT (0.0088 g), 1-ethyl-3-(3-dimethylaminopropyl)carbodiimide hydrochloride (0.0124 g) and N,N-di-isopropylethylamine (0.0215 ml) in dry DMF (0.05 ml) was sonicated for 2 min. A solution of compound of Example 408 (0.025 g) in dry DMF (0.2 ml) was added and the resultant mixture sonicated for a further 2 min. The mixture was then stirred at room temperature for 18 h and concentrated under reduced pressure to give a gum-like residue, which was purified using mass directed preparative h.p.l.c. to give the title compound (0.02 g) as an oil.

Mass spectrum: Found: MH⁺ 590. H.p.l.c. (1) Rt 2.57 min.

Example 410

2-{(1R,5S)-7-[(2S)-2-((3S)-3-{[(6-Chloro-2-naphthyl)sulfonyl]amino}-2-oxopyrrolidin-1-yl)propanoyl]-3,7-diazabicyclo[3.3.1]non-3-yl}-N,N,N-trimethyl-2-oxoethanaminium chloride Using Example 408 and betaine hydrochloride, and the synthetic procedure described for Example 409, the title compound was prepared.

Mass spectrum: Found: MH⁺ 604. H.p.l.c. (1) Rt 2.57 min.

Example 411

6-Chloro-N-((3S)-1-{(1S)-2-[(1R,5S)-3-(N-methylglycyl)-7-diazabicyclo[3.3.1]non-3-yl]-1-methyl-2-oxoethyl}-2-oxopyrrolidin-3-yl)naphthalene-2-sulfonamide Intermediate 99 (0.029 g) was dissolved in DCM (1.5 ml) and treated with trifluoroacetic acid (0.5 ml). The resultant mixture was stirred at room temperature for 1.5 h and then concentrated under reduced pressure. The residue was treated with saturated aqueous sodium bicarbonate (5 ml) and extracted with DCM. The combined organic extracts were dried (over magnesium sulphate), filtered and concentrated under reduced pressure to give the title compound (0.026 g) as a gum.

Mass spectrum: Found: MH⁺ 576. H.p.l.c. (1) Rt 2.61 min.

Example 412

N2-[(6-Chloro-2-naphthyl)sulfonyl]-N2-((3S)-1-{(1S)-2-[(1R,5S)-3,7-diazabicyclo[3.3.1]non-3-yl]-1-methyl-2-oxoethyl}-2-oxopyrrolidin-3-yl)glycinamide formate A mixture of Example 407 (0.0124 g), potassium carbonate (0.009 g) and 2-bromoacetamide (0.0029 g) in dry DMF (0.21 ml) was stirred at room temperature for 19 h, and then additional 2-bromoacetamide (0.0015 g) was added. After stirring for a further 5 h, the mixture was quenched with water (2 ml), extracted with ethyl acetate, dried (over magnesium sulphate) and filtered. The combined organic extracts were concentrated under reduced pressure to give an oil which was treated with trifluoroacetic acid-DCM (2 ml; 1:1), and stirred at room temperature for 5 h. The mixture was concentrated under reduced pressure and the residue was purified using mass directed preparative h.p.l.c. to give the title compound (0.004 g) as an oil.

Mass spectrum: Found: MH$^+$ 562. H.p.l.c. (1) Rt 2.45 min.

Example 413

6-Chloro-N-[(3S)-1-((1S)-1-methyl-2-{(1R,5S)-7-[2-(methylamino)ethyl]-3,7-diazabicyclo[3.3.1]non-3-yl}-2-oxoethyl)-2-oxopyrrolidin-3-yl]naphthalene-2-sulfonamide A mixture of Example 408 (0.0198 g), N-(2-chloroethyl)-N-methylamine hydrochloride (0.076 g) and sodium bicarbonate (0.1 g) in ethanol (0.45 ml) was heated at 80° C. for 20 h. The cooled reaction mixture was diluted with brine, extracted with DCM, dried (over magnesium sulphate) and concentrated under reduced pressure. The resultant residue was purified using mass directed preparative h.p.l.c. to give the title compound (0.008 g) as a clear gum.

Mass spectrum: Found: MH$^+$ 562. H.p.l.c. (1) Rt 2.29 min.

Example 414

6-Chloro-N-[2-(dimethylamino)ethyl]-N-[(3S)-1-((1S)-2-{(1R,5S)-7-[2-(dimethylamino)ethyl]-3,7-diazabicyclo[3.3.1]non-3-yl}-1-methyl-2-oxoethyl)-2-oxopyrrolidin-3-yl]naphthalene-2-sulfonamide Using Example 408 and N,N-dimethylaminoethyl chloride hydrochloride, and the synthetic procedure described for Example 413, the title compound was prepared.

Mass spectrum: Found: MH$^+$ 647. H.p.l.c. (1) Rt 2.33 min.

Example 415

6-Chloro-N-((3S)-1-{(1S)-1-methyl-2-[(1R,5S)-9-oxa-3,7-diazabicyclo[3.3.1]non-3-yl]-2-oxoethyl}-2-oxopyrrolidin-3-yl)naphthalene-2-sulfonamide trifluoroacetate A mixture of 9-oxa-3,7-diazabicyclo[3.3.1]nonane-3-carboxylic acid, 1,1-dimethylethyl ester* (0.0178 g), (2S)-2-((3S)-3-{[(6-chloro-2-naphthyl)sulfonyl]amino}-2-oxopyrrolidin-1-yl)propanoic acid (0.037 g), HOBT (0.0136 g), 1-ethyl-3-(3-dimethylaminopropyl)carbodiimide hydrochloride (0.0194 g) and N,N-di-isopropylethylamine (0.041 ml) in dry DMF (0.3 ml) was stirred at room temperature for 5 days and then concentrated under reduced pressure. The resultant residue was diluted with aqueous sodium hydroxide (0.5M, 5 ml) and extracted with ethyl acetate. The combined organic extracts were concentrated under reduced pressure and the residue purified using preparative thin layer chromatography (20 cm×20 cm 1 mm thick Whatman PKF$_{256}$ SiO$_2$ plate, eluting with ethyl acetate). The resultant material (0.0012 g) was treated with 10% trifluoroacetic add-DCM (10 ml) at room temperature for 3 h and concentrated under reduced pressure to give the title compound (0.0011 g) as an oil.

* The corresponding HCl salt (9-oxa-3,7-diazabicyclo[3.3.1]nonane-3-carboxylic acid, 1,1-dimethylethyl ester, monohydrochloride) has been reported: Bjoere, A; Bjoersne, M; Cladingboel, D; Hoffman, K; Pavey, J; Ponten, F; Strandlund, G; Svensson, P; Thomson, C; Wilstermann, M. PCT Int. Appl. (2001), WO 0128992.

Mass spectrum: Found: MH$^+$ 507. H.p.l.c. (1) Rt 2.52 min.

Example 416

N2-[(6-Chloro-2-naphthyl)sulfonyl]-N2-{(3S)-1-[(1S)-1-methyl-2-oxo-2-piperazin-1-ylethyl]-2-oxopyrrolidin-3-yl}qlycinamide trifluoroacetate Using (2S)-2-((3S)-3-{(2-amino-2-oxoethyl)[(6-chloro-2-naphthyl)sulfonyl]amino}-2-oxopyrrolidin-1-yl)propanoic acid and 1-Boc-piperazine, and the synthetic procedure described for Example 1, provided the Intermediate t-butyl ester. This was subsequently deprotected using trifluoroacetic acid to provide the title compound.

Mass spectrum: Found: MH$^+$ 522. H.p.l.c. (1) Rt 2.39 min.

Example 417

N2-[(6-Chloro-2-naphthyl)sulfonyl]-N2-{(3S)-1-[(1S)-1-methyl-2-(4-methyl-1,4-diazepan-1-yl)-2-oxoethyl]-2-oxopyrrolidin-3-yl}glycinamide formate Using Intermediate 49 and the procedure described for Example 1, the title compound was prepared.

Mass spectrum: Found: MH$^+$ 550. H.p.l.c. (1) Rt 2.45 min.

Using similar chemistry, the following were prepared:

Example 418

N2-[(6-Chloro-2-naphthyl)sulfonyl]-N2-((3S)-1-{(1S)-2-[(2R,6S)-2,6-dimethylmorpholin-4-yl]-1-methyl-2-oxoethyl}-2-oxopyrrolidin-3-yl)glycinamide Mass spectrum: Found: MH$^+$ 551. H.p.l.c. (1) Rt 3.02 min.

Example 419

N2-[(6-Chloro-2-naphthyl)sulfonyl]-N2-((3S)-1-{(1S)-1-methyl-2-[(1S,4S)-2-oxa-5-azabicyclo[2.2.1]hept-5-yl]-2-oxoethyl}-2-oxopyrrolidin-3-yl)glycinamide Mass spectrum: Found: MH$^+$ 535. H.p.l.c. (1) Rt 2.83 min.

Example 420 and Example 421

N2-[(6-Chloro-2-naphthyl)sulfonyl]-N2-{(3S)-1-[(1S)-1-methyl-2-oxo-2-(2-pyridin-4-ylpyrrolidin-1-yl)ethyl]-2-oxopyrrolidin-3-yl}glycinamide [Isomer 1 and Isomer 2]

Isomer 1
Mass spectrum: Found: MH$^+$ 585. H.p.l.c. (1) Rt 2.61 min.

Isomer 2
Mass spectrum: Found: MH$^+$ 585. H.p.l.c. (1) Rt 2.62 min.

Example 422

N2-[(6-Chloro-2-naphthyl)sulfonyl]-N2-{(3S)-1-[(1S)-1-methyl-2-(4-methyl-5-oxo-1,4-diazepan-1-yl)-2-oxoethyl]-2-oxopyrrolidin-3-yl}glycinamide Mass spectrum: Found: MH$^+$ 564. H.p.l.c. (1) Rt 2.70 min.

Example 423 and Example 424

N2-[(6-Chloro-2-naphthyl)sulfonyl]-N2-{(3S)-1-[(1S)-1-methyl-2-oxo-2-(2-pyridin-3-ylpyrrolidin-1-yl)ethyl]-2-oxopyrrolidin-3-yl}glycinamide [Isomer 1 and Isomer 2]

Isomer 1

Mass spectrum: Found: MH$^+$ 584. H.p.l.c. (1) Rt 2.70 min.

Isomer 2

Mass spectrum: Found: MH$^+$ 584. H.p.l.c. (1) Rt 2.73 min.

Example 425

N2-[(6-Chloro-2-naphthyl)sulfonyl]-N2-((3S)-1-{(1S)-1-methyl-2-[2-(4-methylpyridin-2-yl)pyrrolidin-1-yl]-2-oxoethyl}-2-oxopyrrolidin-3-yl)glycinamide Mass spectrum: Found: MH$^+$ 599. H.p.l.c. (1) Rt 2.8 min.

Example 426

(E)-2-(3-Chloro-4-hydroxyphenyl)-N-{(3S)-1-[(1S)-1-methyl-2-morpholin-4-yl-2-oxoethyl]-2-oxopyrrolidin-3-yl}ethenesulfonamide Sulphuryl chloride (0.036 ml) was added dropwise to DMF (0.04 ml) at 0° C. and the mixture was stirred at room temperature for 2 h. Intermediate 105 (0.102 g) in cyclohexane (0.2 ml) was added in one portion and the resultant mixture was heated at 90° C. for 6 h. The cooled reaction mixture was poured onto ice and extracted with DCM. The combined organic extracts were dried (over magnesium sulphate) and concentrated under reduced pressure to give a brown oil which was treated with sulphuryl chloride (0.035 ml) and triphenyl phosphine (0.103 g) in dry DCM (ca. 0.5 ml). After stirring for 3 h at room temperature, the mixture was filtered through a SPE silica cartridge preconditioned with cyclohexane. Elution with ethyl acetate gave, after concentration under reduced pressure, an orange-brown solid which was stirred with Intermediate 87 (0.04 g), 4-dimethylaminopyridine (0.021 g), di-isopropylethylamine (0.059 ml) in dry DCM (1 ml). After stirring for 3 days at room temperature under nitrogen, the mixture was concentrated under reduced pressure. The residue was purified initially using SPE (silica) followed by mass directed preparative h.p.l.c. to give the title compound (0.0035 g) as a white solid.

Mass spectrum: Found: MH$^+$ 458. H.p.l.c. (1) Rt 2.58 min.

Example 427

(E)-2-(4-Chloro-3-hydroxyphenyl)-N-{(3S)-1-[(1S)-1-methyl-2-morpholin-4-yl-2-oxoethyl]-2-oxopyrrolidin-3-yl}ethenesulfonamide To a solution of (E)-2-(3-{[tert-butyl(diphenyl)silyl]oxy}-4-chlorophenyl)-N-{(3S)-1-[(1S)-1-methyl-2-morpholin-4-yl-2-oxoethyl]-2-oxopyrrolidin-3-yl}ethenesulfonamide (0.0078 g) in THF (0.3 ml) at −78° C. under nitrogen, tetra n-butylammonium fluoride (1M in THF, 0.014 ml) was added. The mixture was allowed to warm to room tempertaure over 3 days and then concentrated under reduced pressure. The residue was purified using mass directed preparative h.p.l.c. to give the title compound (0.0043 g) as a clear film.

Mass spectrum: Found: MH$^+$ 458. H.p.l.c. (1) Rt 2.67 min.

Example 428

6-Chloro-N-{(3S)-1-[(1S)-1-methyl-2-morpholin-4-yl-2-oxoethyl]-2-oxopyrrolidin-3-yl}-N-(2-morpholin-4-ylethyl)naphthalene-2-sulfonamide formate Example 1 (0.05 g) was dissolved in DMF (1 ml) and treated with chloroethylmorpholine hydrochloride (0.062 g) and potassium carbonate (0.093 g), and stirred at 40° C. for 2 h. The mixture was then heated at 80° C. for 8 h, cooled and treated with ethyl acetate and water. The organic extraxt was dried (over magnesium sulphate) and concentrated under reduced pressure. The residue was purified using mass directed preparative h.p.l.c. to give the title compound (0.018 g) as a white solid.

Mass spectrum: Found: MH$^+$ 579. H.p.l.c. (1) Rt 2.56 min.

Using similar chemistry, the following were prepared:

Example 429

6-Chloro-N-{(3S)-1-[(1S)-1-methyl-2-morpholin-4-yl-2-oxoethyl]-2-oxopyrrolidin-3-yl}-N-(2-pyrrolidin-1-ylethyl)naphthalene-2-sulfonamide formate Mass spectrum: Found: MH$^+$ 563. H.p.l.c. (1) Rt 2.58 min.

Example 430

6-Chloro-N-[2-(dimethylamino)ethyl]-N-{(3S)-1-[(1S)-1-methyl-2-morpholin-4-yl-2-oxoethyl]-2-oxopyrrolidin-3-yl}naphthalene-2-sulfonamide formate Mass spectrum: Found: MH$^+$ 537. H.p.l.c. (1) Rt 2.53 min.

Example 431

N-[2-([(6-Chloro-2-naphthyl)sulfonyl]{(3S)-1-[(1S)-1-methyl-2-morpholin-4-yl-2-oxoethyl]-2-oxopyrrolidin-3-yl}amino)ethyl]acetamide Mass spectrum: Found: MH$^+$ 551. H.p.l.c. (1) Rt 2.91 min.

Example 432

6-Chloro-N-{2-oxo-1-[1-(piperidin-1-ylcarbonyl)propyl]pyrrolidin-3-yl}naphthalene-2-sulfonamide [Isomer 1 and Isomer 2]

Using 2-(3-{[(6-chloro-2-naphthyl)sulfonyl]amino}-2-oxopyrrolidin-1-yl)butanoic acid [Isomer 1 and Isomer 2] and the synthetic procedure described for Example 1, the title compound was prepared.
Mass spectrum: Found: MH$^+$ 478. H.p.l.c. (1) Rt 3.37 min.
Using similar chemistry, the following was prepared:

Example 433

6-Chloro-N-{2-oxo-1-1-(pyrrolidin-1-ylcarbonyl)propyl]pyrrolidin-3-yl}naphthalene-2-sulfonamide [Isomer 1 and Isomer 2]

Mass spectrum: Found: MH$^+$ 464. H.p.l.c. (1) Rt 3.21 min.

Example 434

6-Chloro-N-[1-(1-{[(2S)-2-methylpiperidin-1-yl]carbonyl}propyl)-2-oxopyrrolidin-3-yl]naphthalene-2-sulfonamide [Isomer 3 and Isomer 4]

Using 2-(3-{[(6-chloro-2-naphthyl)sulfonyl]amino}-2-oxopyrrolidin-1-yl)butanoic acid [Isomer 3 and Isomer 4] and the synthetic procedure described for Example 1, the title compound was prepared.
Mass spectrum: Found: MH$^+$ 492. H.p.l.c. (1) Rt 3.13 min.
Using similar chemistry, the following was prepared:

Example 435

6-Chloro-N-{2-oxo-1-[1-(piperidin-1-ylcarbonyl)propyl]pyrrolidin-3-yl}naphthalene-2-sulfonamide [Isomer 3 and Isomer 4]

Mass spectrum: Found: MH$^+$ 478. H.p.l.c. (1) Rt 3.12 min.

Example 436

6-Chloro-N-((3R)-1-{(1S)-1-methyl-2-oxo-2-[(2S)-2-(pyrrolidin-1-ylmethyl)pyrrolidin-1-yl]ethyl}-2-oxopyrrolidin-3-yl)naphthalene-2-sulfonamide formate Using Intermediate 31 and the procedure described for Example 1, the title compound was prepared.
Mass spectrum: Found: MH$^+$ 533. H.p.l.c. (1) Rt 2.63 min.

Example 437

5-Chloro-N-{(3S)-1-[(1S)-1-methyl-2-morpholin-4-yl-2-oxoethyl]-2-oxopyrrolidin-3-yl}-1H-indole-2-sulfonamide Intermediate 64 (0.011 g) was dissolved in 1:1 TFA/DCM (0.5 ml) and allowed to stand at room temperature for 1 h. The mixture was concentrated under reduced pressure and the residue solvents partitioned between saturated aqueous sodium bicarbonate and DCM. The separated organic phase was dried (over magnesium sulphate) and concentrated under a stream of nitrogen to give the title compound (0.0082 g) as white solid.
Mass spectrum: Found: MH$^+$ 455. H.p.l.c. (1) Rt 2.97 min.

Example 438

6-Chloro-N-{(3S)-1-[(1S)-1-methyl-2-morpholin-4-yl-2-oxoethyl]-2-oxopyrrolidin-3-yl}-1,3-benzothiazole-2-sulfonamide Intermediate 66 (0.1 g) was stirred at room temperature in anhydrous acetone (3 ml) and 5% aqueous potassium permanganate (1.35 ml) for 3 h, after which additional acetone (3 ml) and 5% aqueous potassium permanganate (1.35 ml) were added. The reaction mixture was stirred for a further 18 h and filtered through Celite™. The filtrate was concentrated under reduced pressure and the residue purified by mass directed preparative h.p.l.c to give the title compound (0.0062 g) as a white solid.
Mass spectrum: Found: MH$^+$ 473. H.p.l.c. (1) Rt 2.98 min.

Example 439

1-(3-Cyanophenyl)-N-{(3S)-1-[(1S)-1-methyl-2-oxo-2-piperidin-1-ylethyl]-2-oxopyrrolidin-3-yl}methanesulfonamide The title compound was prepared using Intermediate 23 and (3-cyanophenyl)methanesulfonyl chloride, and the synthetic procedure described for Example 386 (Route 1).
Mass spectrum: Found: MH$^+$ 419. H.p.l.c. (1) Rt min.

Example 440

5-Chloro-N-{(3S)-1-[(1S)-1-methyl-2-morpholin-4-yl-2-oxoethyl]-2-oxopyrrolidin-3-yl}thieno[2,3-b]pyridine-2-sulfonamide The title compound was prepared using Intermediates 57 and 87, and the synthetic procedure described for Example 386 (Route 1). Mass spectrum: Found: MH$^+$ 473. H.p.l.c. (1) Rt 2.64 min.

Example 441

5-Chloro-N-{(3S)-1-[(1S)-1-methyl-2-morpholin-4-yl-2-oxoethyl]-2-oxopyrrolidin-3-yl}thieno[3,2-b]pyridine-2-sulfonamide The title compound was prepared using Intermediates 87 and 118, and the synthetic procedure described for Example 386 (Route 1).
Mass spectrum: Found: MH$^+$ 473. H.p.l.c. (1) Rt 2.53 min.

Example 442

6-Chloro-N-{(3S)-1-[(1S)-1-methyl-2-(4-morpholinyl)-2-oxoethyl]-2-oxopyrrolidinyl}thieno[3,2-b]pyridine-2-sulfonamide The title compound was similarly prepared using Intermediate 87 and 6-chlorothieno[3,2-b]pyridine-2-sulfonyl chloride*, and the synthetic procedure decribed for Example 386 (Route 1).

*Prepared according to the procedure described in U.S. Pat. No. 6,281,227.

Mass spectrum: Found: MH$^+$ 473. H.p.l.c. (I) Rt 2.61 min.

Example 443

(E)-2-(5-Chlorothien-2-yl)-N-methyl-N-{(3S)-1-[(1S)-1-methyl-2-morpholin-4-yl-2-oxoethyl]-2-oxopyrrolidin-3-yl}ethenesulfonamide Sodium hydride (60% dispersion in oil, 0.011 g) was added to trimethysulphonium iodide (0.059 g) in dimethylsulphoxide (2 ml) between 5–10° C., and the resultant mixture was stirred at room temperature for 30 min. Example 386 (0.1 g) in dry THF (2 ml) was added between 5–10° C., and the solution stirred at room temperature for 2.25 h, at 50° C. for 70 h, cooled to room temperature and poured onto ice/water. The aqueous mixture was extracted with ethyl acetate and the combined, dried (over magnesium sulphate) organic extracts were concentrated under reduced pressure. The residue was purified using mass directed preparative h.p.l.c. to give the title compound (0.038 g) as a colourless oil.

Mass spectrum: Found: MH$^+$ 462. H.p.l.c. (1) Rt 2.82 min.

In Vitro Assay for Inhibition of Factor Xa

Compounds of the present invention were tested for their Factor Xa inhibitory activity as determined in vitro by their ability to inhibit human Factor Xa in a chromogenic assay, using N-α-benzyloxycarbonyl-D-Arg-Gly-Arg-p-nitroanilide as the chromogenic substrate. Compounds were diluted from a 10 mM stock solution in dimethylsulfoxide at appropriate concentrations. Assay was performed at room temperature using buffer consisting of: 50 mM Tris-HCl, 150 mM NaCl, 5 mM CaCl2, pH 7.4. containing human Factor Xa (final conc. Of 0.0015 U.ml-1). Compound and enzyme were preincubated for 15 min prior to addition of the substrate (final conc. of 200 μM). The reaction was stopped after 30 min with the addition of soybean trypsin inhibitor or H-D-PHE-PRO-ARG-Chloromethylketone. BioTek EL340 or Tecan SpectraFluor Plus plate readers were used to monitor the absorbance at 405 nM. To obtain IC50 values the data were analysed using ActivityBase® and XLfit®.

All of the synthetic Example compounds tested exhibited measurable FXa inhibitory activity. Preferably compounds have an IC$_{50}$ value of less than 2 μM, more preferably compounds have an IC$_{50}$ value of less than 0.1 μM.

Measurement of Prothrombin Time (PT)—Test 1

Blood was collected into a sodium citrate solution (ratio 9:1) to give a final concentration of 0.38% citrate. Plasma was generated by centrifugation of citrated blood samples at 1200×g for 20 min at 4° C.

The PT test was performed at 37° C. in plastic cuvettes containing a magnetic ball bearing. 50 μL of citrated plasma and either 25 μL of 2.8% DMSO for control or 25 μL of test compound (dissolved in DMSO and diluted in water and 2.8% DMSO to give 0.4% DMSO final in assay) at a concentration of 7-times the final desired concentration was pippetted into each cuvette. This mixture was incubated for 1 min at 37° C. before adding 100 μL of thromboplastin mixture (comprising lyophilised rabbit thromboplastin and calcium chloride which was reconstituted in distilled water as per manufacturer's [Sigma] instructions). On addition of the thromboplastin mixture, the timer was automatically started and continued until the plasma clotted. The time to clotting was recorded (normal range for human plasma is 10–13 seconds).

Method for Measurement of Prothrombin Time (PT)—Test 2

Blood is collected into a sodium citrate solution (ratio 9:1) to give a final concentration of 0.38% citrate. Plasma is generated by centrifugation of citrated blood samples at 1200×g for 20 min at 4° C.

The PT test is performed at 37° C. in plastic cassettes and using a MCA210 Microsample Coagulation Analyzer (Bio/Data Corporation). For assay, 25 ul of plasma containing test compound at concentrations ranging from 0.1 to 100 uM (made from a 1 mM stock solution in 10% DMSO and plasma) and 25 ul of Thromboplastin C Plus (Dade Berhing) are automatically injected into the cassette. Upon addition of the Thromboplastin C Plus, the instrument determines and records the time to clot (normal range for human plasma is 10–13 seconds).

General Purification and Analytical Methods

Analytical HPLC was conducted on a Supelcosil LCABZ+PLUS column (3 μm, 3.3 cm×4.6 mm ID) eluting with 0.1% HCO$_2$H and 0.01 M ammonium acetate in water (solvent A), and 95% acetonitrile and 0.05% HCO$_2$H in water (solvent B), using the following elution gradient 0–0.7 minutes 0% B, 0.7–4.2 minutes 0→100% B, 4.2–5.3 minutes 100% B, 5.3–5.5 minutes 100→0% B at a flow rate of 3 ml/minutes (System 1). The mass spectra (MS) were recorded on a Fisons VG Platform mass spectrometer using electrospray positive ionisation [(ES+ve to give MH$^+$ and M(NH$^4$)$^+$ molecular ions] or electrospray negative ionisation [(ES-ve to give (M-H)$^-$ molecular ion] modes.

$^1$H nmr spectra were recorded using a Bruker DPX 400 MHz spectrometer using tetramethylsilane as the external standard.

Biotage™ chromatography refers to purification carried out using equipment sold by Dyax Corporation (either the Flash 40i or Flash 150i) and cartridges pre-packed with KPSil.

Mass directed autoprep refers to methods where the material was purified by high performance liquid chromatography on a HPLCABZ+5 μm column (5 cm×10 mm i.d.) with 0.1% HCO$_2$H in water and 95% MeCN, 5% water (0.5% HCO$_2$H) utilising the following gradient elution conditions: 0–1.0 minutes 5% B, 1.0–8.0 minutes 5→30% B, 8.0–8.9 minutes 30% B, 8.9–9.0 minutes 30→95% B, 9.0–9.9 minutes 95% B, 9.9–10 minutes 95→0% B at a flow rate of 8 ml minutes$^{-1}$ (System 2). The Gilson 202-fracton collector was triggered by a VG Platform Mass Spectrometer on detecting the mass of interest.

Hydrpophobic frits refers to filtration tubes sold by Whatman.

SPE (solid phase extraction) refers to the use of cartridges sold by International Sorbent Technology Ltd.

TLC (thin layer chromatography) refers to the use of TLC plates sold by Merck coated with silica gel 60 F$_{254}$.

LC/MS System (3)

Method 2 was conducted on a Waters Xtera RP18 column (3 µm, 15 cm×2.1 mm ID) eluting with solvent A (0.1% HCO2H and water) and solvent B (100% acetonitrile, 0.1% HCO2H and reserpine 2.5 µgml-1) at 20° C. The following elution gradient was ran: 0–2.0 minutes 0% B; 2.0–18.0 minutes 0–100% B; 18.0–20.0 minutes 100% B; 20.0–22.0 minutes 100–0% B; 22.0–30.0 minutes 0% B, at a flow rate of 0.4 ml/minutes. The mass spectra (MS) were recorded on a Micromass QTOF 2 spectrometer using electrospray positive ionisation [ES+ve to give MH+].

Note: The number given in brackets in the Examples and Intermediates above, e.g. H.p.l.c. (1), specifies the LC/MS method used.

The invention claimed is:

1. A compound of formula (Ic):

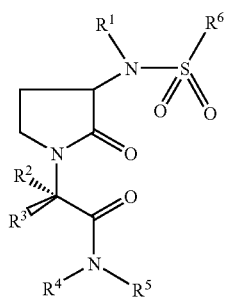

wherein:
R$^1$ represents hydrogen, —C$_{1-6}$alkyl, —C$_{3-6}$alkenyl, —C$_{3-6}$alkynyl, —C$_{2-3}$alkylOH, —C$_{2-3}$alkylNR$^b$R$^a$, —C$_{2-3}$alkylNHCOR$^a$, —C$_{2-3}$alkylNHCO$_2$R$^b$, —C$_{2-3}$alkylNHSO$_2$R$^b$, —C$_{2-3}$alkylNHCONR$^b$R$^c$, —C$_{2-3}$alkyl OCONR$^b$R$^c$, —C$_{2-3}$alkylOC$_{1-6}$alkyl, —C$_{2-3}$alkylOCH$_2$phenyl, phenyl or 5- or 6-membered aromatic heterocyclic group consisting of at least one heteroatom selected from O, N or S, the phenyl or aromatic heterocyclic group being optionally substituted by one or more substitutents selected from: —C$_{1-3}$ alkyl, —C$_{1-3}$alkoxy, —C$_{1-3}$alkylOH, halogen, —CN, —CF$_3$, —NH$_2$, —CO$_2$H and —OH, or R$^1$ represents a group X—W;

X represents —C$_{1-3}$alkylene-, propenylene, propynylene;

W represents —CN, —CO$_2$H, —CONR$^b$R$^c$, —COC$_{1-6}$alkyl, —CO$_2$C$_{1-6}$alkyl, —CO$_2$C$_{3-6}$alkenyl, phenyl or 5- or 6-membered aromatic or non-aromatic heterocyclic group consisting of at least one heteroatom selected from O, N or S, the phenyl or aromatic or non-aromatic heterocyclic group being optionally substituted by one or more substitutents selected from: —C$_{1-3}$alkyl, —C$_{1-3}$ alkoxy, —C$_{1-3}$alkylOH, halogen, —CN, —CF$_3$, —NH$_2$, —CO$_2$H, and —OH;

R$^a$ represents hydrogen, —C$_{1-3}$alkyl, phenyl or a 5- or 6-membered heterocyclic group consisting of at least one heteroatom selected from O, N or S, the phenyl or heterocyclic group being optionally substituted by one or more substituents selected from: —C$_{1-3}$alkyl, —C$_{1-3}$alkoxy, —C$_{1-3}$alkylOH, halogen, —CN, —CF$_3$, —NH$_2$, —CO$_2$H and —OH;

R$^b$ and R$^c$ independently represent hydrogen or —C$_{1-4}$alkyl;

R$^2$ and R$^3$ independently represent hydrogen, —C$_{1-3}$alkyl or —CF$_3$, with the proviso that one of R$^2$ and R$^3$ is —C$_{1-3}$alkyl or —CF$_3$ and the other is hydrogen;

R$^4$ and R$^5$, together with the N atom to which they are bonded, form a 6-membered non-aromatic heterocyclic ring, consisting of an additional O atom and optionally substituted by:

(i) one or more substitutents selected from: —NH$_2$, —CF$_3$, F, —OH, =O, —CO$_2$H, —C$_{1-6}$alkyl, —C$_{1-6}$alkoxy, —C$_{1-6}$alkylOH, —(C$_{1-3}$alkyl)NR$^b$R$^c$, —(C$_{0-3}$alkyl)CONR$^b$R$^c$, —NHSO$_2$CF$_3$, —NHSO$_2$(C$_{0-3}$alkyl)R$^a$, —NHCH$_2$COCH$_2$O(C$_{1-3}$alkyl), —(C$_{0-3}$alkyl)CO$_2$C$_{1-4}$alkyl, —CONHC$_{2-3}$alkylOH, —CH$_2$NHC$_{2-3}$alkylOH, —CH$_2$OC$_{1-3}$alkyl, —COCH$_2$NR$^b$R$^c$, —COCH$_2$N$^+$(CH$_3$)$_3$ and —CH$_2$SO$_2$C$_{1-3}$alkyl;

(ii) a group —NHCOR$^d$ or —NR$^b$R$^d$,

R$^d$ represents —C$_{1-6}$alkyl, —C$_{2-6}$alkynyl, —C$_{1-6}$alkoxy, —C$_{1-6}$alkylOH, —C$_{1-3}$alkylCO$_2$H, —C$_{1-3}$alkylNR$^b$R$^c$, —C$_{1-3}$alkylCO$_2$C$_{1-3}$alkyl, —C$_{1-3}$alkylCONR$^b$R$^c$ and —C$_{1-3}$alkylOC$_{1-3}$alkyl;

(iii) a group —Y—R$^e$,

Y represents —C$_{1-3}$alkylene-, —NHCO—, —NHCO$_2$C$_{1-3}$ alkylene-, —NHC$_{1-3}$alkylene-, —CO—, —C$_{1-3}$alkylNH—, —C$_{1-3}$alkylNHCO—, —C$_{1-3}$alkylNHSO$_2$—, —CH$_2$NHSO$_2$CH$_2$— or a direct link, R$^e$ represents phenyl, phenyl, a 5- or 6-membered heterocycle consisting of at least one heteroatom selected from O, N or S, or a 5- or 6-membered cycloalkyl, each of which is optionally substituted by one or more substituents selected from: —C$_{1-3}$alkyl, —C$_{1-3}$alkoxy, —C$_{1-3}$alkylOH, halogen, —CN, —CF$_3$, —NH$_2$, —CO$_2$H and —OH; or (iv) a second ring R$^f$ which is fused to the non-aromatic heterocyclic ring formed by R$^4$ and R$^5$, wherein R$^f$ represents phenyl, a 5- or 6-membered cycloalkyl group or a 5- or 6-membered aromatic heterocyclic group consisting of at least one heteroatom selected from O, N or S, and the fused bicyclic group is optionally substituted by one or more substituents selected from: —C$_{1-3}$alkyl, —C$_{1-3}$alkoxy, —C$_{1-3}$alkylOH, halogen, —CN, —CF$_3$, —NH$_2$, —CO$_2$H and —OH;

with the proviso that where the substituent on the non-aromatic ring formed by R$^4$ and R$^5$ is —NH$_2$, —OH, —C$_{1-6}$alkoxy, —NHSO$_2$CF$_3$, —NHSO$_2$(C$_{0-3}$alkyl)R$^a$, —NHCOR$^d$, —NR$^b$R$^d$, —NHCOR$^e$, —NHCO$_2$C$_{1-3}$alkyleneR$^e$ or —NHC$_{1-3}$alkyleneR$^e$, —NHCH$_2$COCH$_2$O(C$_{1-3}$alkyl), the substituent is not attached to a ring carbon atom adjacent to a heteroatom;

R$^6$ represents:

a group —R$^g$R$^h$;

wherein R$^g$ represents a thienyl group and R$^h$ represents phenyl or a 5- or 6-membered aromatic heterocyclic group consisting of at least one heteroatom selected from O, N or S, the phenyl or aromatic heterocyclic group being optionally substituted by one or more substituents selected from: —C$_{1-3}$alkyl, —C$_{1-3}$alkoxy, halogen, —CN, —CF$_3$, —NH$_2$, —CO$_2$H and —OH;

and pharmaceutically acceptable derivatives thereof.

2. A compound of formula (I)

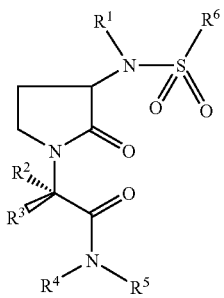

wherein:
R$^1$ represents hydrogen, —C$_{1-6}$alkyl, —C$_{2-6}$alkenyl, —C$_{2-6}$alkynyl, —C$_{2-6}$alkylOH, —C$_{2-3}$alkylNR$^b$R$^a$, —C$_{2-3}$alkylNHCOR$^a$, —C$_{2-3}$alkylNHCO$_2$R$^b$, —C$_{2-3}$alkylNHSO$_2$R$^b$, —C$_{2-3}$alkylNHCONR$^b$R$^c$ or a group X—W;

X represents —C$_{1-3}$alkylene-, propenylene, propynylene;
W represents —CN, —CO$_2$H, —CONR$^b$R$^c$, —COC$_{1-6}$alkyl, —CO$_2$C$_{1-6}$alkyl, —CO$_2$C$_{2-6}$alkenyl, —OCONR$^b$R$^c$, —OC$_{1-6}$alkyl, —OCH$_2$phenyl, phenyl or 5- or 6-membered aromatic heterocyclic group consisting of at least one heteroatom selected from O, N or S, the phenyl or aromatic heterocyclic group being optionally substituted by one or more substitutents selected from: —C$_{1-3}$alkyl, —C$_{1-3}$alkoxy, —C$_{1-3}$alkylOH, halogen, —CN, —CF$_3$, —NH$_2$, —CO$_2$H and —OH;

R$^a$ represents hydrogen, —C$_{1-3}$alkyl, phenyl or a 5- or 6-membered heterocyclic group consisting of at least one heteroatom selected from O, N or S, the phenyl or heterocyclic group being optionally substituted by one or more substituents selected from: —C$_{1-3}$alkyl, —C$_{1-3}$alkoxy, —C$_{1-3}$alkylOH, halogen, —CN, —CF$_3$, —NH$_2$, —CO$_2$H and —OH;

R$^b$ and R$^c$ independently represent hydrogen or —C$_{1-3}$alkyl;

R$^2$ and R$^3$ independently represent hydrogen, —C$_{1-3}$alkyl or —CF$_3$, with the proviso that when one of R$^2$ and R$^3$ is —C$_{1-3}$alkyl or —CF$_3$, the other is hydrogen;

R$^4$ and R$^5$, together with the N atom to which they are bonded, form a 6-membered non-aromatic heterocyclic ring, consisting of an additional O atom and optionally substituted by: (i) one or more substitutents selected from: —NH$_2$, —CF$_3$, F, —OH, =O, —CO$_2$H, —C$_{1-6}$alkyl, —C$_{1-6}$alkoxy, —C$_{1-6}$alkylOH, —(C$_{1-3}$alkyl)NR$^b$R$^c$, —(C$_{0-3}$alkyl)CONR$^b$R$^c$, —NHSO$_2$CF$_3$, —NHSO$^2$(C$_{0-3}$alkyl)R$^a$ and (C$_{0-3}$alkyl)CO$_2$C$_{1-3}$alkyl;

(ii) a group —NHCOR$^d$ or —NR$^b$R$^d$,
R$^d$ represents —C$_{1-6}$alkyl, —C$_{2-6}$alkynyl, —C$_{1-6}$alkoxy, —C$_{1-6}$alkylOH, —C$_{1-3}$alkylCO$_2$H, —C$_{1-3}$alkylNR$^b$R$^c$, —C$_{1-3}$alkylCO$_2$C$_{1-3}$alkyl or —C$_{1-3}$alkylCONR$^b$R$^c$;

(iii) a group —Y—R$^e$,
Y represents —C$_{1-3}$alkylene-, —NHCO—, —NHCO$_2$C$_{1-3}$ alkylene-, —NHC$_{1-3}$alkylene-, —CO—, —C$_{1-3}$alkylNH—, —C$_{1-3}$alkylNHCO—, —C$_{1-3}$alkylNHSO$_2$—, —CH$_2$NHSO$_2$CH$_2$— or a direct link,
R$^e$ represents phenyl, a 5- or 6-membered cycloalkyl or a 5- or 6-membered heterocycle consisting of at least one heteroatom selected from O, N or S, each of which is optionally substituted by one or more substituents selected from: —C$_{1-3}$alkyl, —C$_{1-3}$alkoxy, —C$_{1-3}$alkylOH, halogen, —CN, —CF$_3$, —NH$_2$, —CO$_2$H and —OH; or (iv) a second ring R$^f$ which is fused to the non-aromatic heterocyclic ring formed by R$^4$ and R$^5$, wherein R$^f$ represents phenyl, a 5- or 6-membered cycloalkyl group or a 5- or 6-membered aromatic heterocyclic group consisting of at least one heteroatom selected from O, N or S, and the fused bicyclic group is optionally substituted by one or more substituents selected from: —C$_{1-3}$alkyl, —C$_{1-3}$alkoxy, —C$_{1-3}$alkylOH, halogen, —CN, —CF$_3$, —NH$_2$, —CO$_2$H and —OH;

with the proviso that where the substituent on the non-aromatic ring formed by R$^4$ and R$^5$ is —NH$_2$, —OH, —C$_{1-6}$alkoxy, —NHSO$_2$CF$_3$, —NHSO$_2$(C$_{0-3}$alkyl)R$^a$, —NHCOR$^d$, —NR$^b$R$^d$, —NHCOR$^e$, —NHCO$_2$C$_{1-3}$alkyleneR$^e$ or —NHC$_{1-3}$alkyleneR$^e$, the substituent is not attached to a ring carbon atom adjacent to a heteroatom;

R$^6$ represents:
a group —R$^g$R$^h$;
wherein R$^g$ and R$^h$ independently represent phenyl or a 5- or 6-membered aromatic heterocyclic group consisting of at least one heteroatom selected from O, N or S, the phenyl or aromatic heterocyclic group being optionally substituted by one or more substituents selected from: —C$_{1-3}$alkyl, —C$_{1-3}$alkoxy, halogen, —CN, —CF$_3$, —NH$_2$, —CO$_2$H and —OH;
and pharmaceutically acceptable salts or solvates thereof.

3. A compound as claimed in claim 1 or claim 2 wherein R$^1$ represents hydrogen, —C$_{1-6}$alkyl, —C$_{2-6}$alkenyl or a group X—W wherein X represents —C$_{1-3}$alkylene- and W represents —CN, —CO$_2$H, —CONR$^b$R$^c$, —COC$_{1-6}$alkyl, —CO$_2$C$_{1-6}$alkyl or a 5- or 6-membered aromatic heterocyclic group consisting of at least one heteroatom selected from O, N or S.

4. A compound as claimed in claim 1 wherein R$^1$ represents hydrogen, —C$_{1-6}$alkyl, —C$_{3-6}$alkenyl, —C$_{2-3}$alkylNR$^b$R$^a$, —C$_{2-3}$alkylNHCOR$^a$, phenyl or a 5- or 6-membered aromatic heterocycle, or R$^1$ represents a group X—W wherein X represents —C$_{1-6}$alkylene- and W represents —CN, —CO$_2$H, —CONR$^b$R$^c$, —COC$_{1-6}$alkyl, —CO$_2$C$_{1-6}$alkyl or a 5- or 6-membered aromatic or non-aromatic heterocyclic group consisting of at least one heteroatom selected from O, N or S.

5. A compound as claimed in claim 1 wherein R$^2$ represents —C$_{1-3}$alkyl or hydrogen.

6. A compound as claimed in claim 1 wherein R$^3$ represents —C$_{1-3}$alkyl or hydrogen.

7. A compound as claimed in claim 1 wherein R$^4$ and R$^5$, together with the N atom to which they are bonded, form a morpholine group optionally substituted by:

(i) one or more subsituents selected from: —NH$_2$, —CF$_3$, —OH, —CO$_2$H, —C$_{1-6}$alkyl, —C$_{1-6}$alkoxy, —C$_{1-6}$alkylOH, —(C$_{1-3}$alkyl)—NR$^b$R$^c$, —(C$_{0-3}$alkyl)CONR$^b$R$^c$ and —NHSO$_2$CF$_3$;

(ii) a group NHCOR$^d$ wherein R$^d$ represents —C$_{1-6}$alkyl, —C$_{2-6}$alkynyl, —C$_{1-6}$alkoxy, —C$_{1-3}$alkylCO$_2$H, —C$_{1-3}$ alkylNR$^b$R$^c$, —C$_{1-3}$alkylCO$_2$C$_{1-3}$alkyl or —C$_{1-3}$ alkylCONR$^b$R$^c$ or a group NHR$^d$ wherein R$^d$ represents —C$_{1-6}$alkyl or —C$_{1-6}$alkylOH;

(iii) a group —Y—R$^e$, Y represents —C$_{1-3}$alkylene-, —NHCO—, —NHCO$_2$C$_{1-3}$alkylene-, —NHC$_{1-3}$alkylene- or —C$_{1-3}$alkylNHSO$_2$—, R$^e$ represents imidazole, pyrrole, pyrazole, pyridine, pyrimidine, furan, oxazole, 1,2,4-triazole, phenyl or pyrrolidine optionally substituted by —$C_{1-3}$alkyl, $NH_2$ or —$C_{1-3}$alkylOH;

(iv) a second ring $R^f$ which is fused to the non-aromatic heterocyclic ring formed by $R^4$ and $R^5$, wherein $R^f$ represents cyclohexyl;

with the proviso that where the substituent on the non-aromatic ring formed by $R^4$ and $R^5$ is —$NH_2$, —OH, —$C_{1-6}$alkoxy, —$NHSO_2CF_3$, —$NHCOR^d$, —$NR^bR^d$, —$NHCOR^e$, —$NHCO_2C_{1-3}$alkyleneR$^e$ or —$NHC_{1-3}$alkyleneR$^e$, the substituent is not attached to a ring carbon atom adjacent to a heteroatom.

8. A compound as claimed in claim 1 wherein $R^4$ and $R^5$, together with the N atom to which they are bonded, form a unsubstituted morpholine.

9. A compound as claimed in claim 1 wherein $R^6$ represents

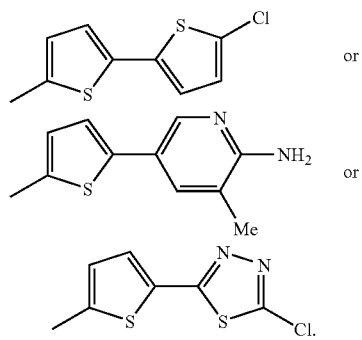

or

10. A compound selected from:

N²-[(5'-Chloro-2,2'-bithien-5-yl)sulfonyl]-N2-{(3S)-1-[(1S)-1-methyl-2-morpholin-4-yl-2-oxoethyl]-2-oxopyrrolidin-3-yl}glycinamide;

N-[(5'-Chloro-2,2'-bithien-5-yl)sulfonyl]-N-{(3S)-1-[(1S)-1-methyl-2-morpholin-4-yl-2-oxoethyl]-2-oxopyrrolidin-3-yl}glycine;

5'-Chloro-N-{(3S)-1-[(1S)-1-methyl-2-morpholin-4-yl-2-oxoethyl]-2-oxopyrrolidin-3-yl}-2,2'-bithiophene-5-sulfonamide;

5'-Chloro-N-(cyanomethyl)-N-{(3S)-1-[(1S)-1-methyl-2-morpholin-4-yl-2-oxoethyl]-2-oxopyrrolidin-3-yl}-2,2'-bithiophene-5-sulfonamide;

Methyl N-[(5'-chloro-2,2'-bithien-5-yl)sulfonyl]-N-{(3S)-1-[(1S)-1-methyl-2-morpholin-4-yl-2-oxoethyl]-2-oxopyrrolidin-3-yl}glycinate;

5'-Chloro-N-{(3S)-1-[(1S)-1-methyl-2-morpholin-4-yl-2-oxoethyl]-2-oxopyrrolidin-3-yl}-N-(2-oxobutyl)-2,2'-bithiophene-5-sulfonamide; and 5-(5-Chloro-1,3,4-thiadiazol-2-yl)-N-{(3S)-1-[(1S)-1-methyl-2-morpholin-4-yl-2-oxoethyl]-2-oxopyrrolidin-3-yl}thiophene-2-sulfonamide.

11. A pharmaceutical composition consisting of a compound according to claim 1 together with a pharmaceutical carrier and/or excipient.

* * * * *

UNITED STATES PATENT AND TRADEMARK OFFICE
CERTIFICATE OF CORRECTION

PATENT NO. : 7,084,139 B2  
APPLICATION NO. : 10/479534  
DATED : August 1, 2006  
INVENTOR(S) : Chan et al.

Page 1 of 1

It is certified that error appears in the above-identified patent and that said Letters Patent is hereby corrected as shown below:

Claim 2 (Column 169, Line 52) should read as follows:

-- $R^b R^c$, -($C_{0-3}$alkyl)$CONR^b R^c$, -$NHSO_2CF_3$, -$NHSO_2$ --

Claim 2 (Column 170, Line 23) should read as follows:

-- wherein $R^g$ represents a thienyl group and $R^h$ represents phenyl or a 5- --

Claim 8 (Column 171, Line 13) should read as follows:

-- together with the N atom to which they are bonded, form an --

Signed and Sealed this

Fifteenth Day of April, 2008

JON W. DUDAS  
*Director of the United States Patent and Trademark Office*